United States Patent
Chern et al.

(10) Patent No.: US 11,535,598 B2
(45) Date of Patent: Dec. 27, 2022

(54) HISTONE DEACETYLASES (HDACS) INHIBITORS

(71) Applicant: ANNJI PHARMACEUTICAL CO., LTD., Taipei (TW)

(72) Inventors: Ji-Wang Chern, Taipei (TW); Chao-Wu Yu, Taipei (TW); Jia-Rong Liu, Taipei (TW); Yi-Hsun Ho, Taipei (TW); Chia-Yu Wu, Taipei (TW); Chan-Hui Huang, Taipei (TW); Pei-Yun Hung, Taipei (TW)

(73) Assignee: AnnJi Pharmaceutical Co., Ltd., Taipei (TW)

( * ) Notice: Subject to any disclaimer, the term of this patent is extended or adjusted under 35 U.S.C. 154(b) by 135 days.

(21) Appl. No.: 16/494,284

(22) PCT Filed: May 15, 2018

(86) PCT No.: PCT/US2018/032848
§ 371 (c)(1),
(2) Date: Sep. 14, 2019

(87) PCT Pub. No.: WO2018/213364
PCT Pub. Date: Nov. 22, 2018

(65) Prior Publication Data
US 2021/0355089 A1 Nov. 18, 2021

Related U.S. Application Data

(60) Provisional application No. 62/507,196, filed on May 16, 2017.

(51) Int. Cl.
| | |
|---|---|
| *C07D 239/96* | (2006.01) |
| *C07D 401/04* | (2006.01) |
| *C07D 403/06* | (2006.01) |
| *C07D 405/06* | (2006.01) |
| *C07D 409/06* | (2006.01) |
| *C07D 471/04* | (2006.01) |
| *C07D 495/04* | (2006.01) |

(52) U.S. Cl.
CPC ......... *C07D 239/96* (2013.01); *C07D 401/04* (2013.01); *C07D 403/06* (2013.01); *C07D 405/06* (2013.01); *C07D 409/06* (2013.01); *C07D 471/04* (2013.01); *C07D 495/04* (2013.01)

(58) Field of Classification Search
CPC .................................................. C07D 239/96
See application file for complete search history.

(56) References Cited

U.S. PATENT DOCUMENTS

| | | |
|---|---|---|
| 2012/0094997 A1 | 4/2012 | England et al. |
| 2015/0196563 A1 | 7/2015 | Chern et al. |

FOREIGN PATENT DOCUMENTS

| | | |
|---|---|---|
| JP | 2003-137866 A | 5/2003 |
| WO | 2013184806 A1 | 12/2013 |

OTHER PUBLICATIONS

Yu et al. J.Med. Chem. 62, p. 857-874. (Year: 2019).*
Li et al. Journal of Hematology & Oncology (2018) 11:111. (Year: 2018).*
Office Action issued in corresponding Canadian Application No. 3063111, dated Feb. 23, 2021 (4 pages).
C. Yu et al., "Quinazolin-4-one Derivatives as Selective Histone Deacetylase-6 Inhibitors for the Treatment of Alzheimer's Disease," Journal of Medical Chemistry, vol. 56, No. 17, pp. 6715-6791, Sep. 12, 2013 (17 pages).
Extended European Search Report issued in corresponding European Application No. 18801840.2; dated Nov. 3, 2020 (8 pages).
(Continued)

*Primary Examiner* — Erich A Leeser

(74) *Attorney, Agent, or Firm* — Osha Bergman Watanabe & Burton LLP

(57) ABSTRACT

Histone deacetylases (HDACs) inhibitors are disclosed according to the following structural formula.

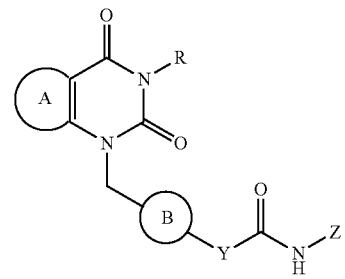

The moiety A is a benzene ring, optionally substituted. The moiety B is a benzene ring attached at the 1,4 or 1,3 position, or a cyclohexane ring attached at the 1,4 position, optionally substituted. R and Z are further substituents. The HDACs inhibitors possess cytotoxicities to various cancer cell lines. They are useful for treating a tumor associated with deregulation of the activity of histone deacetylases in a subject in need thereof, in one embodiment, the HDACs inhibitors of the invention are useful for treating glioma, breast cancer, colon cancer, target cell lung cancer, adenocarcinoma of the lung, small cell lung cancer, stomach cancer, liver cancer, ovary adenocarcinoma, pancreas carcinoma, prostate carcinoma, promyiocytic leukemia, chronic myelocytic leukemia, or acute lymphocytic leukemia in a subject in need thereof.

20 Claims, 3 Drawing Sheets

(56) References Cited

OTHER PUBLICATIONS

International Search Report for PCT/US2018/032848, dated Jul. 16, 2018.
Written Opinion of International Search Authority for PCT/US2018/032848, dated Jul. 16, 2018.
Office Action issued in corresponding BR Application No. BR1120190241116 with English translation dated Sep. 6, 2022 (7 pages).
Smil, David V. et al. "Novel HDAC6 isoform selective chiral small molecule histone deacetylase inhibitors" Bioorganic & Medicinal Chemistry Letters 19 (2009) 688-692 (5 pages).
Office Action issued in corresponding Chinese Application No. 201880030154.1, dated Apr. 15, 2022 (12 pages).
"Bicyclic-Capped Histone Deacetylase 6 Inhibitors with Improved Activity in a Model of Axonal Charcot-Marie-Tooth Disease", Sida Shen et al., ACS Chem Neurosci, vol. 7, No. 2, pp. 240-258. (45 pages).

\* cited by examiner

HISTONE DEACETYLASES (HDACS) INHIBITORS

REFERENCE TO RELATED APPLICATION

This application is a national stage application (under 35 U.S.C. 371) of PCT/US 18/032848 filed on 15 May 2018, which claims priority to US provisional application 62/507,196 filed on 16 May 2017, all of which are herein incorporated by reference in their entireties,

FIELD OF THE INVENTION

The present invention relates generally to histone deacetylases inhibitors.

BACKGROUND OF THE INVENTION

WO2008040934, WO2008068170, WO/2008/087514, WO/2009/026446, WO/2009/045440, WO/2011/011186, WO/2012/117421, WO/2012/106343, WO/2013/078544, U.S. Pat. Nos. 8,431,538; 8,188,138; 8,058,273 and 7,803,800 disclose histone deacetylases (HDACs), inhibitors having antitumor activities and antineurondegenerative activities.

SUMMARY OF THE INVENTION

In one aspect, the invention relates to a compound of Formula I

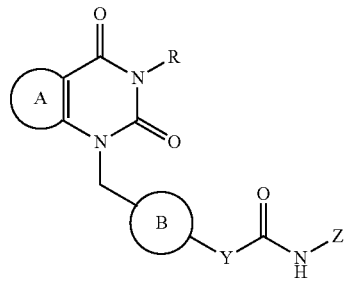

Formula I or a pharmaceutically acceptable salt thereof, wherein
R is $(C_1-C_6)$alkyl, $(C_3-C_6)$alkenyl, phenyl$(C_3-C_6)$alkenyl, $(C_{3-6})$cycloalkyl, (C3-C6)cycloalkenyl(C1-C6)alky $(C_1-C_6)$alkyl$(C_3-C_6)$cycloalkyl, $(C_5)$heterocycloalkyl, $(C_1-C_6)$alkyl $(C_6-C_{18})$aryl, cyclopropyl-$C_6H_5$, $(C_1-C_6)$alkoxy$(C_1-C_6)$alkyl, halo$(C_1-C_6)$alkyl, halo$(C_3-C_6)$cycloalkyl, $(C_6-C_{18})$aryl, halophenyl, halo$(C_1-C_6)$alkylphenyl, halo$(C_1-C_6)$alkyl$(C_6-C_{18})$aryl$(C_1-C_6)$alkoxy, halo$(C_1-C_6)$alkylphenoxy$(C_1-C_6)$alkyl, halo$(C_1-C_6)$alkylhalophenyl, $(C_1-C_6)$alkylhalo$(C_1-C_6)$alkylphenyl, hydroxyphenyl, nitrophenyl, nitrophenyl$(C_1-C_6)$alkyl, aminophenyl$(C_1-C_6)$alkyl, N—$(C_1-C_6)$alkylamino$(C_6-C_{18})$aryl$(C_1-C_6)$alkyl; $(C_1-C_6)$alkylbenzoic acid, hydroxyl$(C_1-C_6)$alkyl, hydroxyl$(C_3-C_6)$cycloalkyl$(C_1-C_6)$alkyl, hydroxy $(C_6-C_{18})$aryl$(C_1-C_6)$alkyl, hydroxyl$(C_1-C_6)$alkyl$(C_6-C_{18})$aryl, $(C_1-C_6)$alkoxy$(C_6-C_{18})$aryl, $(C_6-C_{18})$aryl$(C_1-C_6)$alkyl, $(C_3-C_{18})$heteroaryl$(C_1-C_6)$alkyl, halo$(C_6-C_{18})$aryl$(C_1-C_6)$alkyl, halo$(C_1-C_6)$alkoxy$(C_6-C_{18})$aryl, halo$(C_1-C_6)$alkoxy $(C_6-C_{18})$aryl$(C_1-C_6)$alkyl, halo$(C_1-C_6)$alkyl$(C_6-C_{18})$aryl$(C_1-C_6)$alkyl, $(C_1-C_6)$akylamino$(C_6-C_{18})$aryl$(C_1-C_6)$alkyl, morpholinyl$(C_1-C_6)$alkyl, morpholinyl$(C_1-C_6)$alkyl$(C_6-C_{18})$aryl, morpholinyl$(C_1-C_6)$alkyl$(C_6-C_{18})$aryl$(C_1-C_6)$alkyl, morpholinyl$(C_6-C_{18})$aryl$(C_1-C_6)$alkyl, piperidinyl, piperidinyl$(C_1-C_6)$alkyl, N—$(C_1-C_6)$alkylpiperidinyl, N,N-di$(C_1-C_6)$alkylpiperidinyl, piperidinyl-N—$(C_1-C_6)$alkoxy$(C_6-C_{18})$aryl$(C_1-C_6)$alkyl, piperidinyl$(C_1-C_6)$alkyl$(C_6-C_{18})$aryl$(C_1-C_6)$alkyl, pyridine, $(C_1-C_6)$alkylpyridine, $(C_1-C_6)$alkyl imidazole, hydroxyl$(C_6-C_{18})$aryl$(C_1-C_6)$alkyl, N,N-dimethyl$(C_6-C_{18})$aryl$(C_1-C_6)$alkyl, $(C_1-C_6)$alkoxy$(C_6-C_{18})$aryl$(C_1-C_6)$alkyl, hydroxyl$(C_1-C_6)$alkoxy$(C_6-C_{18})$aryl$(C_1-C_6)$alkyl, methylenedioxyphenyl$(C_1-C_6)$alkyl, or $(C_6-C_{18})$aryl$(C_1-C_6)$alkoxy;

The heterocyclic moiety

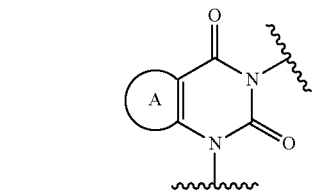

is optionally substituted with one or more $R^a$ or $R^b$, or $R^a$ and $R^b$, and is selected from the group consisting of

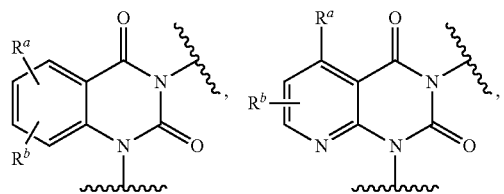

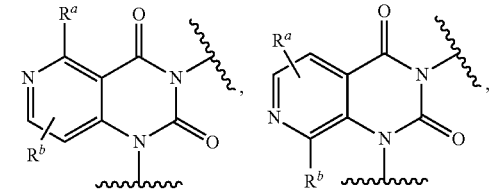

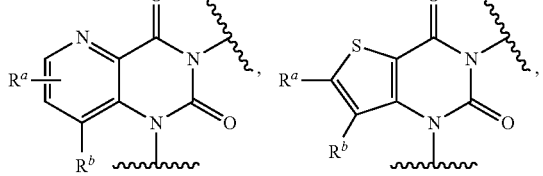

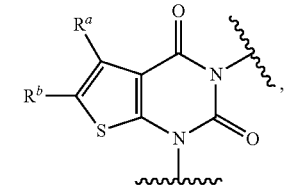

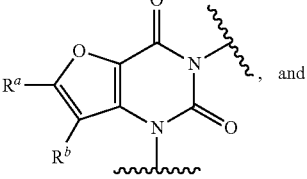, and

-continued

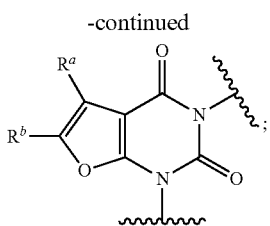

in which $R^a$ and $R^b$ are independently selected from the group consisting of hydrogen, halogen, $(C_1$-$C_6)$alky, $(C_6$-$C_{18})$aryl, $(C_3$-$C_{18})$heteroaryl, $(C_3$-$C_6)$cycloalkyl, $(C_1$-$C_6)$alkoxy, $(C_1$-$C_6)$alkoxy$(C_1$-$C_6)$alkoxy, aryloxy, hydroxyl, —$NO_2$, —CN, —$CF_3$ and —$CH_2CF_3$;

The moiety

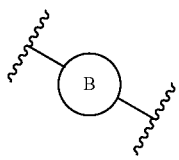

is selected from the group consisting of

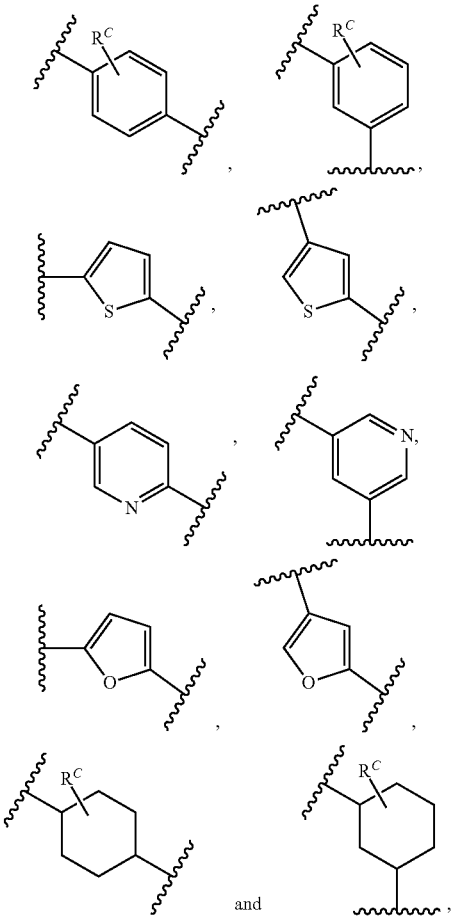

in which $R^c$ is optionally present and is hydrogen, halogen, (C1-C6)alkyl, or (C1-C6)alkoxyl;

Y is absent or is selected from the group consisting of —$CH_2$—, —$CF_2$—, —CFH—, —CH═CH—, and —$CH_2CH_2$—; and Z is —OH, —O—C(═O)—$CH_3$, —O-Valine, —O-Valine hydrochloride salt, —O-Valine trifluoroacetic acid salt, or —O—C(═O)—CH(NH2)-CH($CH_3$)$_2$ hydrochloride or trifluoroacetic acid salt.

In one embodiment, R is methyl, 2-Me-$C_6H_4$, —$CH_2$Ph, —$C_6H_5$, —$CH_2CH_2C_6H_5$, $(CH_2)_4C_6H_5$, —$CH_2CH_2$-(4-F—$C_6H_4$), —$CH_2$CH-(2-OMe-$C_6H_4$), —$CH_2CH_2$-(2-OH—$C_6H_4$), —$CH_2$CH-(2-thiophene), 2-F—$C_6H_4$, 3-F—$C_6H_4$, 4-F—$C_6H_4$, 2-Cl—$C_6H_4$, 4-Cl—$C_6H_4$, —$CH_2CH_2$-(2-F—$C_6H_4$), —$CH_2CH_2$-(3-F—$CH_4$), —$CH_2CH_2$-(4-F—$C_6H_4$), —$CH_2CH_2$-(4-Cl—$C_6H_4$), —$CH_2CH_2$OH, —$CH_2CH_2$OH—$C_6H_5$, —$CH_2CH_2$-(3-Cl-4-OMe-$C_6H_3$), —$CH_2CH_2$-(4-NHMe-$C_4H_4$), —$CH_2CH_2$-(4-morpholine-$C_6H_4$), —$OCH_2C_6H_5$, 4-OH—$C_6H_4$, —$CH_2CH_2$-(4-OH—$C_6H_4$), 4-OMe-$C_6H_4$, 2-OMe-$C_6H_4$, $CH_2CH_2$-(3-OMe-$C_6H_4$), —$CH_2CH_2$-(4-OMe-$C_6H_4$), 2-NO—$C_6$H4, cyclopropyl-$C_6H_5$, —$CH_2$-(4-$CF_3$—$C_6H_4$), —$CH_2$CH-(4-$CF_3$—$C_6H_4$), 2-F-3-$CF_3$—$C_6H_3$, 2-F-5-$CF_3$—$C_6H_3$, 2,4,5-tri-F—$C_6H_2$, —$CH_2CH_2CF_3$, —$CH_2CF_3$, —$CH_2CH_2$OMe, 2-$CF_3$—$C_6H_4$, —$CH_2$-(2-$CF_3$—$C_6H_4$), —$CH_2CH_2$-(2-$CF_3$—$C_6H_4$), —$CH_2$-(3-$CF_3$—$C_6H_4$), —$CH_2CH_2$-(3-$CF_3$—$C_6H_4$), 2,4-di-F—$C_6H_3$, —$CH_2CH_2$-(2-Br—$C_4H_4$), $CH_2CH_2$-(4-Br—$C_6H_4$), 2-t-Bu-$C_6H_4$, 2,6-di-iso-propyl-$C_6H_3$, 2-ethyl-$C_6H_4$, 2-Me-3-$CF_3$—$C_6H_3$, —$CH_2CH_2$-(6-(1,3-benzodioxole)), —$CH_2CH_2$-(3,4-diOMe-$C_6H_3$), 2,6-di-Me-$C_6H_3$, 2-methyl-$C_6H_4$, cyclopropyl, cyclohexyl, 3-$CF_3$—$C_6H_4$, 3,3-di-F-cyclobutyl, 2-$OCF_3$—$C_6H_4$, 2-pyridine, 3-pyridine, 4-pyridine, —$CH_2CH_2$-(2-pyridine), —$CH_2CH_2$-(3-pyridine), —$CH_2CH_2$-(4-pyridine), $CH_2$-(2-$OCF_3$—$C_6H_4$), 3-piperidine, 3-(N,N-di-Me-piperidinium), 3-(N-Et-piperidine), —$CH_2CH_2$-(4-($OCH_2CH_2$OH)—$C_6H_4$), —$CH_2CH_2$-(3,4-di-OH—$C_6H_3$), —$CH_2$-cyclopropyl, 2-F-cyclopentyl, —$CH_2CH_2$—(N-morpholine), 4-CH—(N-morpholine)-$C_6$Ha, $CH_2CH_2$—(O-3-$CF_3$—$C_6H_4$), propyl-2-CHs, $CH_2CH_2$-(4-$CH_2$—(N-morpholine)-$C_6H_4$), 4-(N-methyl-piperidine), —$CH_2CH_2$-(4-$CH_2$—(N-piperidine)-$C_6H_4$), —$CH_2CH_2$-(4-$OCH_2$CH—N-piperidine-$C_6H_4$), $CH_2CH_2$-(4-$NO_2$—$C_6H_4$), —$CH_2CH_2$-(4-$NH_2$—$C_6H_4$), —$CH_2CH_2$-(4-COOH—$C_6H_4$), (4-Cl-2,6-di-Me-$C_6H_2$), (4-Br-2,6-di-Me-$C_6H_2$), —$CH_2CH_2$—(N-imidazole), —$CH_2CHCH_2$, —$CH_2CH_2$-(cyclohexene), $CH_2CHCHC_6H_5$, $CH_2CH_2$-(1,2-OH-cyclohexane), or $CH_2CHFC_6H_5$.

In another embodiment, the moiety

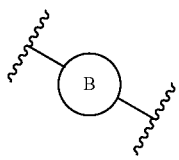

is $C_6H_4$, 3-F—$C_6H_2$, 2-F—$C_6H_3$, $C_6H_8$, or $CH_2CH_2$-(3-$CF_3$—$C_6H_4$).

In another embodiment, $R^a$ and $R^b$ are independently selected from the group consisting of H, —OH, —F, —Cl, —CF3, —CN, Me, —OMe, —$OCH_2CH_2$OMe, or cyclopropyl.

In another embodiment, R is methyl, phenyl, 4-chlorophenyl, 4-fluorophenyl, 4-hydroxyphenyl, 4-methoxyphenyl, 2-hydroxyphenyl, 2-methoxyphenyl, benzyl, 2-phenylethyl, 2-(4-hydroxyphenyl)ethyl, 2-(4-methoxyphenyl)

ethyl, 2-(4-fluorophenyl)ethyl, 2-thiophenylethyl, 3-phenylpropyl, or 2-(4-methoxyphenyl)ethyl.

In another embodiment, R is phenyl, benzyl, 2-phenylethyl, 2-(4-hydroxyphenyl)ethyl, 3-phenylpropyl, or 2-(4-methoxyphenyl)ethyl.

In another embodiment, a compound or a pharmaceutically acceptable salt thereof according to the invention is as listed in Table 5.

In another aspect, the invention relates to use of a compound or a pharmaceutically acceptable salt thereof according to the invention in the manufacture of a medicament for the treatment of a tumor associated with deregulation of the activity of histone deacetylases in a subject in need thereof. In one embodiment, the tumor is selected from the group consisting of glioma, pancreatic carcinoma, hepatocellular carcinoma, colon tumor, breast tumor, prostate tumor, lymphoma and cutaneous tumor. The cutaneous tumor may be melanomas or basal carcinomas.

In another aspect, the invention relates to use of a compound or a pharmaceutically acceptable salt thereof according to the invention in the manufacture of a medicament for the treatment of glioma, breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, or acute lymphocytic leukemia in a subject in need thereof.

In another aspect, the invention relates to use of a compound or a pharmaceutically acceptable salt thereof according to the invention in the manufacture of a medicament for treatment of a disease or a condition wherein inhibition of HDAC provides a benefit.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
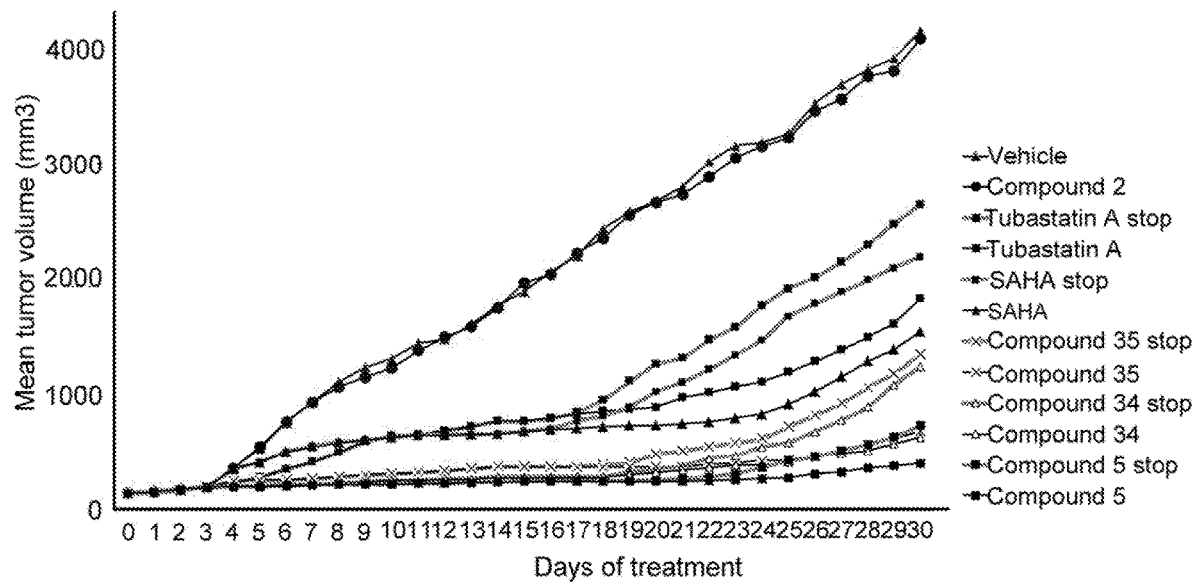
FIG. 1 shows plots of mean tumor volume vs. days of treatment for xenografted nude mouse model of prostate cancer cell line treated with vehicle. Compound 2 (10 Days, 10 mg/kg), Tubastatin A (14 Days, 10 mg/kg), Tubastatin A (30 Days, 10 mg/kg), SAHA (14 Days, 10 mg/kg), SAHA (30 Days, 10 mg/kg), Compound 35 (14 Days, 10 mg/kg), Compound 35 (30 Days, 10 mg/kg), Compound 34 (14 Days, 10 mg/kg), Compound 34 (30 Days, 10 mg/kg), Compound 5 (14 Days, 10 mg/kg), Compound 5 (30 days, 10 mg/kg).
Figure 2:
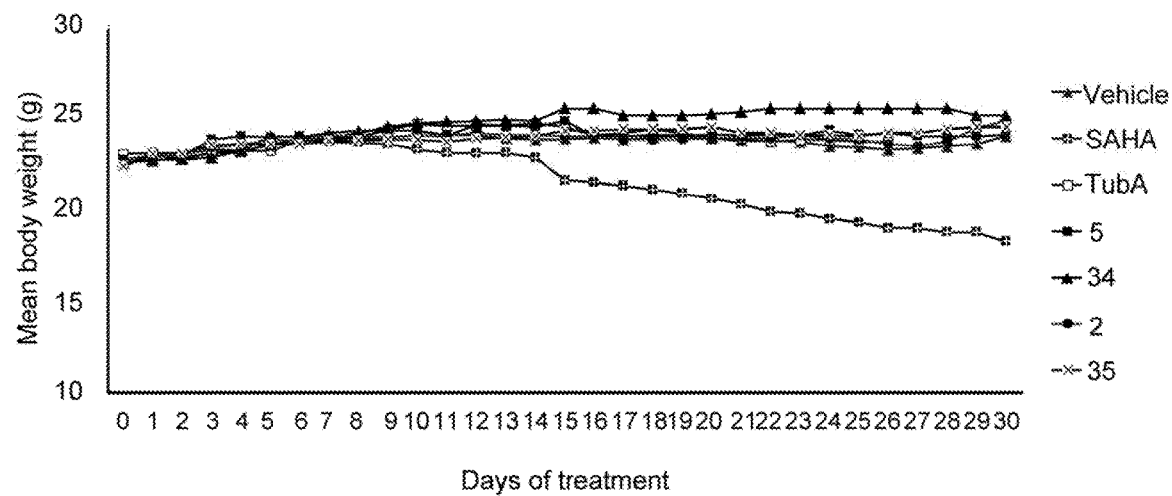
FIG. 2 shows plots of mean body weight vs. days of treatment for xenografted nude mouse model of prostate cancer cell line treated with vehicle SAHA (30 Days, 10 mg/kg), Tubastatin A (30 Days, 10 mg/kg), Compound 5 (30 Days, 10 mg/kg), Compound 34 (30 Days, 10 mg/kg), Compound 2 (30 Days, 10 mg/kg), Compound 35 (30 Days, 10 mg/kg).
Figure 3:
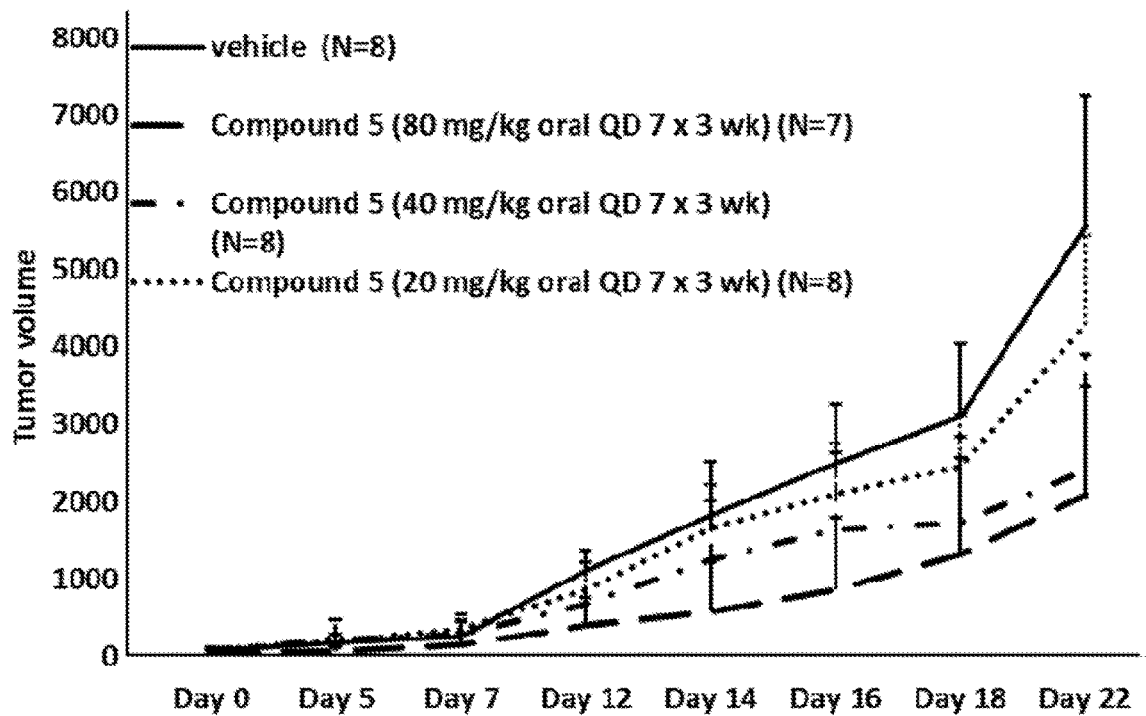
FIG. 3 shows plots of mean tumor volume vs. days of Treatment for syngeneic xenografted mouse model of lung, cancer cell line treated with vehicle. Compound 5 via oral for 21 days.
Figure 4:
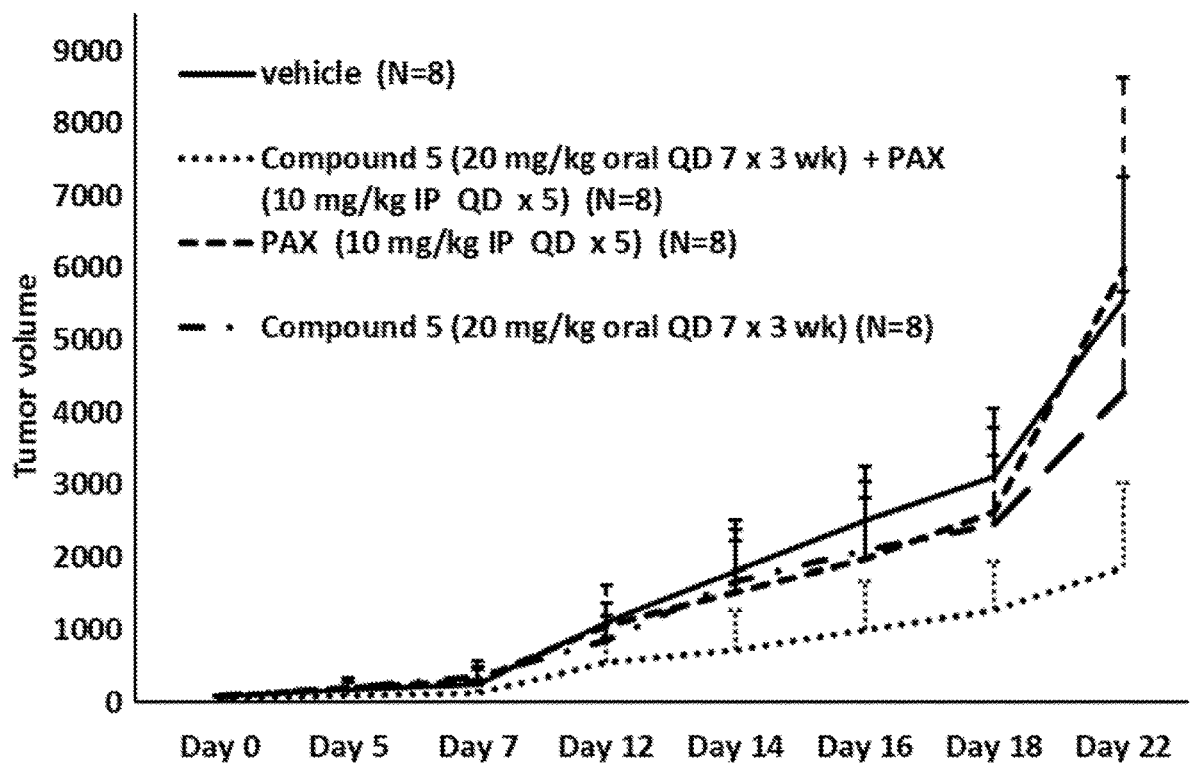
FIG. 4 shows plots of mean tumor volume vs. days of treatment for syngeneic xenografted mouse model of lung cancer cell line treated with vehicle, Paclitaxel (5 Days, 10 mg/kg), Compound 5 (21 Days, 20 mg/kg), Paclitaxel (5 Days, 10 mg/kg) combined with Compound 5 (21 Days, 20 mg/kg).
Figure 5:
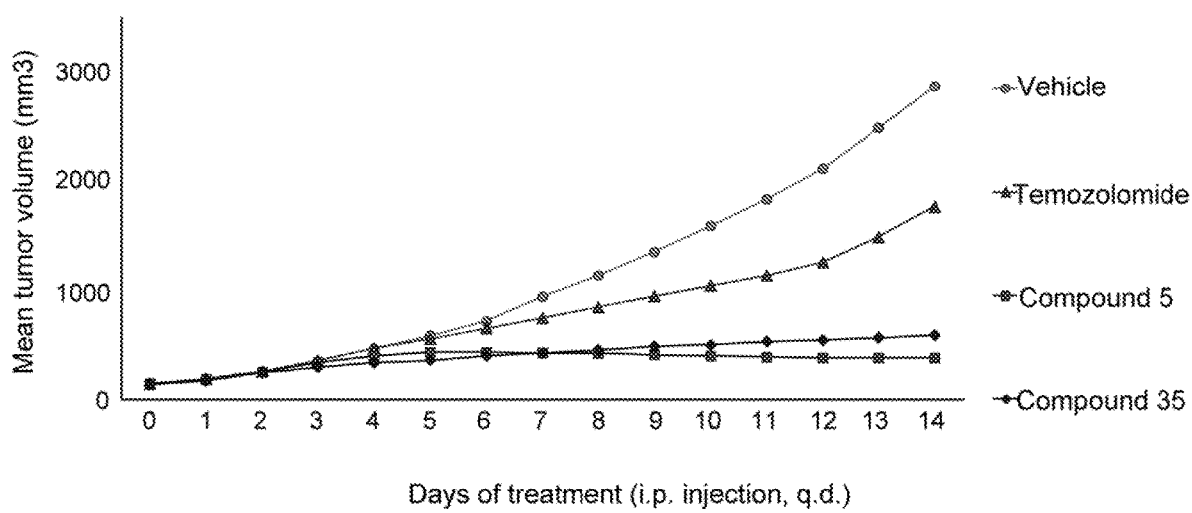
FIG. 5 shows plots of mean tumor volume vs. Days of Treatment for Xenografted nude mice model of glioblastoma cancer cell line treated with vehicle, Temozolomide (5 Days, 10 mg/kg), Compound 35 (14 Days, 10 mg/kg), Compound 5 (14 Days, 10 mg/kg).

Unless otherwise defined, all technical and scientific terms used herein have the same meaning as commonly understood by one of ordinary skill in the art to which this invention pertains. In the case of conflict, the present document, including definitions will control.

As used herein, the singular forms "a," "an" and "the" include plural reference useless the context dearly dictates otherwise.

A dash ("-") that is not between two letters or symbols is used to indicate a point of attachment for a moiety or substituent. For example, the moiety —$CONH_2$ is attached through the carbon atom.

The term "amino" refers to —$NH_2$. The amino group can be optionally substituted as defined herein for the term "substituted."

The term "alkyl" refers to a $C_1$-$C_{18}$ hydrocarbon containing normal, secondary, tertiary or cyclic carbon atoms. Examples are methyl, ethyl, 1-propyl, 2-propyl, 1-butyl, 2-methyl-1-propyl (iso-butyl, —$CH_2CH(CH_3)_2$), 2-butyl (sec-butyl, —$CH(CH_3)CH_2CH_3$), 2-methyl-2-propyl (tert-butyl, —$C(CH_3)_3$), 1-pentyl, 2-pentyl, 3-pentyl, 2-methyl-2-butyl, 3-methyl-2-butyl, 3-methyl-1-butyl, 2-methy-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methy-3-pentyl, 2,3-dimethyl-2-butyl, 3,3-dimethyl-2-butyl.

The alkyl can be a monovalent hydrocarbon radical, as described and exemplified above, or it can be a divalent hydrocarbon radical (i.e., alkylene).

The term "alkenyl" refers to a $C_2$-$C_{18}$ hydrocarbon containing normal, secondary, tertiary or cyclic carbon atoms with at least one site of unsaturation, i.e., a carbon-carbon, $sp^2$ double bond. Examples include, hut are not limited to: ethylene or vinyl (—$CH=CH_2$), allyl, (—$CH_2CH=CH_2$), cyclopentenyl (—$C_5H_7$), and 5-hexenyl (—$CH_2CH_2CH_2CH_2CH=CH_2$). The alkenyl can be a monovalent hydrocarbon radical, as described and exemplified above, or it can be a divalent hydrocarbon radical (i.e., alkenylene).

The term "alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene (—CH$_2$—) 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and the like.

The term "alkoxy" refers to the group alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphtyl, dihydrophenanthrenyl, fluorenyl, or anthryl). Preferred aryls include phenyl, naphthyl and the like. The aryl can optionally be a divalent radical, thereby providing an aryl ene.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sulfino, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

The terms "aryloxy" and "arylalkoxy" refer to, respectively, an aryl group bonded to an oxygen atom and an aralkyl group bonded to the oxygen atom at the alkyl moeity. Examples include but are not limited to phenoxy, naphthyloxy, and benzyloxy.

The term "carboxyl" refers to —COOH.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sultino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

As used herein, the term "halogen" or "halo" refer to fluoro, chloro, bromo, and iodo, the term "halogen" refers to fluorine, chlorine, bromine, and iodine.

As used herein, the term "heteroaryl" is defined herein as a monocycle, bicycle, or tricyclic ring system containing one, two, or three aromatic rings and containing at least one nitrogen, oxygen, or sulfur atom in an aromatic ring, and which can be unsubstituted or substituted. The heteroaryl can optionally be a divalent radical, thereby providing a heteroarylene.

Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocycle aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl, or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

The term "oxo" refers to =O.

The term "substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, acyloxy, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino-benzoyloxy, benzyl, benzyloxy, benzyloxycarbonyl, benzylthio, carbamoyl, carbamate, isocyanato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy. When a substituent is oxo(i.e., =O) or thioxo (i.e., =S) group, then two hydrogens on the atom are replaced.

The term "(C$_m$-C$_n$)", wherein m, n are integers, and n>m, means that all integer unit amounts within the range m to n are specifically disclosed as part of the invention. Thus, by "(C$_m$-C$_n$)", it means that C$_m$, C$_{m+1}$, C$_{m+2}$, ..., C$_{n-2}$, C$_{n-1}$, C$_n$, (C$_m$-C$_{m+1}$), (C$_m$-C$_{m+2}$), (C$_m$-C$_{m+3}$), ..., (C$_m$-C$_{n-2}$), (C$_m$-C$_{n-1}$), (C$_m$-C$_n$); (C$_{m+1}$-C$_{m+2}$), (C$_{m+1}$-C$_{m+3}$), (C$_{m+1}$-

$C_{m+4}$), ..., ($C_{m+1}$-$C_{n-2}$), ($C_{m+1}$-$C_{n-1}$), ($C_{m+1}$-$C_n$), ..., ($C_{n-2}$-$C_{n-1}$), ($C_{n-2}$-$C_n$); and ($C_{n-1}$-$C_n$) are included as embodiments of this invention.

By "($C_1$-$C_6$)", it means that all integer unit amounts within the range 1 to 6 are specifically disclosed as part of the invention. Thus, $C_1$, $C_2$, $C_3$, $C_4$, $C_5$, $C_6$, ($C_1$-$C_2$), ($C_1$-$C_3$), ($C_1$-$C_4$), ($C_1$-$C_5$), ($C_1$-$C_6$); ($C_2$-$C_3$), ($C_2$-$C_4$), ($C_2$-$C_5$), ($C_2$-$C_6$); ($C_3$-$C_4$), ($C_3$-$C_5$), ($C_3$-$C_6$); ($C_4$-$C_5$), ($C_4$-$C_6$); and ($C_5$-$C_6$) units amounts are included as embodiments of this invention.

By "($C_3$-$C_6$)", means that all integer unit amounts within the range 3 to 6 are specifically disclosed as part of the invention. Thus, $C_3$, $C_4$, $C_5$, $C_6$; ($C_3$-$C_4$), ($C_3$-$C_5$), ($C_3$-$C_6$); ($C_4$-$C_5$), ($C_4$-$C_6$); and ($C_5$-$C_6$) units amounts are included as embodiments of this invention.

By "($C_3$-$C_{18}$)", it means that all integer unit amounts within the range 3 to 18 are specifically disclosed as part of the invention. Thus, $C_3$, $C_4$, $C_5$, $C_6$, $C_7$, $C_8$, $C_9$, $C_{10}$, $C_{11}$, $C_{12}$ .... $C_{16}$, $C_{17}$, $C_{18}$; ($C_3$-$C_4$), ($C_3$-$C_5$), ($C_3$-$C_6$), ($C_3$-$C_7$), ($C_3$-$C_8$), ($C_3$-$C_9$) ... ($C_3$-$C_{18}$); ($C_4$-$C_5$), ($C_4$-$C_6$), ($C_4$-$C_7$), ($C_4$-$C_8$), ($C_4$-$C_9$) ... ($C_4$-$C_{18}$); ($C_5$-$C_6$), ($C_5$-$C_7$), ($C_5$-$C_8$), ($C_5$-$C_9$); ($C_5$-$C_{10}$), ($C_5$-$C_{11}$), ($C_5$-$C_{12}$) ... ($C_5$-$C_{18}$); ($C_6$-$C_7$), ($C_6$-$C_8$), ($C_6$-$C_9$) ... ($C_6$-$C_{18}$); ($C_7$-$C_8$), ($C_6$-$C_9$), ($C_6$-$C_{10}$) ... ($C_6$-$C_{18}$); ... ($C_{16}$-$C_{17}$), ($C_{16}$-$C_{18}$) and ($C_{17}$-$C_{18}$) units amounts are included as embodiments of this invention.

By "($C_6$-$C_{18}$)", it means that all integer unit amounts within the range 6 to 18 are specifically disclosed as part of the invention. Thus, $C_6$, $C_7$, $C_8$, $C_9$, $C_{10}$, $C_{11}$, $C_{12}$ ... $C_{16}$, $C_{17}$, $C_{18}$; ($C_6$-$C_7$), ($C_6$-$C_8$), ($C_6$-$C_9$), ($C_6$-$C_{10}$), ($C_6$-$C_{11}$), ($C_6$-$C_{12}$) ... ($C_6$-$C_{18}$); ($C_7$-$C_8$), ($C_7$-$C_9$), ($C_9$-$C_{10}$), ($C_7$-$C_{12}$) ... ($C_7$-$C_{18}$); ($C_8$-$C_9$), ($C_8$-$C_{10}$), ($C_8$-$C_{11}$), ($C_8$-$C_{12}$); ($C_9$-$C_{10}$), ($C_9$-$C_{11}$), ($C_9$-$C_{12}$) ... ($C_9$-$C_{18}$); ($C_{10}$-$C_{11}$), ($C_{10}$-$C_{12}$), ($C_{10}$-$C_{13}$) ... ($C_{10}$-$C_{18}$); ($C_{11}$-$C_{12}$), ($C_{11}$-$C_{13}$), ($C_{11}$-$C_{14}$) ... ($C_{11}$-$C_{18}$); ... ($C_{16}$-$C_{17}$), ($C_{16}$-$C_{18}$) and ($C_{17}$-$C_{18}$) units amounts are included as embodiments of this invention.

Methods of Making Compounds of Formula I
Synthesis

Compounds of formula I were prepared using the following schemes:

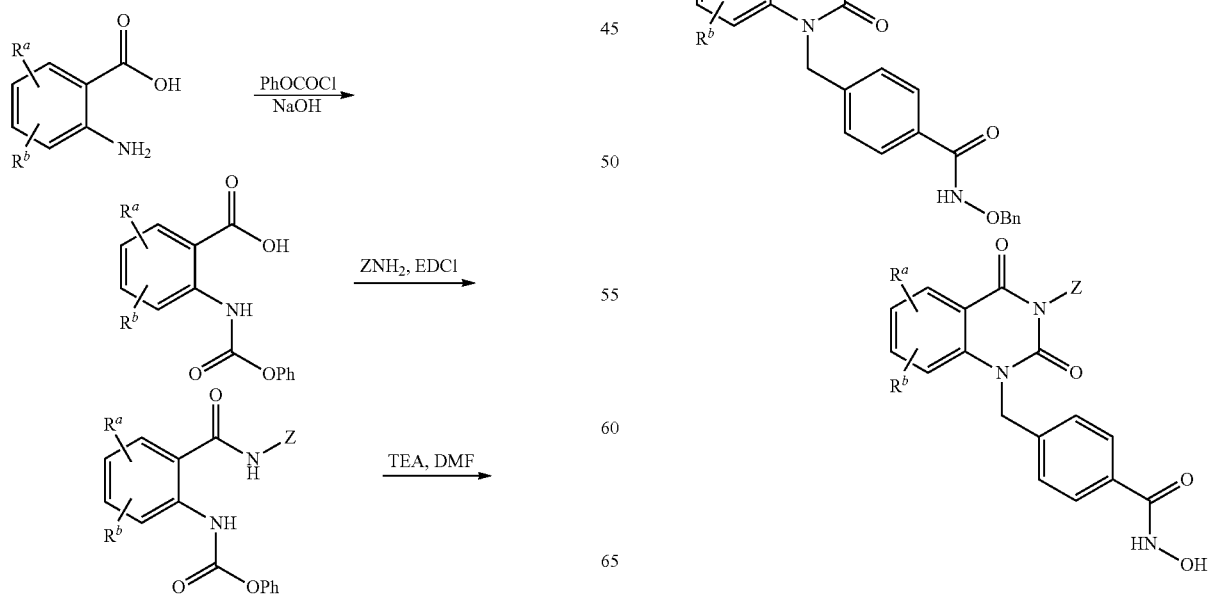

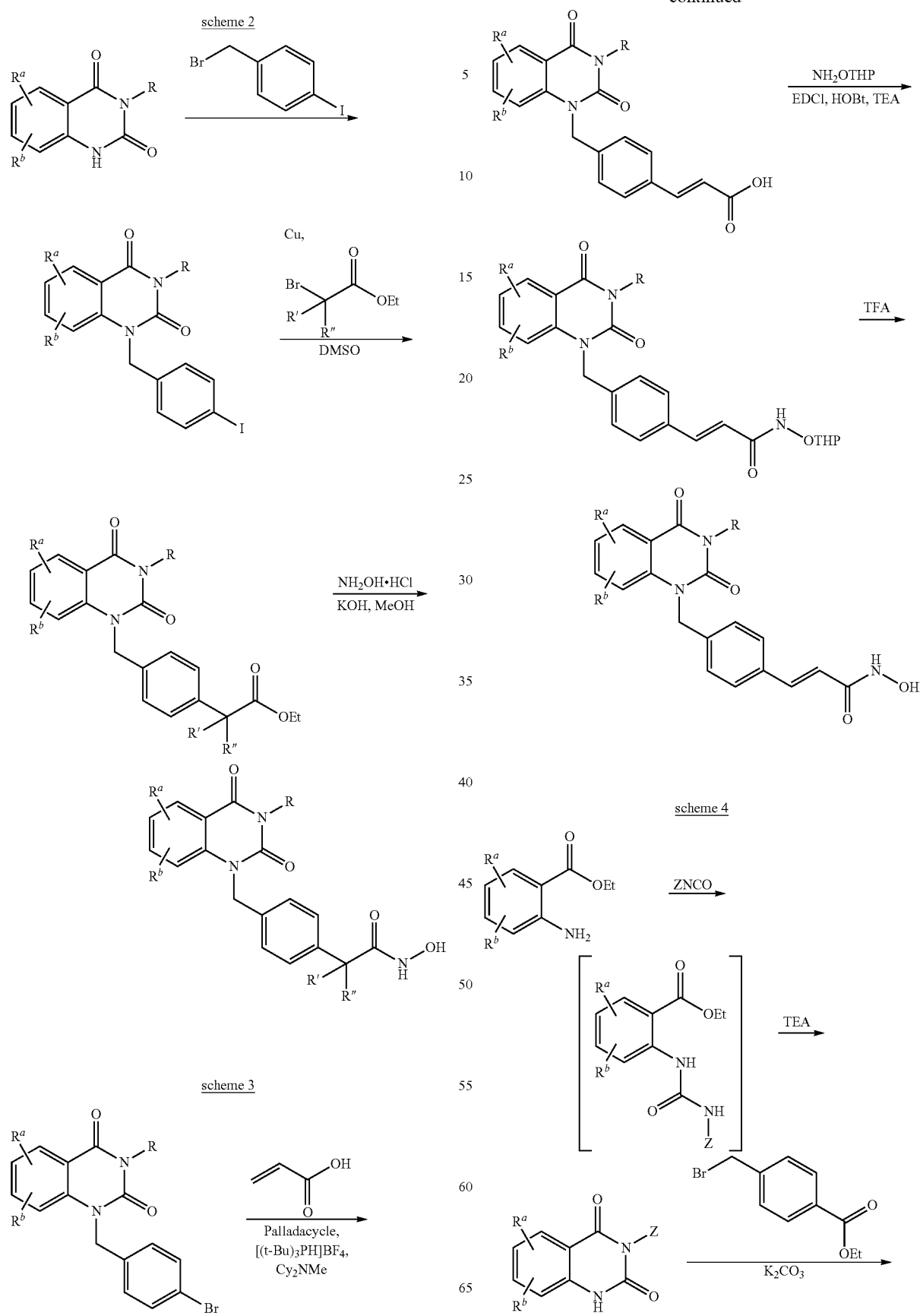

-continued

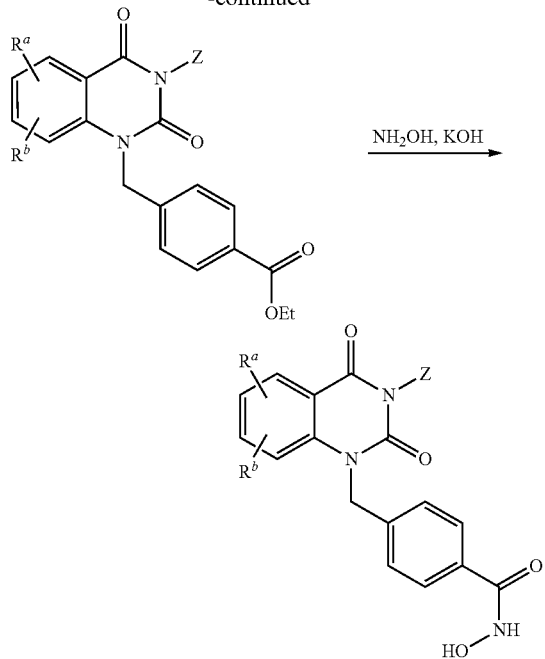

EXAMPLES

Example 1: Preparation of 4-((7-fluoro-2,4-dioxo-3-phenethyl-3,4-dihydroquinazolin-(2H)-yl)methyl)-N-hydroxybenzamide (Compound 1)

Steps 1 to 3: Preparation of 7-fluoro-3-phenethylquinazoline-2,4(1H,3H)-dione 4-fluoro anthranilic acid (10.00 g, 63.17 mmol) mixed with phenyl chloroformate (9.6 mL, 75.51 mmol) in dioxane (120 mL) was added dropwise with 1 N NaOH (126 mL) under ice bath for 1 h. The resulting solution was poured to ice water (200 mL) and filtered to get crude solid. Then the solid mixed with EDCI (13.30 g, 69.45 mmol) and HOBt (9.58 g, 69.48 mmol) in dichloromethane (150 mL) was stirred at it for 0.5 h.

Then phenethylamine (8.44 mL, 66.33 mmol) was added to reaction mixture and kept stirring for 4 h. The mixture was evaporated to dry and added with triethylamine (8.67 mL, 62.55 mmol) and DMF (50 mL), and the mixture was irradiated with microwave to reflux for 20 min. The resulting solution was poured to ice water (250 mL) to get solid formed. The solution was filtered and washed with excess of water to give tide compound as beige solid (6.80 g, three steps 37.9%).

Step 4: Preparation of ethyl 4-((7-fluoro-2,4-dioxo-3-phenethyl-3,4-dihydroquinazolin-1(2H)-yl)methyl) benzoate The beige solid (2.40 g, 8.44 mmol) from previous step suspended in DMF (35 mL) under ice bath was added with NaH (0.46 g, 11.5 mmol) and kept stirring for 1 h. After 1 h, ethyl 4-(bromomethyl)benzoate (4.45 g, 17.57 mmol) was added to the reaction mixture and kept stirring for 9 h from ice bath to room temperature. Alter 9 h. the resulting mixture was poured to ice water (150 mL) and then filtered to get beige solid. The solid was purified by column chromatography eluting with EtOAc/Hexanes=¼ to get title compound as white solid (2.35 g, 62.4%).

Steps 5 and 6: Preparation of N-(benzyloxy)-4-((7-fluoro-2,4-dioxo-3-phenethyl-3,4-dihydroquinazolin-1(2H)-yl)methyl)benzamide

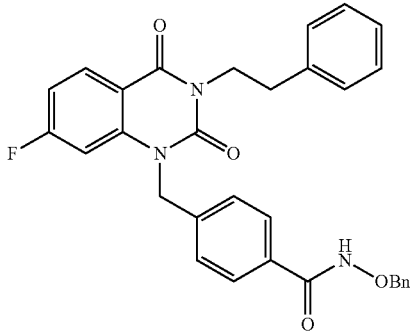 [SMILES: O=C(NOCc1ccccc1)c1ccc(Cn2c(=O)n(CCc3ccccc3)c(=O)c3ccc(F)cc32)cc1]

The white solid (1.40 g, 3.14 mmol) from step 4 dissolved in mixture of THF (20 mL) and MeOH (4 mL) was added with aqueous 2.5 M LiOH (5 mL) and stirred at rt for 17 h. After 17 h, the solution was neutralized with 1 N (10 mL) and evaporated to remove most organic solvent. Then the rest solution was extracted with dichloromethane (3×30 mL). The dichloromethane solution dried over MgSO$_4$ was evaporated to get white solid. The dried solid was mixed with EDCI (0.66 g, 3.45 mmol) and HOBt (0.47 g, 3.41 mmol) in dichloromethane (30 mL) and stirred at rt for 0.5 h. After 0.5 h, NH$_2$OBn.HCl (0.50 g, 3.13 mmol) and tritely famine (0.48 mL 3.46 mmol) were added to reaction mixture and kept stirring tsar 12 h. After 12 h, the solution was washed with water (3×30 mL) and dried over MgSO$_4$. Then

Step 7: Preparation of 4-((7-fluoro-2,4-dioxo-3-phenethyl-3,4-dihydroquinazolin-1(2H)-yl)methyl)-N-hydroxybenzamide (Compound 1)

The solid (0.7 g, 1.34 mmol) from previous step mixed with palladium on charcoal, 10% (70 mg) in mixture of MeOH (24 mL) and THF (8 mL) under balloon of H$_2$ (1 atm) was stirred at rt for 3 h. After 3 h, the solution was filtered by celite, and the filtrate was purified by column chromatography to get title compound (g, %). R$_f$=0.47 (MeOH/CH$_2$Cl$_2$=1/19); $^1$H NMR (400 MHz, DMSO-d$_6$) δ 9.01 (br s, 1H), 11.17 (br s, 1H), 8.12 (dd, J=9.2 Hz and 6.4 Hz, 1H), 7.68-7.70 (m, 2H), 7.19-7.30 (m, 7H), 7.09-7.13 (m, 2H), 5.36 (s, 2H), 4.20 (dd, J=7.6 Hz, 2H), 2.93 (dd, J=7.6 Hz, 2H), $^{13}$C NMR (100 MHz, DMSO-d$_6$) δ 166.0 (d, J=250.0 Hz), 163.9, 160.1, 150.6, 141.6 (d, J=12.0 Hz), 139.0, 138.4, 131.8, 131.2 (d, J=11.0 Hz), 128.7, 128.4, 127.2, 126.4, 126.3, 112.0 (br s), 110.8 (d, J=23.0 Hz), 101.9 (d, J=28.0 Hz), 46.2, 42.5, 33.0; ESIMS(−), m/z 431.9 [M−1]$^-$. Anal. Calcd for (C$_{24}$H$_{20}$FN$_3$O$_4$·1/2 H$_2$O): C, 63.15, H, 4.78, N, 9.50. Found: C, 65.24, H, 4.68, N, 9.53.

Example 2: Preparation of 4-((7-cyano-2,4-dioxo-3-phenethyl-3,4-dihydroquinazolin-1(2H)-yl)ethyl)-N-hydroxybenzamide (Compound 3)

Steps 1 to 3: Preparation of 7-chloro-3-phenethylquinazoline-2,4(1H,3H)-dione

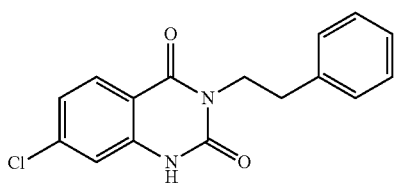 [SMILES: O=c1[nH]c2cc(Cl)ccc2c(=O)n1CCc1ccccc1]

The title compound was prepared from 4-chloroanthranilic acid (6.0 g, 20.57 mmol) by using the similar procedure described above of the step 1, step 2, and step 3 of example 1 to give white solid (5.2 g, three steps 79.6%); R$_f$=0.65 (EtOAc/Hexanes=1:1); $^1$H NMR (400 MHz, DMSO-d$_6$) δ 7.89 (d, J=8.4 Hz, 1H), 7.16-7.30 (m, 7H), 4.06 (dd, J=8.0 Hz, 1H), 2.84 (dd, J=8.0 Hz, 2H); $^{13}$C NMR (100 MHz, DMSO-d$_6$) δ 161.0, 149.8, 140.4, 139.2, 138.5, 129.4, 128.5, 128.4, 126.1, 122.6, 114.4, 112.6, 41.3, 33.2.

Step 4: Preparation of Ethyl 4-((7-2,4-dioxo-3-phenethyl-3,4-dihydroquinazolin-1(2H)-yl)methyl)benzoate

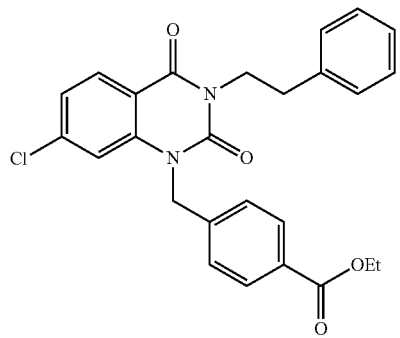 [SMILES: CCOC(=O)c1ccc(Cn2c(=O)n(CCc3ccccc3)c(=O)c3ccc(Cl)cc32)cc1]

The title compound was prepared from the solid (6.00 g, 19.95 mmol) of previous step by using the similar procedure described above of the step 4 of example 1 to give white solid (6.87 g, 74.4%).

Steps 5 and 6: Preparation of N-(benzyloxy)-4-((7-chloro-2,4-dioxo-3-phenethyl-3,4-dihydroquinazolin-1(2H)-yl)ethyl)benzamide

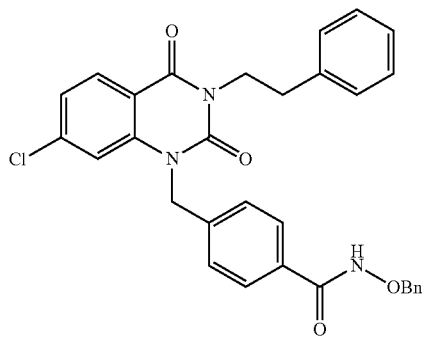 [SMILES: O=C(NOCc1ccccc1)c1ccc(Cn2c(=O)n(CCc3ccccc3)c(=O)c3ccc(Cl)cc32)cc1]

The title compound was prepared from the solid (8.00 g, 17.28 mmol) of previous step by using the similar procedure described above of the step 5 and step 6 of example 1 to give white solid (9.01 g, 96.6%).

Steps 7 and 8: Preparation of 4-((7-cyano-2,4-dioxo-3-phenethyl-3,4-dihydroquinazolin-1(2H)-yl)methyl)-N-hydroxybenzamide (Compound 3)

The solid (3.00 g, 5.55 mmol) from step 6 mixed with Zn(CN)$_2$ (132 g, 11.02 mmol), Pd$_2$(dba)$_3$ (0.26 g, 0.27 mmol), and XPhos (0.16 g, 0.33 mmol) in DMF (60 mL) was irradiated with microwave 200 W to reflux for 20 min. The resulting solution was poured to ice water (200 mL) and filtered to get light green solid. The solid suspended dichloromethane (50 was washed with water (3×50 mL), then the organic layer was filtered, dried over MgSO$_4$, and evaporated to give light gray solid. The solid mixed with pentamethyl benzene (5.00 g, 33.39 mmol) in dichloromethane (50 mL) under ice bath was added dropwise with BBr$_3$ (1 Min THE) (28 mL) for 20 min and kept stirring under ice bath for 40 min. The resulting solution was quenched with 10 mL of MeOH/DCM (3:7) under ice bath and warmed to rt. The solution was evaporated to dry and purified by column chromatography to give title compound as light yellow solid (1.24 g, 50.7%). $R_f$=0.31 (MeOH/CH$_2$Cl$_1$=2:98); $^1$H NMR (400 MHz, DMSO-d$_6$) δ 11.18 (br s, 1H), 9.02 (br s, 1H), 8.19 (d, 8.0 Hz, 1H), 7.78 (br s, 1H), 7.65-7.70 (m, 3H), 7.21-7.30 (m, 7H), 5.41 (s, 2H), 4.21 (dd, 7.6 Hz, 2H), 2.93 (dd, J=7.6 Hz, 2H); $^{13}$C NMR (100 MHz, DMSO-d$_6$) δ 163.9, 150.1, 150.3, 139.8, 138.9, 138.3, 131.9, 129.2, 128.7, 128.4, 127.2, 126.48, 126.42, 125.8, 118.8, 118.5, 117.7, 116.9, 46.1, 42.8, 32.9 ESIMS(−), m/z 438.9 [M−1]$^-$.

Example 3: Preparation of 2-(4-((2,4-dioxo-3-phenethyl-3,4-dihydroquinazolin-1(2H)-yl)methyl)phenyl)-2,2-difluoro-N-hydroxyacetamide (Compound 20)

Step 1: Preparation of 1-(4-iodobenzyl)-3-phenethylquinazoline-2,4(1H,3H)-dione

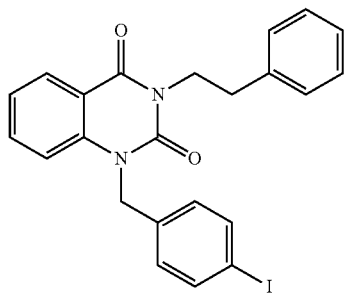 [SMILES: O=c1c2ccccc2n(Cc2ccc(I)cc2)c(=O)n1CCc1ccccc1]

NaH (0.63 g, 15.75 mmol) was added portionwise to 3-phenethylquinazoline-2,4(1H,3H)-dione (3.5 g, 13.14 mmol) in DMF (0.45 mL), and the solution was stirred under ice bath for 0.5 h. Then 4-iodobenzyl bromide (4.22 z, 13.79 mmol) was added to the above solution and stirred from ice bath to rt for 4 h. The resulting solution was poured to water and filtered to get title compound as white solid. (5.40 g, 85%).

Step 2: Preparation of Ethyl 2-(4-((2,4-dioxo-3-phenethyl-3,4-dihydroquinazolin-1(2H)-yl)methyl)phenyl)-2,2-difluoroacetate

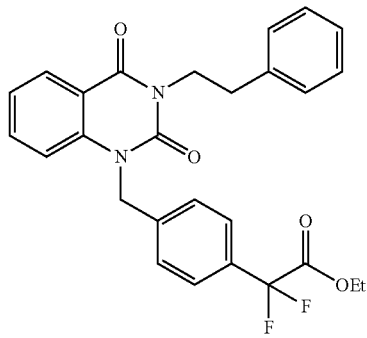 [SMILES: CCOC(=O)C(F)(F)c1ccc(Cn2c(=O)n(CCc3ccccc3)c(=O)c3ccccc32)cc1]

Cu (0.1 g, 1.57 mmol) was added to a solution of 1-(4-iodobenzyl)-3-phenethylquinazoline-2,4(1H,3H)-dione (0.3 g, 0.62 mmol) and BrCF$_2$CO$_2$Et (0.08 mL, 0.61 mmol) DMSO (3.00 mL) and stirring at 60° C. for 15 h. The resulting solution was poured to ice water and filtered to get blue solid. The blue solid was purified by column doted with EtOAc/Hexanes (1:4) to get the title compound as white solid (60 mg, 20%).

Step 3: Preparation of 2-(4-((2,4-dioxo-3-phenethyl-3,4-dihydroquinazolin-1(2H)-yl)methyl)phenyl)-2,2-difluoro-N-hydroxyacetamide (Compound 20)

NH$_2$OH.HCl (3.0 g, 41.9 mmol) suspended in MeOH (14 mL) was added by solution of KOH (2.3 g, 41.0 mmol) dissolved in MeOH (30 mL), and the mixed solution was filtered and added dropwise for 20 mill to solution of ethyl 2,2-difluoro-2-(4-((3,4-dihydro-2,4-dioxo-3-phenethylquinazolin-1(2H)-yl)methyl)phenyl)acetate (1.0 g, 2.1 mmol) under ice bath. The reaction mixture was stirred from ice bath to rt for 11 h. The resulting solution was poured to ice water (150 mL) and filtered to get white solid. The solid was purified by column eluted by MeOH/DCM=⁴⁄₉₆ to get title compound as white solid (0.5 g, 51%).

Example 4: Preparation of (E)-3-(4-((7-fluoro-2,4-dioxo-3-phenethyl-3,4-dihydroquinazolin-1(2H)-yl)methyl)phenyl)-N-hydroxyacrylamide (Compound 45)

Step 1: Preparation of (E)-3-(4-((7-fluoro-2,4-dioxo-3-phenethyl-3,4-dihydroquinazolin-1(2H)-yl)methyl)phenyl)acrylic Acid

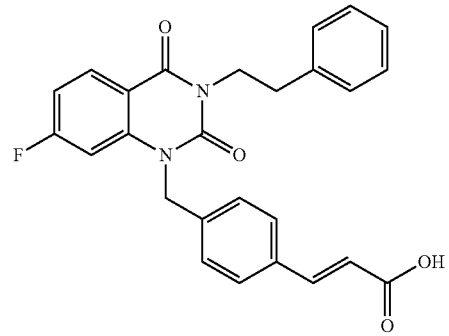 [SMILES: O=C(O)/C=C/c1ccc(Cn2c(=O)n(CCc3ccccc3)c(=O)c3ccc(F)cc32)cc1]

1-(4-bromobenzyl)-7-fluoro-3-phenethylquinazoline-2,4 (1H,3H)-dione (3.00 g, 6.62 mmol) was mixed With Herrmann's Palladacycle (0.12 g, 0.02 eq), [(t-Bu)$_3$PH]BF$_4$ (0.08 g, 0.04 eq), Cy$_2$NMe 97% (1.61 mL, 1.1 eq), acrylic acid (0.45 mL, 1 eq) in DMF (20 mL) under Argon and irradiated with μW 100 W to reflux for 10 min. The resulting solution was filtered by celite and then poured into excess water (100 mL). The mixture solution was neutralized with NaHCO$_{3(aq)}$ to pH 3-4. The precipitation was filtered to get carboxylic acid solid. The crude solid was put to next step without further purification.

Step 2: Preparation of (E)-N-(benzyloxy)-3-(4-((7-fluoro-2,4-dioxo-3-phenethyl-3,4-dihydroquinazolin-1(2H)-yl)methyl)phenyl)acrylamide

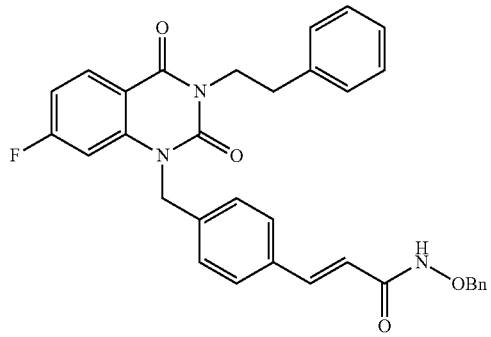 [SMILES: O=C(/C=C/c1ccc(Cn2c(=O)n(CCc3ccccc3)c(=O)c3ccc(F)cc32)cc1)NOCc1ccccc1]

The crude carboxylic acid (2.00 g, 4.50 mmol) was mixed with EDCI (1.29 g, 1.5 eq) and HOBt (0.62 g, 1 eq) in DMF (15 mL) and stirred at rt for 30 min. Then NH$_2$OTHP (1 eq) was added and continued stirring for 5-8 hr at rt. The resulting solution was evaporated and extracted with DCM/H$_2$O. The mixture of DCM layer was purified by flash column chromatography (silica gel: ϕ3.5×9.5 cm; eluted by EtOAc/Hexanes=1/1) to get white solid, 1.24 g.

Step 3: Preparation of (E)-3-(4-((7-fluoro-2,4-dioxo-3-phenethyl-3,4-dihydroquinazolin-1(2H)-yl)methyl)phenyl)-N-hydroxyacrylamide (Compound 45)

The solid (from step 2) (0.50 g, 0.92 mmol) and TFA (4.23 mL 60 eq) was dissolved in MeOH (25 was stirred at 50° C. for 5-8 hr. After reaction the precipitation was neutralized with NaHCO$_{3(aq)}$ to pH=5-6, then filtered and washed with MeOH and water to get target compound. The solid was recrystallized from DCM and MeOH to give compound 45 as orange solid 0.36 g, 43% (three steps), R$_f$=0.18 (MeOH/DCM=5/95); mp 179-182° C.; $^1$H NMR (400 MHz, DMSO-d$_6$) δ 10.70 (br s, 1H), 9.05 (br s, 1H), 8.11 (t, J=6.0 Hz, 1H), 7.51 (d, J=8.0 Hz, 2 Hz), 7.43 (d, J=16.0 Hz, 1H), 7.30-7.09 (m, 9H), 6.43 (d, J=16.0 Hz, 1H), 5.34 (s, 2H), 4.21 (t, J=8.0 Hz, 2H), 2.94 (t, J=6.0 Hz, 2H); $^{13}$C NMR (100 MHz, DMSO-d$_6$) δ 167.3, 164.8, 162.7, 160.1, 150.7, 141.7, 141.6, 138.4, 137.8, 137.2, 134.0, 131.3, 131.2, 128.7, 128.4, 128.3, 127.8, 127.1, 126.4, 119.1, 112.0, 110.9, 110.7, 102.1, 101.9, 46.2, 42.5, 33.1.

Example 5: Preparation of 4-((3-(2-fluorophenyl)-2,4-dioxo-3,4-dihydroquinazolin-1(2H)-yl)methyl)-N-hydroxybenzamide (Compound 55)

Step 1: Preparation of 3-(2-fluorophenyl)quinazoline-2,4(1H,3H)-dione

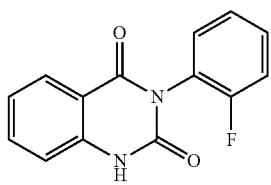 [SMILES: O=c1[nH]c2ccccc2c(=O)n1-c1ccccc1F]

To neat methyl 2-aminobenzoate (91.5 mL, 700 mmol, 1.0 eq) at 0° C., 2-fluorophenyl isocyanate (88.2 mL, 1.1 eq) was added and stirred at 0° C., 5 mM, MeOH (280 mL, 2.5 M) and TEA (295.7 mL, 3.0 eq) was added and stirred under 65° C., 45 min. The slurry crude was cooled to 0° C., and filtrated. The solid was washed with EtOAc/Hexanes=1/1 (500 mL) and pentane 300 mL, and dried under vacuum to provide white fine solid product 161.2 g, 90%.

Step 2: Preparation of Ethyl 4-((3-(2-fluorophenyl)-2,4-dioxo-3,4-dihydroquinazolin-1(2H)-yl)methyl)benzoate

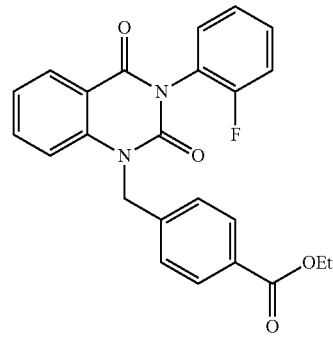 [SMILES: CCOC(=O)c1ccc(Cn2c(=O)n(-c3ccccc3F)c(=O)c3ccccc32)cc1]

To a solution of ethyl 4-(bromomethyl)benzoate (165.1 g, 1.1 eq) in acetone (1240 mL, 0.5 M), 3-(2-fluorophenyl)quinazoline-2,4(1H,3H)-dione (158.9 g, 620 mmol, 1.0 eq), and K$_2$CO$_3$ (258.4 g, 3.0 eq) was added and stirred under 60° C., 1.5 h. The crude mixture was concentrated in vacuo and extracted with DCM/H$_2$O=1.5 L/1.5 L. The organic layer was dried over MgSO4 and evaporated under vacuum till little precipitate was observed, Et$_3$O (500 mL) and pentane (250 mL) was added and filtrated. The solid was washed with pentane and dried under vacuum to provide white fine solid product 232.4 g, 93%

Step 3: Preparation of 4-((3-(2-fluorophenyl)-2,4-dioxo-3,4-dihydroquinazolin-1(2H)-yl)methyl)-N-hydroxybenzamide (Compound 55)

To a generally mixed slurry solution of KOH (19.8 g, 2.0 eq) in NH$_2$OH$_{(2\ M\ in\ MeOH)}$ (750 mL, 10.0 eq), ethyl 4-((3-(2-fluorophenyl)-2,4-dioxo-3,4-dihydroquinazolin-1(2H)-yl)methyl)benzoate (60.7 g, 150 mmol, 1.0 eq) was added and stirred wider 30° C., 2.5 h. H$_2$O (1.5 L) was added and extracted with EtOAc (1.5 L*4). The organic layer was dried over MgSO4, evaporated under vacuum, and re-precipitated with EtOAc/Hexanes=500 mL/1000 mL. The slurry solution was filtrated, washed with pentane and dried under vacuum to provide white solid product 25.3 g, 42%. R$_f$=0.39 (MeOH/DCM=10/90). mp 188.1-189.0° C. $^1$H NMR (400 MHz, DMSO, 25° C.) δ 11.20 (bs, 1H), 9.06 (bs, 1H), 8.11 (pseudo dd, 1H, J=7.7 Hz, J=1.3 Hz), 7.69-7.78 (m, 3H), 7.58-7.66 (m, 1H), 7.50-7.58 (m, 1H), 7.28-7.48 (m, 6H), 5.45 (pseudo dd, 2H, J=38.6 Hz, J=17.1 Hz). ESIMS(+), m/z 406 [M+H]$^+$. HPLC 98.3%.

The following compounds were prepared according to the procedure given in abo e Examples.

Example 6: Preparation of N-hydroxy-4-((7-methoxy-2,4-dioxo-3-phenethyl-3,4-dihydroquinazolin-1(2H)-yl)methyl)benzamide (Compound 2)

R$_f$=0.43 (MeOH/CH$_2$Cl$_2$=1/19); mp 198-200° C. (dec); $^1$H NMR (600 MHz, DMSO-d$_6$) δ 11.15 (br s, 1H), 8.99 (s, 1H), 7.98 (d, J=8.4 Hz, 1H), 7.68 (d, J=8.4 Hz, 1H), 7.26-7.30 (m, 4H), 7.21-7.23 (m, 3H), 6.86 (dd, J=8.4 Hz, 2.4 Hz, 1H), 6.62 (d, J=2.4 Hz, 1H), 5.37 (s, 2H), 4.21 (dd, J=7.8 Hz, 7.2 Hz, 2H), 3.74 (s, 3H), 2.93 (dd, J=7.8 Hz, 7.2 Hz, 2H); $^{13}$C NMR (150 MHz, DMSO-d$_6$) δ 164.4, 163.9, 160.3, 150.9, 141.1, 139.5, 138.5, 131.8, 130.1, 128.7, 128.3, 127.2, 126.4, 126.2, 109.8, 108.4, 99.5, 55.7, 45.9, 42.2, 33.1; ESIMS(−), m/z 444.0 [M−1]$^−$. Anal. Calcd for (C$_{25}$H$_{23}$N$_3$O$_5$); C, 67.41, H, 5.20, N, 943. Found: C, 67.17, H, 5.30, N, 9.24.

Example 7: Preparation of N-hydroxy-4-((7-hydroxy-2,4-dioxo-3-phenethyl-3,4-dihydroquinazolin-1(2H)-yl)methyl)benzamide (Compound 4)

Step 1: Preparation of Ethyl 4-((3,4-dihydro-7-hydroxy-2,4-dioxo-3-phenethylquinazolin-1(2H)-yl)methyl)benzoate

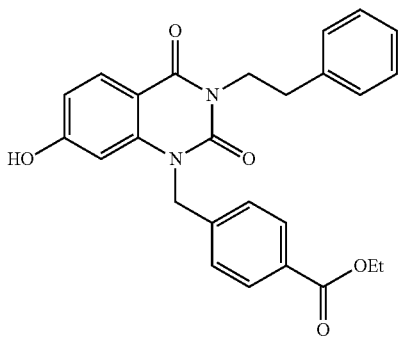 [SMILES: CCOC(=O)c1ccc(Cn2c(=O)n(CCc3ccccc3)c(=O)c3ccc(O)cc32)cc1]

4-((7-chloro-3,4-dihydro-2,4-dioxo-3-phenethylquinazolin-1(2H)-yl)methy)benzoate (3.5 g, 7.56 mmol) mixed with palladacycle ((3.142 g, 0.02 eq), XPhos ((3.294 g, 0.08 eq), and Cs$_2$CO$_3$ (739 g, eq) in mixture of DMF 35 mL) and H$_2$O (3.5 mL) under Ar was irradiated with μW (200 W) to reflux for 2×30 min. The resulting mixture was evaporated to dry and suspended in EtOAc (50 mL) to washed with H$_2$O (3×50 mL). The EtOAc solution dried over MgSO$_4$ was filtered. The filtrate was concentrated to around 15 ml to get white solid formed. The suspension was filtered to get beige solid. The precipitation and filtration was repeated three times to get 10 as white solid (3.04 g, 90.5%). R$_f$=0.27 (EtOAc/Hexanes=1/1); mp 203-205° C. (dec); $^1$H NMR (600 MHz, DMSO-d$_6$) δ 10.61 (br s, 1H), 7.90 (dd, J=8.4, 6.6 Hz, 3H), 7.27-7.33 (m, 4H), 7.19-7.23 (m, 3H), 6.67 (dd, J=8.4, 1.8 Hz, 1H), 6.43 (d, J=1.8 Hz, 1H), 5.33 (s, 2H), 4.29 (q, J=72 Hz, 2H), 4.19 (dd, J=7.8, 7.2 Hz, 2H), 2.92 (dd, J=7.8, 7.8 Hz, 2H), 1.29 (t, J=7.2 Hz, 3H); $^{13}$C NMR (150 MHz, DMSO-d$_6$) δ 165.3, 163.5, 160.4, 150.9, 141.8, 141.3, 138.5, 130.2, 129.4, 128.8, 128.6, 128.3, 126.5, 126.2, 111.7, 107.0, 100.2, 60.6, 46.2, 42.1, 33.2, 14.1: ESIMS(−), m/z 443.1 [M−1]$^−$; Anal. Calcd for (C$_{26}$H$_{24}$N$_2$O$_5$.0.2 H$_2$O); C, 69.69, H, 5.49, N, 6.25. Found: C, 69.60, H, 5.70, N, 6.27.

Steps 2 to 4: Preparation of 4-((3,4-dihydro-7-hydroxy-2,4-dioxo-3-phenethylquinazolin-1(2H)-yl)methyl)-N-hydroxybenzamide (Compound 4)

Starting from ethyl 4-((3,4-dihydro-7-hydroxy-2,4-dioxo-3-phenethylquinazolin-1(2H)-yl)methyl)benzoate and similar procedures of step 5, 6, and 7 in example 1 were followed to yield compound 4 as white solid. Yield 59.6% R$_f$=0.18 (MeOH/CH$_2$Cl$_2$=1/19); mp 205-207° C. (dec); $^1$H NMR (400 MHz, DMSO-d$_6$) δ 7.84 (d, J=8.8 Hz, 1H), 7.69-7.71 (m, 2H), 7.21-730 (m, 7H), 6.61 (d, J=8.4 Hz, 1H), 6.38 (s, 1H), 5.25 (s, 2H), 4.19 (dd, J=7.6 Hz, 2H), 2.92 (dd, J=7.2 Hz, 2H); $^{13}$C NMR (100 MHz, DMSO-d$_6$) δ 165.8, 163.8, 160.5, 151.1, 141.5, 139.5, 138.7, 131.9, 130.0, 128.7, 128.4, 127.2, 126.36, 126.32, 112.6, 105.7, 100.5, 46.1, 42.1, 33.4; ESIMS(−), m/z 429.9 [M−1]$^−$. Anal. Calcd for (C$_{24}$H$_{21}$N$_3$O$_5$.H$_2$O); C, 64.13, H, 5.16, N, 9.35. Found: C, 64.24, H, 4.88, N, 9.11.

Example 8: Preparation of 4-((2,4-dioxo-3-phenethyl-3,4-dihydroquinazolin-1(2H)-yl)methyl)-N-hydroxybenzamide (Compound 5)

The similar procedures of example 1 were followed to yield compound 5 as brown solid. R$_f$=0.20 (MeOH/CH$_2$Cl$_2$=2/98); $^1$H NMR (400 MHz, DMSO-d$_6$) δ 11.18 (br s, 1H), 9.02 (s, 1H), 8.06 (d, J=7.6 Hz, 1H), 7.68-7.70 (m, 2H), 7.63 (dd, J=7.6 Hz, 7.2 Hz, 1H), 720-7.30 (m, 9H), 5.37 (s, 2H), 4.23 (dd, J=7.6 Hz, 2H), 2.95 (dd, J=7.6 Hz, 2H); $^{13}$C NMR (100 MHz, DMSO-d$_6$) δ 163.9, 160.9, 150.6, 139.5, 139.4, 138.5, 135.2, 131.8, 128.7, 128.4, 128.0, 127.2, 126.4, 126.3, 122.9, 115.1, 114.8, 46.0, 42.4, 33.1; ESIMS(−), m/z 413.9 [M−1]$^−$. Anal. Calcd for (C$_{24}$H$_{21}$N$_3$O$_4$): C, 69.39; H, 5.10; N, 10.11. Found: C, 69.31; H, 5.14; N, 10.11.

Example 9: Preparation of 3-((2,4-dioxo-3-phenethyl-3,4-dihydroquinazolin-1(2H)-yl)methyl)-N-hydroxybenzamide (Compound 6)

The similar procedures of example 1 were followed to yield compound 6. R$_f$=0.19 (MeOH/CH$_2$Cl$_2$=2/98); mp 188-190° C. (dec); $^1$H NMR (400 MHz, DMSO-d$_6$) δ 11.24 (br s, 1H), 9.06 (s, 1H), 8.07 (d, J=7.2 Hz, 1H), 7.64-7.70 (m, 3H), 7.20-7.42 (m, 9H), 5.39 (s, 2H), 4.24 (dd, J=7.6 Hz, 2H), 2.95 (dd, J=7.6 Hz, 2H); $^{13}$C NMR (100 MHz, DMSO-d$_6$) δ 163.9, 160.9, 150.6, 139.5, 138.5, 136.6, 135.2, 133.2, 129.1, 128.8, 128.6, 128.4, 128.0, 126.3, 125.8, 125.0, 122.9, 115.1, 114.8, 46.2, 42.5, 33.2; ESIMS(−), m/z 413.9 [M−1]$^−$. Anal. Calcd for (C$_{24}$H$_{21}$N$_3$O$_4$.0.6 H$_2$O): C, 67.63; H, 5.25; N, 9.86. Found: C, 67.56; H, 4.86; N, 9.61.

Example 10: Preparation of 3-((7-cyano-2,4-dioxo-3-phenethyl-3,4-dihydroquinazolin-1(2H)-yl)methyl)-N-hydroxybenzamide (Compound 7)

The similar procedures of example 2 were hollowed to yield compound 7. R$_f$=0.42 (MeOH/CH$_2$Cl$_2$=1/19); mp 166-168° C.; $^1$H NMR (400 MHz, DMSO-d$_6$) δ 11.19 (br s, 1H), 9.03 (br s, 1H), 8.20 (d, J=8.0 Hz, 1H), 7.83 (s, 1H), 7.64-7.68 (m, 3H), 7.35-7.43 (m, 2H), 7.22-7.30 (m, 5H), 5.43 (s, 2H), 4.21 (dd, J=7.6 Hz, 2H), 2.93 (dd, J=7.6 Hz, 2H); $^{13}$C NMR (100 MHz, DMSO-d$_6$) δ 163.8, 160.1, 150.3, 139.9, 138.3, 136.0, 133.1, 129.1, 128.7, 128.6, 128.4, 126.3, 125.88, 125.85, 124.9, 118.8, 118.4, 117.7, 116.9, 114.5, 46.2, 42.8, 33.0; ESIMS(−), m/z 438.9 [M−1]$^−$. Anal. Calcd for (C$_{25}$H$_{20}$N$_4$O$_4$.0.4 H$_2$O): C, 67.08; H, 4.68; N, 12.52. Found: C, 67.13; H, 4.59; N, 12.19.

Example 11: Preparation of 4-((7-chloro-2,4-dioxo-3-phenethyl-3,4-dihydroquinazolin-1(2H)-yl)methyl)-N-hydroxybenzamide (Compound 8)

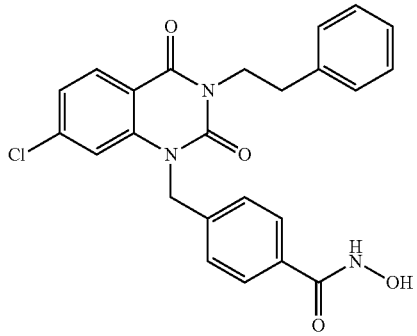 [SMILES: O=C(NO)c1ccc(Cn2c(=O)n(CCc3ccccc3)c(=O)c3ccc(Cl)cc32)cc1]

The similar procedures of example 2 were followed to yield compound 8. $R_f$=0.45 (MeOH/CH$_2$Cl$_2$=1/19); mp 185-187° C. (dec); $^1$H NMR (400 MHz, DMSO-d$_6$) δ 8.05 (d, J=8.4 Hz, 1H), 7.69-7.71 (m, 2H), 7.21-7.31 (m, 9H), 5.39 (s, 2H), 4.20 (dd, J=7.2 Hz, 2H), 2.93 (dd, J=7.2 Hz, 2H); $^{13}$C NMR (100 MHz, DMSO-d$_6$) δ 163.7, 160.2, 150.5, 140.5, 139.8, 138.9, 138.4, 132.0, 129.9, 128.7, 128.4, 127.2, 126.35, 126.33, 123.1, 114.5, 114.0, 46.0, 42.5, 33.0; ESIMS(−), m/z 447.9 [M−1]$^−$. Anal. Calcd for (C$_{24}$H$_{20}$ClN$_3$O$_4$); C, 64.07; H, 4.48; N, 9.34. Found: C, 64.12; H, 4.52; N, 9.31.

Example 12: Preparation of 4-((6-chloro-2,4-dioxo-3-phenethyl-3,4-dihydroquinazolin-1(2H)-yl)methyl)-N-hydroxybenzamide (Compound 9)

The similar procedures of example 2 were followed to yield compound 9 as white solid. $R_f$=0.27 (MeOH/CH$_2$Cl$_2$=1/19); mp 190-192° C.; $^1$H NMR (400 MHz, DMSO-d$_6$) δ 11.18 (br s, 1H), 9.02 (br s, 1H), 7.98 (d, J=2.4 Hz, 1H), 7.66-7.70 (m, 3H), 7.21-7.30 (m, 8H), 5.37 (s, 2H), 4.21 (dd, J=7.6 Hz, 2H), 2.94 (dd, J=7.6 Hz, 2H); $^{13}$C NMR (100 MHz, DMSO-d$_6$) δ 163.8, 159.9, 150.3, 139.1, 138.39, 138.38, 134.8, 131.8, 128.7, 128.4, 127.23, 127.21, 126.8, 117.1, 116.6, 46.2, 42.6, 32.9, 126.3 (2C); ESIMS(−), m/z 447.9 [M−1]$^−$; Anal. Calcd for (C$_{24}$H$_{20}$ClN$_3$O$_4$): C, 64.07; H, 4.48; N, 9.34. Found: C, 63.75; H, 4.40; N, 9.18.

Example 13: Preparation of 4-((7-chloro-3-methyl-2,4-dioxo-3,4-dihydroquinazolin-1(2H)-yl)methyl)-N-hydroxybenzamide (Compound 10)

$^1$H NMR (400 MHz, DMSO-d$_6$) δ 8.03 (d, J=8.4 Hz, 1H), 7.70 (d, J=8.0 Hz, 2H), 7.37 (d, J=8.0 Hz, 2H), 7.27-7.30 (m, 2H), 5.41 (s, 2H), 3.34 (s, 3H); $^{13}$C NMR (100 MHz, DMSO-d$_6$) δ 163.7, 160.6, 150.8, 140.5, 139.6, 139.0, 131.9, 129.8, 127.2, 126.3, 123.0, 114.4, 114.1, 46.1, 28.3; ESIMS(−), m/z=358 [M−H]$^−$. Anal. Calcd for (C$_{17}$H$_{14}$ClN$_3$O$_4$.0.2 H$_2$O): C, 56.19: H, 3.99; N, 11.56. Found: C, 56.18; H, 3.87; N, 11.37.

Example 14: Preparation of 4-((3-benzyl-2,4-dioxo-3,4-dihydroquinolin-1(2H)-yl)methyl)-N-hydroxybenzamide (Compound 11)

$^1$H NMR (400 MHz, DMSO-d$_6$) δ 11.16 (br s, 1H), 9.01 (br s, 1H), 8.09 (d, J=7.6 Hz, 1H), 7.63-7.71 (m, 3H), 7.22-7.37 (m, 9H), 5.42 (s, 2H), 5.20 (s, 2H); $^{13}$C NMR (100 MHz, DMSO-d$_6$) δ 163.9, 161.1, 150.8, 139.5, 139.4, 137.1, 135.3, 131.8, 128.3, 128.1, 127.4, 127.2, 127.1, 126.3, 123.0, 115.0, 114.9, 46.2, 44.4; ESIMS(−), m/z=400 [M−H]$^−$. Anal. Calcd for (C$_{23}$H$_{19}$N$_3$O$_4$.0.8 H$_2$O): C, 66.43: H, 4.99; N, 10.11. Found: C, 66.50; H, 4.66; N, 9.93.

Example 15: Preparation of 4-((2,4-dioxo-3-phenethyl-3,4-dihydropyrido[2,3-d]pyrimidin-1(2H)-yl)methyl)-N-hydroxybenzamide (Compound 12)

$^1$H NMR (400 MHz, DMSO-d$_6$) δ 8.66 (dd, J=4.4, 1.2 Hz, 1H), 8.39 (dd, J=7.6, 1.2 Hz, 1H), 7.66 (d, J=8.0 Hz, 2H), 7.17-7.35 (m, 8H), 5.43 (s, 2H), 4.16 (t, J=7.6 Hz, 2H), 2.90 (t, J=7.6 Hz, 2H); $^{13}$C NMR (100 MHz, DMSO-d$_6$) δ 163.7, 160.5, 154.2, 150.6, 150.2, 139.2, 138.4, 137.4, 133.0, 128.7, 128.4, 126.7, 126.6, 126.4, 119.4, 110.5, 48.6, 44.7, 42.5, 33.0; ESIMS(−), m/z=415 [M−H]$^−$. Anal. Calcd. for (C$_{23}$H$_{20}$N$_4$O$_4$.1.2 H$_2$O): C, 63.06; H, 5.15; N, 12.79. Found: C, 62.97; H, 4.90; N, 12.47.

Example 16: Preparation of 4-((2,4-dioxo-3-phenethyl-7-(trifluoromethyl)-3,4-dihydroquinazolin-1(2H)-yl)methyl)-N-hydroxybenzamide (Compound 13)

$^1$H NMR (400 MHz, DMSO-d$_6$) δ 11.20 (br s, 1H), 9.03 (br s, 1H), 8.25 (d, J=8.4 Hz, 1H), 7.69 (d, J=8.0 Hz, 2H), 7.58 (d, J=8.4 Hz, 1H), 7.50 (s, 1H), 7.22-7.31 (m, 7H), 5.47 (s, 2H), 4.23 (t, J=7.2 Hz, 2H), 2.95 (t, J=7.2 Hz, 2H); $^{13}$C NMR (100 MHz, DMSO-d$_6$) δ 163.8, 160.2, 150.5, 139.9, 139.1, 138.4, 134.5, 134.1, 131.8, 129.6, 128.7, 128.4, 127.2, 126.45, 126.40, 124.6, 121.9, 119.14, 119.10, 118.3, 111.9, 111.8, 46.1, 42.7, 0.9; ESIMS(−), m/z 482 [M−H]$^−$. Anal Calcd for (C$_{25}$H$_{20}$F$_3$N$_3$O$_4$): C, 62.11; H, 4.17; N, 8.69. Found: C, 62.13; H, 4.13; N, 8.64.

Example 17: Preparation of 4-((3-(4-fluorophenethyl)-2,4-dioxo-3,4-dihydroquinazolin-1(2H)-yl)methyl)-N-hydroxybenzamide (Compound 14)

$^1$H NMR (400 MHz, DMSO-d$_6$) δ 11.15 (br s, 1H), 9.01 (br s, 1H), 8.06 (dd, J=8.0, 1.2 Hz, 1H), 7.69 (d, J=8.4 Hz, 1H), 7.62 (dd, J=8.4, 7.6 Hz, 1H), 7.20-7.28 (m, 6H), 7.09 (dd, J=9.2, 8.4 Hz, 2H), 5.37 (s, 2H), 4.22 (t, J=7.6 Hz, 2H), 2.94 (t, J=7.6 Hz, 2H); $^{13}$C NMR (100 MHz, DMSO-d$_6$) δ 163.9, 162.1, 160.9, 159.7, 150.6, 139.4, 135.2, 134.7, 134.6, 131.8, 130.6, 130.5, 128.0, 127.2, 126.4, 126.2, 122.9, 115.19, 115.10, 114.9, 114.8, 46.0, 42.4, 32.2; ESIMS(−), m/z=432 [M−H]$^−$. Anal. Calcd for (C$_{24}$H$_{20}$FN$_3$O$_4$): C, 66.51; H, 4.65; N, 9.69. Found: C, 66.20; H, 4.46; N, 9.48.

Example 18: Preparation of N-hydroxy-4-((3-(2-methoxyphenethyl)-2,4-dioxo-3,4-dihydroquinazolin-1(2H)-yl)methyl)benzamide (Compound 15)

$^1$H NMR (400 MHz, DMSO-d$_6$) δ 8.99 (br s, 1H), 8.04 (dd, J=8.0, 1.2 Hz, 1H), 7.68 (d, J=8.0 Hz, 2H), 7.61 (dd, J=7.6, 7.2 Hz, 1H), 7.17-7.26 (m, 5H), 7.06 (d, J=7.2 Hz, 1H), 6.90 (d, J=8.0 Hz, 1H), 6.83 (dd, J=7.6, 7.2 Hz, 1H), 5.33 (s, 2H), 4.26 (t, J=7.2 Hz, 2H), 3.64 (s, 3H), 2.94 (t, 7.2 Hz, 2H), 11.16 (br s, 1H); $^{13}$C NMR (100 MHz, DMSO-d$_6$) δ 164.0, 161.0, 157.5, 150.7, 139.6, 139.5, 135.2, 131.8, 130.3, 128.1, 127.9, 127.3, 126.6, 126.5, 123.0, 120.3, 115.2, 114.7, 110.7, 55.2, 46.1, 41.3, 27.9; ESIMS(−), m/z=444 [M−H]⁻. Anal. Calcd for $C_{25}H_{23}N_3O_5 \cdot 0.5\ H_2O$); C, 66.07; H, 532; N, 9.25. Found: C, 66.12; H, 5.33; N, 9.17.

Example 19: Preparation of 2-(4-((2,4-dioxo-3-phenethyl-3,4-dihydroquinazolin-1(2H)-yl)methyl)phenyl)-N-hydroxyacetamide (Compound 16)

The similar procedures of example 3 were followed to yield compound 16. $^1$H NMR (400 MHz, DMSO-d$_6$) δ 8.76 (br s, 8.05 (dd, J=8.0, 1.2 Hz, 1H), 7.63 (ddd, J=8.4, 8.4, 1.2 Hz, 1H), 7.12-7.30 (m, 1H), 5.31 (s, 2H), 4.23 (t, J=7.6 Hz, 2H), 3.23 (s, 2H), 2.94 (t, J=7.6 Hz, 2H), 10.60 (br s, 1H); $^{13}$C NMR (100 MHz, DMSO-d$_6$) δ 166.8, 160.9, 150.6, 139.5, 138.5, 135.2, 135.0, 134.3, 129.2, 128.7, 128.3, 127.9, 126.34, 126.32, 122.8, 115.0, 114.9, 45.9, 42.4, 38.9, 33.1; ESIMS(−), m/z=428 [M−H]⁻. Anal. Calcd for ($C_{23}H_{23}N_3O_4$); C, 69.92; H, 5.40; N, 9.78. Found: C, 70.03; H, 5.52; N, 9.44.

Example 20: Preparation of 4-((6-fluoro-2,4-dioxo-3-phenethyl-3,4-dihydroquinolin-1(2H)-yl)methyl)-N-hydroxybenzamide (Compound 17)

The similar procedures of example 1 were followed to yield compound 17. $^1$H NMR (400 MHz, DMSO-d$_6$) δ 11.21 (br s, 1H), 9.05 (br s, 1H), 7.68-7.77 (m, 3H), 7.54 (s, 1H), 7.21-7.28 (m, 8H), s, 2H), 4.21 (t, J=6.8 Hz, 2H), 2.94 (t, J=6.8 Hz, 2H); $^{13}$C NMR (100 MHz, DMSO-d$_6$) δ 163.8, 160.19, 160.16, 158.7, 156.3, 150.3, 139.3, 138.4, 136.2, 131.8, 128.7, 128.4, 127.2, 126.4, 126.3, 122.9, 122.7, 117.4, 117.3, 116.5, 116.4, 113.2, 113.0, 46.3, 42.7, 33.0; ESIMS(−), m/z=432 [M−H]⁻. Anal. Calcd for ($C_{24}H_{20}FN_3O_4 \cdot 0.1\ H_2O$): C, 66.23; H, 4.68; N, 9.65. Found: C, 66.07; H, 4.77; N, 9.32.

Example 21: Preparation of N-hydroxy-4-((3-(2-hydroxyphenethyl)-2,4-dioxo-3,4-dihydroquinazolin-1(2H)-yl)methyl)benzamide (Compound 18)

$^1$H NMR (400 MHz, DMSO-d$_6$) δ 11.19 (br s, 1H), 9.32 (br s, 1H), 9.03 (br s, 1H), 8.04 (d, J=7.6 Hz, 1H), 7.67 (d, J=8.0 Hz, 2H), 7.61 (dd, J=7.6, 7.6 Hz, 1H), 7.22-7.26 (m, 3H), 7.17 (d, J=8.4 Hz, 1H), 6.97-7.02 (m, 2H), 6.75 (d, J=8.0 Hz, 1H), 6.66 (dd, J=7.6, 7.2 Hz, 1H), 5.34 (s, 2H), 4.25 (t, J=6.8 Hz, 2H), 2.90 (t, J=6.8 Hz, 2H); $^{13}$C NMR (100 MHz, DMSO-d$_6$) δ 164.0, 161.0, 155.6, 150.7, 139.6, 139.5, 135.2, 131.7, 130.3, 128.1, 127.4, 127.3, 126.5, 124.9, 122.9, 118.9, 115.2, 114.9, 114.8, 46.1, 41.3, 27.8; ESIMS(+), m/z=454 [M+H]⁺.

Example 22: Preparation of 2-(4-((2,4-dioxo-3-phenethyl-3,4-dihydroquinazolin-1(2H)-yl)methyl)-3-fluorophenyl)-N-hydroxyacetamide (Compound 19)

$^1$H NMR (400 MHz, DMSO-d$_6$) δ 10.64 (br s, 1H), 8.83 (br s, 1H), 0.07 (dd, J=8.0, 0.8 Hz, 1H), 7.66 (ddd, J=8.0, 8.0, 0.8 Hz, 1H), 7.12-7.29 (m, 8H), 6.97 (dd, J=8.0, 0.8 Hz, 1H), 6.88 (dd, 8.0, 8.0 Hz, 1H), 5.33 (S, 214), 4.20 (1.1=7.6 Hz, 210, 3.27 (s, 2H), 2.92 (t, J=7.6 Hz, 2H); $^{13}$C NMR (100 MHz, DMSO-d$_6$) δ 166.4, 160.8, 160.7, 158.2, 150.4, 139.4, 138.4, 137.78, 137.70, 135.3, 128.6, 128.4, 128.0, 127.58, 127.54, 126.3, 125.8, 125.3, 123.0, 121.0, 120.9, 115.9, 115.7, 115.0, 114.4, 42.4, 40.7, 40.6, 38.6, 33.1; ESIMS(−), m/z=446 [M−H]⁻. Anal. Calcd for ($C_{25}H_{22}FN_3O_4$): C, 67.11; H, 4.96; N, 9.39. Found: C, 67.26; H, 4.99; N, 9.22.

Example 23: Preparation of 4-((2,4-dioxo-3-phenethyl-3,4-dihydrothieno[2,3-d]pyrimidin-1(2H)-yl)methyl)-N-hydroxybenzamide (Compound 21)

$^1$H NMR (400 MHz, DMSO-d$_6$) δ 11.20 (br s, 1H), 9.04 (br s, 1H), 7.71 (d, J=8.0 Hz, 2H), 7.15-7.31 (m, 9H), 5.19 (s, 2H), 4.15 (t, J=7.6 Hz, 2H), 2.90 (t, J=7.6 Hz, 2H); $^{13}$C NMR (100 MHz, DMSO-d$_6$) δ 163.7, 157.5, 152.3, 150.5, 138.4, 137.9, 132.3, 128.7, 128.4, 127.2, 127.1, 126.3, 123.1, 118.2, 115.2, 50.5, 42.2, 33.1; ESIMS(−), m/z=420 [M−H]⁻. Anal Calcd for ($C_{22}H_{19}N_3O_4S \cdot 0.5\ H_2O$): C, 61.38; H, 4.68: N, 9.76. Found: C, 61.44; H, 4.60; N, 9.63.

Example 24: Preparation of N-hydroxy-4-((7-methyl-2,4-dioxo-3-phenethyl-3,4-dihydroquinazolin-1(2H)-yl)methyl)benzamide (Compound 22)

$^1$H NMR (400 MHz, DMSO-d$_6$) δ 11.16 (br s, 1H), 8.99 (br s, 1H), 7.94 (d, J=8.0 Hz, 1H), 7.68 (d, J=8.0 Hz, 2H), 7.20-7.30 (m, 7H), 7.07-7.09 (m, 2H), 5.35 (s, 2H), 4.21 (t, J=7.6 Hz, 2H), 2.93 (t, J=7.6 Hz, 2H), 2.30 (s, 3H); $^{13}$C NMR (100 MHz, DMSO-d$_6$) δ 163.8, 160.7, 150.6, 146.0, 139.59, 139.55, 138.4, 131.7, 128.7, 128.3, 127.9, 127.2, 126.36, 126.30, 124.1, 114.6, 112.7, 45.9, 42.3, 33.1, 21.6; ESIMS(+), m/z=430 [M+H]⁺. Anal Calcd for ($C_{25}H_{23}N_3O_4$): C, 69.92; H, 5.40; N, 9.78. Found: C, 6930; H, 5.23; N, 9.74.

Example 25: Preparation of 2-(4-((7-cyano-2,4-dioxo-3,4-phenethyl-3,4-dihydroquinazolin-1(2H)-yl)methyl)phenyl)-N-hydroxyacetamide (Compound 23)

$^1$H NMR (400 MHz, DMSO-d$_6$) δ 11.61 (br s, 1H), 8.77 (br s, 1H), 8.18 (d, J=8.0 Hz, 1H), 7.79 (s, 1H) 7.64 (d, J=8.4 Hz, 1H), 7.15-7.30 (m, 9H), 5.34 (s, 2H), 4.21 (t, J=7.6 Hz, 2H), 3.24 (s, 2H), 2.93 (t, J=7.6 Hz, 2H); $^{13}$C NMR. (100 MHz, DMSO-d$_6$) δ 166.9, 160.0, 150.2, 139.8, 138.3, 135.2, 133.7, 129.2, 129.1, 128.7, 128.4, 126.4, 126.3, 125.7, 118.9, 118.4, 117.7, 116.8, 46.0, 42.7, 38.9, 32.9; ESIMS(+), m/z=477.1 [M+Na]⁺. Anal. Calcd for ($C_{26}H_{22}N_4O_4$): C, 68.71; H, 4.88; N, 12.33. Found: C, 68.55; H, 4.86; N, 12.14.

Example 26: Preparation of 4-((2,4-dioxo-3-(2-(thiophen-2-yl)ethyl)-3,4-dihydroquinazolin-1(2H)-yl)methyl)-N-hydroxybenzamide (Compound 24)

$^1$H NMR (400 MHz, DMSO-d$_6$) δ 11.16 (br s, 1H), 9.00 (br s, 1H), 8.06 (d, J=7.6 Hz, 1H), 7.62-7.69 (m, 3H), 7.21-7.35 (m, 5H), 6.89-6.95 (m, 2H), 5.38 (s, 2H), 4.25 (t, J=7.2 Hz, 2H), 3.18 (t, 7.2 Hz, 2H); $^{13}$C NMR (100 MHz, DMSO-d$_6$) δ 163.9, 160.9, 150.6, 140.3, 139.4, 135.2, 131.8, 128.0, 127.2, 127.2, 127.0, 126.4, 125.6, 124.4, 123.0, 115.1, 114.8, 46.0, 42.5, 27.1; ESIMS(+), m/z=422 [M+H]⁺.

Example 27: Preparation of 4-((2,4-dioxo-3-phenethyl-3,4-dihydroquinazolin-1(2H)-yl)methyl)-N-hydroxythiophene-2-carboxamide (Compound 25)

$^1$H NMR (400 MHz, DMSO-d$_6$) δ 11.14 (br s, 1H), 9.06 (br s, 1H), 8.06 (dd, J=7.6, 1.2 Hz, 1H), 7.69 (ddd, J=8.8, 8.4, 0.8 Hz, 1H), 7.60 (br s, 1H), 7.50 (br s, 1H), 7.40 (d, J=8.4 Hz, 1H), 7.18-7.31 (m, 6H), 5.30 (s, 2H), 4.21 (t, J=7.6 Hz, 2H), 2.93 (t, J=7.6 Hz, 2H); $^{13}$C NMR (100 MHz, DMSO-d$_6$) δ 160.8, 159.2, 150.2, 139.3, 137.8, 137.5, 135.2, 128.6, 128.4, 128.0, 126.9, 126.8, 126.3, 122.9, 115.0, 114.7, 42.5, 42.3, 33.2; ESIMS(+), m/z=444.1 [M+Na]⁺. Anal. Calcd for ($C_{22}H_{19}N_3O_4S$): C, 62.69; H, 4.54; N, 9.97. Found: C, 62.93; H, 4.60; N, 9.97.

Example 28: Preparation of 4-((3-(3-fluorophenethyl)-2,4-dioxo-3,4-dihydroquinazolin-1(2H)-yl)methyl)-N-hydroxybenzamide (Compound 26)

$^1$H NMR (400 MHz, DMSO-d$_6$) δ 11.17 (br s, 1H), 9.01 (br s, 1H), 8.06 (dd, J=8.0, 1.2 Hz, 1H), 7.61-7.69 (m, 3H), 7.19-7.34 (gin, 511), 7.01-7.07 (m, 3H), 5.37 (s, 2H), 4.25 (t, J=7.6 Hz, 2H), 2.98 (t, J=7.6 Hz, 2H); $^{13}$C NMR (100 MHz, DMSO-d$_6$) δ 163.93, 163.39, 160.97, 160.94, 150.6, 141.5, 141.4, 139.49, 139.46, 135.2, 131.8, 130.28, 130.20, 128.0, 127.2, 126.4, 124.92, 124.90, 123.0, 115.5, 115.3, 115.1, 114.8, 113.0, 46.0, 42.1, 32.7; ESIMS(+), m/z=434.1 [M+H]⁺. Anal. Calcd for ($C_{24}H_{20}FN_3O_4$); C, 66.51; H, 4.65; N, 9.69. Found: C, 66.85; H, 4.69; N, 9.76.

Example 29: Preparation of 4-((7-cyclopropyl-2,4-dioxo-3-phenethyl-3,4-dihydroquinazolin-1(2H)-yl)methyl)-N-hydroxybenzamide (Compound 27)

$^1$H NMR (400 MHz, DMSO-d$_6$) δ 11.18 (br s, 1H), 9.02 (br s, 1H), 7.90 (d, J=8.0 Hz, 1H), 7.69 (d, J=8.0 Hz, 1H), 7.20-730 (m, 7H), 6.86-6.91 (m, 2H), 5.38 (s, 2H), 4.21 (t, J=7.6 Hz, 2H), 2.93 (t, J=7.6 Hz, 2H), 1.89-1.93 (m, 1H), 0.97-1.0 (m, 2H), 0.64-0.66 (m, 2H); $^{13}$C NMR (100 MHz, DMSO-d$_6$) δ 163.8, 160.6, 152.6, 150.7, 139.7, 139.4, 138.5, 131.7, 128.7, 128.3, 128.0, 127.2, 126.4, 126.3, 119.8, 112.5, 111.2, 45.8, 42.3, 33.1, 15.7, 10.8; ESIMS(+), m/z=456.1 [M+H]⁺. Anal. Calcd for ($C_{27}H_{25}N_3O_4 \cdot 0.5 H_2O$): C, 69.81; H, 5.64; N, 9.05. Found: C, 69.80; H, 5.71; N, 8.96.

Example 30: Preparation of 4-((3-(3-chloro-4-methoxyphenethyl)-2,4-dioxo-3,4-dihydroquinazolin-1(2H)-yl)methyl)-N-hydroxybenzamide (Compound 28)

$^1$H NMR (400 MHz, DMSO-d$_6$) δ 11.16 (br s, 1H), 9.02 (br s, 1H), 8.06 (d, J=7.6 Hz, 1H), 7.61-7.68 (m, 3H), 7.02-7.35 (m, 7H), 5.37 (s, 2H), 4.19 (t, J=7.2 Hz, 2H), 3.79 (s, 3H), 2.89 (t, J=7.2 Hz, 2H); $^{13}$C NMR (100 MHz, DMSO-d$_6$) δ 163.9, 160.9, 1510, 150.6, 139.4, 135.2, 131.8, 131.7, 128.5, 128.0, 127.2, 126.6, 126.3, 123.0, 120.7, 115.1, 114.8, 112.7, 55.9, 46.0, 42.4, 31.9; ESIMS(+), m/z=502.1 [M+Na]⁺.

Example 31: Preparation of N-hydroxy-4-((3-(3-(methylamino)phenethyl)-2,4-dioxo-3,4-dihydroquinazolin-1(2H)-yl)methyl)benzamide (Compound 29)

$^1$H NMR (400 MHz, DMSO-d$_6$) δ 11.14 (br s, 1H), 9.00 (br s, 1H), 8.07 (dd, J=8.0, 1.2 Hz, 1H), 7.61-7.69 (m, 3H), 7.20-7.30 (m, 4H), 6.94 (d, J=8.0 Hz, 1H), 6.45 (d, J=8.4 Hz, 2H), 5.46 (q, J=4.8 Hz, 1H), 5.39 (s, 2H), 4.13 (t, J=7.6 Hz, 2H), 2.77 (t, J=7.6 Hz, 2H), 2.62 (d, J=4.8 Hz, 3H); $^{13}$C NMR (100 MHz, DMSO-d$_6$) δ 164.4, 161.4, 151.1, 148.9, 140.04, 140.00, 135.7, 132.3, 129.6, 128.5, 127.7, 126.9, 125.5, 123.4, 115.7, 115.3, 112.2, 46.5, 43.4, 32.8, 30.3; ESIMS(−), m/z=443.1 [M−H]⁻.

Example 32: Preparation of N-hydroxy-4-((3-(4-morpholinophenethyl)-2,4-dioxo-3,4-dihydroquinazolin-1(2H)-yl)methyl)benzamide (Compound 30)

$^1$H NMR (400 MHz, DMSO-d$_6$) δ 2.84 (br s, 2H), 3.03 (br s, 4H), 3.71 (br s, 4H), 4.17 (br s, 2H), 5.38 (s, 2H), 6.85 (d, J=6.4 Hz, 2H), 7.08 (d, J=6.8 Hz, 2H), 7.21-7.26 (m, 4H), 7.63-7.70 (m, 3H), 8.06 (d, J=6.4 Hz, 1H), 9.03 (br s, 1H), 11.16 (br s, 1H); $^{13}$C NMR (100 MHz, DMSO-d$_6$) δ 32.2, 42.7, 46.0, 48.6, 66.0, 114.8, 115.1, 115.6, 122.9, 126.4, 127.1, 128.0, 128.4, 128.9, 129.2, 131.8, 135.2, 139.4, 149.6, 150.6, 160.9, 163.9; ESIMS(−), m/z=499 [M−H]⁻.

Example 33: Preparation of 4-((3-(benzyloxy)-2,4-dioxo-3,4-dihydroquinazolin-1(2H)-yl)methyl)-N-hydroxybenzamide (Compound 31)

$^1$H NMR (400 MHz, DMSO-d$_6$) δ 5.19 (s, 2H), 5.41 (s, 2H), 7.23 (d, J=8.4 Hz, 1H), 7.30 (dd, J=7.6, 7.2 Hz, 1H), 7.36-7.46 (m, 5H), 7.57-7.59 (m, 2H), 7.64-7.71 (m, 3H), 8.10 (d, J=7.6 Hz, 1H), 9.03 (br s, 1H), 11.20 (br s, 1H); $^{13}$C NMR (100 MHz, DMSO-d$_6$) δ 46.3, 77.4, 115.1, 115.6, 123.2, 126.4, 127.2, 127.9, 128.3, 128.9, 129.6, 131.8, 134.3, 135.3, 138.9, 139.2, 149.1, 158.2, 163.9: ESIMS(+), m/z=418 [M+H]⁺.

Example 34: Preparation of 5-(2,4-dioxo-3-phenethyl-3,4-dihydroquinazolin-1(2H)-yl)methyl)-N-hydroxythiophene-2-carboxamide (Compound 32)

$^1$H NMR (400 MHz, DMSO-d$_6$) δ 2.91 (d, J=7.6 Hz, 2H), 4.19 (d, J=7.6 Hz, 2H), 5.49 (s, 2H), 7.15-7.30 (m, 7H), 7.45 (br s, 1H), 7.56 (d, J=8.8 HZ, 1H), 7.72 (ddd, J=8.8, 8.8, 1.6 Hz, 1H), 8.04 (dd, J=8.0, 1.2 Hz, 1H), 9.10 (br s, 1H), 11.19 (br s, 1H); $^{13}$C NMR (100 MHz, DMSO-d$_6$) δ 46.3, 77.4, 115.1, 115.6, 123.2, 126.4, 127.2, 127.9, 128.3, 128.9, 129.6, 131.8, 134.3, 135.3, 138.9, 139.2, 149.1, 158.2, 163.9: ESIMS(−), m/z=420 [M−H]⁻. Anal. Calcd for ($C_{22}H_{19}N_3O_4S$): C, 62.69; H, 4.54; N, 9.97. Found: C, 62.86; H, 4.89; N, 9.61.

Example 35: Preparation of N-hydroxy-4-((3-(4-methoxyphenethyl)-2,4-dioxo-3,4-dihydroquinazolin-1(2H)-yl)methyl)benzamide (Compound 33)

$^1$H NMR (400 MHz, DMSO-d$_6$) δ 2.87 (t, J=7.6 Hz, 2H), 3.70 (s, 3H), 4.19 (t, J=7.6 Hz, 2H), 5.38 (s, 2H), 6.84 (d, J=8.4 Hz, 2H), 7.14 (d, J=8.4 Hz, 2H), 7.20-7.28 (m, 4H), 7.61-7.68 (m, 3H), 8.07 (d, J=8.0 Hz, 1H), 8.99 (br s, 1H), 11.14 (br s, 1H); $^{13}$C NMR (100 MHz, DMSO-d$_6$) δ 32.2, 40.1, 46.0, 54.9, 113.8, 114.8, 115.1, 122.9, 126.3, 127.2, 128.0, 129.6, 130.3, 131.8, 135.1, 139.4, 150.6, 157.8, 160.8;

Example 36: Preparation of N-hydroxy-4-((3-(4-hydroxyphenethyl)-2,4-dioxo-3,4-dihydroquinazolin-1(2H)-yl)methyl)benzamide (Compound 34)

$^1$H NMR (400 MHz, DMSO-d$_6$) δ 2.82 (t, J=7.2 Hz, 2H), 4.15 (t, J=7.2 Hz, 2H), 5.38 (s, 2H), 6.67 (d, J=8.4 Hz, 2H), 7.01 (d, J=8.4 Hz, 2H), 7.19-7.29 (m, 4H), 7.60-7.69 (m, 3H), 8.06 (d, J=8.0 Hz, 1H), 9.03 (br s, 1H), 9.23 (br s, 1H), 11.15 (br s, 1H); $^{13}$C NMR (100 MHz, DMSO-d$_6$) δ 32.3, 42.8, 46.0, 114.8, 115.1, 115.2, 123.0, 126.4, 127.2, 128.0, 128.5, 129.6, 131.8, 135.2, 139.4, 139.5, 150.6, 155.8, 160.9, 164.0; ESIMS(−), m/z=430 [M−H]⁻

Example 37: Preparation of 4-((2,4-dioxo-phenyl-3,4-dihydroquinolin-1(2H)-yl)methyl)-N-hydroxybenzamide (Compound 35)

$^1$H NMR (400 MHz, DMSO-d$_6$) δ 2.91 (d, J=7.6 Hz, 2H), 4.19 (d, J=7.6 Hz, 2H), 5.49 (s, 2H), 7.15-7.30 (m, 7H), 7.45

(br s, 1H), 7.56 (d, J=8.8 Hz, 1H), 7.72 (ddd, J=8.8, 8.8, 1.6 Hz, 1H), 8.04 (dd, J=8.0, 1.2 Hz, 1H), 9.10 (br s, 1H), 11.19 (br s, 1H); $^{13}$C NMR (100 MHz, DMSO-d$_6$) δ 46.7, 115.5, 116.4, 123.4, 127.0, 127.7, 128.7, 129.3, 129.4, 129.5, 132.3, 135.9, 136.8, 140.0, 140.4, 151.4, 161.9, 164.4; ESIMS(−), m/z=386 [M−H]$^-$.

Example 38: Preparation of N-hydroxy-4-((3-(4-methoxyphenyl)-2,4-dioxo-3,4-dihydroquinazolin-1(2H)-yl)methyl)benzamide (Compound 36)

White solid; R$_f$=0.34 (MeOH/Cl$_2$=⅑); mp 258-269° C. (dec); $^1$H NMR (400 MHz, DMSO-d$_6$) δ 3.80 (s, 3H), 5.41 (s, 2H), 7.03 (d, J=8.0 Hz, 2H), 7.25-7.33 (m, 4H), 7.45 (d, J=8.4 Hz, 2H), 7.65-7.72 (m, 3H), 9.03 (s, 1H), 11.19 (s, 1H); $^{13}$C NMR (100 MHz, DMSO-d$_6$) δ 46.3, 55.3, 114.0, 115.0, 115.9, 122.9, 126.6, 127.2, 128.2, 128.8, 130.0, 131.8, 135.3, 139.5, 139.9, 151.2, 158.9, 161.6, 164.0; ESIMS(+), m/z 418.1 [M+1]$^+$; Anal. Calcd for (C$_{23}$H$_{19}$N$_3$O$_5$); C, 66.18; H, 4.59; N, 10.07. Found: C, 66.03; H, 4.35; N, 9.75.

Example 39: Preparation of 4-((3-(4-chlorophenyl)-2,4-dioxo-3,4-dihydroquinazolin-1(2H)-yl)methyl)-N-hydroxybenzamide (Compound 37)

White solid; R$_f$=0.29 (MeOH/CH$_2$Cl$_2$=1:9); mp 258-260° C. (dec); $^1$H NMR (400 MHz, DMSO-d$_6$) δ 5.41 (s, 2H), 7.25-7.31 (m, 2H), 7.47 (dd, J=8.2, 3.4 Hz, 4H), 7.57 (d, J=8.4 Hz, 2H), 7.67-7.71 (m, 3H), 8.08 (d, J=7.6 Hz, 1H), 9.02 (s, 1H), 11.18 (s, 1H); $^{13}$C NMR (100 MHz, DMSO-d$_6$) δ 46.3, 115.0, 115.9, 123.0, 126.6, 127.2, 128.2, 128.9, 131.0, 131.8, 132.8, 135.2, 135.5, 139.4, 139.9, 150.8, 161.3, 163.9; ESIMS(−), m/z 419.9 [M−H]$^-$; Anal. Calcd for (C$_{22}$H$_{16}$ClN$_3$O$_4$): C, 62.54; H, 3.82; N, 9.96. Found: C, 62.30; H, 3.63: N, 9.83.

Example 40: Preparation of 4-((3-(4-fluorophenyl)-2,4-dioxo-3,4-dihydroquinazolin-1(2H)-yl)methyl)-N-hydroxybenzamide (Compound 38)

White solid; R$_f$=0.44 (MeOH/CH$_2$Cl$_2$=⅑); mp 257° C. (dec); $^1$H NMR (200 MHz, DMSO-d$_6$) δ 5.42 (s, 2H), 7.26-7.36 (m, 4H), 7.47-7.52 (m, 4H), 7.67-7.74 (m, 3H), 8.09 (dd, J=7.2, 0.8 Hz, 1H), 9.06 (s, 1H), 11.22 (s, 1H); $^{13}$C NMR (100 MHz, DMSO-d$_6$) δ 46.3, 115.0, 115.6, 115.8, 115.9, 123.0, 126.6, 127.2, 128.2, 131.1, 131.2, 131.8, 132.5 (2C), 135.4, 139.5, 139.9, 151.0, 160.4, 161.5, 162.9, 164.0; ESIMS(+), 406.1 [M+1]$^+$; Anal. Calcd for (C$_{22}$H$_{16}$FN$_3$O$_4$): C, 65.18; H, 3.98; N, 10.37. Found: C, 65.19; H, 3.95; N, 10.21.

Example 41: Preparation of N-hydroxy-4-((3-(2-methoxyphenyl)-2,4-dioxo-3,4-dihydroquinazolin-1(2H)-yl)methyl)benzamide (Compound 39)

White solid; R$_f$=0.29 (MeOH/CH$_2$Cl$_2$=⅑); mp 238-239° C. (dec); $^1$H NMR (200 MHz, DMSO-d$_6$) δ 11.21 (s, 1H), 9.07 (s, 1H), 8.08 (d, J=7.6 Hz, 1H), 7.75 (d, J=8.0 Hz, 2H), 7.71 (t, J=7.8 Hz, 1H), 7.40-7.46 (m, 4H), 7.33 (d, J=8.4 Hz, 1H), 7.29 (t, J=7.6 Hz, 1H), 7.18 (d, J=8.0 Hz, 1H), 7.07 (t, J=7.4 Hz, 1H), 5.44 (s, 2H), 3.76 (s, 3H); $^{13}$C NMR (100 MHz, DMSO-d$_6$) δ 164.0, 160.9, 154.7, 150.5, 139.8, 139.5, 135.6, 131.9, 130.2, 130.0, 128.3, 127.4, 126.5, 124.6, 123.2, 120.5, 115.5, 115.1, 112.1, 55.8, 46.0; ESIMS(+), ESIMS(+), m/z 418.1 [M+1]$^+$; Anal. Calcd for (C$_{22}$H$_{16}$FN$_3$O$_4$) C, 66.18; H, 4.59; N, 10.07. Found: C, 66.55; H, 4.31; N, 10.35.

Example 42: Preparation of (E)-3-(4-((2,4-dioxo-3-phenethyl-3,4-dihydroquinazolin-1(2H)-yl)methyl)phenyl)-N-hydroxyacrylamide (Compound 40)

White solid; R$_f$=0.21 (EtOAc/Hexanes 3/1); mp 203-206° C.; IR(ATR): 3347, 2950, 2838, 1640 cm$^{-1}$; $^1$H NMR (200 MHz, DMSO-d$_6$) δ 10.76 (br s, 1H), 8.06 (d, J=8.0 Hz, 1H), 7.64 (t, J=7.7 Hz, 1H), 7.48 (t, J=6.9 Hz, 2H), 7.38-7.21 (m, 10H), 6.42 (s, 1H), 5.35 (s, 2H), 4.23 (t, J=8.0 Hz, 2H), 2.95 (t, J=7.0 Hz, 2H); $^{13}$C NMR (50 MHz, DMSO-d$_6$) δ 162.7, 160.9, 150.6, 139.5, 138.5, 137.9, 137.7, 135.2, 133.9, 128.7, 128.4, 128.0, 127.8, 127.0, 166.3, 123.0, 119.0, 115.1, 114.9, 46.1, 42.5, 33.1; ESIMS(−), m/z 440 [M−H]$^-$; Anal. Calcd for (C$_{26}$H$_{23}$N$_3$O$_4$): C, 70.73; H, 5.25; N, 9.52. Found: C, 70.46; H, 5.41; N, 9.39.

Example 43: Preparation of (E)-3-(4-((3-(4-chlorophenethyl)-2,4-dioxo-3,4-dihydroquinazolin-1(2H)-yl)methyl)phenyl)-N-hydroxyacrylamide (Compound 41)

White solid; R$_f$=0.22 (MeOH/DCM 5/95); mp 193-196° C.; IR(ATR): 3358, 3268, 2949, 2839, 1630 cm$^{-1}$; $^1$H NMR (200 MHz, DMSO-d$_6$) δ 10.77 (br s, 1H), 9.02 (br s, 1H), 8.06 (dd, J=7.6, 1.0 Hz, 1H), 7.64 (t, J=7.0 Hz, 1H), 7.49 (t, J=8.0 Hz, 2H), 7.36-7.18 (m, 9H), 6.41 (d, J=14.0 Hz, 1H), 5.34 (s, 2H), 4.24 (t, J=7.0 Hz, 2H), 2.95 (t, J=7.0 Hz, 2H); $^{13}$C NMR (50 MHz, DMSO-d$_6$) δ 162.7, 160.9, 150.7, 139.5, 137.9, 137.7, 137.6, 135.3, 133.9, 131.0, 130.7, 128.4, 128.0, 127.8, 177.0, 123.0, 119.0, 115.1, 114.9, 46.1, 42.3, 32.4; ESIMS(+), m/z 476 [M+H]$^+$; Anal. Calcd for (C$_{26}$H$_{22}$ClN$_3$O$_4$): C, 65.62; H, 4.66; N, 8.83. Found: C, 65.11; 11, 4.52; N, 8.70.

Example 44: Preparation of (E)-3-(4-((3-(4-fluorophenethyl)-2,4-dioxo-3,4-dihydroquinazolin-1(2H)-yl)methyl)phenyl)-N-hydroxyacrylamide (Compound 42)

White solid; R$_f$=0.24 (MeOH/DCM=5/95); mp 198-200° C.; IR(ATR): 3358, 3278, 2945, 2836, 1643 cm$^{-1}$; $^1$H NMR (400 MHz, DMSO-d$_6$) δ 10.77 (br s, 1H), 9.04 (br s, 1H), 8.06 (dd, J=7.8, 1.4 Hz, 1H), 7.66-7.62 (m, 1H), 7.50 (d, J=8.0 Hz, 2H), 7.41 (d, J=16 Hz, 1H), 7.27-7.21 (m, 6H), 7.10 (t, J=8.8 Hz, 2H), 6.41 (d, J=16 Hz, 1H), 5.34 (s, 2H), 4.22 (t, J=7.4 Hz, 2H), 2.94 (t, J=7.2 Hz, 2H); $^{13}$C NMR (100 MHz, DMSO-d$_6$) δ 162.7, 162.2, 160.9, 159.8, 150.6, 139.5, 137.9, 137.7, 135.3, 134.7, 134.7, 133.9, 130.6, 130.6, 128.0, 127.8, 127.0, 123.0, 119.0, 115.2, 115.1, 115.0, 114.9, 46.1, 42.4, 32.3; ESIMS(−), m/z 458 [M−H]$^-$; Anal. Calcd for (C$_{26}$H$_{22}$FN$_3$O$_4$) C, 67.97; H, 4.83; N, 9.15. Found: C, 67.90; H, 4.80; N, 8.95.

Example 45: Preparation of (E)-N-hydroxy-3-(4-((3-(4-methoxyphenethyl)-2,4-dioxo-3,4-dihydroquinazolin-1(2H)-yl)methyl)phenyl)acrylamide (Compound 43)

White solid; R$_f$=0.28 (MeOH/DCM=5/95); mp 164-167° C.; IR(ATR); 3250, 2919, 2849, 1698, 1649, 1608 cm$^{-1}$; $^1$H NMR (200 MHz, DMSO-d$_6$) δ 10.77 (br s, 1H), 9.02 (br s, 1H), 8.06 (d, J=7.6 Hz, 1H), 7.64 (t, J=7.1 Hz, 1H), 7.52-7.11 (m, 9H), 6.84 (d, J=8.6 Hz, 2H), 6.41 (d, J=15.8

Hz, 1H), 5.35 (s, 2H), 4.19 (t, J=7.0 Hz, 2H), 3.70 (s, 3H), 2.88 (t, J=7.0 Hz, 2H); $^{13}$C NMR (50 MHz, DMSO-$d_6$) δ 162.8, 161.0, 157.9, 150.7, 139.5, 138.0, 137.8, 135.3, 133.9, 130.4, 129.8, 128.1, 127.9, 127.1, 123.1, 119.0, 115.1, 114.9, 113.9, 55.0, 46.1, 42.7, 32.3; ESIMS(+), m/z 472 [M+H]$^+$, 494 [M+Na]$^+$; Anal. Calcd for ($C_{27}H_{25}N_3O_5$.5 $H_2O$): C, 67.49; H, 5.45; N, 8.74. Found: C, 67.31; H, 5.31; N, 8.66.

Example 46: Preparation of (E)-N-hydroxy-3-(4-((3-(4-hydroxyphenethyl)-2,4-dioxo-3,4-dihydroquinazolin-1(2H)-yl)methyl)phenyl)acrylamide (Compound 44)

White solid; $R_f$=0.22 (10% MeOH in DCM); mp 211-214° C.; IR(ATR): 3353, 3227, 2919, 2850, 1707, 1675, 1636, 1607 cm$^{-1}$; $^1$H NMR (200 MHz, DMSO-$d_6$) δ 9.57 (br s, 2H), 8.06 (dd, J=6.0, 2.0 Hz, 1H), 7.63 (t, J=7.0 Hz, 1H), 7.51 (d, J=8.0 Hz, 2H), 7.41 (d, J=16.0 Hz, 1H), 7.29-7.20 (m, 4H), 7.01 (d, J=8.0 Hz, 2H), 6.67 (d, J=8.0 Hz, 2H), 6.42 (d, J=16.0 Hz, 1H), 5.34 (s, 2H), 4.18 (t, J=7.0 Hz, 2H), 2.83 (t, J=8.0 Hz, 2H); $^{13}$C NMR (50 MHz, DMSO-$d_6$) δ 162.7, 160.9, 155.9, 150.7, 139.5, 137.9, 137.7, 135.2, 133.9, 129.7, 128.5, 128.0, 127.9, 127.1, 123.0, 119.0, 115.2, 114.9, 46.1, 42.8, 32.3; ESIMS(−), m/z 456 [M−H]$^-$; Anal. Calcd for ($C_{26}H_{23}N_3O_5$): C, 68.26; H, 5.07; N, 9.19. Found: C, 68.39; H, 5.27; N, 8.88.

Example 47: Preparation of (E)-3-(4-((3-(4-chlorophenethyl)-7-fluoro-2,4-dioxo-3,4-dihydroquinazolin-1(2H)-yl)methyl)phenyl)-N-hydroxyacrylamide (Compound 46)

$R_f$=0.14 (MeOH/DCM=5/95); mp 192-194° C.; IR(ATR): 3288, 2921, 2850, 1702, 1666, 1646, 1623 cm$^{-1}$; $^1$H NMR (200 MHz, DMSO-$d_6$) δ 10.78 (br s, 1H), 9.04 (br s, 1H), 8.11 (dd, J=8.9, 6.6 Hz, 1H), 7.54-7.31 (m, 5H), 7.25-7.07 (m, 6H), 6.42 (d, J=16 Hz, 1H), 5.32 (s, 2H), 2.94 (t, J=7.2 Hz, 2H), 4.21 (t, J=7.2 Hz, 2H); $^{13}$C NMR (50 MHz, DMSO-$d_6$) δ 167.4, 164.9, 162.7, 160.2, 150.7, 141.7, 141.6, 137.9, 137.5, 137.3, 134.0, 131.3, 131.2, 131.1, 130.7, 128.4, 127.9, 127.1, 119.1, 112.0, 112.01, 111.0, 110.8, 102.2, 101.9, 45.2, 42.3, 32.4; ESIMS(−), m/z 492 [M−H]; Anal. Calcd for ($C_{26}H_{21}ClFN_3O_4$.0.2 $H_2O$): C, 62.77; H, 4.34; N, 8.45. Found: C, 62.56; H, 4.48; N, 8.19.

Example 48: Preparation of (E)-3-(4-((7-fluoro-3-(4-fluorophenethyl)-2,4-dioxo-3,4-dihydroquinazolin-1(2H)-yl)methyl)phenyl)-N-hydroxyacrylamide (Compound 47)

$R_f$=0.13 (EtOAc/Hexanes=2H); mp 201-204° C.; IR(ATR): 3275, 2918, 2849, 1701, 1646, 1622, 1595 cm$^{-1}$; $^1$H NMR (200 MHz, DMSO-$d_6$) δ 10.78 (br s, 1H), 9.04 (br s, 1H), 8.11 (t, J=8.0 Hz, 1H), 7.51 (d, J=8.0 Hz, 2H), 7.42 (d, J=16.0 Hz, 1H), 7.25-7.05 (m, 8H), 6.42 (d, J=16.0 Hz, 1H), 5.33 (s, 2H), 4.20 (t, J=7.0 Hz, 2H), 2.93 (t, J=7.0 Hz, 2H); $^{13}$C NMR (50 MHz, DMSO-$d_6$) δ 168.6, 163.6, 163.4, 162.3, 1603.2, 158.6, 150.7, 141.8, 141.5, 137.9, 137.3, 134.6, 134.6, 134.0, 131.3, 131.1, 130.7, 130.5, 127.1, 127.0, 119.1, 115.3, 114.9, 112.0, 112.0, 111.1, 110.6, 102.3, 101.8, 82.0, 46.2, 42.5, 32.2; ESIMS(m/z 476 [M−H]$^-$; Anal. Calcd for ($C_{26}N_{21}F_2N_3O_4$): C, 65.40; H, 4.43; N, 8.80. Found: C, 65.47; H, 4.63; N, 8.76.

Example 49: Preparation of (E)-3-(4-((7-fluoro-3-(4-methoxyphenethyl)-2,4-dioxo-3,4-dihydroquinazolin-1(2H)-yl)methyl)phenyl)-N-hydroxyacrylamide (Compound 48)

White solid; $R_f$=0.32 (EtOAc/Hexanes=2/1); mp 196-198° C.; IR(ATR): 3367, 2949, 2836, 1705, 1671, 1660, 1645, 1621 cm$^{-1}$; $^1$H NMR (200 MHz, DMSO-$d_6$) δ 10.78 (br s, 1H), 9.04 (br s, 1H), 8.12 (dd, J=10.0, 6 Hz, 1H), 7.51 (d, J=8.0 Hz, 2H), 7.42 (d, J=16.0 Hz, 1H), 7.23 (d, J=8.0 Hz, 2H), 7.16-7.08 (m, 4H), 6.84 (d, J=8.0 Hz, 2H), 6.41 (d, J=16.0 Hz, 1H), 5.34 (s, 2H), 4.17 (t, J=7.0 Hz, 2H), 3.7 (s, 3H), 2.86 (t, J=7.0 Hz, 2H); $^{13}$C NMR (50 MHz, DMSO-$d_6$) δ 168.7, 163.7, 162.8, 160.3, 158.0, 150.8, 141.9, 141.6, 138.0, 137.4, 134.1, 131.5, 131.2, 130.4, 129.9, 128.0, 127.2, 119.1, 114.0, 112.2, 112.1, 111.2, 110.7, 102.4, 101.9, 55.1, 46.3, 42.8, 32.3; ESIMS(−), m/z 488 [M−H]$^-$; Anal. Calcd for ($C_{27}H_{24}FN_3O_5$): C, 66.25; H, 4.94; N, 8.58. Found: C, 66.05; H, 5.03; N, 8.31.

Example 50: Preparation of (E)-3-(4-((7-fluor-3-(4-hydroxyphenethyl)-2,4-dioxo-3,4-dihydroquinazolin-1(2H)-yl)methyl)phenyl)-N-hydroxyacrylamide (Compound 49)

$R_f$=0.24 (EtOAc/Hexanes=2/1); mp 188-190° C.; IR(ATR): 3246, 2922, 2850, 1701, 1647, 1620, 1598 cm$^{-1}$; $^1$H NMR (400 MHz, DMSO-$d_6$) δ 10.76 (br s, 1H), 9.23 (br s, 1H), 9.02 (br s, 1H), 8.11 (t, J=7.4 Hz, 1H), 7.52 (d, J=8.0 Hz, 2H), 7.42 (d, J=16.0 Hz, 1H), 7.23 (d, J=8.0 Hz, 2H), 7.11 (t, J=8.8 Hz, 2H), 7.00 (d, J=8.0 Hz, 2H), 6.67 (d, J=8.0 Hz, 2H), 6.43 (d 16.0 Hz, 1H), 5.33 (s, 4.15 (t, J=7.4 Hz, 2H), 2.82 (t, J=7.2 Hz, 2H); $^{13}$C NMR (100 MHz, DMSO-$d_6$) δ 167.3, 164.8, 162.7, 160.1, 155.8, 150.7, 141.7, 141.5, 137.9, 137.3, 134.0, 131.2, 131.1, 129.6, 128.4, 127.8, 127.1, 119.1, 115.2, 112.02, 112.01, 110.9, 110.6, 102.1, 101.8, 46.2, 42.8, 32.2; ESIMS(−), m/z 474 [M−H]$^-$, Anal. Calcd for ($C_{26}H_{22}FN_3O_5$.0.6 $H_2O$): C, 64.22; H, 4.81; N, 8.64. Found: C, 64.00; H, 5.01; N, 8.27.

Example 51: Preparation of (E)-3-(4-((7-chloro-2,4-dioxo-3-phenethyl-3,4-dihydroquinazolin-(2H)-yl)methyl)phenyl)-N-hydroxyacrylamide (Compound 50)

$R_f$=0.24 (EtOAc/Hexanes=2/1); mp 207-210° C.; IR(ATR); 3355, 3281, 2920, 2850, 1702, 1647, 1605 cm$^{-1}$; $^1$H NMR (200 MHz, DMSO-$d_6$) δ 10.77 (br s, 1H), 9.05 (br s, 1H), 8.05 (d, J=8.0 Hz, 1H), 7.52 (d, J=8.0 Hz, 2H), 7.47-7.22 (m, 10H), 6.43 (d, J=16 Hz, 1H), 5.37 (s, 2H), 4.21 (t, J=8.0 Hz, 2H), 2.94 (t, J=7.0 Hz, 2H); $^{13}$C NMR (50 MHz, DMSO-$d_6$) δ 162.7, 160.3, 150.6, 140.6, 139.9, 138.4, 137.9, 137.1, 134.0, 130.0, 128.8, 128.5, 127.9, 127.0, 126.4, 123.2, 119.1, 114.6, 114.1, 46.1, 42.6, 33.0; ESIMS (−), m/z 474 [M−H]$^-$; Anal. Calcd for ($C_{26}H_{22}ClN_3O_4$.0.1 $H_2O$): C, 65.37; H, 4.68; N, 8.80. Found: C, 65.18; H, 0.91; N, 8.50.

Example 52: Preparation of (E)-3-(4-((7-chloro-3-(4-hydroxyphenethyl)-2,4-dioxo-3,4-dihydroquinazolin-1(2H)-yl)methyl)phenyl)-N-hydroxyacrylamide (Compound 51)

$R_f$=0.15 (EtOAcHexanes=2/1); mp 199-202° C.; IR(ATR): 3330, 3194, 3028, 2852, 1708, 1655, 1636, 1603 cm⁻¹; ¹H NMR (200 MHz, DMSO-d$_6$) δ 10.77 (br s, 1H), 9.25 (br s, 1H), 8.04 (d, J=8.6 Hz, 1H), 7.52 (d, J=7.8 Hz, 2H), 7.42 (J=16.0 Hz, 1H), 7.3 (d, J=8.0 Hz, 2H), 7.22 (d, 7.8 Hz, 2H), 6.99 (d, J=8.0 Hz, 2H), 6.66 (d, J=8.0 Hz, 2H), 6.42 (d, J=16.0 Hz, 1H), 5.35 (s, 2H), 4.14 (t, J=6.8 Hz, 2H), 2.81 (t, J=6.7 Hz, 2H); ¹³C NMR (50 MHz, DMSO-d$_6$) δ 162.7, 160.3, 155.9, 150.6, 140.6, 139.9, 137.9, 137.3, 134.0, 130.0, 129.7, 128.4, 127.9, 127.0, 123.2, 119.1, 115.2, 114.6, 114.1, 46.1, 42.9, 32.2; ESIMS(−), m/z 490 [M−H]⁻; Anal. Calcd for (C$_{26}$H$_{22}$ClN$_3$O$_5$): C, 63.48; H, 4.51; N, 8.54. Found: C, 63.43; H, 4.58; N, 8.22.

Example 53: Preparation of (E)-3-(4-((2,4-dioxo-3-phenyl-3,4-dihydroquinazolin-1(2H)-yl)methyl)phenyl)-N-hydroxyacrylamide (Compound 52)

R$_f$=0.20 (MeOH/DCM=3/97); mp 229-231° C.; IR(ATR); 3256, 1698, 1657, 1641, 1606 cm⁻¹, ¹H NMR (200 MHz, DMSO-d$_6$) δ 10.76 (br s, 1H), 9.04 (br s, 1H), 8.08 (d, J=7.0 Hz, 1H), 7.69 (t, J=7.4 Hz, 1H), 7.55-7.25 (m, 12H), 6.42 (d, J=16.0 Hz, 1H), 5.39 (s, 2H); ¹³C NMR (50 MHz, DMSO-d$_6$) δ 162.8, 161.5, 151.0, 140.0, 138.0, 137.8, 136.3, 135.5, 133.9, 129.1, 128.9, 128.3, 127.9, 127.3, 123.0, 119.0, 115.9, 115.1, 46.3; ESIMS(−), m/z 412 [M−H]; Anal. Calcd for (C$_{24}$H$_{19}$N$_3$O$_4$): C, 69.72; H, 4.63; N, 10.16. Found: C, 69.97; H, 4.64: N, 10.06.

Example 54: Preparation or (E)-N-hydroxy-3-(4-((3-(4-methoxyphenyl)-2,4-diox 3,4-dihydroquinazolin-1(2H)-yl)methyl)phenyl)acrylamide (Compound 53)

White solid; R$_f$=0.21 (MeOH/DCM=5/95); mp 181-184° C.; IR(ATR); 3264, 2923, 2848, 2360, 1706, 1658, 1607 cm⁻¹; ¹H NMR (200 MHz, DMSO-d$_6$) δ 10.77 (br s, 1H), 9.05 (br s, 1H), 8.07 (d, J=6.8 Hz, 1H), 7.68 (t, J=7.4 Hz, 1H), 7.55-7.23 (m, 9H), 7.02 (d, J=8.8 Hz, 2H), 6.44 (d, J=16.0 Hz, 1H), 5.38 (s, 2H), 3.80 (s, 314); ¹³C NMR (50 MHz, DMSO-d$_6$) δ 162.7, 161.6, 158.9, 151.2, 139.9, 137.9, 137.8, 135.4, 133.9, 130.0, 128.8, 128.2, 127.8, 127.2, 122.9, 119.0, 115.9, 115.0, 114.1, 55.3, 46.3; ESIMS(−), m/z 442 [M−H]⁻; Anal. Calcd for (C$_2$H$_{21}$N$_3$O$_5$.0.1 H$_2$O): C, 67.71; H, 4.77; N, 9.48. Found: C, 67.05; H, 4.77; N, 9.32.

Example 55: Preparation of (E)-N-hydroxy-3-(4-((3-(4-hydroxyphenyl)-2,4-dioxo-3,4-dihydroquinazolin-1(2H)-yl methyl)phenyl)acrylamide (Compound 54)

R$_f$=0.13 (MeOH/DCM=5/95); mp 244-247° C.; IR(ATR): 3287, 2950, 2838, 1702, 1654, 1605 cm⁻¹; ¹H NMR (200 MHz, DMSO-d$_6$) δ 10.75 s, 1H), 9.64 (br s, 9.03 (br s, 1H), 8.06 (d, 8.0 Hz, 1H), 7.67 (t, J=7.0 Hz, 1H), 7.51 (t, J=7.6 Hz, 2H), 7.41-7.14 (m, 7H), 6.83 (d, J=8.0 Hz, 2H), 6.41 (d, J=16.0 Hz, 1H), 5.38 (s, 2H); ¹³C NMR (100 MHz, DMSO-d$_6$) δ 162.7, 161.6, 157.1, 151.2, 139.9, 137.9, 137.8, 1353, 133.9, 129.8, 128.2, 127.8, 127.3, 127.2, 122.9, 119.0, 115.8, 115.3, 115.0, 46.3; ESIMS(−) m/z 428 [M−H]⁻; Anal. Calcd for (C$_{24}$H$_{19}$N$_3$O$_5$.0.1 H$_2$O): C, 66.85; H, 4.49; N, 9.74. Found: C, 66.47; H, 4.68; N, 936.

Example 56: Preparation of N-hydroxy-4-((3-(2-nitrophenyl)-2,4-dioxo-3,4-dihydroquinazolin-1(2H)-yl)methyl)benzamide (Compound 56)=

R$_f$=0.19 (MeOH/DCM 5%); ¹H NMR (400 MHz, DMSO) δ 11.20 (br s, 1H, NH), 9.06 (br s, 1H, OH), 838-8.21 (m, 1H, Ar—H), 8.17-8.05 (m, 8.04-7.92 (m, 1H, Ar—H), 7.92-7.65 (m, 5H, Ar—H), 7.49-726 (m, 4H, Ar—H), 5.53 (d, 1H, CH, J=17.2 Hz), 5.42 (d, 1H, CH, J=17.1 Hz). ESIMS(+), m/z 433 [M+H]⁺. HPLC 95.9%

Example 57: Preparation of 4-((2,4-dioxo-3-(2-phenylcyclopropyl)-3,4-dihydroquinazolin-(2H)-yl)methyl)-N-hydroxybenzamide (Compound 57)

R$_f$=0.19 (MeOH/DCM 5%); mp 122.0-124.5° C.; ¹H NMR (400 MHz, DMSO) δ 11.19 (s, 1H, NH), 9.03 (s, 1H, OH), 8.07 (dd, 1H, Ar—H, J=8.0 Hz, 1.4 Hz), 7.74-7.67 (m, 2H, Ar—H), 7.67-7.57 (m, 1H, Ar—H), 7.45-7.37 (m, 2H, Ar—H), 735-7.15 (m, 7H, Ar—H), 5.49-5.31 (m, 2H, CH$_2$), 2.92-2.80 (m, 1H, CH), 2.41-2.29 (m, 1H, CH), 1.69-1.57 (m, 1H, CH), 1.51-1.40 (m, 1H, CH). ¹³C NMR (100 MHz, DMSO) δ 164.0, 162.1, 151.5, 140.8, 139.74, 139.66, 135.0, 131.8, 128.1, 128.0, 127.2, 126.7, 126.5, 126.0, 122.7, 115.9, 114.8, 46.1, 34.4, 25.6, 17.1. HPLC>99.5%.

Example 58: Preparation of N-hydroxy-4-((3-(2-hydroxyethyl)-2,4-dioxo-3,4-dihydroquinazolin-1(2H)-yl)methyl)benzamide (Compound 58)

R$_f$=0.24 (MeOH/DCM=10%); mp 189.2-192.8° C.; ¹H NMR (400 MHz, DMSO) δ 8.14-7.95 (m, 1H, Ar—H), 7.83-7.52 (m, 3H, Ar—H), 7.40-6.98 (m, 4H, Ar—H), 5.37 (s, 2H, CH$_2$), 4.84 (s, 1H, OH), 4.23-3.94 (m, 2H, CH$_2$), 3.75-3.49 (m, 2H, CH$_2$). ESIMS(+), m/z 356 [M+H]⁺. HPLC 97.5%.

Example 59: Preparation of N-hydroxy-4-((3-(2-hydroxy-2-phenylethyl)-2,4-dioxo-3,4-dihydroquinazolin-1(2H)-yl)methyl)benzamide (Compound 59)

R$_f$=0.06 (MeOH/DCM=5%); mp 205.6-206.8° C.; ¹H NMR (400 MHz, DMSO) δ 11.21 (s, 1H, NH), 9.05 (s, 1H, OH), 8.08 (pseudo d, 1H, Ar—H, J=7.8 Hz), 7.69 (pseudo d, 2H, Ar—H, J=8.1 Hz), 7.67-7.60 (an, 1H, Ar—H), 7.41-7.15 (m, 9H, Ar—H), 5.57 (d, 1H, OH, J=4.6 Hz), 5.49-5.29 (m, 2H, CH$_2$), 5.12-4.97 (m, 1H, CH), 4.34 (dd, 1H, CH, J=12.8 Hz, 8.7 Hz), 4.04 (dd, 1H, CH, J=12.8 Hz, 5.0 Hz). ESIMS (+), m/z 432 [M+H]⁺. HPLC>99%

Example 60: Preparation of 4-((7-fluoro-3-(2-fluorophenyl)-2,4-dioxo-3,4-dihydroquinazolin-1(2H)-yl)methyl)-N-hydroxybenzamide (Compound 60)

R$_f$=0.36 (MeOH/DCM 10%); mp 129.5-134.0° C.; ¹H NMR (400 MHz, DMSO) δ 11.21 (s, 1H, NH), 9.06 (s, 1H, (1H), 8.17 (dd, 1H, Ar—H, J=8.7 Hz, 6.4 Hz), 7.73 (d, 2H, Ar—H, 8.3 Hz), 7.61 (m, 1H, Ar—H, J=7.7 Hz, 1.6 Hz), 7.58-7.49 (m, 1H, Ar—H), 7.47-7.40 (in 3H, Ar—H), 7.39-7.32 (m, 1H, Ar—H), 7.27 (dd, 1H, Ar—H, J=11.1 Hz, 2.1 Hz), 7.20 (td, 1H, Ar—H, J=8.5 Hz, 2.1 Hz), 5.49 (d, 1H, CH, J=17.2 Hz), 5.39 (d, 1H, CH, J=17.1 Hz). ESIMS(+), m/z 424 [M+H]⁺. HPLC 98%

Example 61: Preparation of 4-((7-chloro-3-(2-fluorophenyl)-2,4-dioxo-3,4-dihydroquinazolin-1(2H)-yl)methyl)-N-hydroxybenzamide (Compound 61)

R$_f$=0.43 (MeOH/DCM 1/9); mp 186.4-189.3° C. ¹H NMR (400 MHz, DMSO) δ 11.2.1 (s, 1H, NH), 9.06 (s, 1H, OH), 8.11 (d, 1H, Ar—H, J=8.4 Hz), 7.73 d, 2H, Ar—H, J=8.3 Hz), 7.61 (td, 1H, Ar—H, J=7.7 Hz, 1.6 Hz), 7.58-7.49 (m,

1H, Ar—H), 7.49-7.30 (m, 6H, Ar—H), 5.51 (d, 1H, CH, J=17.2 Hz), 5.42 (d, 1H, CH, J=17.2 Hz). ESIMS(+), m/z 438 [M–H]$^-$. HPLC 99%

Example 62: Preparation of 4-((2,4-dioxo-3-(4-(trifluoromethyl)benzyl)-3,4-dihydroquinazolin-1(2H)-yl)methyl)-N-hydroxybenzamide (Compound 62)

$R_f$=0.71 (MeOH/CH$_2$Cl$_2$=1/9); $^1$H NMR (400 MHz, DMSO-d$_6$) δ 11.21 (s, 1H), 9.12 (s, 1H), 8.08 (d, J=5.92 Hz, 1H), 7.87 (d, J=7.6 Hz, 1H), 7.72-7.60 (m, 214), 7.49 (d, J=8.1 Hz, 2H), 7.35-7.21 (m, 6H), 5.39 (s, 2H), 5.21 (s, 2H); ESIMS(+), m/z [M+Na]$^+$ 508. HPLC 97%

Example 63: Preparation of 4-((2,4-dioxo-3-(4-(trifluoromethyl)phenethyl)-3,4-dihydroquinazolin-1(2H)-yl)methyl)-N-hydroxybenzamide (Compound 63)

$R_f$=0.71 (MeOH/CH$_2$Cl$_2$=1/9); $^1$H NMR (400 MHz, DMSO-d$_6$) δ 11.17 (s, 1H), 9.03 (s, 1H), 8.07 (d, J=6.3 Hz, 1H), 7.76-7.60 (m, 5H), 7.48 (d, J=7.9 Hz, 2H), 7.37-7.20 (m, 4H), 5.37 (s, 2H), 4.26 (t, J=7.7 Hz, 1H), 3.05 (d, J=7.3 Hz, 1H); ESIMS(+), m/z [M+H]$^+$ 484. HPLC 94%

Example 64: Preparation of 4-((2,4-dioxo-3-phenyl-7-(trifluoromethyl)-3,4-dihydroquinazolin-1(2H)-yl)methyl)-N-hydroxybenzamide (Compound 64)

$R_f$=0.49 (MeOH/CH$_2$Cl$_2$=1/9); $^1$H NMR (400 MHz, DMSO-d$_6$) δ 11.19 (s, 1H), 9.03 (s, 1H), 8.28 (d, J=8.1 Hz, 1H), 7.71 (d, J=8.2 Hz, 2H), 7.62 (d, J=8.3 Hz, 1H), 7.54-7.40 (m, 8H), 5.51 (s, 2H): ESIMS(+), m/z [M+H]$_+$; HPLC 95%

Example 65: Preparation of 4-((2,4-dioxo-3-(2,4,5-trifluorophenyl)-3,4-dihydroquinazolin-1(2H)-yl)methyl)-N-hydroxybenzamide (Compound 65)

$R_f$=0.23 (MeOH/CH$_2$Cl$_2$=1/9); $^1$H NMR (400 MHz, DMSO-d$_6$) δ 11.19 (s, 1H), 9.04 (s, 1H), 8.11 (d, J=7.92 Hz, 1H), 7.98-7.65 (m, 5H), 7.55-7.28 (m, 4H), 5.52 (d, J=17.0 Hz, 1H), 5.37 (d, J=17.1 Hz, 1H); ESIMS(+), m/z [M+H]$^+$ 442. HPLC 93%

Example 66: Preparation of 4-((3-(2-fluorophenethyl)-2,4-dioxo-3,4-dihydroquinazolin-1(2H)-yl)methyl)-N-hydroxybenzamide (Compound 66)

$R_f$=0.77 (MeOH/CH$_2$Cl$_2$=5/95); $^1$H NMR (400 MHz, DMSO-d$_6$) δ 11.16 (s, 1H), 9.01 (s, 1H), 8.03 (d, J=7.8 Hz, 1H), 7.73-7.56 (m, 3H), 7.29-7.05 (m, 8H), 5.32 (s, 2H), 4.24 (t, J=7.0 Hz, 2H), 2.99 (t, J=7.0 Hz, 2H); ESIMS(+), m/z [M+Na]$^+$ 454. HPLC 95%

Example 67: Preparation of 4-((2,4-dioxo-3-(3,3,3-trifluoropropyl)-3,4-dihydroquinazolin-1(2H)-yl)methyl)-N-hydroxybenzamide (Compound 67)

$R_f$=0.60 (MeOH/CH$_2$Cl$_2$=5/95); $^1$H NMR (400 MHz, DMSO-d$_6$) δ 11.16 (s, 1H), 9.01 (s, 1H), 8.08 (d, J=7.8 Hz, 1H), 7.67 (t, J=6.8 Hz, 2H), 7.36 (d, J=8.0 Hz, 2H), 7.33-7.19 (m, 2H), 5.41 (s, 2H), 4.24 (t, J=7.1 Hz, 2H), 2.74-2.64 (m, 2H); ESIMS(+), m/z [M+H]$^+$ 408. HPLC 98%

Example 68: Preparation of 4-((2,4-dioxo-3-(2,2,2-trifluoroethyl)-3,4-dihydroquinazolin-1(2H)-yl)methyl)-N-hydroxybenzamide (Compound 68)

$R_f$=0.69 (MeOH/CH$_2$Cl$_2$=5/95); $^1$H NMR (400 MHz, DMSO-d$_6$) δ 11.16 (s, 1H), 9.02 (s, 1H), 8.10 (dd, J=7.7 Hz, 1.4 Hz, 1H), 7.68 (d, J=8.3 Hz, 3H), 7.42-7.25 (m, 4H), 5.43 (s, 2H), 4.83 (q, 9.1 Hz, 2H); ESIMS(+), m/z [M+Na]$^+$ 416. HPLC 98%

Example 69: Preparation of 4-((8-fluoro-2,4-dioxo-3-phenethyl-3,4-dihydroquinazolin-1(2H)-yl)methyl)-N-hydroxybenzamide (Compound 69)

$R_f$=0.71 (MeOH/Cl$_2$=5/95); $^1$H NMR (400 MHz, DMSO-d$_6$) δ 11.16 (s, 1H), 9.00 (s, 7.94 (d, J=7.9 Hz, 1H), 7.66 (d, J=8.2 Hz, 2H), 7.61-7.49 (m, 1H), 7.31-7.15 (m, 8H), 5.39 (s, 2H), 4.19 (t, J=7.5 Hz, 2H), 2.92 (t, J=7.6 Hz, 2H); ESIMS(+), m/z [M+H]$^+$ 434. HPLC 97%

Example 70: Preparation of 4-((2,4-dioxo-3-(2-(pyridin-2-yl)ethyl)-3,4-dihydroquinazolin-1(2H)-yl)methyl)-N-hydroxybenzamide (Compound 70)

$R_f$=0.57 (MeOH/CH$_2$Cl$_2$=5/95); $^1$H NMR (400 MHz, DMSO-d$_6$) δ 11.16 (s, 1H), 9.00 (s, 1H), 7.94 (d, J=7.9 Hz, 1H), 7.66 (d, J=8.2 Hz, 2H), 7.54 (dd, J=14.5 Hz, 8.0 Hz, 1H), 7.29-7.21 (m, 8H), 5.39 (s, 2H), 4.19 (t, J=7.5 Hz, 2H), 2.92 (t, J=7.6 Hz, 2H); ESIMS (+) m/z [M+H]$^+$ 417. HPLC 97%.

Example 71: Preparation of 4-((2,4-dioxo-3-(2-(pyridin-3-yl)ethyl)-3,4-dihydroquinazolin-1(2H)-yl)methyl)-N-hydroxybenzamide (Compound 71)

$R_f$=0.71 (MeOH/CH$_2$Cl$_2$=1/9); $^1$H NMR (400 MHz, DMSO-d$_6$) δ 11.20 (s, 1H), 9.05 (s, 1H), 8.45-8.38 (m, 2H), 8.05 (d, J=7.9 Hz, 1H), 7.75-7.62 (m, 4H), 7.36-7.15 (m, 5H), 5.36 (s, 2H), 4.26 (t, J=7.1 Hz, 2H), 2.99 (t, J=7.1 Hz, 2H); ESIMS(+), m/z [M+H]$^+$ 417. HPLC 98%

Example 72: Preparation of 4-((3-(2-fluoro-5-(trifluoromethyl)phenyl)-2,4-dioxo-3,4-dihydroquinazolin-1(2H)-yl)methyl)-N-hydroxybenzamide (Compound 72)

$R_f$=0.43 (MeOH/CH$_2$Cl$_2$=5/95); $^1$H NMR (400 MHz, DMSO-d$_6$) δ 11.19 (s, 1H), 9.09 (s, 1H), 8.15-8.01 (m, 1H), 8.11 (dd, J=8.0 Hz, 1.4 Hz, 1H), 8.03-7.92 (m, 1H), 7.77-7.68 (m, 4H), 7.45 (d, J=8.2 Hz, 2H), 7.40-7.30 (m, 2H), 5.53 (d, J=17.1 Hz, 1H), 5.38 (d, J=17.2 Hz, 1H); ESIMS(+), m/z [M+H]$^+$ 474. HPLC 95%.

Example 73: Preparation of 4-((2,4-dioxo-3-(2-(pyridin-4-yl)ethyl)-3,4-dihydroquinazolin-1(2H-yl)methyl)-N-hydroxybezamide (Compound 73)

$R_f$=0.83 (MeOH/CH$_2$Cl$_2$=1/9); $^1$H NMR (400 MHz, DMSO-d$_6$) δ 11.17 (s, 1H), 9.04 (s, 8.48-8.42 (m, 2H), 8.06 (dd, J=7.8 Hz, 1.3 Hz, 1H), 7.73.4-7.59 (m, 3H), 7.29-7.18 (m, 6H), 5.37 (s, 2H), 4.28 (t, J=7.3 Hz, 2H), 2.99 (t, J=7.2 Hz, 2H); ESIMS(+), m/z [M+H]$^+$ 417. HPLC 95%

Example 74: Preparation of N-hydroxy-4-((3-(2-methoxyethyl)-2,4-dioxo-3,4-dihydroquinazolin-1(2H)-yl)methyl)benzamide (Compound 74)

$R_f$=0.51 (MeOH/CH$_2$O$_2$=5/95); $^1$H NMR (400 MHz, DMSO-d$_6$) δ 11.18 (s, 1H), 9.05 (s, 1H), 8.10-8.04 (m, 1H), 7.73-7.62 (m, 3H), 7.40-7.20 (m, 4H), 5.41 (s, 2H), 4.20 (t, J=6.1 Hz, 2H), 3.58 (t, J=6.1 Hz, 2H), 3.25 (s, 3H); ESIMS (+) [M+Na]$^+$ 392. HPLC 96%

Example 75: Preparation of 4-((2,4-dioxo-3-(3-(trifluoromethyl)benzyl)-3,4-dihydroquinazolin-1(2H)-yl)methyl)-N-hydroxybenzamide (Compound 75)

$R_f$=0.54 (MeOH/CH$_2$Cl$_2$=5.95); $^1$H NMR (400 MHz, DMSO-d$_6$) δ 11.19 (s, 1H), 9.05 (s, 1H), 8.09 (d, J=7.0 Hz, 1H), 7.77-7.52 (m, 7H), 7.43-7.23 (m, 4H), 5.42 (s, 2H), 5.27 (s, 2H); ESIMS(+), m/z [M+Na]$^+$ 492. HPLC 99%

Example 76: Preparation of 4-((3-(2-bromophenethyl)-2,4-dioxo-3,4-dihydroquinazolin-1(2H)-yl)methyl)-N-hydroxybenzamide (Compound 76)

$R_f$=0.51 (MeOH/CH$_2$Cl$_2$=5.95); $^1$H NMR (400 MHz, DMSO-d$_6$) δ 11.19 (s, 1H), 9.04 (s, 1H), 8.10-8.00 (m, 1H), 7.72-7.51 (m, 4H), 7.33-7.11 (m, 7H), 5.32 (s, 2H), 4.28 (t, J=6.9 Hz, 2H), 3.09 (t, J=6.9 Hz, 2H); ESIMS(+) m/z [M+H]$^+$495. HPLC 98%

Example 77: Preparation of 4-((2,4-dioxo-3-(2-(trifluoromethyl)benzyl)-3,4-dihydroquinazolin-1(2H)-yl)methyl)-N-hydroxybenzamide (Compound 77)

$R_f$=0.54 (MeOH/CH$_2$Cl$_2$=5/95); $^1$H NMR (400 MHz, DMSO-d$_6$) δ 11.20 (s, 1H), 9.05 (s, 1H), 8.14-8.07 (m, 1H), 7.79-7.65 (m, 4H), 7.59-7.54 (m, 1H), 7.52-7.36 (m, 3H), 7.36-7.22 (m, 3H), 5.37 (s, 2H), 5.43 (s, 2H); ESIMS(+), m/z [M+H]$^+$ 470. HPLC 100%

Example 78: Preparation of 4-((3-(2-fluoro-3-(trifluoromethyl)phenyl)-2,4-dioxo-3,4-dihydroquinazolin-1(2H)-yl)methyl)-N-hydroxybenzamide (Compound 78)

$R_f$=0.43 (MeOH/CH$_2$Cl$_2$=5/95); $^1$H NMR (400 MHz, DMSO-d$_6$) δ 11.22 (s, 1H), 9.08 (s, 1H), 8.16-8.09 (m, 1H), 8.02 (t, J=7.1 Hz, 1H), 7.94 (t, J=7.0 Hz, 1H), 7.79-7.68 (m, 3H), 7.6 (t, J=8.0 Hz, 1H), 7.45 (d, J=8.2 Hz, 2H), 7.40-7.3 (m, 1), 5.59-5.34 (m, 2H), ESIMS (+) m/z [M+H]$^+$ 474, HPLC 98%

Example 79: Preparation of (E)-3-(4-(4-((2,4-dioxo-3-(3-(trifluoromethyl)phenethyl)-3,4-dihydroquinazolin-1(2H)-yl)methyl)phenyl)-N-hydroxyacrylamide (Compound 79)

$R_f$=0.54 (MeOH/CH$_2$Cl$_2$=1/9); $^1$H NMR (400 MHz, DMSO-d$_6$) δ 10.78 (s, 1H), 9.06 (s, 1H), 8.05 (d, J 7.8 Hz, 1H), 7.70-7.36 (m, 8H), 7.32-7.10 (m, 4H), 6.42 (d, J=15.8 Hz, 1H), 5.34 (s, 2H), 4.27 (t, J=7.3 Hz, 1H), 3.07 (t, J=7.3 Hz, 1H); ESIMS (+) m/z [M−H]$^-$ 508.

Example 80: Preparation of 4-((3-(2,6-diisopropylphenyl)-2,4-dioxo-3,4-dihydroquinazolin-1(2H)-yl)methyl)-N-hydroxybenzamide (Compound 80)

$R_f$=0.71 (MeOH/CH$_2$Cl$_2$=5/95); $^1$H NMR (400 MHz, DMSO-d$_6$) δ 11.2 (s, 1H), 9.06 (s, 1H), 8.12 (d, J=7.7 Hz, 1H), 7.73 (d, J=7.9 Hz, 3H), 7.55-7.25 (m, 7H), 5.47 (s, 2H), 2.68 (s, 2H), 1.08 (s, 12H); ESIMS(+), m/z [M+H]$^+$ 472. HPLC 95%

Example 81: Preparation of 4-((3-(2-ethylphenyl)-2,4-dioxo-3,4-dihydroquinazolin-1(2H)-yl)methyl)-N-hydroxybenzamide (Compound 81)

$R_f$=0.51 (MeOH/CH$_2$Cl$_2$=5/95); $^1$H NMR (400 MHz, DMSO-d$_6$) δ 11.19 (S, 1H), 9.05 (s, 1H), 8.09 (s, 1H), 7.71 (d, J=5.8 Hz, 3H), 7.63-7.17 (m, 8H), 5.43 (s, 2H), 2.47-7.34 (m, 2H), 1.06 (d, J=7.1 Hz, 3H); ESIMS(+), m/z [M+H]$^+$ 416. HPLC 97%

Example 82: Preparation of (E)-3-(4-((3-(2-fluorophenyl)-2,4-dioxo-3,4-dihydroquinazolin-1(2H)methyl)phenyl)-N-hydroxyacrylamide (Compound 82)

$R_f$=0.43 (MeOH/CH$_2$Cl$_2$=5/95); $^1$H NMR (400 MHz, DMSO-d$_6$) δ 10.8 (s, 1H), 8.10 (d, J=7.7 Hz, 1H), 7.73 (t, J=7.7 Hz, 1H), 7.66-7.49 (m, 4H), 7.48-7.28 (m, 7H), 6.44 (d, J=15.8 Hz, 1H), 5.46 (d, J=17.0 Hz, 1H), 5.38 (d, J=17.1 Hz, 1H); ESIMS (+) m/z [M+H]$^+$ 432. HPLC 98%

Example 83: Preparation of N-hydroxy-4-((3-(2-methyl-3-(trifluoromethyl)phenyl)-2,4-dioxo-3,4-dihydroquinazolin-1(2H)-yl)methyl)benzamide (Compound 83)

$R_f$=0.69 (MeOH/CH$_2$Cl$_2$=5/95); $^1$H NMR (400 MHz, DMSO-d$_6$) δ 11.4 (s, 1H), 8.12 (d, J=7.7 Hz, 1H), 7.88-7.68 (m, 5H), 7.57 (t, J=8.0 Hz, 1H), 7.47 (d, J=8.2 Hz, 2H), 0.38-7.30 (m, 2H), 5.46 (q, J=17.0 Hz, 2H), 2.23 (s, 3H); ESIMS (+) m/z [M+H]$^+$ 470. HPLC 98%

Example 84: Preparation of N-hydroxy-4-((3-(3-methoxyphenethyl)-2,4-dioxo-3,4-dihydroquinazolin-1(2H)-yl)methyl)benzamide (Compound 84)

$F_f$=0.57 (MeOH/CH$_2$Cl$_2$=5/95); $^1$H NMR (400 MHz, DMSO-d$_6$) δ 11.19 (s, 1H), 9.04 (s, 1H), 8.06 (dd, J=8.1 Hz, 3.9 Hz, 1H), 7.73-7.56 (m, 3H), 7.36-7.12 (m, 5H), 6.85-6.70 (m, 3H), 5.37 (s, 2H), 4.21 (t, J=7.6 Hz, 2H), 3.67 (s, 3H), 2.91 (t, J=7.5 Hz, 2H); ESIMS(+), m/z [M+Na]$^+$ 468. HPLC 99%

Example 85: Preparation of 4-((3-(2-(benzo[d][1,3]dioxol-5-yl)ethyl)-2,4-dioxo-3,4-dihydroquinazolin-1(2H)-yl)methyl)-N-hydroxybenzamide (Compound 85)

$R_f$=0.67 (MeOH/CH$_2$Cl$_2$=5/95); $^1$H NMR (400 MHz, DMSO-d$_6$) δ 11.18 (s, 1H), 9.04 (s, 1H), 8.06 (dd, J=7.8 Hz, 1.5 Hz, 1H), 7.73-7.59 (m, 3H), 7.35-7.18 (m, 4H), 6.84-6.77 (m, 2H), 6.64 (dd, J=8.0 Hz, 1.4 Hz, 1H), 5.95 (s, 2H), 5.38 (s, 2H), 4.18 (t, J=7.5 Hz, 2H), 2.86 (t, J=7.5 Hz, 2H); ESIMS (+) m/z [M+H]$^+$ 460. HPLC 95%

Example 86: Preparation of 4-((3-(3,4-dimethoxyphenethyl)-2,4-dioxo-3,4-dihydroquinazolin-1(2H)-yl)methyl)-N-hydroxybenzamide (Compound 86)

$R_f$=0.77 (MeOH/CH$_2$Cl$_2$=5/95); $^3$H NMR (400 MHz, DMSO-d$_6$) δ 11.18 (s, 1H), 9.05 (s, 1H), 8.07 (dd, J=7.9, 1.5 Hz, 1H), 7.74-7.57 (m, 3H), 7.35-7.18 (m, 4H), 6.92-6.69 (m, 3H), 5.39 (s, 2H), 4.21 (t, J=7.6 Hz, 2H), 3.70 (s, 3H), 3.66 (s, 3H), 2.88 (t, J=7.6 Hz, 2H); ESNS (+) m/z [M+H]$^+$ 476. HPLC 98%.

Example 87: Preparation of 4-((6-fluoro-7-hydroxy-2,4-dioxo-3-(3-(trifluoromethyl)phenethyl)-3,4-dihydroquinazolin-1(2H)-yl)methyl)-N-hydroxybenzamide (Compound 87)

$R_f$=0.75 (MeOH/CH$_2$Cl$_2$=1/9); $^1$H NMR (400 MHz, DMSO-d$_6$) δ 11.22 (s, 1H), 9.06 (s, 1H), 7.77-7.65 (m, 3H), 7.64-7.46 (m, 4H), 7.23 (d, J=8.1 Hz, 2H), 6.65 (d, J 7.0 Hz, 1H), 5.26 (s, 2H), 4.22 (t, J=7.2 Hz, 2H), 3.04 (t, J=7.2 Hz, 2H); ESIMS (+) m/z [M+H]$^+$ 518. HPLC 97%

Example 88: Preparation of 4-((3-(4-bromophenethyl)-2,4-dioxo-3,4-dihydroquinazolin-1(2H)-yl)methyl)-N-hydroxybenzamide (Compound 88)

$R_f$=0.81 (MeOH/CH$_2$Cl$_2$=5/95); $^1$H NMR (400 MHz, DMSO-d$_6$) δ 11.2 (s, 1H), 9.09 (s, 1H), 8.05 (dd, J=7.9 Hz, 1.4 Hz, 1H), 7.79-7.57 (m, 3H), 7.51-7.40 (m, 2H), 7.36-7.09 (m, 6H), 5.37 (s, 2H), 4.21 (t, J=7.7 Hz, 2H), 2.92 (t, J=7.4 Hz, 2H); ESIMS(+), m/z [M+Na]$^+$ 516. HPLC 95%

Example 89: Preparation of 4-((3-(2,6-dimethylphenyl)-2,4-dioxo-3,4-dihydroquinazolin-1(2H)-yl)methyl)-N-hydroxybenzamide (Compound 89)

$R_f$=0.93 (MeOH/CH$_2$Cl$_2$=5/95); $^1$H NMR (400 MHz, DMSO-d$_6$) δ 11.19 (s, 1H), 9.06 (s, 1H), 8.12 (d, J=6.8 Hz, 1H), 7.82-7.68 (m, 3H), 7.47-7.16 (m, 7H), 5.47 (s, 2H), 2.05 (s, 6H); ESIMS(+), m/z [M+H]$^+$ 416. HPLC 99%

Example 90: Preparation of 4-((2,4-dioxo-3-(2-(trifluoromethoxy)phenyl)-3,4-dihydroquinazolin-1(2H)-yl)methyl)-N-hydroxybenzamide (Compound 90)

$R_f$=0.33 (MeOH/CH$_2$Cl$_2$=5/95); $^1$H NMR (400 MHz, DMSO-d$_6$) δ 11.23 (s, 1H), 9.07 (s, 1H), 8.09 (dd, J=7.8 Hz, 1.4 Hz, 1H), 7.79-7.56 (m, 5H), 7.56-7.42 (m, 4H), 735-7.19 (m, 2H), 5.42 (s, 2H); ESIMS(+), m/z [M+H]$^+$ 472. HPLC 98%

Example 91: Preparation of 4-((2,4-dioxo-3-(o-tolyl)-3,4-dihydroquinazolin-1(2H)-yl)methyl)-N-hydroxybenzamide (Compound 91)

$R_f$=0.59 (MeOH/CH$_2$Cl$_2$=1/9); $^1$H NMR (400 MHz, DMSO-d$_6$) δ 11.17 (br s, 1H), 9.12 s, 1H), 8.20-8.00 (m, 1H), 7.82-7.64 (m, 3H), 7.48-7.28 (m, 8H), 5.43 (s, 2H), 2.09 (s, 3H); ESIMS(+), m/z 402.2 [M+H]$^+$. HPLC 96%.

Example 92: Preparation of 4-((3-cyclohexyl-2,4-dioxo-3,4-dihydroquinazolin-1(2H)-yl)methyl)-N-hydroxybenzamide (Compound 92)

$R_f$=0.45 (MeOH/CH$_2$Cl$_2$=1/9); $^1$H NMR (400 MHz, DMSO d$_6$) δ 11.16 (br s, 1H), 9.13 (br s, 1H), 8.04 (d, J=7.6 Hz, 1H), 7.76-7.56 (m, 3H), 7.33 (d, J=7.6 Hz, 2H), 7.26-7.17 (m, 2H), 5.37 (s, 2H), 4.92-4.75 (m, 1H), 2.47-2.31 (m, 2H), 1.84-1.75 (m, 2H), 1.71-1.57 (m, 3H), 1.37-1.25 (m, 2H)), 1.21-1.07 (m, 1H); ESIMS(+), m/z 394.1 [M+H]$^+$. HPLC 98%.

Example 93: Preparation of N-hydroxy-4-((3-(1-methylpiperidin-4-yl)-2,4-dioxo-3,4-dihydroquinazolin-1(2H)-yl)methyl)benzamide (Compound 93)

$R_f$=0.58 (MeOH/CH$_2$Cl$_2$=3/7); $^1$H NMR (400 MHz, DMSO-d$_6$) δ 11.17 (br s, 1H), 9.04 (br s, 1H), 8.05 (d, J=7.8 Hz, 1H), 7.68 (d, J=8.0 Hz, 2H), 7.62 (t, J=7.8 Hz, 1H), 7.34 (d, J=8.0 Hz, 2H), 7.24 (t, J=7.6 Hz, 1H), 7.19 (d, J=8.4 Hz, 1H), 5.37 (s, 2H), 4.87-4.73 (m, 1H), 2.86 (d, J=11.0 Hz, 2H), 2.72-2.61 (m, 2H), 2.17 (s, 3H), 2.02-1.87 (m, 2H), 1.67-1.50 (m, 2H); ESIMS(+), m/z 409.1 [M+H]$^+$. HPLC 98%.

Example 94: Preparation of 4-((2,4-dioxo-3-(pyridin-4-yl)-3,4-dihydroquinazolin-1(2H)-yl)methyl)-N-hydroxybenzamide (Compound 94)

$R_f$=0.30 (MeOH/CH$_2$Cl$_2$=1/9); $^1$H NMR (400 MHz, DMSO-d$_6$) δ 11.20 (s, 1H), 9.04 (s, 1H), 8.74 (d, J=4.9 Hz, 2H), 8.09 (d, J=7.8 Hz, 1H), 7.73-7.68 (m, 3H), 7.54 (d, J=4.8 Hz, 2H), 7.48 (d, J=8.0 Hz, 2H), 7.34-7.26 (m, 2H), 5.42 (s, 2H); ESIMS(+), m/z 389.1 [M+H]$^+$; HPLC 94%.

Example 95: Preparation of 4-((2,4-dioxo-3-(3-(trifluoromethyl)phenyl)-3,4-dihydroquinazolin-1(2H)-yl)methyl)-N-hydroxybenzamide (Compound 95)

$R_f$=0.58 (MeOH/CH$_2$Cl$_2$=1/9): $^1$H NMR (400 MHz, DMSO-d$_6$) δ 11.20 (s, 1H), 9.03 (br s, 1H), 8.09 (dd, J=7.8 Hz, 1.4 Hz, 1H), 7.94 (s, 7.85-7.74 (m, 3H), 7.73-7.67 (m, 3H), 7.48 (d, J=8.2 Hz, 2H), 7.33-7.24 (m, 2H), 5.42 (s, 2H); ESIMS(+), m/z 455.9 [M+H]$^+$; HPLC 95%.

Example 96: Preparation of 4-((2,4-dioxo-3-(pyridin-3-yl)-3,4-dihydroquinazolin-1(2H)-yl)methyl)-N-hydroxybenzamide (Compound 96)

$R_f$=0.23 (MeOH/CH$_2$Cl$_2$=1/9); $^1$H NMR (400 MHz, DMSO-d$_6$) δ 11.21 (br s, 1H), 8.77 (d, J=2.3 Hz, 1H), 8.71 (dd, J=4.9 Hz, 1.2 Hz, 1H), 8.13-8.09 (m, 2H), 7.75-7.69 (m, 4H), 7.49 (d, J=8.2 Hz, 2H), 7.34-7.28 (m, 2H), 5.44 (s, 2H); ESIMS(+), m/z 388.9 [M+H]$^+$; HPLC>99%.

Example 97: Preparation of 4-((3-(3,3-difluorocyclobutyl)-2,4-dioxo-3,4-dihydroquinazolin-1(2H)-yl)methyl)-N-hydroxybenzamide (Compound 97)

$R_f$=0.40 (MeOH/CH$_2$Cl$_2$=1/9), $^1$H NMR (400 MHz, DMSO-d$_6$) δ 11.17 (s, 1H), 9.03 (s, 1H), 8.06 (dd, J=7.8 Hz, 1.4 Hz, 1H), 7.70-7.60 (m, 3H), 7.39 (d, J==8.2 Hz, 2H), 7.26 (t, J=7.6 Hz, 1H), 7.19 (d, J=8.5 Hz, 1H), 5.38 (s, 2H), 5.23-5.13 (m, 1H), 3.58-3.41 (m, 2H), 2.97-2.87 (m, 2H); ESIMS(+), m/z 424.1 [M+Na]$^+$. HPLC 93%.

Example 98: Preparation of 4-((2,4-dioxo-3-(piperidin-3-yl)-3,4-dihydroquinazolin-1(2H)-yl)methyl)-N-hydroxybenzamide (Compound 98)

$R_f$=0.17 (MeOH/CH$_2$Cl$_2$=3/7); $^1$H NMR (400 MHz, DMSO-d$_6$) δ 8.04 (d, J=7.8 Hz, 1H), 7.69 (d, J=7.8 Hz, 2H), 7.62 (t, J=7.8 Hz, 1H), 7.34 (d, J=8.0 Hz, 2H), 7.26-7.17 (m, 2H), 5.37 (s, 2H), 4.93-4.80 (m, 1H), 3.43 (t, J=11.3 Hz, 1H), 2.83 (d, J=11.4 Hz, 2H), 2.57-2.44 (m, 1H), 2.36 (t, J=11.8 Hz, 1H), 1.78-1.66 (m, 2H), 1.55-1.40 (m, 1H); ESIMS(+), m/z 395.2 [M+H]$^+$. HPLC 94%

Example 99: Preparation of N-acetoxy-4-((2,4-dioxo-3-phenethyl-3,4-dihydroquinazolin-1(2H)-yl)methyl)benzamide (Compound 99)

$R_f$=0.52 (MeOH/CH$_2$Cl$_1$=1/9); $^1$H NMR (200 MHz, DMSO-d$_6$) δ 12.29 (br s, 1H), 8.08 (d, J=7.8 Hz, 1H), 7.74 (d, J=8.1 Hz, 2H), 7.69-7.58 (m, 1H), 7.36-7.17 (m, 9H), 5.41 (s, 2H), 4.24 (t, J=7.5 Hz, 2H), 2.95 (t, J=7.4 Hz, 2H), 2.21 (s, 3H); ESIMS(−), m/z 456.2 [M−H]⁻. HPLC 96%.

Example 100: Preparation of 4-((2,4-dioxo-3-(3-(trifluoromethyl)phenethyl)-3,4-dihydroquinazolin-1(2H)-yl)methyl)-N-hydroxybenzamide (Compound 100)

$R_f$=0.36 (MeOH/CH$_2$Cl$_2$=1/9); $^1$H NMR (200 MHz, DMSO-d$_6$) δ 11.18 (s, 1H), 9.03 (s, 1H), 8.05 (dd, J=7.8 Hz, 1.6 Hz, 1H), 7.73-7.62 (m, 3H), 7.61-7.50 (m, 4H), 7.30-7.18 (m, 4H), 5.37 (s, 2H), 4.27 (t, J=7.1 Hz, NI), 3.07 (t, J=7.3 Hz, 2H); ESIMS(+), m/z 506.2 [M+Na]⁺. HPLC 98%.

Example 0.101: Preparation of 4-((2,4-dioxo-3-(2-(trifluoromethoxy)benzyl)-3,4-dihydroquinazolin-1(2H)-yl)methyl)-N-hydroxybenzamide (Compound 101)

$R_f$=0.45 (MeOH/CH$_2$Cl$_2$=1:9), $^1$H NMR (400 MHz, DMSO-d$_6$) δ 11.18 (s, 1H), 9.02 (s, 1H), 8.09 (dd, J=7.8 Hz, 1.4 Hz, 1H), 7.71-7.66 (m, 3H), 7.41-7.36 (m, 4H), 7.35-7.27 (m, 4H), 5.42 (s, 2H), 5.25 (s, 2H); ESIMS(+), m/z 508.1 [M+Na]⁺. HPLC 99%

Example 102: Preparation of 4-((2,4-dioxo-3-(2-(trifluoromethyl)phenethyl)-3,4-dihydroquinazolin-1(2H)-yl)methyl)-N-hydroxybenzamide (Compound 102)

$R_f$=0.41 (MeOH/CH$_2$Cl$_2$=1/9); $^1$H NMR (400 MHz, DMSO-d$_6$) δ 11.19 (s, 1H), 9.04 (d, J=1.4 Hz, 1H), 8.07 (dd, J=7.8 Hz, 1.4 Hz, 1H), 7.71-7.59 (m, 5H), 7.49-7.42 (m, 2H), 7.29-7.20 (m, 4H), 5.36 (s, 2H), 4.27 (t, J=7.2 Hz, 2H), 3.13 (t, J=7.0 Hz, 2H); ESIMS(−), m/z 482.2 [M−H]⁻; HPLC 95%.

Example 103: Preparation of N-acetoxy-4-((2,4-dioxo-3-(3-(trifluoromethyl)phenethyl)-3,4-dihydroquinazolin-1(2H)-yl)methyl)benzamide (Compound 103)

$R_f$=0.54 (MeOH/CH$_2$Cl$_2$=1/9); $^1$H NMR (400 MHz, DMSO-d$_6$) δ 12.28 (s, 1H), 8.06 (dd, J=7.8 Hz, 1.5 Hz, 1H), 7.74 (d, J=8.3 Hz, 2H), 7.66-7.61 (m, 1H), 7.59-7.50 (m, 4H), 7.34 (d, J=8.3 Hz, 2H), 7.26 (t, J=7.5 Hz, 1H), 7.20 (d, J=8.5 Hz, 1H), 5.40 (s, 2H), 4.27 (t, J=7.4 Hz, 2H), 3.07 (t, J=7.3 Hz, 2H), 2.21 (s, 3H); ESIMS(−), m/z 524.2 [M−H]⁻. HPLC 97%.

Example 104: Preparation of 3-(1-(4-(hydroxycarbamoyl)benzyl)-2,4-dioxo-1,2-dihydroquinazolin-3(4H)-yl)-1,1-dimethylpiperidin-1-ium (Compound 104)

$R_f$=0.11 (MeOH/CH$_2$Cl$_2$=1/9); $^1$H NMR (400 MHz, DMSO-d$_6$) δ 9.06 (br s, 1H), 8.06 (d, J=7.8 Hz, 1H), 7.72 (d, 8.2 Hz, 2H), 7.68-7.64 (m, 1H), 7.38 (d, J=8.0 Hz, 2H), 7.28 (t, J=7.5 Hz, 1H), 7.23 (d, J=8.5 Hz, 1H), 5.44-5.33 (m, 3H), 4.08 (t, J=12.1 Hz, 1H), 3.61-3.55 (m, 2H), 3.36-3.25 (m, 7H), 2.59-2.51 (m, 1H), 2.20-2.06 (m, 1H), 1.96-1.86 (m, 2H); ESIMS(+), m/z 423.3 [M+H]⁺. HPLC 94.1%.

Example 105: Preparation of 4-((3-(1-ethylpiperidin-3-yl)-2,4-dioxo-3,4-dihydroquinazolin-1(2H)-yl)methyl)-N-hydroxybenzamide (Compound 105)

$R_f$=0.14 (MeOH/CH$_2$Cl$_2$=1/9); $^1$H NMR (400 MHz, DMSO-d$_6$) δ 11.17 (br s, 1H), 9.06 (br s, 1H), 8.05 (dd, J 7.9 Hz, 1.4 Hz, 1H), 7.69 (d, J=8.2 Hz, 2H), 7.65-7.60 (m, 1H), 7.35 (d, J=8.2 Hz, 2H), 7.24 (t, J=7.5 Hz, 1H), 7.19 (d, J=8.5 Hz, 1H), 5.37 (s, 2H), 5.04-4.94 (m, 1H), 2.89-2.78 (m, 3H), 2.45-2.29 (m, 3H), 1.85 (t, J=11.2 Hz, 1H), 1.77-1.67 (m, 2H), 1.60-1.48 (m, 1H), 0.99 (t, J=7.1 Hz, 3H); ESIMS(+), m/z 423.2 [M+H]⁺. HPLC 99%.

Example 106: Preparation of N-hydroxy-4-((3-(4-(2-hydroxyethoxy)phenethyl)-2,4-dioxo-3,4-dihydroquinazolin-1(2H)-yl)methyl)benzamide (Compound 106)

$R_f$=0.30 (MeOH/CH$_2$Cl$_2$=1/9); $^1$H NMR (400 MHz, DMSO-d$_6$) δ 11.21 (s, 1H), 9.09 (s, 1H), 8.06 (dd, J=7.9 Hz, 1.3 Hz, 1H), 7.68-7.60 (m, 3H), 7.28-7.24 (m, 3H), 7.19 (d, J=8.5 Hz, 1H), 7.11 (d, J=8.5 Hz, 2H), 6.84 (d, J=8.6 Hz, 2H), 5.37 (s, 2H), 4.94 (t, J=5.5 Hz, 1H), 4.18 (t, J=7.6 Hz, 2H), 3.91 (t, J=4.9 Hz, 2H), 3.68 (q, J=5.1 Hz, 2H), 2.86 (t, J=7.6 Hz, 2H); ESIMS(−), m/z 474.3 [M−H]⁻. HPLC 100%.

Example 107: Preparation of 1-((4-((2,4-dioxo-3-(3-(trifluoromethyl)phenethyl)-3,4-dihydroquinazolin-1(2H)-yl)methyl)benzamido)oxy)-3-methyl-1-oxobutan-2-aminium Chloride (Compound 107)

$R_f$=0.43 (MeOH/CH$_2$Cl$_2$=1/9); $^1$H NMR (400 MHz, DMSO-d$_6$) δ 12.97 (s, 1H), 8.78 (s, 3H), 8.07-8.04 (m, 1H), 7.81 (d, J=8.3 Hz, 2H), 7.66-7.61 (m, 1H), 7.56-7.52 (m, 3H), 7.35 (d, J=8.3 Hz, 2H), 7.26 (t, J=7.4 Hz, 2H), 7.21 (d, J=8.5 Hz, 1H), 5.41 (s, 2H), 4.29-4.22 (m, 3H), 3.07 (t, J=7.3 Hz, 2H), 2.37-2.27 (m, 1H), 1.12 (d, J=7.0 Hz, 3H), 1.07 (d, J=6.9 Hz, 3H); HPLC 100%

Example 108: Preparation of 4-((2,4-dioxo-3-phenethyl-3,4-dihydroquinazolin-1(2H)-yl)methyl)-N-hydroxy-3-methoxybenzamide (Compound 108)

$R_f$=0.43 (MeOH/CH$_2$Cl$_1$=1/9); $^1$H NMR (400 MHz, DMSO-d$_6$) δ 11.22 (s, 1H), 9.07 (s, 1H), 8.08 (d, J=7.8 Hz, 1H), 7.63 (t, J=7.8 Hz, 1H), 7.42 (s, 1H), 7.31-7.19 (m, 7H), 7.03 (d, J=8.5 Hz, 1H), 6.77 (d, J=7.8 Hz, 1H), 5.24 (s, 2H), 4.21 (t, J=7.6 Hz, 2H), 3.95 (s, 3H), 2.93 (t, J=7.6 Hz, 2H); ESIMS(−), m/z 444.3 [M−H]⁻. HPLC 100%

Example 109: Preparation of 4-((2,4-dioxo-3-phenethyl-3,4-dihydroquinazolin-1(2H)-yl)methyl)-N-hydroxy-2-methylbenzamide (Compound 109)

$R_f$=0.32 (MeOH/CH$_2$Cl$_2$=1/9); $^1$H NMR (400 MHz, DMSO-d$_6$) δ 10.80 (s, 1H), 9.05 (s, 1H), 8.05 (dd, J=7.8 Hz, 1.3 Hz, 1H), 7.68-7.63 (m, 1H), 7.59-7.49 (m, 4H), 7.28-7.17 (m, 4H), 6.97 (d, J=7.9 Hz, 1H), 5.32 (s, 2H), 4.26 (t, J=7.4 Hz, 2H), 3.06 (t, J=7.3 Hz, 2H), 2.28 (s, 3H); ESIMS(−), m/z 496.1 [M−H]⁻. HPLC 98%

Example 110: Preparation of 4-((2,4-dioxo-3-phenethyl-3,4-dihydroquinazolin-1(2H)-yl)methyl)-2-fluoro-N-hydroxybenzamide (Compound 110)

$R_f$=0.48 (MeOH/CH$_2$Cl$_2$=1/9); $^1$H NMR (400 MHz, DMSO-d$_6$) δ 10.96 (s, 1H), 9.21 (s, 1H), 8.08 (dd, J=7.8 Hz, 1.4 Hz, 1H), 7.68-7.63 (m, 1H), 7.47 (t, J=7.6 Hz, 1H), 7.31-7.19 (m, 8H), 7.09 (d, J=8.3 Hz, 1H), 5.38 (s, 2H), 4.21 (t, J=7.7 Hz, 2H), 2.94 (t, J=7.6 Hz, 2H); ESIMS(−), m/z 432.1 [M−H]⁻. HPLC 99%.

Example 111: Preparation of 4-((3-(3,4-dihydroxyphenethyl)-2,4-dioxo-3,4-dihydroquinazolin-1(2H)-yl)methyl)-N-hydroxybenzamide (Compound 111)

$R_f$=0.12 (MeOH/CH$_2$Cl$_2$=1/9); $^1$H NMR (400 MHz, DMSO-d$_6$) δ 11.15 (s, 1H), 9.04 (s, 1H), 8.85 (s, 1H), 8.72 (s, 1H), 8.07 (dd, J=7.9 Hz, 1.5 Hz, 1H), 7.69 (d, J=8.2 Hz, 2H), 7.66-7.61 (m, 1H), 7.30 (d, 8.2 Hz, 2H), 7.26 (t, J=7.6 Hz, 1H), 7.21 (d, J=8.5 Hz, 1H), 6.65-6.60 (m, 2H), 6.45 (dd, J=8.0 Hz, 1.9 Hz, 1H), 5.39 (s, 2H), 4.13 (t, J=7.7 Hz, 2H), 2.74 (t, J=7.7 Hz, 2H); ESIMS(−), m/z 446.1 [M−H]$^-$. HPLC 99%.

Example 112: Preparation of 4-((2,4-dioxo-3-(3-(trifluoromethyl)phenethyl)-3,4-dihydroquinazolin-1(2H)-yl)methyl)-N-hydroxycyclohexanecarboxamide (Compound 112)

$R_f$=0.31 (MeOH/CH$_2$Cl$_2$=1/9); $^1$H NMR (400 MHz, DMSO-d$_6$) δ 10.36 (s, 1H), 8.64 (s, 1H), 8.03 (dd, J=7.8 Hz, 1.4 Hz, 1H), 7.77-7.71 (m, 1H), 7.54-7.45 (m, 5H), 7.27 (t, J=7.5 Hz, 1H), 4.21 (t, J=7.2 Hz, 2H), 3.93 (d, J=6.4 Hz, 2H), 3.01 (t, J=7.1 Hz, 2H), 1.91 (t, J=11.9 Hz, 1H), 1.71-1.55 (m, 5H), 1.32-1.20 (m, 2H), 1.08-0.95 (m, 2H); ESIMS(+), m/z 490.3 [M+H]$^+$. HPLC 96%

Example 113: Preparation of 4-((3-(2-chlorophenyl)-2,4-dioxo-3,4-dihydroquinazolin-1(2H)-yl)methyl)-N-hydroxybenzamide (Compound 113)

$R_f$=0.38 (MeOH/CH$_2$Cl$_2$=1/9); $^1$H NMR (400 MHz, DMSO-d$_6$) δ 11.15 (br s, 1H), 9.08 (br s, 1H), 8.10 (d, J=7.7 Hz, 1H), 7.76-7.69 (m, 3H), 7.69-7.63 (m, 2H), 7.54-7.49 (m, 2H), 7.43-7.29 (m, 4H), 5.52-5.37 (m, 2H); ESIMS(+), m/z 422.1 [M+H]$^+$. HPLC 95%.

Example 114: Preparation of 4-((3-(3-fluorophenyl)-2,4-dioxo-3,4-dihyd quinazolin-1(2H)-yl)methyl)-N-hydroxybenzamide (Compound 114)

$R_f$=0.54 (MeOH/CH$_2$Cl$_2$=1/9); $^1$H NMR (400 MHz, DMSO-d$_6$) δ 11.23 (br s, 1H), 9.10 (br s, 1H), 8.08 (d, J=7.3 Hz, 1H), 7.76-7.63 (m, 3H), 7.58-7.51 (m, 1H), 7.49-7.37 (m, 3H), 7.34-7.25 (m, 4H), 5.40 (s, 2H); ESIMS(+), m/z 406.1 [M+H]$^+$. HPLC 94%.

Example 115: Preparation of N-acetoxy-4-((3-(2-fluorophenyl)-2,4-dioxo-3,4-dihydroquinazolin-1(2H)-yl)methyl)benzamide (Compound 115)

$R_f$=0.47 (MeOH/CH$_2$Cl$_2$=1/9); $^1$H NMR (400 MHz, DMSO-d$_6$) δ 12.30 (s, 1H), 8.11 (dd, J=8.0 Hz, 1.4 Hz, 1H), 7.79 (d, J=8.3 Hz, 2H), 7.75-7.70 (m, 1H), 7.65-7.59 (m, 1H), 7.56-7.48 (m, 3H), 7.45-7.39 (m, 1H), 7.38-7.31 (m, 3H), 5.57-5.40 (m, 2H), 2.21 (s, 3H); ESIMS(−), m/z 446.0 [M−H]$^-$. HPLC 97%.

Example 116: Preparation of 1-((4-((2,4-dioxo-3-phenethyl-4-dihydroquinazolin-1(2H)-yl)methyl)benzamido)oxy)-3-methyl-1-oxobutan-2-aminium Trifluoroacetate (Compound 116)

$R_f$=0.26 (MeOH/DCM=1/9); $^1$H NMR (400 MHz, DMSO-d$_6$) δ 12.79 (br s, 1H), 8.59 (br s, 3H), 8.07 (dd, J=8.0 Hz, 1.6 Hz, 1H), 7.77 (d, J=8.4 Hz, 2H), 7.63 (ddd, J=8.0 Hz, 7.6 Hz, 1.6 Hz, 1H), 7.37-7.20 (m, 9H), 5.42 (s, 2H), 4.30 (br d, J=3.6 Hz, 1H) 4.23 (dcl, 1==8.0 Hz, 6.8 Hz, 2H), 2.95 (dd, J=7.6 Hz, 7.6 Hz, 2H), 2.25-2.30 (m, 1H), 1.10 (d, J=6.8 Hz, 3H), 1.06 (d, J=6.8 Hz, 3H).

Example 117: Preparation of 4-((3-cyclopropyl-2,4-dioxo-3,4-dihydroquinazolin-1(2H)-yl)methyl)-N-hydroxybenzamide (Compound 117)

$R_f$=0.36 (MeOH/CH$_2$Cl$_2$=1/9); $^1$H NMR (400 MHz, DMSO-d$_6$) δ 7.99 (dd, J=8.0 Hz, 1.6 Hz, 1H), 7.64 (d, J=8.0 Hz, 2H), 7.58-7.54 (m, 1H), 7.32 (d, J=7.6 Hz, 2H), 7.20-7.12 (m, 2H), 5.33 (s, 2H), 2.74-2.70 (m, 1H), 1.03-0.98 (m, 2H), 0.76-032 (m, 2H); ESIMS(+), m/z=352 [M+H]$^+$; HPLC 98%

Example 118: Preparation of 4-((3-(cyclopropylmethyl)-2,4-dioxo-3,4-dihydroquinazolin-1(2H)-yl)methyl)-N-hydroxybenzamide (Compound 118)

$R_f$=0.45 (MeOH/CH$_2$Cl$_2$=1/9); $^1$H NMR (400 MHz, DMSO-d$_6$) δ 8.04 (dd, J=8.0 Hz, 1.2 Hz, 1H), 7.67-7.59 (m, 3H), 7.32-7.20 (m, 4H), 5.38 (s, 2H), 3.86 (d, J=6.8 Hz, 2H), 1.22-1.17 (m, 1H), 0.42-0.34 (m, 4H); ESIMS(+), m/z 366 [M+H]$^+$; HPLC 98%.

Example 119: Preparation of 4-((2,4-dioxo-3-(4-(2-(piperidin-1-yl)ethoxy)phenethyl)-3,4-dihydroquinazolin-1(2H)-yl)methyl)-N-hydroxybenzamide (Compound 119)

$R_f$=0.20 (MeOH/CH$_2$Cl$_2$=1/9); $^1$H NMR (400 MHz, DMSO-d$_6$) δ 8.06 (d, J 7.6 Hz, 1H), 7.68-7.61 (m, 3H), 7.28-7.20 (m, 4H), 7.12 (d, J=8.4 Hz, 2H), 6.84 (d, J=8.4 Hz, 2H), 5.38 (br s, 2H), 4.17 (dd, J=8.0 Hz, 7.2 Hz, 2H), 3.99 (dd, J=6.0 Hz, 6.0 Hz, 2H), 2.86 (dd, J=7.6 Hz, 7.6 Hz, 2H), 2.62 (dd, J=6.0 Hz, 5.6 Hz, 2H), 2.40 (br s, 4H), 1.49-1.44 (m, 4H), 1.35 (br d, J=5.2 Hz, 2H); ESIMS(+), m/z=543 [M+H]$^+$; HPLC 96%.

Example 120: Preparation of N-hydroxy-4-((6-(2-methoxyethoxy)-2,4-dioxo-3-phenethyl-3,4-dihydroquinazolin-1(2H)methyl)benzamide (Compound 120)

$R_f$=0.34 (MeOH/CH$_2$Cl$_2$=1/9); $^1$H NMR (400 MHz, DMSO-d$_6$) δ 11.10 (br s, 1H), 9.03 (br s, 1H), 7.67 (d, J=8.0 Hz, 2H), 7.50 (d, J=2.8 Hz, 1H), 7.31-7.13 (m, 9H), 5.35 (br s, 2H), 4.22 (dd, J=8.4 Hz, 6.4 Hz, 2H), 4.12 (br d, J=3.2 Hz, 2H), 3.64 (br d, J=4.0 Hz, 2H), 3.27 (s, 3H), 2.94 (dd, 7.6 Hz, 7.2 Hz, 2H).

Example 121: Preparation of 6-((2,4-dioxo-3-(3-(trifluoromethyl)phenethyl)-3,4-dihydroquinazolin-1(2H)-yl)methyl)-N-hydroxynicotinamide (Compound 121)

$R_f$=0.37 (MeOH/CH$_2$Cl$_2$=1/9); $^1$H NMR (400 MHz, DMSO-d$_6$) d 11.3 (br s, 1H), 9.19 (br s, 1H), 8.75 (d, J=1.2 Hz, 1H), 8.01 (d, J=8.0 Hz, 2H), 7.62-7.47 (m, 5H), 7.33 (d, J=8.0 Hz, 1H), 7.22 (d, J=8.0 Hz, 7.6 Hz, 2H), 5.44 (s, 2H), 4.20 (dd, J=8.0 Hz, 6.8 Hz, 2H), 3.00 (dd, J=7.6 Hz, 6.8 Hz, 2H).

Example 122: Preparation of 4-((3-(2-fluorocyclopentyl)-2,4-dioxo-3,4-dihydroquinazolin-1(2H)-yl)methyl)-N-hydroxybenzamide (Compound 122)

$R_f$=0.42 (MeOH/CH$_2$Cl$_2$=1/9); $^1$H NMR (400 MHz, DMSO-d$_6$) δ 11.16 (br s, 1H), 9.02 (br s, 1H), 8.03 (d, J=7.6

Hz, 1H), 7.67-7.59 (m, 3H), 7.35 (d, J=8.0 Hz, 2H), 7.24-7.16 (m, 2H), 5.56-5.32 (m, 4H), 2.27-2.15 (m, 1H), 1.98-1.72 (m, 5H); ESIMS(–), m/z=396 [M–H]−.

Example 123: Preparation of N-hydroxy-4-((3-(2-morpholinoethyl)-2,4-dioxo-3,4-dihydroquinazolin-1(2H)-yl)methyl)benzamide (Compound 123)

$R_f$ 0.32 (MeOH/CH$_2$Cl$_2$=1/9); $^1$H NMR (400 MHz, DMSO-d$_6$) δ 8.06 (dd, J=7.6 Hz, 1.2 Hz, 1H), 7.69 (d, J=8.4 Hz, 2H), 7.65-7.61 (m, 1H), 7.35 (d, J=8.0 Hz, 2H), 7.27-7.22 (m, 2H), 5.40 (s, 2H), 4.13 (dd, J=6.4 Hz, 6.4 Hz, 2H), 3.52-3.49 (m, 4H), 2.56 (dd, J=6.4 Hz, 6.4 Hz, 2H), 2.43 (br s, 4H); ESIMS(+), m/z=425 [M+H]$^+$.

Example 124: Preparation of 4-((3-(2,4-difluorophenyl)-2,4-dioxo-3,4-dihydroquinazolin-1(2H)-yl)methyl)-N-hydroxybenzamide (Compound 124)

$R_f$=0.40 (MeOH/CH$_2$Cl$_2$=1/9); $^1$H NMR (400 MHz, DMSO-d$_6$) d 11.18 (br s, 1H), 9.04 (br s, 1H), 8.07 (d, J=7.6 Hz, 1H), 7.77-7.64 (m, 4H), 7.49-7.21 (m, 6H), 5.46 (d, J=17.2 Hz, 1H), 5.35 (d, J=16.8 Hz, 1H); ESIMS(+), m/z=446 [M+Na]$^+$.

Example 125: Preparation of 4-((2,4-dioxo-3-(pyridin-2-yl)-3,4-dihydroquinazolin-1(2H)-yl)methyl)-N-hydroxybenzamide (Compound 125)

$R_f$=0.28 (MeOH/CH$_2$Cl$_2$=1/9): $^1$H NMR (400 MHz, DMSO-d$_6$) d 11.18 (br s, 1H), 14.33 (br s, 1H), 9.04 (br s, 1H), 8.06-7.98 (m, 2H), 7.69-7.28 (m, 9H), 5.39 (br s, 2H).

Example 126: Preparation of 4-((2,4-dioxo-3-(2-(trifluoromethyl)phenyl)-3,4-dihydroquinazolin-1(2H)-yl)methyl)-N-hydroxybenzamide (Compound 126)

$R_f$=0.35 (MeOH/CH$_2$Cl$_2$=1/9); $^1$H NMR (400 MHz, DMSO-d$_6$) d 8.06 (dd, J=7.6 Hz, 1.2 Hz, 1H), 7.89-7.82 (m, 2H), 7.75-7.68 (m, 5H), 7.37-7.27 (m, 4H), 5.47 (d, J=16.4 Hz, 1H), 5.34 (d, J=16.8 Hz, 1H); ESIMS(+), m/z=456 [M+H]$^+$; HPLC 94%.

Example 127: Preparation of 4-((3-(2-(tert-butyl)phenyl)-2,4-dioxo-3,4-dihydroquinazolin-1(2H)methyl)-N-hydroxybenzamide (Compound 127)

$R_f$=0.37 (MeOH/CH$_2$Cl$_2$=1/9): $^1$H NMR (400 MHz, DMSO-d$_6$) d 11.17 (br s, 1H), 9.03 (br s, 1H), 8.07 (d, J=7.2 Hz, 1H), 7.70-7.66 (m, 3H), 7.57 (d, J=8.0 Hz, 1H), 7.40-7.24 (m, 7H), 5.46 (d, J=16.8 Hz, 1H), 5.37 (d, J=17.2 Hz, 1H), 1.18 (s, 9H); ESIMS(+), m/z=444 [M+H]$^+$; HPLC 98%.

Example 128: Preparation of N-hydroxy-4-((3-(4-(morpholinomethyl)phenyl)-2,4-dioxo-3,4-dihydroquinazolin-1(2H)-yl)methyl)benzamide (Compound 128)

$R_f$=0.28 (MeOH/CH$_2$Cl$_2$=1/9); $^1$H NMR (400 MHz, DMSO-d$_6$) d 11.19 (br s, 1H), 9.033 (br s, 1H), 8.07 (br s, 1H), 7.79-7.61 (m, 3H), 7.43-7.27 (m, 8H), 5.40 (br s, 2H), 3.59 (br s, 8H), 2.42 (br s, 2H); ESIMS(+), m/z=487 [M+H]$^+$; HPLC 97%.

Example 129: Preparation of 4-((2,4-dioxo-3-(2-(3-(trifluoromethyl)phenoxy)ethyl)-3,4-dihydroquinazolin-1(2H)-yl)methyl)-N-hydroxybenzamide (Compound 129)

$R_f$=0.34 (MeOH/CH$_2$Cl$_2$=1/9); $^1$H NMR (400 MHz, DMSO-d$_6$) d 11.15 (br s, 1H), 9.01 (br s, 1H), 8.05 (d, J=7.6 Hz, 1H), 7.65-7.60 (m, 3H), 7.49-7.45 (m, 1H), 7.38-7.32 (m, 2H), 7.26-7.18 (m, 5H), 5.38 (br s, 2H), 4.38-4.31 (m, 4H): ESIMS(+), m/z=500 [M+H]$^+$; HPLC 99%.

Example 130: Preparation of 4-((2,4-dioxo-3-(2-phenylpropyl)-3,4-dihydroquinazolin-1(2H)-yl)methyl)-N-hydroxybenzamide (Compound 130)

$R_f$=0.22 (MeOH/CH$_2$Cl$_2$=5/95); $^1$H NMR (400 MHz, DMSO-d$_6$) d 11.15 (br s, 1H), 9.00 (br s, 1H), 8.00 (dd, J=8.0 Hz, 1.2 Hz, 1H), 7.63 (d, J=8.4 Hz, 2H), 7.60-7.55 (m, J=7.25-7.11 (m, 9H), 5.36 (d, J=17.2 Hz, 1H), 5.24 (d, J=16.8 Hz, 1H), 4.20 (dd, J=8.0, 8.0 Hz, 1H), 4.09 (dd, J=7.6 Hz, 7.6 Hz, 1H), 3.35-3.29 (m, 1H), 1.22 (d, J=6.8 Hz, 1H); ESIMS(+), m/z=430 [M+H]$^+$; HPLC 98%.

Example 131: Preparation N-hydroxy-4-((3-(4-(morpholinomethyl)phenethyl)-4-dioxo-3,4-dihydroquinazolin-1(2H)-yl)methyl)benzamide (Compound 131)

$R_f$=0.32 (MeOH/CH$_2$Cl$_2$=1/9); $^1$H NMR (400 MHz, DMSO-d$_6$) δ 11.1 (s, 1H), 10.12 (br s, 1H), 9.02 (br s, 1H), 8.01 (dd, J=8.0 Hz, 1.6 Hz, 1H), 7.67-7.59 (m, 3H), 7.38 (d, J=8.0 Hz, 2H), 7.33-7.19 (m, 6H), 5.37 (s, 2H), 4.25-4.17 (m, 4H), 3.86 (br s, 2H), 3.59 (br s, 2H), 3.05 (br s, 4H), 2.94 (dd, J=7.6, 7.2 Hz, 2H); ESIMS(+), m/z=515 [M+H]$^+$; HPLC 96%.

Example 132: Preparation of 4-((2,4-dioxo-3-(4-(piperidin-1-ylmethyl)phenyl)-3,4-dihydroquinazolin-1(2H)-yl)methyl)-N-hydroxybenzamide (Compound 132)

$R_f$=0.14 (MeOH/CH$_2$Cl$_2$=1/9); $^1$H NMR (400 MHz, DMSO-d$_6$) d 11.14 (br s, 1H), 9.00 (br s, 1H), 8.01 (dd, J=8.0 Hz, 1.6 Hz, 1H), 7.65 (d, J=8.4 Hz, 2H), 7.66-7.58 (m, 1H), 7.27 (d, J=8.4 Hz, 2H), 7.25-7.11 (m, 6H), 5.35 (br s, 2H), 4.17 (dd, J=8.0 Hz, 7.6 Hz, 2H), 3.12 (s, 2H), 2.88 (dd, J=8.0 Hz, 7.6 Hz, 2H), 2.24 (br s, 4H), 1.42-1.40 (m, 4H), 1.32 (br s, 2H); ESIMS(+), m/z=513 [M+H]$^+$; HPLC 100%.

Example 133: Preparation of N-hydroxy-4-((3-(4-nitrophenethyl)-2,4-dioxo-3,4-dihydroquinazolin-1(2H)-yl)methyl)benzamide (Compound 133)

$R_f$=0.38 (MeOH/CH$_2$Cl$_2$=1:10). $^1$H NMR (400 MHz, DMSO-d$_6$) δ 11.2 (s, 1H) 9.05 (s, 1H), 8.17 (d, J=8.7 Hz, 2H), 8.07 (dd, J=7.9 Hz, 1.6 Hz, 1H), 7.36-7.69 (m, 3H), 7.55 (d, J=8.7 Hz, 2H), 7.22-731 (m, 4H), 5.38 (s, 2H), 4.29 (t, J=6.8 Hz, 2H), 3.11 (t, J=7.3 Hz, 2H); ESIMS(+) m/z 483 [M+Na]$^+$; HPLC 99%.

Example 134: Preparation of 4-((3-(4-aminophenethyl)-2,4-dioxo-3,4-dihydroquinolin-1(2H)-yl)methyl)-N-hydroxybenzamide (Compound 134)

$R_f$=0.2 (MeOH/CH$_2$Cl$_3$=1:10); $^1$H NMR (400 MHz, DMSO-d$_6$) δ 11.17 (s, 1H), 9.04 (s, 1H), 8.08 (dd, J=7.8 Hz, 1.5 Hz, 1H), 7.62-7.71 (m, 3H), 7.21-7.32 (m, 4H), 6.89 (d,

J=8.3 Hz, 2H), 6.52 (d, J=8.3 Hz, 2H), 5.40 (s, 2H), 5.11 (s, 2H), 4.14 (t, J=7.6 Hz, 2H), 2.76 (t, J=7.8 Hz, 2H); m/z 431 [M+H]$^+$; HPLC 94%.

Example 135: Preparation of 4-(2-(1-(4-(hydroxycarbamoyl)benzyl)-2,4-dioxo-1,2-dihydroquinazolin-3(4H)-yl)ethyl)benzoic Acid (Compound 135)

$R_f$=0.01 (MeOH/CH$_2$Cl$_2$=1:10); 1H NMR (400 MHz, DMSO-d$_6$) δ 12.67 (s, 1H) 11.16 (s, 1H), 9.02 (s, 1H), 8.07 (d, J 7.5 Hz, 1H), 7.88 (d, J=8.0 Hz, 2H), 7.70-7.65 (m, 3H), 7.22-7.39 (m, 6H), 5.40 (s, 2H), 4.26 (t, J=7.2 Hz, 2H), 3.03 (t, J=7.6 Hz, 2H); ESIMS(+) m/z 460 [M+H]+; HPLC 95%.

Example 136 Preparation of 4-((3-(4-chloro-2,6-dimethylphenyl)-2,4-dioxo-3,4-dihydroquinazolin-1(2H)-yl)methyl)-N-hydroxybenzamide (Compound 136)

$R_f$=0.5 (MeOH/CH$_2$Cl$_2$=1:10); $^1$H NMR (400 MHz, DMSO-d$_6$) δ 11.17 (s, 1H), 9.03 (s, 1H), 8.13 (d, J=7.8 Hz, 1H), 7.72-7.78 (m, 3H), 7.34-7.43 (m, 6H), 5.47 (s, 2H), 2.06 (s, 6H); ESIMS(±) m/z 450 [M+H]$^+$; HPLC 97%.

Example 137: Preparation of 4-((3-(4-bromo-2,6-dimethylphenyl)-2,4-dioxo-3,4-dihydroquinazolin-1(2H)-yl)methyl)-N-hydroxybenzamide (Compound 137)

$R_f$=0.37 (MeOH/DCM=1/10); $^1$H NMR (400 MHz, DMSO-d$_6$) δ 11.17 (s, 1H), 9.03 (s, 1H), 8.13 (dd, J=7.9 Hz, 1.3 Hz, 1H), 7.72-7.78 (m, 3H), 7.47 (s, 2H), 7.33-7.43 (m, 4H), 5.47 (s, 2H), 2.06 (s, 6H); ESIMS(−) m/z 494 [M+H]$^+$; HPLC 100%.

Example 138: Preparation of 4-((3-(2-(1H-imidazol-1-yl)ethyl)-2,4-dioxo-3,4-dihydroquinazolin-1(2H)-yl)methyl)-N-hydroxybenzamide (Compound 138)

$R_f$=0.23 (MeOH/CH$_2$Cl$_2$=1/9); $^1$H NMR (400 MHz, DMSO-d$_6$) δ 11.20 (s, 1H), 9.06 (br s, 1H), 8.04 (dd, J=7.8, 1.4 Hz, 1H), 7.69 (d, J=8.2 Hz, 2H), 7.66-7.61 (m, 1H), 7.59 (s, 1H), 7.30-7.19 (m, 4H), 7.13 (s, 1H), 6.85 (s, 1H), 5.35 (s, 2H), 4.37-4.29 (m, 4H); ESIMS(+) m/z 406 [M+H]$^+$. HPLC 97%.

Example 139: Preparation of 4-((2,4-dioxo-3-phenethyl-3,4-dihydroquinazolin-1(2H)-yl)methyl)-3-fluoro-N-hydroxybenzamide (Compound 139)

$R_f$=0.47 (MeOH/CH$_2$Cl$_2$=1/9); $^1$H NMR (400 MHz, DMSO-d$_6$) δ 11.31 (s, 1H), 9.16 (s, 1H), 8.09 (d, J=0.8 Hz, 1H), 7.67 (t, J=7.8 Hz, 1H), 7.59 (d, J=11.1 Hz, 1H), 7.47 (d, J=8.1 Hz, 1H), 7.32-7.26 (m, 3H), 7.24-7.18 (m, 4H), 7.03 (t, J=7.8 Hz, 1H), 5.39 (s, 2H), 4.20 (t, J=7.7 Hz, 2H), 2.92 (t, J=7.7 Hz, 2H); ESIMS(+) m/z 456 [M+H]$^+$. HPLC 99%.

Example 140: Preparation of N-hydroxy-4-((7-methoxy-2,4-dioxo-3-(3-(trifluoromethyl)phenethyl)-3,4-dihydroquinazolin-1(2H)-yl)methyl)-2-methylbenzamide (Compound 140)

$R_f$=0.29 (MeOH/CH$_2$Cl$_2$=1/9); $^1$H NMR (400 MHz, DMSO-d$_6$) δ 10.79 (s, 1H), 9.05 (s, 1H), 7.96 (d, J=8.8 Hz, 1H), 7.59-7.49 (m, 4H), 7.25-7.17 (m, 2H), 7.00 (d, J=7.7 Hz, 1H), 6.86 (dd, J=8.8, 2.1 Hz, 1H), 6.65 (d, J=2.0 Hz, 1H), 5.32 (s, 2H), 4.24 (t, J=7.3 Hz, 2H), 3.76 (s, 3H), 3.05 (t, J=7.3 Hz, 2H), 2.28 (s, 3H); ESIMS(+) m/z 528 [M+H]$^+$; HPLC 100%.

Example 141: Preparation of 4-((2,4-dioxo-3-(4-phenylbutyl)-3,4-dihydroquinazolin-1(2H)-yl)methyl)-N-hydroxybenzamide (Compound 141)

$R_f$=0.61 (MeOH/CH$_2$Cl$_2$=5:95); $^1$H NMR (400 MHz, DMSO-d$_6$) δ 11.19 (s, 1H), 9.06 (s 1H), 8.05 (dd, J==7.8, 1.4 Hz, 1H), 7.57-7.75 (m, 3H), 7.07-7.39 (m, 9H), 5.39 (s, 2H), 4.01 (t, J=6.7 Hz, 2H), 2.59 (t, J=7.2 Hz, 2H), 1.49-1.72 (m, 4H); ESIMS (+) m/z 444 [M+H]$^+$; HPLC 98.6%.

Example 142: Preparation of 4-((3-allyl-2,4-dioxo-3,4-dihydroquinazolin-1(2H)-yl)methyl)-N-hydroxybenzamide (Compound 142)

$R_f$=0.45 (MeOH/CH$_2$Cl$_2$=5:95); $^1$H NMR (400 MHz, DMSO-d$_6$) δ 11.19 (s, 1H), 9.07 (s, 1H), 8.07 (dd, J=7.9, 1.5 Hz, 1H), 7.59-7.75 (m, 3H), 7.35 (d, J=8.2 Hz, 2H), 7.20-7.32 (m, 2H), 5.84-6.0 (m, 1H), 5.4 (s, 2H), 5.06-5.22 (m, 2H), 4.6 (d, J=5.2 Hz, 2H); ESIMS (+) m/z 444 [M+H]$^+$. HPLC 99%.

Example 143: Preparation of 4-((3-(2-(cyclohex-1-en-1-yl)ethyl)-2,4-dioxo-3,4-dihydroquinazolin-1(2H)-yl)methyl)-N-hydroxybenzamide (Compound 143)

$R_f$=0.49 (MeOH/CH$_2$Cl$_2$=1:9); $^1$H NMR (400 MHz, DMSO-d$_6$) δ 11.2 (s, 1H), 9.07 (s, 1H), 8.04 (dd, J=7.9, 1.3 Hz, 1H), 7.55-7.73 (m, 3H), 7.14-7.38 (m, 4H), 5.37 (s, 2H), 5.24 (s, 1H), 4.05 (t, J=7.0 Hz, 2H), 3.13 (d, J=5.2 Hz, 1H), 2.21 (t, J=6.7 Hz, 2H), 1.97 (s, 2H), 1.8 (s, 2H), 1.33-1.56 (m, 4H); ESIMS (+) m/z 420 [M+H]$^+$. HPLC 99%.

Example 144: Preparation of (E)-4-((3-cinnamyl-2,4-dioxo-3,4-dihydroquinazolin-1(2H)-yl)methyl)-N-hydroxybenzamide (Compound 144)

$R_f$=0.71 (MeOH/CH$_2$Cl$_2$=1:9); $^1$H NMR (400 MHz, DMSO-d$_6$) δ 11.18 (s, 1H), 9.04 (s, 1H), 8.09 (dd, J=7.8, 1.5 Hz, 1H), 7.59-7.74 (m, 3H), 7.34-7.49 (m, 4H), 7.14-7.34 (m, 5H), 6.52-6.65 (m, 1H), 6.32-6.46 (m, 1H), 5.43 (s, 2H), 4.78 (d, J=5.4 Hz, 2H); ESIMS (+) m/z 428 [M+H]$^+$. HPLC 95%.

Example 145: Preparation of 4-((3-(2-(1,2-dihydroxycyclohexyl)ethyl)-2,4-dioxo-3,4-dihydroquinazolin-1(2H)-yl)methyl)-N-hydroxybenzamide (Compound 145)

$R_f$=0.09 (MeOH/CH$_2$Cl$_2$=5:95); $^1$H NMR (400 MHz, DMSO-d$_6$) δ 11.16 (s, 1H), 9.01 (s, 1H), 8.06 (dd, J=7.8, 1.3 Hz, 1H), 7.56-7.77 (m, 3H), 7.35 (d, J=8.2 Hz, 2H), 7.17-7.31 (m, 2H), 5.4 (s, 2H), 4.0-4.24 (m, 2H), 3.74 (s, 1H), 3.23 (q, J=5.6 Hz, 1H), 1.88-2.0 (m, 1H), 1.6-1.84 (m, 2H), 138-1.6 (m, 4H), 1.08-71.38 (m, 3H); ESIMS (+) m/z 454 [M+H]$^+$. HPLC 99%.

Example 146: Preparation of 4-((8-chloro-2,4-dioxo-3-phenethyl-3,4-dihydroquinazolin-1(2H)-yl)methyl)-N-hydroxybenzamide (Compound 146)

$R_f$=0.44 (MeOH/CH$_2$Cl$_2$=1:9); $^1$H NMR (400 MHz, DMSO-d$_6$) δ 11.2 (s, 1H), 9.05 (s, 1H), 8.1 (dd, J=7.8, 1.5

Hz, 1H), 7.61-7.81 (m, 3H), 7.11-7.37 (m, 8H), 5.5 (s, 2H), 4.13 (t, J=7.6 Hz, 2H), 2.89 (t, J=7.6 Hz, 2H); ESIMS (+) m/z 450 [M+H]$^+$. HPLC 99%.

Example 147: Preparation of 4-((3-(2-fluoro-2-phenylethyl)-2,4-dioxo-3,4-dihydroquinazolin-1(2H)-yl)methyl)-N-hydroxybenzamide (Compound 147)

$R_f$=0.56 (MeOH/CH$_2$Cl$_2$=1:9); $^1$H NMR (400 MHz, DMSO-d$_6$) δ 11.18 (s, 1H), 9.05 (s, 1H), 8.09 (dd, J=7.8, 1.5 Hz, 1H), 7.57-7.79 (m, 3H), 7.20-7.55 (m, 9H), 5.87 (ddd, J=54.5, 8.7, 3.5 Hz, 1H), 5.41 (s, 2H), 4.71 (ddd, J=17.1, 12.4, 8.9 Hz, 1H), 4.21 4.71 (ddd, J=31.8, 13.9, 3.5 Hz, 1H); ESIMS (+) m/z [M+H]$^+$ 434. HPLC 95%.

Example 148. Enzymatic Assay

The IC$_{50}$ values for aforementioned compounds against HDACs were determined. HDAC 1 to 11 can be assayed by using acetylated AMC-labeled peptide substrate. The Substrate 1, a fluorogenic peptide from p53 residues 379-382 (RHKKAc) is used for all MAC 1 to 11 but HDAC8, which has a substrate II (RHKAcKAc), a fluorogenic diacyl peptide based on residues 179-382 of p53. Compounds were tested in 10-dose 1050 mode in duplicate with 3-fold serial dilution starting at 10 µM.

Human HDAC1 GenBank Accession No. NM_004964): Full length with C-terminal GST tag, MW=79.9 kDa, Human HDAC2 (GenBank Accession No. Q92769): Full length with C-terminal His tag, MW=60 kDa. Human HDAC3/NcoR2 (GenBank Accession No. NM_13038883 for HDAC3, GenBank Accession No. NM_006312 for NcoR2): Complex of human HDAC3, full length with C-terminal His tag, MW=49.7 kDa, and human NCOR2, N-terminal GST tag, MW=39 kDa. Human HDAC6 (GenBank Accession No. BC069243): Full length with N-terminal GST tag, MW=159 kDa. Human HDAC8 (GenBank Accession No. NM018486): Full length, MW=42 kDa, expressed in an *E. coli* expression system. Human HDAC10 (GenBank Accession No. NM_032019): Amino acids 1-631 with N-terminal GST tag, MW=96 kDa. Human HDAC11 (GenBank Accession No. NM_BC009676) with N-terminal GST tag, MW=66 kDa, expressed in baculovirus expression system, Control Inhibitor for HDAC is Trichostatin A (TSA); Biomol Cat #GR 309.

Human HDAC1, Human HDAC2, Human HDAC3/NcoR2, Human HDAC6, Human HDAC10, and Human HDAC11 were all expressed by baculovirus expression system in Sf9 cells.

Reaction Condition: Assay Buffer: 50 mM Tris-HCl, pH 8.0, 137 mM NaCl, 2.7 mM KCl, 1 mM MgCl$_2$, Before use, add 1 mg/mL BSA. HDAC1: 75 nM; HDAC2: 5 mM; HDAC3: 2.3 nM; HDAC6: 13 nM; HDAC8: 119 nM; HDAC10: 781 nM; HDAC11: 781 nM. 50 µM HDAC substrate. 1% DMSO final. Incubation for 2 hours at 30° C.

HDAC Enzymatic Assay. These compounds had inhibitory effects on human historic deacetylases (HDAC) 1, 2, 3, 6, 8, 10 and 11.

Because these compound showed selective inhibitions on HDAC6, the HDAC6-selective inhibitors may be used for treating autoimmunity, cancer, and many neurodegenerative diseases. (S. Minucci et all, *Nat. Rev, Cancer.* 2006, 6, 38-51; L. Wang et al., *Nat. Rev. Drug Discov.* 2009, 8, 969-81; J. P. Dompierre et al., *J. Neurosci,* 2007, 27, 3571-83; and A. G. Kazantsev et al., *Nat. Rev. Drug Discov.* 2008, 7, 854-68.)

Materials

All cell lines were purchased from BCRC (Bioresource Collection and Research Center, Taiwan) U87MG (BCRC 60360), HepG2 (BCRC 60025), A549 (BCRC 60074), PANC1 (BCRC 60284), A375 (BCRC 60039), LNCaP (BCRC 60088), 22Rv1 (BCRC 60545), FHs173 we (BCRC 60229) and Vero (BCRC 60013).

Tables 1 and 2 illustrate HDAC inhibition activities of the compounds according to the invention.

TABLE 1

| Cpd No. | HDAC subtypes IC50 (nM) | | | |
|---|---|---|---|---|
| | HDAC1 | HDAC8 | HDAC6 | HDAC11 |
| 1 | 9410 | 95 | 8 | 15400 |
| 2 | 12000 | 731 | 51 | ND |
| 3 | 11990 | 1300 | 13500 | ND |
| 4 | 8275 | 2751 | 28 | 5501 |
| 5 | 11160 | 376 | 4 | 13900 |
| 6 | >10000 | 653 | 4296 | >10000 |
| 7 | >10000 | 235 | 4450 | ND |
| 8 | 9540 | 1640 | 21 | ND |
| 9 | 18860 | ND | 35 | ND |
| 10 | 2720 | 523 | 4 | ND |
| 11 | 15820 | 486 | 24 | 37500 |
| 12 | 11150 | 1068 | 28 | 25050 |
| 13 | 8021 | 1442 | 635 | 7392 |
| 14 | 10810 | 1049 | 23 | 14730 |
| 15 | 10430 | 525 | 11 | 34370 |
| Trichostatin A | 7 | 175 | 1 | 12 |

All compounds were tested in 10-dose IC$_{50}$ mode with a 3-fold serial dilution.
ND stands for Not Determined

TABLE 2

| compound number | HDAC subtypes IC50 (nM) | | | |
|---|---|---|---|---|
| | HDAC1 | HDAC8 | HDAC6 | HDAC11 |
| 17 | 13410 | 1155 | 57 | 16740 |
| 18 | 8830 | 400 | 6 | 16700 |
| 21 | 6655 | 169 | 15 | 5686 |
| 22 | 10870 | 2521 | 170 | 52050 |
| 24 | 10700 | 287 | 11 | 10020 |
| 25 | >30000 | 1191 | 1194 | 128900 |
| 26 | 13170 | 428 | 10 | 10660 |
| 27 | 14500 | 3060 | 168 | 10500 |
| 28 | ND | ND | ND | ND |
| 29 | 4380 | 1420 | 25 | 3800 |
| 30 | 9790 | 979 | 14 | 22750 |
| Trichostatin A | 7 | 175 | 1 | 12 |

All compounds were tested in 10-dose IC$_{50}$ mode with a 3-fold serial dilution.

Example 149. Cell Proliferation Assay—MTT

Cells were seeded in 96-well plates at a density of 5×10$^3$ cells per well and allowed to attach for 24 h before compound treatment. A series dilutions of the testing compounds, SAHA, and Tubastatin A were added to the culture medium so that the final concentration of DMSO) was 0.1% in all reactions. At end of the treatment period 72 h, 20 µl (5 mg/mL) 3-(4,5-dimethylthiazol-2-yl)-2,5-diphenyl-tetrazolium bromide (MTT) reagent was added each well. After 4 h incubation at 37° C., the supernatant was aspirated and the formazan crystals were dissolved in 100 µl of DMSO at 37° C. for 10 min with gentle agitation. The absorbance was measured at 570 nm using the Molecular Devices Microplate Reader. Results were presented as mean±standard error mean (SEM) from at least three independent experiments. IC$_{50}$ values were calculated from the relative viability values and concentrations by regression analysis. Tables 3 and 4 show the cytotoxicity of HDAC inhibitors against cancer cell lines and normal human cell line.

TABLE 3

Cytotoxicity IC50 (μM), MTT assay, 72 hr treated

| Cpd. No. | Glioblastoma U87MG | Prostate LNCap | Lung A549 | Pancreas PANC1 | Liver HepG2 | Human normal FHsWe |
|---|---|---|---|---|---|---|
| 2 | >10 | >10 | >10 | >10 | >10 | >200 |
| 3 | >10 | >10 | >10 | >10 | >10 | >200 |
| 4 | 4.28 ± 0.67 | 2.97 ± 0.22 | 8.04 ± 0.28 | 6.54 ± 0.11 | 6.12 ± 0.33 | 147.12 ± 0.51 |
| 5 | 1.56 ± 0.14 | 0.44 ± 0.07 | 3.75 ± 0.39 | 4.15 ± 0.27 | 1.93 ± 0.25 | 83.21 ± 0.62 |
| 6 | 3.75 ± 0.13 | 3.40 ± 0.21 | 4.03 ± 0.12 | 5.12 ± 0.32 | 3.41 ± 0.34 | 69.23 ± 0.27 |
| 8 | 2.10 ± 0.06 | 1.07 ± 0.14 | 2.28 ± 0.27 | 3.52 ± 0.09 | 2.74 ± 0.29 | 75.79 ± 0.12 |
| 9 | 2.26 ± 0.13 | 1.01 ± 0.11 | 2.45 ± 0.51 | 4.05 ± 0.12 | 2.03 ± 0.47 | 70.34 ± 0.12 |
| 10 | 7.63 ± 0.12 | 4.72 ± 0.16 | 8.15 ± 0.17 | 9.04 ± 0.21 | 6.65 ± 0.22 | 85.33 ± 0.34 |
| 11 | 4.08 ± 0.11 | 2.93 ± 0.62 | 4.78 ± 0.11 | 6.13 ± 0.17 | 4.39 ± 0.07 | 89.18 ± 0.62 |
| 12 | 9.12 ± 0.23 | 7.53 ± 0.23 | >10 | >10 | >10 | 159.12 ± 0.44 |
| 13 | 5.87 ± 0.14 | 5.92 ± 0.21 | 7.22 ± 0.29 | 8.29 ± 0.43 | 5.48 ± 0.27 | 131.72 ± 0.25 |
| 14 | 6.31 ± 0.63 | 4.25 ± 0.21 | 6.35 ± 0.11 | >10 | 6.82 ± 0.12 | 83.81 ± 0.19 |
| 15 | 7.08 ± 0.80 | 5.71 ± 0.32 | 5.69 ± 0.21 | >10 | 7.11 ± 0.28 | 55.44 ± 0.09 |
| 16 | 6.28 ± 0.12 | 6.05 ± 0.31 | 7.07 ± 0.42 | 8.73 ± 0.24 | 6.99 ± 1.07 | 163.18 ± 0.27 |
| 17 | 6.13 ± 0.78 | 5.74 ± 0.51 | 8.96 ± 0.17 | 8.47 ± 0.04 | 6.64 ± 0.92 | 100.53 ± 0.37 |
| 19 | 2.64 ± 0.04 | 1.87 ± 0.18 | 2.98 ± 0.12 | 4.29 ± 0.08 | 2.75 ± 0.02 | 32.7 ± 0.03 |
| 20 | 9.67 ± 0.66 | 9.97 ± 0.08 | >10 | >10 | 7.43 ± 0.27 | >200 |
| 21 | 2.93 ± 0.13 | 0.98 ± 0.06 | 3.22 ± 0.31 | 4.72 ± 0.37 | 3.55 ± 0.14 | 63.11 ± 0.17 |
| 22 | 5.68 ± 0.19 | 5.38 ± 0.41 | 7.44 ± 0.12 | 8.73 ± 0.71 | 6.82 ± 0.44 | 135.08 ± 0.39 |
| 23 | 4.12 ± 0.06 | 4.05 ± 0.07 | 4.21 ± 0.03 | 5.12 ± 0.11 | 4.24 ± 0.03 | 92.11 ± 0.69 |
| 24 | 4.18 ± 0.22 | 3.83 ± 0.17 | 4.69 ± 0.17 | >10 | 4.11 ± 0.27 | 60.41 ± 0.22 |
| 25 | 5.23 ± 0.21 | 5.77 ± 0.46 | 6.25 ± 0.33 | 8.13 ± 0.28 | 5.31 ± 0.37 | 105.11 ± 0.25 |
| 26 | 3.77 ± 0.25 | 0.96 ± 0.02 | 4.58 ± 0.21 | 5.03 ± 0.19 | 4.03 ± 0.11 | 84.34 ± 0.73 |
| SAHA | 3.46 ± 0.37 | 4.55 ± 0.21 | 4.63 ± 0.11 | 6.32 ± 0.31 | 3.27 ± 0.83 | 16.75 |
| Tubastatin A | >10 | >10 | >10 | >10 | >10 | 46.54 |

TABLE 4

Cytotoxicity IC50 (μM), MTT assay, 72 hr treated

| Cpd. No | Monkey normal Vero | Leukemia HL60 | Leukemia MV4-11 | Leukemia MOLM13 |
|---|---|---|---|---|
| 2 | >10 | ND | ND | ND |
| 3 | >10 | >10 | >10 | >10 |
| 4 | 156.39 ± 0.42 | 0.67 ± 0.09 | 0.75 ± 0.11 | 0.81 ± 0.09 |
| 5 | 91.38 ± 0.47 | 0.25 ± 0.03 | 0.17 ± 0.05 | 0.16 ± 0.03 |
| 6 | 78.42 ± 0.22 | ND | ND | ND |
| 8 | 85.74 ± 0.17 | 0.44 ± 0.04 | 0.37 ± 0.02 | 0.48 ± 0.08 |
| 9 | 77.51 ± 0.14 | 2.71 ± 0.05 | 2.78 ± 0.03 | 2.82 ± 0.07 |
| 10 | 93.24 ± 0.37 | ND | ND | ND |
| 11 | 97.25 ± 0.31 | ND | ND | ND |
| 12 | 166.37 ± 0.39 | ND | ND | ND |
| 13 | 146.17 ± 0.41 | 0.87 ± 0.12 | 0.83 ± 0.11 | 0.92 ± 0.07 |
| 14 | 116.01 ± 0.23 | 1.37 ± 0.07 | 1.77 ± 0.05 | 1.62 ± 0.09 |
| 15 | 96.92 ± 0.11 | 1.22 ± 0.08 | 1.65 ± 0.03 | 1.47 ± 0.07 |
| 16 | 160.31 ± 0.23 | 2.77 ± 0.04 | 3.04 ± 0.08 | 3.29 ± 0.16 |
| 17 | 123.25 ± 0.33 | 2.37 ± 0.11 | 3.13 ± 0.09 | 356 ± 0.09 |
| 19 | 37.82 ± 0.03 | 1.68 ± 0.09 | 1.87 ± 0.03 | 1.74 ± 0.08 |
| 20 | >200 | ND | ND | ND |
| 21 | 81.51 ± 0.18 | ND | ND | ND |
| 22 | 127.39 ± 0.28 | 1.46 ± 0.08 | 1.64 ± 0.07 | 1.77 ± 0.05 |
| 23 | 95.27 ± 0.58 | 1.25 ± 0.08 | 1.19 ± 0.07 | 2.32 ± 0.07 |
| 24 | 76.31 ± 0.32 | ND | ND | ND |
| 25 | 106.32 ± 0.29 | ND | ND | ND |
| 26 | 93.26 ± 0.25 | 3.12 ± 0.08 | 3.71 ± 0.11 | 4.01 ± 0.06 |
| SAHA | 26.64 | 1.85 ± 0.08 | 1.29 ± 0.13 | 1.43 ± 0.06 |
| Tubastatin A | 39.86 | ND | ND | ND |

Xenografted nude mice model of prostate cancer cell line. Forty-five male nude mice (BALB/cAnN.Cg-Foxn1nu/CrI-Narl, 4-6 weeks old) were used. Mice were subcutaneously injected in the left flank with 1×10⁶ LNCaP human prostatic carcinoma in PBS through a 1 cm long 25 G needle. When LNCaP xenografts had reached an average volume of 150 mm3, animals were randomized into groups of five mice. Compounds were prepared in PBS daily fresh and injected i.p. (10 mL/kg of body weight). The tumor sizes were measured by two perpendicular diameters (Length and Width) and tumor volumes (me) were determined by the formula length×width$^2$×1/2. The mouse body weight was determined as an indicator of tolerability on the same days. TGI was calculated according to the formula [1−(T−T0)/(C−C0)]×100, where T and T0 are the mean tumor volumes on Day 30 and Day 1, respectively, for the experimental group, and C and C0 are those for the vehicle control group. After 14 or 30 days of treatment, the animals were sacrificed on Day 30 by cervical dislocation. Tumor samples were harvested from animals and post-fixed in 4% paraformaldehyde and weighted. Animal studies were carried out in accordance with the guidelines.

LL/2 syngeneic xenograft model. The 7 weeks old B6 mice were injected s.c. with 100 μL of LL/2 cell suspensions, equivalent to 5×10⁶ cells. Paclitaxel was treated via i.p. injection at 10 mg/kg once daily for five days. AJ20064 was dosed orally, at 20 mg/kg, 40 mg/kg and 80 mg/kg once daily for 21 consecutive days. Tumor volumes were measured twice weekly throughout the duration of the experiment and tumor growth inhibition (TGI) was assessed at the end of the third cycle of therapy.

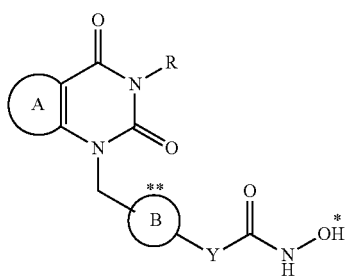

Formula I

*: may be substituted.
**: Unless mentioned, B group was 1,4 disubstituted.

TABLE 5

| Cpd No. | Chemical Name | Structure | Substituents of Formula I |
|---|---|---|---|
| 1 | 4-((7-fluoro-2,4-dioxo-3-phenethyl-3,4-dihydroquinazolin-1(2H)-yl)methyl)-N-hydroxybenzamide | 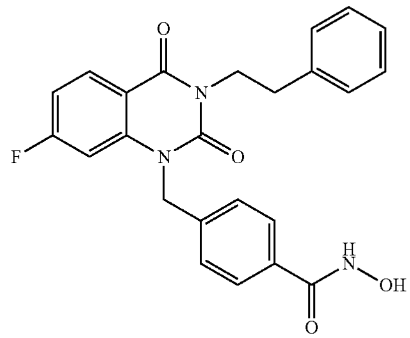 [SMILES: O=C(NO)c1ccc(Cn2c(=O)n(CCc3ccccc3)c(=O)c3ccc(F)cc32)cc1] | A = 7-F—$C_6H_3$<br>B = $C_6H_4$<br>R = $CH_2CH_2C_6H_5$<br>Y = null |
| 2 | N-hydroxy-4-((7-methoxy-2,4-dioxo-3-phenethyl-3,4-dihydroquinazol-1(2H)-yl)methyl)benzamide | 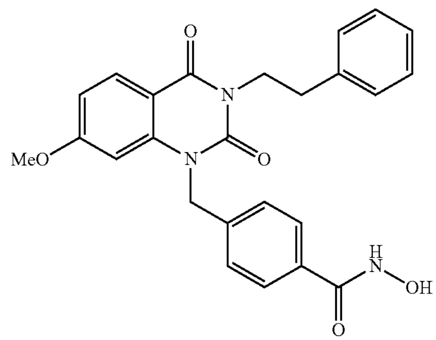 [SMILES: COc1ccc2c(=O)n(CCc3ccccc3)c(=O)n(Cc3ccc(C(=O)NO)cc3)c2c1] | A = 7-OMe—$C_6H_3$<br>B = $C_6H_4$<br>R = $CH_2CH_2C_6H_5$<br>Y = null |
| 3 | 4-((7-cyano-2,4-dioxo-3-phenethyl-3,4-dihydroquinazolin-1(2H)-yl)methyl)-N-hydroxybenzamide | 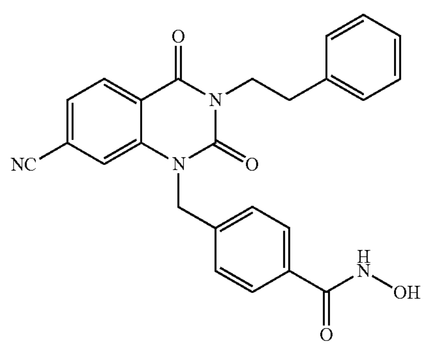 [SMILES: N#Cc1ccc2c(=O)n(CCc3ccccc3)c(=O)n(Cc3ccc(C(=O)NO)cc3)c2c1] | A = 7-CN—$C_6H_3$<br>B = $C_6H_4$<br>R = $CH_2CH_2C_6H_5$<br>Y = null |
| 4 | N-hydroxy-4-((7-hydroxy-2,4-dioxo-3-phenethyl-3,4-dihydroquinazolin-1(2H)-yl)methyl)benzamide | 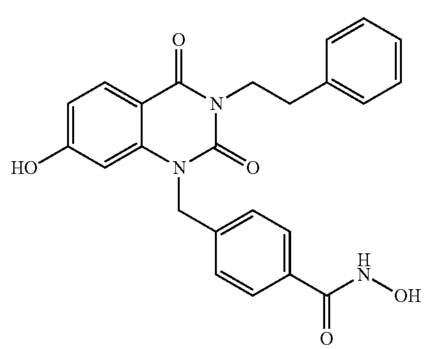 | A = 7-OH—$C_6H_3$<br>B = $C_6H_4$<br>R = $CH_2CH_2C_6H_5$<br>Y = null |

TABLE 5-continued

| Cpd No. | Chemical Name | Structure | Substituents of Formula I |
|---|---|---|---|
| 5 | 4-((2,4-dioxo-3-phenethyl-3,4-dihydroquinazolin-1(2H)-yl)methyl)-N-hydroxybenzamide | 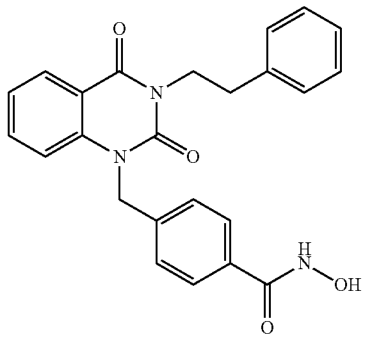 [SMILES: O=C(NO)c1ccc(Cn2c(=O)n(CCc3ccccc3)c(=O)c3ccccc32)cc1] | A = C$_6$H$_4$<br>B = C$_6$H$_4$<br>R = CH$_2$CH$_2$C$_6$H$_5$<br>Y = null |
| 6 | 3-((2,4-dioxo-3-phenethyl-3,4-dihydroquinazolin-1(2H)-yl)methyl)-N-hydroxybenzamide | 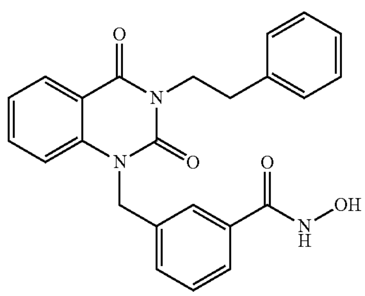 [SMILES: O=C(NO)c1cccc(Cn2c(=O)n(CCc3ccccc3)c(=O)c3ccccc32)c1] | A = C$_6$H$_4$<br>B = 1,3-substituted-C$_6$H$_4$<br>R = CH$_2$CH$_2$C$_6$H$_5$<br>Y = null |
| 7 | 3-((7-cyano-2,4-dioxo-3-phenethyl-3,4-dihydroquinazolin-1(2H)-yl)methyl)-N-hydroxybenzamide | 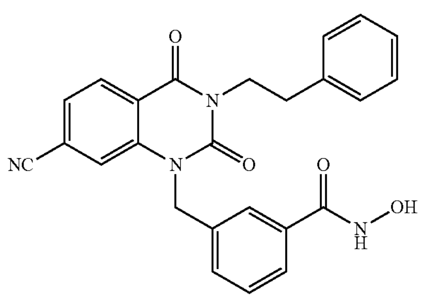 [SMILES: N#Cc1ccc2c(=O)n(CCc3ccccc3)c(=O)n(Cc3cccc(C(=O)NO)c3)c2c1] | A = 7-CN—C$_6$H$_3$<br>B = 1,3-substituted-C$_6$H$_4$<br>R = CH$_2$CH$_2$C$_6$H$_5$<br>Y = null |
| 8 | 4-((7-chloro-2,4-dioxo-3-phenethyl-3,4-dihydroquinazolin-1(2H)-yl)methyl)-N-hydroxybenzamide | 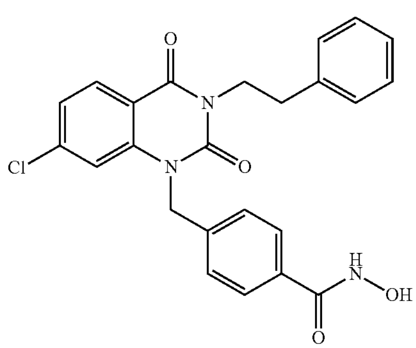 [SMILES: O=C(NO)c1ccc(Cn2c(=O)n(CCc3ccccc3)c(=O)c3ccc(Cl)cc32)cc1] | A = 7-Cl—C$_6$H$_3$<br>B = C$_6$H$_4$<br>R = CH$_2$CH$_2$C$_6$H$_5$<br>Y = null |

TABLE 5-continued

| Cpd No. | Chemical Name | Structure | Substituents of Formula I |
|---|---|---|---|
| 9 | 4-((6-chloro-2,4-dioxo-3-phenethyl-3,4-dihydroquinazolin-1(2H)-yl)methyl)-N-hydroxybenzamide | 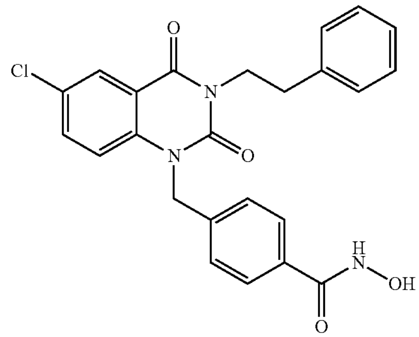 [SMILES: O=C(NO)c1ccc(Cn2c(=O)n(CCc3ccccc3)c(=O)c3cc(Cl)ccc32)cc1] | A = 6-Cl—C$_6$H$_3$<br>B = C$_6$H$_4$<br>R = CH$_2$CH$_2$C$_6$H$_5$<br>Y = null |
| 10 | 4-((7-chloro-3-methyl-2,4-dioxo-3,4-dihydroquinazolin-1(2H)-yl)methyl)-N-hydroxybenzamide | 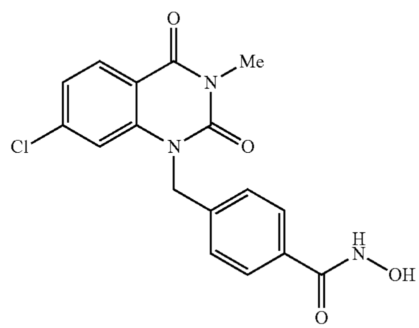 [SMILES: Cn1c(=O)c2ccc(Cl)cc2n(Cc2ccc(C(=O)NO)cc2)c1=O] | A = 7-Cl—C$_6$H$_3$<br>B = C$_6$H$_4$<br>R = Me<br>Y = null |
| 11 | 4-((3-benzyl-2,4-dioxo-3,4-dihydroquinazolin-1(2H)-yl)methyl)-N-hydroxybenzamide | 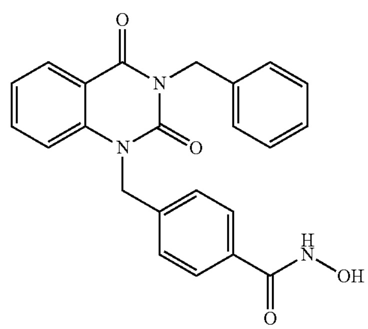 [SMILES: O=C(NO)c1ccc(Cn2c(=O)n(Cc3ccccc3)c(=O)c3ccccc32)cc1] | A = C$_6$H$_4$<br>B = C$_6$H$_4$<br>R = CH$_2$Ph<br>Y = null |
| 12 | 4-((2,4-dioxo-3-phenethyl-3,4-dihydropyrido[2,3-d]pyrimidin-1(2H)-yl)methyl)-N-hydroxybenzamide | 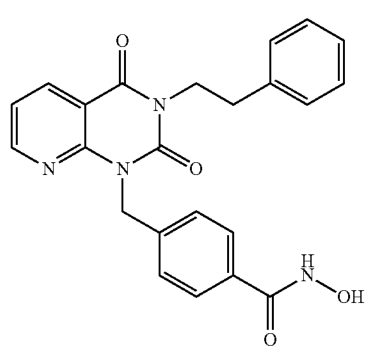 [SMILES: O=C(NO)c1ccc(Cn2c(=O)n(CCc3ccccc3)c(=O)c3cccnc32)cc1] | A = 8-pyridine<br>B = C$_6$H$_4$<br>R = CH$_2$CH$_2$C$_6$H$_5$<br>Y = null |

TABLE 5-continued

| Cpd No. | Chemical Name | Structure | Substituents of Formula I |
|---|---|---|---|
| 13 | 4-((2,4-dioxo-3-phenethyl-7-(trifluoromethyl)-3,4-dihydroquinazolin-1(2H)-yl)methyl)-N-hydroxybenzamide | 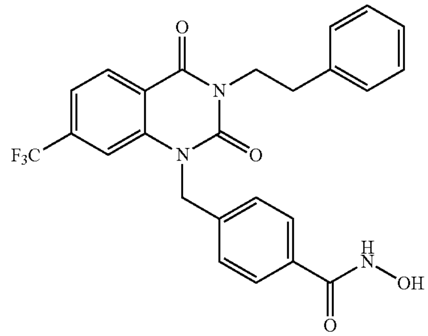 [SMILES: O=C(NO)c1ccc(Cn2c(=O)n(CCc3ccccc3)c(=O)c3ccc(C(F)(F)F)cc32)cc1] | A = 7-CF$_3$—C$_6$H$_3$<br>B = C$_6$H$_4$<br>R = CH$_2$CH$_2$C$_6$H$_5$<br>Y = null |
| 14 | 4-((3-(4-fluorophenethyl)-2,4-dioxo-3,4-dihydroquinazolin-1(2H)-yl)methyl)-N-hydroxybenzamide | 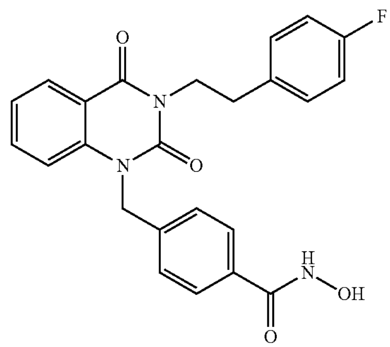 [SMILES: O=C(NO)c1ccc(Cn2c(=O)n(CCc3ccc(F)cc3)c(=O)c3ccccc32)cc1] | A = C$_6$H$_4$<br>B = C$_6$H$_4$<br>R = CH$_2$CH$_2$-(4-F—C$_6$H$_4$)<br>Y = null |
| 15 | N-hydroxy-4-((3-(2-methoxyphenethyl)-2,4-dioxo-3,4-dihydroquinazolin-1(2H)-yl)methyl)benzamide | 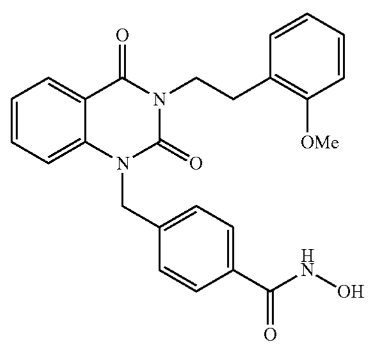 [SMILES: COc1ccccc1CCn1c(=O)c2ccccc2n(Cc2ccc(C(=O)NO)cc2)c1=O] | A = C$_6$H$_4$<br>B = C$_6$H$_4$<br>R = CH$_2$CH$_2$-(2-OMe—C$_6$H$_4$)<br>Y = null |
| 16 | 2-(4-((2,4-dioxo-3-phenethyl-3,4-dihydroquinazolin-1(2H)-yl)methyl)phenyl)-N-hydroxyacetamide | 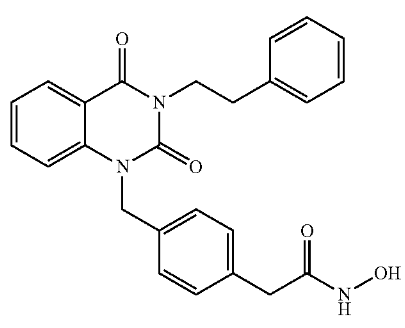 [SMILES: O=C(Cc1ccc(Cn2c(=O)n(CCc3ccccc3)c(=O)c3ccccc32)cc1)NO] | A = C$_6$H$_4$<br>B = C$_6$H$_4$<br>R = CH$_2$CH$_2$C$_6$H$_5$<br>Y = Me |

TABLE 5-continued

| Cpd No. | Chemical Name | Structure | Substituents of Formula I |
|---|---|---|---|
| 17 | 4-((6-fluoro-2,4-dioxo-3-phenethyl-3,4-dihydroquinazolin-1(2H)-yl)methyl)-N-hydroxybenzamide | 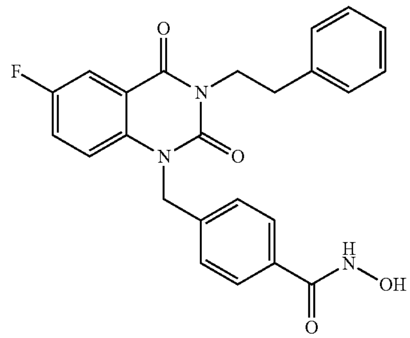 [SMILES: O=C(NO)c1ccc(Cn2c(=O)n(CCc3ccccc3)c(=O)c3cc(F)ccc32)cc1] | A = 6-F—$C_6H_3$<br>B = $C_6H_4$<br>R = $CH_2CH_2C_6H_5$<br>Y = null |
| 18 | N-hydroxy-4-((3-(2-hydroxyphenethyl)-2,4-dioxo-3,4-dihydroquinazolin-1(2H)-yl)methyl)benzamide | 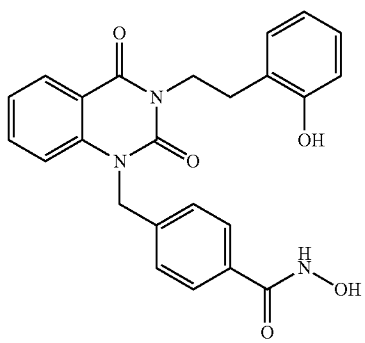 [SMILES: O=C(NO)c1ccc(Cn2c(=O)n(CCc3ccccc3O)c(=O)c3ccccc32)cc1] | A = $C_6H_4$<br>B = $C_6H_4$<br>R = $CH_2CH_2$-(2-OH—$C_6H_4$)<br>Y = null |
| 19 | 2-(4-((2,4-dioxo-3-phenethyl-3,4-dihydroquinazolin-1(2H)-yl)methyl)-3-fluorophenyl)-N-hydroxyacetamide | 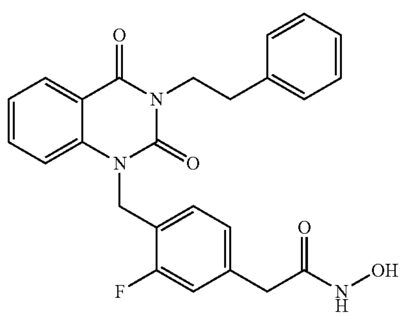 [SMILES: O=C(Cc1ccc(Cn2c(=O)n(CCc3ccccc3)c(=O)c3ccccc32)c(F)c1)NO] | A = $C_6H_4$<br>B = 3-F—$C_6H_3$<br>R = $CH_2CH_2C_6H_5$<br>Y = Me |
| 20 | 2-(4-((2,4-dioxo-3-phenethyl-3,4-dihydroquinazolin-1(2H)-yl)methyl)phenyl)-2,2-difluoro-N-hydroxyacetamide | 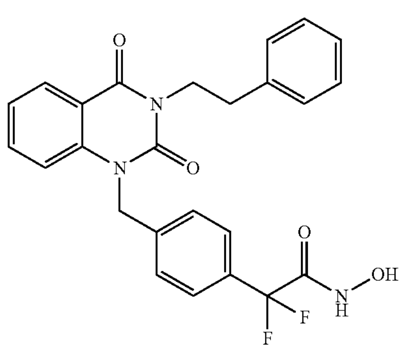 [SMILES: O=C(NO)C(F)(F)c1ccc(Cn2c(=O)n(CCc3ccccc3)c(=O)c3ccccc32)cc1] | A = $C_6H_4$<br>B = $C_6H_4$<br>R = $CH_2CH_2C_6H_5$<br>Y = $CF_2$ |

TABLE 5-continued

| Cpd No. | Chemical Name | Structure | Substituents of Formula I |
|---|---|---|---|
| 21 | 4-((2,4-dioxo-3-phenethyl-3,4-dihydrothieno[2,3-d]pyrimidin-1(2H)-yl)methyl)-N-hydroxybenzamide | 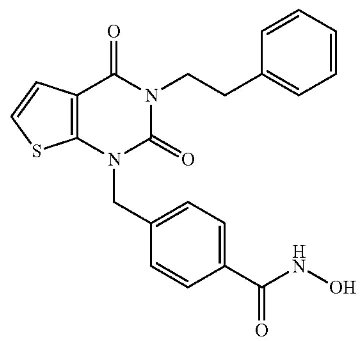 [SMILES: O=C(NO)c1ccc(Cn2c(=O)n(CCc3ccccc3)c(=O)c3ccsc32)cc1] | A = 7-thiophene<br>B = $C_6H_4$<br>R = $CH_2CH_2C_6H_5$<br>Y = null |
| 22 | N-hydroxy-4-((7-methyl-2,4-dioxo-3-phenethyl-3,4-dihydroquinazolin-1(2H)-yl)methyl)benzamide | 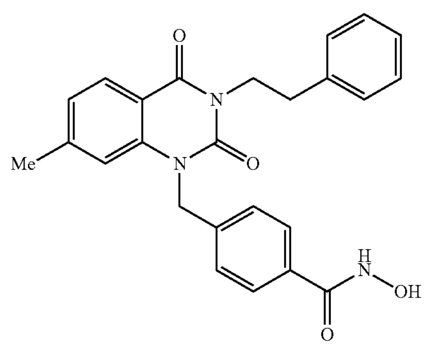 | A = 7-Me—$C_6H_3$<br>B = $C_6H_4$<br>R = $CH_2CH_2C_6H_5$<br>Y = null |
| 23 | 2-(4-((7-cyano-2,4-dioxo-3-phenethyl-3,4-dihydroquinazolin-1(2H)-yl)methyl)phenyl)-N-hydroxyacetamide | 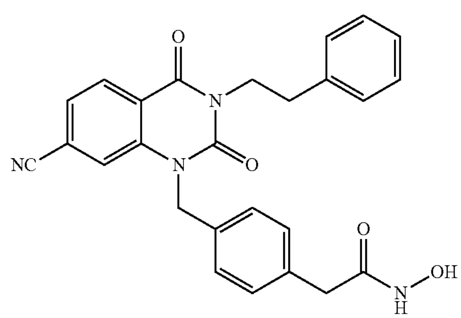 [SMILES: N#Cc1ccc2c(=O)n(CCc3ccccc3)c(=O)n(Cc3ccc(CC(=O)NO)cc3)c2c1] | A = 7-CN—$C_6H_3$<br>B = $C_6H_4$<br>R = $CH_2CH_2C_6H_5$<br>Y = Me |
| 24 | 4-((2,4-dioxo-3-(2-(thiophen-2-yl)ethyl)-3,4-dihydroquinazolin-1(2H)-yl)methyl)-N-hydroxybenzamide | 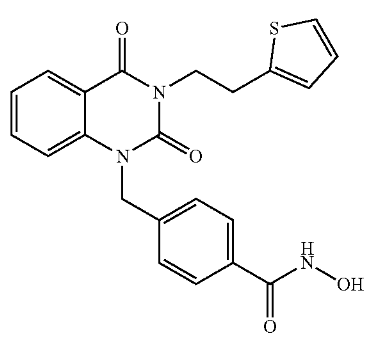 [SMILES: O=C(NO)c1ccc(Cn2c(=O)n(CCc3cccs3)c(=O)c3ccccc32)cc1] | A = $C_6H_4$<br>B = $C_6H_4$<br>R = $CH_2CH_2$-(2-thiophene<br>Y = null |

TABLE 5-continued

| Cpd No. | Chemical Name | Structure | Substituents of Formula I |
|---|---|---|---|
| 25 | 4-((2,4-dioxo-3-phenethyl-3,4-dihydroquinazolin-1(2H)-yl)methyl)-N-hydroxythiophene-2-carboxamide | 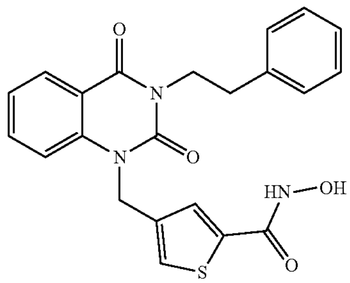 [SMILES: O=C(NO)c1cc(Cn2c(=O)n(CCc3ccccc3)c(=O)c3ccccc32)cs1] | A = $C_6H_4$<br>B = 2,4-thiophene<br>R = $CH_2CH_2C_6H_5$<br>Y = null |
| 26 | 4-((3-(3-fluorophenethyl)-2,4-dioxo-3,4-dihydroquinazolin-1(2H)-yl)methyl)-N-hydroxybenzamide | 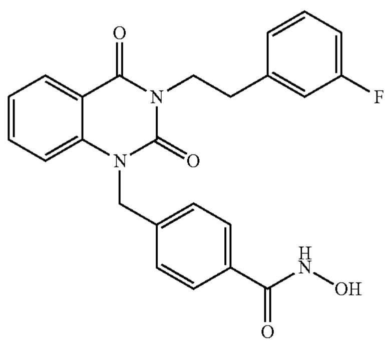 [SMILES: O=C(NO)c1ccc(Cn2c(=O)n(CCc3cccc(F)c3)c(=O)c3ccccc32)cc1] | A = $C_6H_4$<br>B = $C_6H_4$<br>R = $CH_2CH_2$-(3-F—$C_6H_4$)<br>Y = null |
| 27 | 4-((7-cyclopropyl-2,4-dioxo-3-phenethyl-3,4-dihydroquinazolin-1(2H)-yl)methyl)-N-hydroxybenzamide | 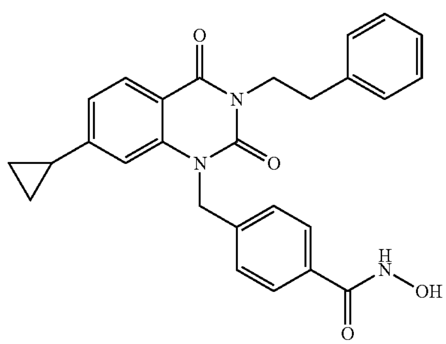 [SMILES: O=C(NO)c1ccc(Cn2c(=O)n(CCc3ccccc3)c(=O)c3ccc(C4CC4)cc32)cc1] | A = 7-cyclopropyl-$C_6H_3$<br>B = $C_6H_4$<br>R = $CH_2CH_2C_6H_5$<br>Y = null |
| 28 | 4-((3-(3-chloro-4-methoxyphenethyl)-2,4-dioxo-3,4-dihydroquinazolin-1(2H)-yl)methyl)-N-hydroxybenzamide | 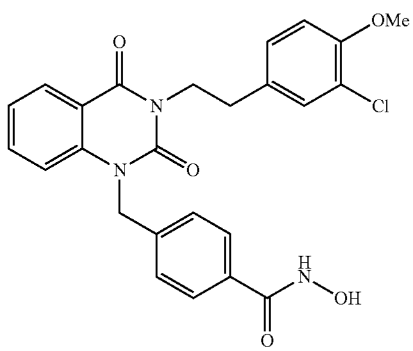 [SMILES: COc1ccc(CCn2c(=O)c3ccccc3n(Cc3ccc(C(=O)NO)cc3)c2=O)cc1Cl] | A = $C_6H_4$<br>B = $C_6H_4$<br>R = $CH_2CH_2$-(3-Cl-4-OMe—$C_6H_3$)<br>Y = null |

TABLE 5-continued

| Cpd No. | Chemical Name | Structure | Substituents of Formula I |
|---|---|---|---|
| 29 | N-hydroxy-4-((3-(4-(methylamino)phenethyl)-2,4-dioxo-3,4-dihydroquinazolin-1(2H)-yl)methyl)benzamide | 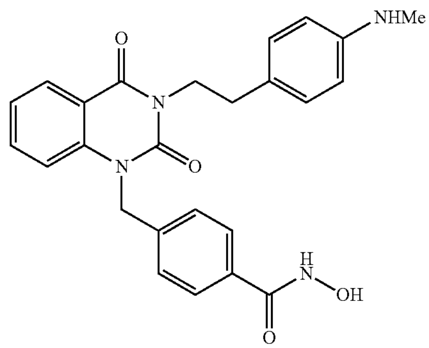 [SMILES: CNc1ccc(CCn2c(=O)c3ccccc3n(Cc3ccc(C(=O)NO)cc3)c2=O)cc1] | A = $C_6H_4$<br>B = $C_6H_4$<br>R = $CH_2CH_2$-(4-NHMe—$C_6H_4$)<br>Y = null |
| 30 | N-hydroxy-4-((3-(4-morpholinophenethyl)-2,4-dioxo-3,4-dihydroquinazolin-1(2H)-yl)methyl)benzamide | 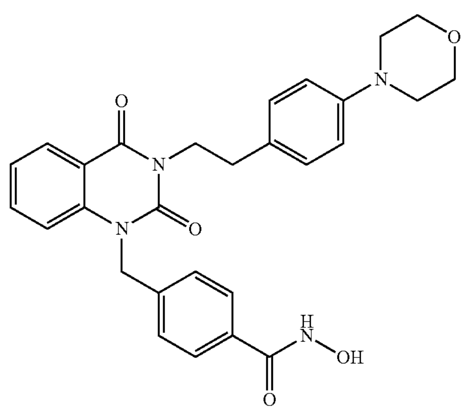 [SMILES: O=C(NO)c1ccc(Cn2c(=O)n(CCc3ccc(N4CCOCC4)cc3)c(=O)c3ccccc32)cc1] | A = $C_6H_4$<br>B = $C_6H_4$<br>R = $CH_2CH_2$-(4-morpholine-$C_6H_4$)<br>Y = null |
| 31 | 4-((3-(benzyloxy)-2,4-dioxo-3,4-dihydroquinazolin-1(2H)-yl)methyl)-N-hydroxybenzamide | 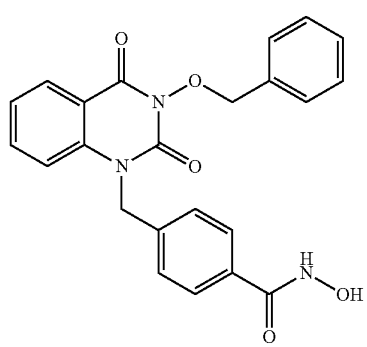 [SMILES: O=C(NO)c1ccc(Cn2c(=O)n(OCc3ccccc3)c(=O)c3ccccc32)cc1] | A = $C_6H_4$<br>B = $C_6H_4$<br>R = $OCH_2Ph$<br>Y = null |
| 32 | 5-((2,4-dioxo-3-phenethyl-3,4-dihydroquinazolin-1(2H)-yl)methyl)-N-hydroxythiophene-2-carboxamide | 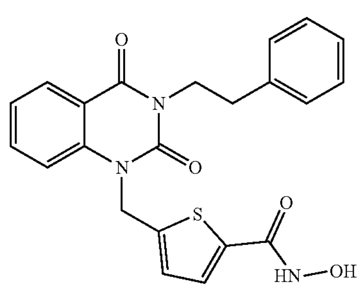 [SMILES: O=C(NO)c1ccc(Cn2c(=O)n(CCc3ccccc3)c(=O)c3ccccc32)s1] | A = $C_6H_4$<br>B = 2,5-thiophene<br>R = $CH_2CH_2C_6H_5$<br>Y = null |

TABLE 5-continued

| Cpd No. | Chemical Name | Structure | Substituents of Formula I |
|---|---|---|---|
| 33 | N-hydroxy-4-((3-(4-methoxyphenethyl)-2,4-dioxo-3,4-dihydroquinazolin-1(2H)-yl)methyl)benzamide | 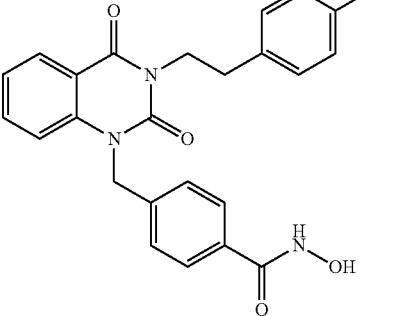 | A = $C_6H_4$<br>B = $C_6H_4$<br>R = $CH_2CH_2$-(4-OMe—$C_6H_4$)<br>Y = null |
| 34 | N-hydroxy-4-((3-(4-hydroxyphenethyl)-2,4-dioxo-3,4-dihydroquinazolin-1(2H)-yl)methyl)benzamide | 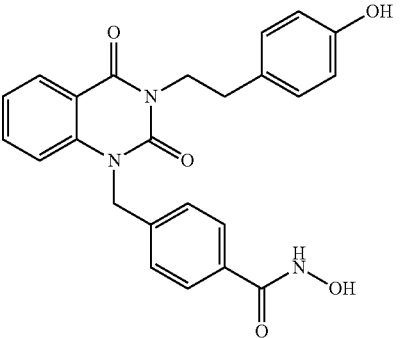 [SMILES: O=C(NO)c1ccc(Cn2c(=O)n(CCc3ccc(O)cc3)c(=O)c3ccccc32)cc1] | A = $C_6H_4$<br>B = $C_6H_4$<br>R = $CH_2CH_2$-(4-OH—$C_6H_4$)<br>Y = null |
| 35 | 4-((2,4-dioxo-3-phenyl-3,4-dihydroquinazolin-1(2H)-yl)methyl)-N-hydroxybenzamide | 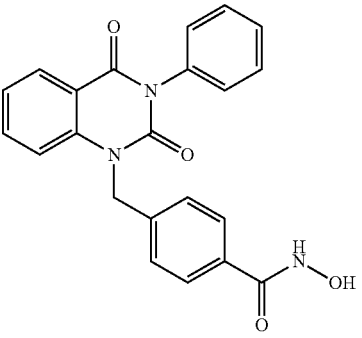 [SMILES: O=C(NO)c1ccc(Cn2c(=O)n(-c3ccccc3)c(=O)c3ccccc32)cc1] | A = $C_6H_4$<br>B = $C_6H_4$<br>R = $C_6H_5$<br>Y = null |
| 36 | N-hydroxy-4-((3-(4-methoxyphenyl)-2,4-dioxo-3,4-dihydroquinazolin-1(2H)-yl)methyl)benzamide | 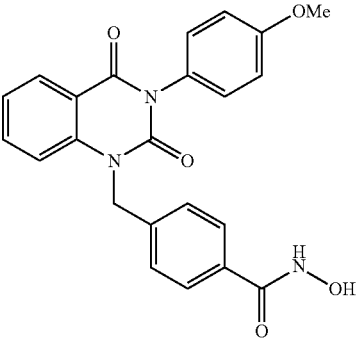 [SMILES: COc1ccc(-n2c(=O)c3ccccc3n(Cc3ccc(C(=O)NO)cc3)c2=O)cc1] | A = $C_6H_4$<br>B = $C_6H_4$<br>R = 4-OMe—$C_6H_4$<br>Y = null |

TABLE 5-continued

| Cpd No. | Chemical Name | Structure | Substituents of Formula I |
|---|---|---|---|
| 37 | 4-((3-(4-chlorophenyl)-2,4-dioxo-3,4-dihydroquinazolin-1(2H)-yl)methyl)-N-hydroxybenzamide | 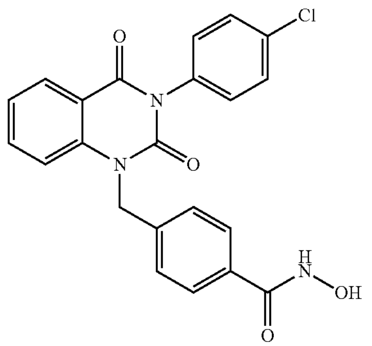 [SMILES: O=C(NO)c1ccc(Cn2c(=O)n(-c3ccc(Cl)cc3)c(=O)c3ccccc32)cc1] | A = C$_6$H$_4$<br>B = C$_6$H$_4$<br>R = 4-Cl—C$_6$H$_4$<br>Y = null |
| 38 | 4-((3-(4-fluorophenyl-2,4-dioxo-3,4-dihydroquinazolin-1(2H)-yl)methyl)-N-hydroxybenzamide | 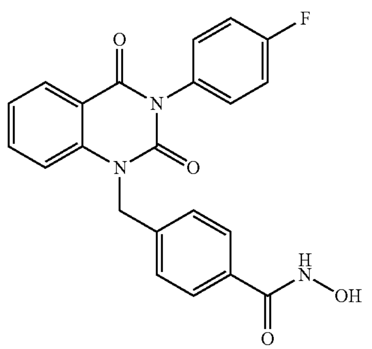 [SMILES: O=C(NO)c1ccc(Cn2c(=O)n(-c3ccc(F)cc3)c(=O)c3ccccc32)cc1] | A = C$_6$H$_4$<br>B = C$_6$H$_4$<br>R = 4-F—C$_6$H$_4$<br>Y = null |
| 39 | N-hydroxy-4-((3-(2-methoxyphenyl)-2,4-dioxo-3,4-dihydroquinazolin-1(2H)-yl)methyl)benzamide | 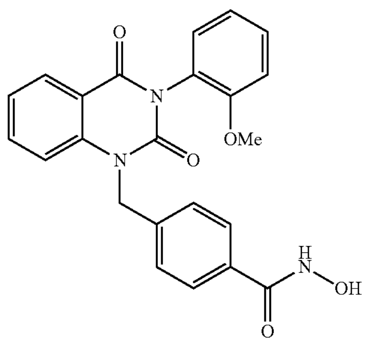 [SMILES: COc1ccccc1-n1c(=O)c2ccccc2n(Cc2ccc(C(=O)NO)cc2)c1=O] | A = C$_6$H$_4$<br>B = C$_6$H$_4$<br>R = 2-OMe—C$_6$H$_4$<br>Y = null |
| 40 | (E)-3-(4-((2,4-dioxo-3-phenethyl-3,4-dihydroquinazolin-1(2H)-yl)methyl)phenyl)-N-hydroxyacrylamide | 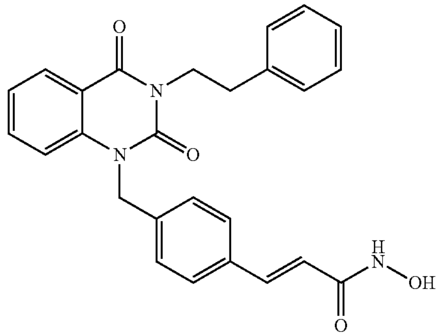 [SMILES: O=C(/C=C/c1ccc(Cn2c(=O)n(CCc3ccccc3)c(=O)c3ccccc32)cc1)NO] | A = C$_6$H$_4$<br>B = C$_6$H$_4$<br>R = CH$_2$CH$_2$C$_6$H$_5$<br>Y = (E)-ethylene |

TABLE 5-continued

| Cpd No. | Chemical Name | Structure | Substituents of Formula I |
|---|---|---|---|
| 41 | (E)-3-(4-((3-(4-chlorophenethyl)-2,4-dioxo-3,4-dihydroquinazolin-1(2H)-yl)methyl)phenyl)-N-hydroxyacrylamide | 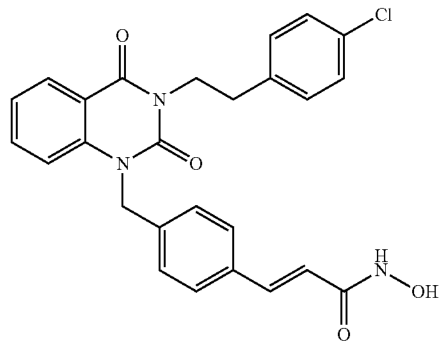 | A = $C_6H_4$<br>B = $C_6H_4$<br>R = $CH_2CH_2$-(4-Cl—$C_6H_4$)<br>Y = (E)-ethylene |
| 42 | (E)-3-(4-((3-(4-fluorophenethyl)-2,4-dioxo-3,4-dihydroquinazolin-1(2H)-yl)methyl)phenyl)-N-hydroxyacrylamide | 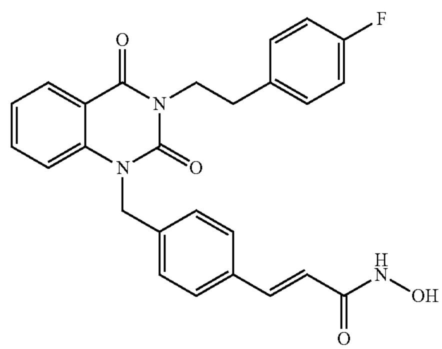 [SMILES: O=C(/C=C/c1ccc(Cn2c(=O)n(CCc3ccc(F)cc3)c(=O)c3ccccc32)cc1)NO] | A = $C_6H_4$<br>B = $C_6H_4$<br>R = $CH_2CH_2$-(4-F—$C_6H_4$)<br>Y = (E)-ethylene |
| 43 | (E)-N-hydroxy-3-(4-((3-(4-methoxyphenethyl)-2,4-dioxo-3,4-dihydroquinazolin-1(2H)-yl)methyl)phenyl)acrylamide | 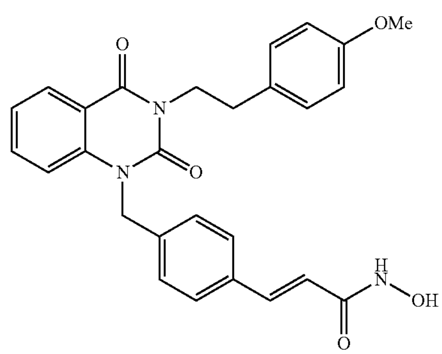 [SMILES: COc1ccc(CCn2c(=O)c3ccccc3n(Cc3ccc(/C=C/C(=O)NO)cc3)c2=O)cc1] | A = $C_6H_4$<br>B = $C_6H_4$<br>R = $CH_2CH_2$-(4-OMe—$C_6H_4$)<br>Y = (E)-ethylene |
| 44 | (E)-N-hydroxy-3-(4-((3-(4-hydroxyphenethyl)-2,4-dioxo-3,4-dihydroquinazolin-1(2H)-yl)methyl)phenyl)acrylamide | 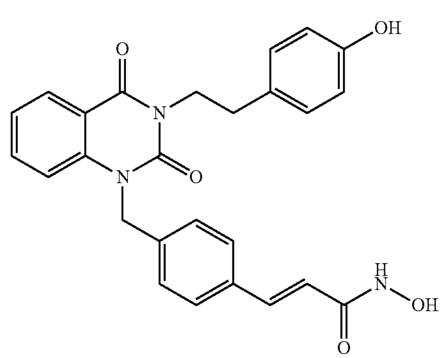 | A = $C_6H_4$<br>B = $C_6H_4$<br>R = $CH_2CH_2$-(4-OH—$C_6H_4$)<br>Y = (E)-ethylene |

TABLE 5-continued

| Cpd No. | Chemical Name | Structure | Substituents of Formula I |
|---|---|---|---|
| 45 | (E)-3-(4-((7-fluoro-2,4-dioxo-3-phenethyl-3,4-dihydroquinazolin-1(2H)-yl)methyl)phenyl)-N-hydroxyacrylamide | 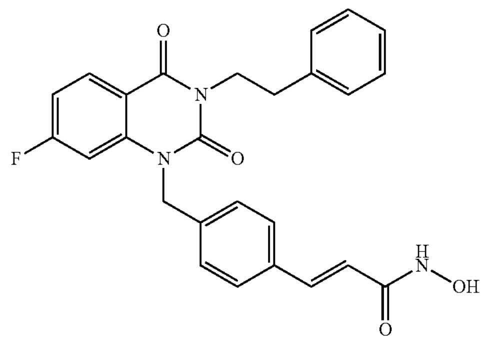 [SMILES: O=C(/C=C/c1ccc(Cn2c(=O)n(CCc3ccccc3)c(=O)c3ccc(F)cc32)cc1)NO] | A = 7-F—C$_6$H$_3$<br>B = C$_6$H$_4$<br>R = CH$_2$CH$_2$C$_6$H$_5$<br>Y = (E)-ethylene |
| 46 | (E)-3-(4-((3-(4-chlorophenethyl)-7-fluoro-2,4-dioxo-3,4-dihydroquinazolin-1(2H)-yl)methyl)phenyl)-N-hydroxyacrylamide | 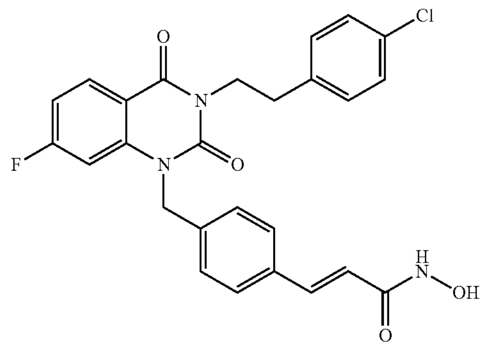 [SMILES: O=C(/C=C/c1ccc(Cn2c(=O)n(CCc3ccc(Cl)cc3)c(=O)c3ccc(F)cc32)cc1)NO] | A = C$_6$H$_4$<br>B = C$_6$H$_4$<br>R = CH$_2$CH$_2$-(4-Cl—C$_6$H$_4$)<br>Y = (E)-ethylene |
| 47 | (E)-3-(4-((7-fluoro-3-(4-fluorophenethyl)-2,4-dioxo-3,4-dihydroquinazolin-1(2H)-yl)methyl)phenyl)-N-hydroxyacrylamide | 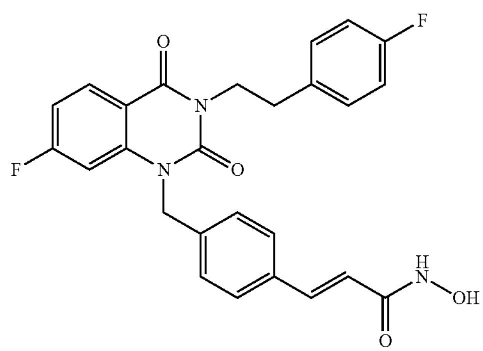 [SMILES: O=C(/C=C/c1ccc(Cn2c(=O)n(CCc3ccc(F)cc3)c(=O)c3ccc(F)cc32)cc1)NO] | A = 7-F—C$_6$H$_3$<br>B = C$_6$H$_4$<br>R = CH$_2$CH$_2$-(4-F—C$_6$H$_4$)<br>Y = (E)-ethylene |
| 48 | (E)-3-(4-((7-fluoro-3-(4-methoxyphenethyl)-2,4-dioxo-3,4-dihydroquinazolin-1(2H)-yl)methyl)phenyl)-N-hydroxyacrylamide | 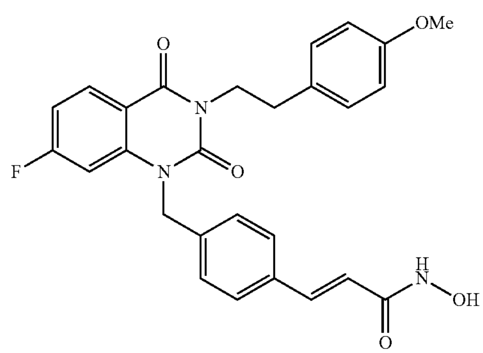 | A = 7-F—C$_6$H$_3$<br>B = C$_6$H$_4$<br>R = CH$_2$CH$_2$-(4-OMe—C$_6$H$_4$)<br>Y = (E)-ethylene |

TABLE 5-continued

| Cpd No. | Chemical Name | Structure | Substituents of Formula I |
|---|---|---|---|
| 49 | (E)-3-(4-((7-fluoro-3-(4-hydroxyphenethyl)-2,4-dioxo-3,4-dihydroquinazolin-1(2H)-yl)methyl)phenyl)-N-hydroxyacrylamide | 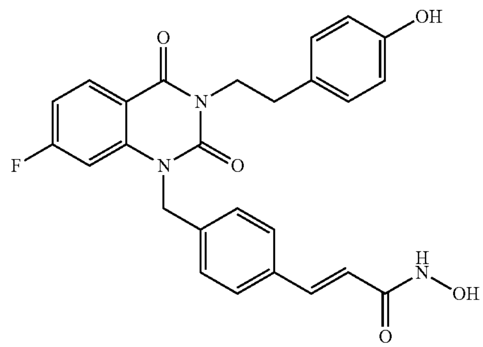 [SMILES: O=C(/C=C/c1ccc(Cn2c(=O)n(CCc3ccc(O)cc3)c(=O)c3ccc(F)cc32)cc1)NO] | A = 7-F—C$_6$H$_3$<br>B = C$_6$H$_4$<br>R = CH$_2$CH$_2$-(4-OH—C$_6$H$_4$)<br>Y = (E)-ethylene |
| 50 | (E)-3-(4-((7-chloro-2,4-dioxo-3-phenethyl-3,4-dihydroquinazolin-1(2H)-yl)methyl)phenyl)-N-hydroxyacrylamide | 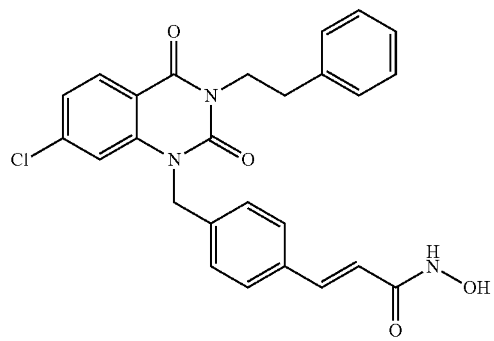 [SMILES: O=C(/C=C/c1ccc(Cn2c(=O)n(CCc3ccccc3)c(=O)c3ccc(Cl)cc32)cc1)NO] | A = 7-Cl—C$_6$H$_3$<br>B = C$_6$H$_4$<br>R = CH$_2$CH$_2$C$_6$H$_5$<br>Y = (E)-ethylene |
| 51 | (E)-3-(4-((7-chloro-3-(4-hydroxyphenethyl)-2,4-dioxo-3,4-dihydroquinazolin-1(2H)-yl)methyl)phenyl)-N-hydroxyacrylamide | 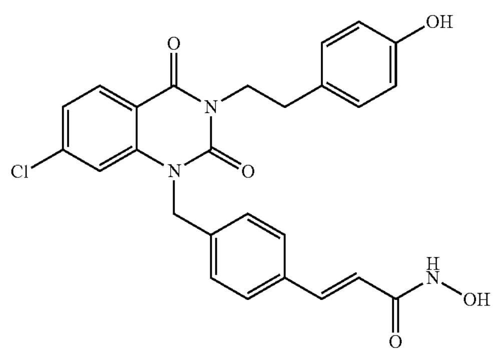 [SMILES: O=C(/C=C/c1ccc(Cn2c(=O)n(CCc3ccc(O)cc3)c(=O)c3ccc(Cl)cc32)cc1)NO] | A = 7-Cl—C$_6$H$_3$<br>B = C$_6$H$_4$<br>R = CH$_2$CH$_2$-(4-OH—C$_6$H$_4$)<br>Y = (E)-ethylene |
| 52 | (E)-3-(4-((2,4-dioxo-3-phenyl-3,4-dihydroquinazolin-1(2H)-y)methyl)phenyl)-N-hydroxyacrylamide | 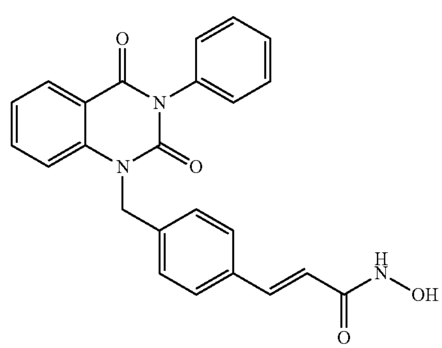 [SMILES: O=C(/C=C/c1ccc(Cn2c(=O)n(-c3ccccc3)c(=O)c3ccccc32)cc1)NO] | A = C$_6$H$_4$<br>B = C$_6$H$_4$<br>R = C$_6$H$_5$<br>Y = (E)-ethylene |

TABLE 5-continued

| Cpd No. | Chemical Name | Structure | Substituents of Formula I |
|---|---|---|---|
| 53 | (E)-N-hydroxy-3-(4-((3-(4-methoxyphenyl)-2,4-dioxo-3,4-dihydroquinazolin-1(2H)-yl)methyl)phenyl)acrylamide | 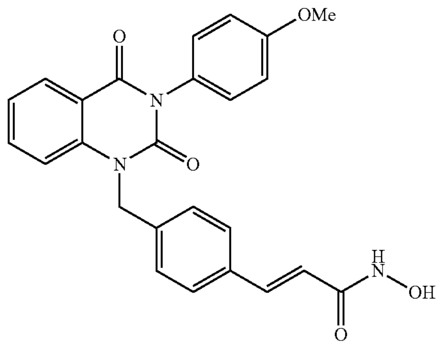 [SMILES: COc1ccc(-n2c(=O)c3ccccc3n(Cc3ccc(/C=C/C(=O)NO)cc3)c2=O)cc1] | A = $C_6H_4$<br>B = $C_6H_4$<br>R = 4-OMe—$C_6H_4$<br>Y = (E)-ethylene |
| 54 | (E)-N-hydroxy-3-(4-((3-(4-hydroxyphenyl)-2,4-dioxo-3,4-dihydroquinazolin-1(2H)-yl)methyl)phenyl)acrylamide | 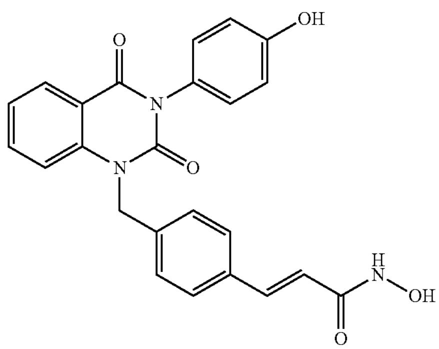 [SMILES: O=C(/C=C/c1ccc(Cn2c(=O)n(-c3ccc(O)cc3)c(=O)c3ccccc32)cc1)NO] | A = $C_6H_4$<br>B = $C_6H_4$<br>R = 4-OH—$C_6H_4$<br>Y = (E)-ethylene |
| 55 | 4-((3-(2-fluorophenyl)-2,4-dioxo-3,4-dihydroquinazolin-1(2H)-yl)methyl)-N-hydroxybenzamide | 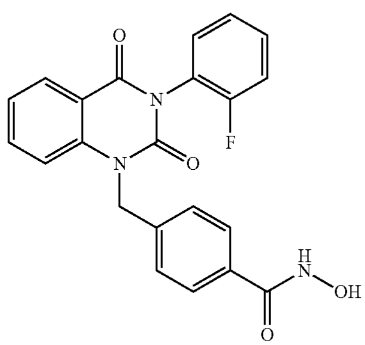 [SMILES: O=C(NO)c1ccc(Cn2c(=O)n(-c3ccccc3F)c(=O)c3ccccc32)cc1] | A = $C_6H_4$<br>B = $C_6H_4$<br>R = 2-F—$C_6H_4$<br>Y = null |
| 56 | N-hydroxy-4-((3-(2-nitrophenyl)-2,4-dioxo-3,4-dihydroquinazolin-1(2H)-yl)methyl)benzamide | 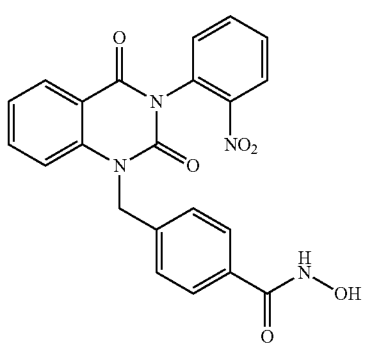 | A = $C_6H_4$<br>B = $C_6H_4$<br>R = 2-$NO_2$—$C_6H_4$<br>Y = null |

TABLE 5-continued

| Cpd No. | Chemical Name | Structure | Substituents of Formula I |
|---|---|---|---|
| 57 | 4-((2,4-dioxo-3-(2-phenylcyclopropyl)-3,4-dihydroquinazolin-1(2H)-yl)methyl)-N-hydroxybenzamide | 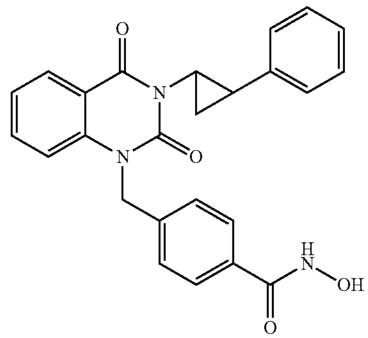 [SMILES: O=C(NO)c1ccc(Cn2c(=O)n(C3CC3c3ccccc3)c(=O)c3ccccc32)cc1] | A = $C_6H_4$<br>B = $C_6H_4$<br>R = cyclopropyl-$C_6H_5$<br>Y = null |
| 58 | N-hydroxy-4-((3-(2-hydroxyethyl)-2,4-dioxo-3,4-dihydroquinazolin-1(2H)-yl)methyl)benzamide | 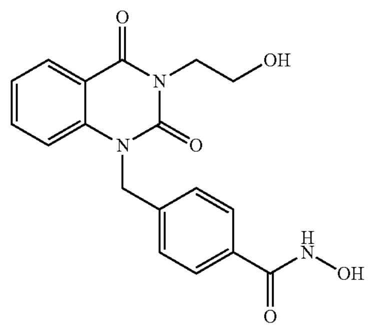 | A = $C_6H_4$<br>B = $C_6H_4$<br>R = $CH_2CH_2OH$<br>Y = null |
| 59 | N-hydroxy-4-((3-(2-hydroxy-2-phenylethyl)-2,4-dioxo-3,4-dihydroquinazolin-1(2H)-yl)methyl)benzamide | 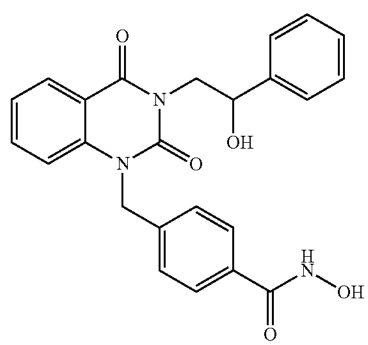 [SMILES: O=C(NO)c1ccc(Cn2c(=O)n(CC(O)c3ccccc3)c(=O)c3ccccc32)cc1] | A = $C_6H_4$<br>B = $C_6H_4$<br>R = $CH_2CH_2OH$—$C_6H_5$<br>Y = null |
| 60 | 4-((7-fluoro-3-(2-fluorophenyl)-2,4-dioxo-3,4-dihydroquinazolin-1(2H)-yl)methyl)-N-hydroxybenzamide | 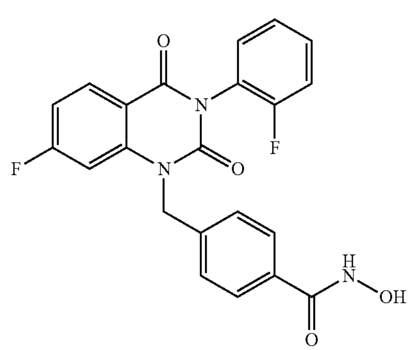 [SMILES: O=C(NO)c1ccc(Cn2c(=O)n(-c3ccccc3F)c(=O)c3ccc(F)cc32)cc1] | A = 7-F—$C_6H_3$<br>B = $C_6H_4$<br>R = 2-F—$C_6H_4$<br>Y = null |

TABLE 5-continued

| Cpd No. | Chemical Name | Structure | Substituents of Formula I |
|---|---|---|---|
| 61 | 4-((7-chloro-3-(2-fluorophenyl)-2,4-dioxo-3,4-dihydroquinazolin-1(2H)-yl)methyl)-N-hydroxybenzamide | 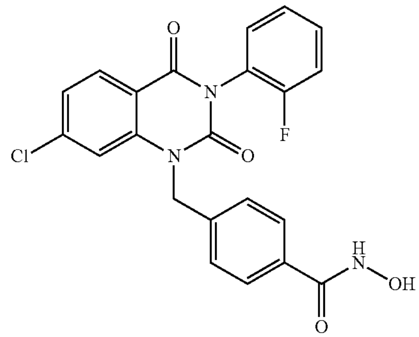 [SMILES: O=C(NO)c1ccc(Cn2c(=O)n(-c3ccccc3F)c(=O)c3ccc(Cl)cc32)cc1] | A = 7-Cl—C$_6$H$_3$<br>B = C$_6$H$_4$<br>R = 2-F—C$_6$H$_4$<br>Y = null |
| 62 | 4-((2,4-dioxo-3-(4-(trifluoromethyl)benzyl)-3,4-dihydroquinazolin-1(2H)-yl)methyl)-N-hydroxybenzamide | 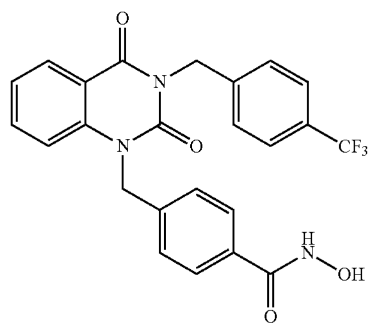 [SMILES: O=C(NO)c1ccc(Cn2c(=O)n(Cc3ccc(C(F)(F)F)cc3)c(=O)c3ccccc32)cc1] | A = C$_6$H$_4$<br>B = C$_6$H$_4$<br>R = CH$_2$-(4-CF$_3$—C$_6$H$_4$)<br>Y = null |
| 63 | 4-((2,4-dioxo-3-(4-(trifluoromethyl)phenethyl)-3,4-dihydroquinazolin-1(2H)-yl)methyl)-N-hydroxybenzamide | 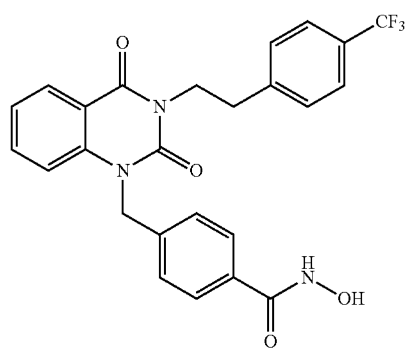 [SMILES: O=C(NO)c1ccc(Cn2c(=O)n(CCc3ccc(C(F)(F)F)cc3)c(=O)c3ccccc32)cc1] | A = C$_6$H$_4$<br>B = C$_6$H$_4$<br>R = CH$_2$CH$_2$-(4-CF$_3$—C$_6$H$_4$)<br>Y = null |
| 64 | 4-((2,4-dioxo-3-phenyl-7-(trifluoromethyl)-3,4-dihydroquinazolin-1(2H)-yl)methyl)-N-hydroxybenzamide | 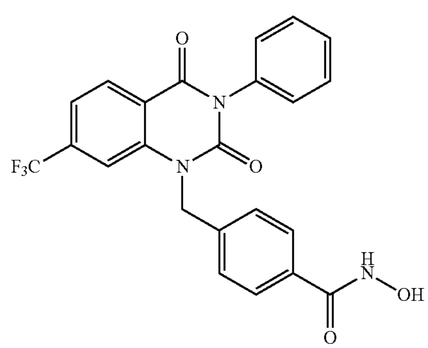 [SMILES: O=C(NO)c1ccc(Cn2c(=O)n(-c3ccccc3)c(=O)c3ccc(C(F)(F)F)cc32)cc1] | A = 7-CF$_3$—C$_6$H$_3$<br>B = C$_6$H$_4$<br>R = C$_6$H$_5$<br>Y = null |

TABLE 5-continued

| Cpd No. | Chemical Name | Structure | Substituents of Formula I |
|---|---|---|---|
| 65 | 4-((2,4-dioxo-3-(2,4,5-trifluorophenyl)-3,4-dihydroquinazolin-1(2H)-yl)methyl)-N-hydroxybenzamide | 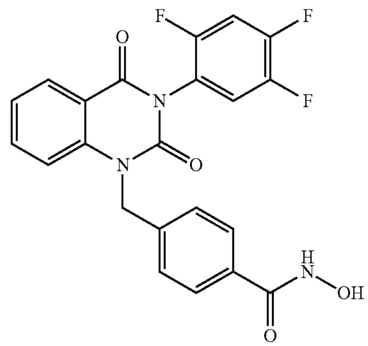 [SMILES: O=C(NO)c1ccc(Cn2c(=O)n(-c3cc(F)c(F)cc3F)c(=O)c3ccccc32)cc1] | A = $C_6H_4$<br>B = $C_6H_4$<br>R = 2,4,5-tri-F—$C_6H_2$<br>Y = null |
| 66 | 4-((3-(2-fluorophenethyl)-2,4-dioxo-3,4-dihydroquinazolin-1(2H)-yl)methyl)-N-hydroxybenzamide | 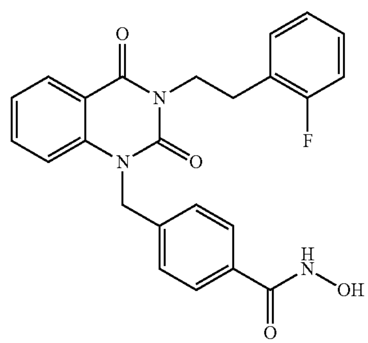 [SMILES: O=C(NO)c1ccc(Cn2c(=O)n(CCc3ccccc3F)c(=O)c3ccccc32)cc1] | A = $C_6H_4$<br>B = $C_6H_4$<br>R = $CH_2CH_2$-(2-F—$C_6H_4$)<br>Y = null |
| 67 | 4-((2,4-dioxo-3-(3,3,3-trifluoropropyl)-3,4-dihydroquinazolin-1(2H)-yl)methyl)-N-hydroxybenzamide | 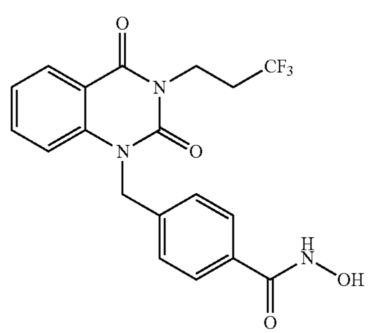 [SMILES: O=C(NO)c1ccc(Cn2c(=O)n(CCC(F)(F)F)c(=O)c3ccccc32)cc1] | A = $C_6H_4$<br>B = $C_6H_4$<br>R = $CH_2CH_2CF_3$<br>Y = null |
| 68 | 4-((2,4-dioxo-3-(2,2,2-trifluoroethyl)-3,4-dihydroquinazolin-1(2H)-yl)methyl)-N-hydroxybenzamide | 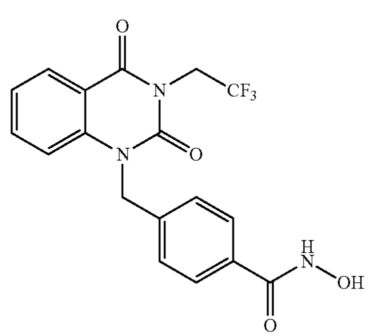 [SMILES: O=C(NO)c1ccc(Cn2c(=O)n(CC(F)(F)F)c(=O)c3ccccc32)cc1] | A = $C_6H_4$<br>B = $C_6H_4$<br>R = $CH_2CF_3$<br>Y = null |

TABLE 5-continued

| Cpd No. | Chemical Name | Structure | Substituents of Formula I |
|---|---|---|---|
| 69 | 4-((8-fluoro-2,4-dioxo-3-phenethyl-3,4-dihydroquinazolin-1(2H)-yl)methyl)-N-hydroxybenzamide | 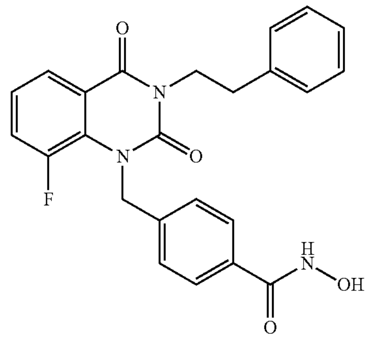 | A = 8-F—C$_6$H$_3$<br>B = C$_6$H$_4$<br>R = CH$_2$CH$_2$C$_6$H$_5$<br>Y = null |
| 70 | 4-((2,4-dioxo-3-(2-(pyridin-2-yl)ethyl)-3,4-dihydroquinazolin-1(2H)-yl)methyl)-N-hydroxybenzamide | 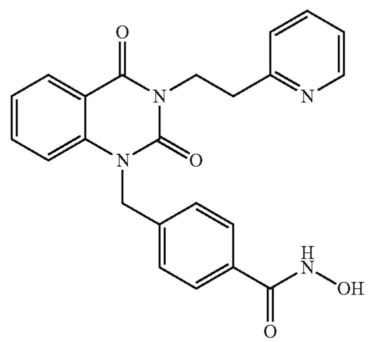 [SMILES: O=C(NO)c1ccc(Cn2c(=O)n(CCc3ccccn3)c(=O)c3ccccc32)cc1] | A = C$_6$H$_4$<br>B = C$_6$H$_4$<br>R = CH$_2$CH$_2$-(2-pyridine)<br>Y = null |
| 71 | 4-((2,4-dioxo-3-(2-(pyridin-3-yl)ethyl)-3,4-dihydroquinazolin-1(2H)-yl)methyl)-N-hydroxybenzamide | 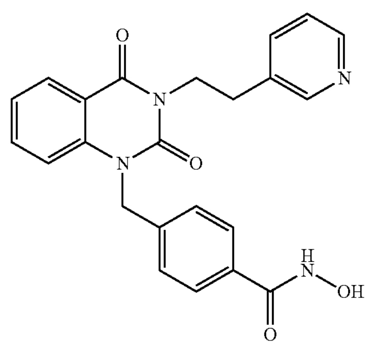 [SMILES: O=C(NO)c1ccc(Cn2c(=O)n(CCc3cccnc3)c(=O)c3ccccc32)cc1] | A = C$_6$H$_4$<br>B = C$_6$H$_4$<br>R = CH$_2$CH$_2$-(3-pyridine)<br>Y = null |
| 72 | 4-((3-(2-fluoro-5-(trifluoromethyl)phenyl)-2,4-dioxo-3,4-dihydroquinazolin-1(2H)-yl)methyl)-N-hydroxybenzamide | 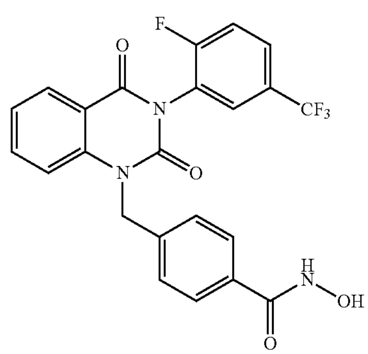 [SMILES: O=C(NO)c1ccc(Cn2c(=O)n(-c3cc(C(F)(F)F)ccc3F)c(=O)c3ccccc32)cc1] | A = C$_6$H$_4$<br>B = C$_6$H$_4$<br>R = 2-F-5-CF$_3$—C$_6$H$_3$<br>Y = null |

TABLE 5-continued

| Cpd No. | Chemical Name | Structure | Substituents of Formula I |
|---|---|---|---|
| 73 | 4-((2,4-dioxo-3-(2-(pyridin-4-yl)ethyl)-3,4-dihydroquinazolin-1(2H)-yl)methyl)-N-hydroxybenzamide | 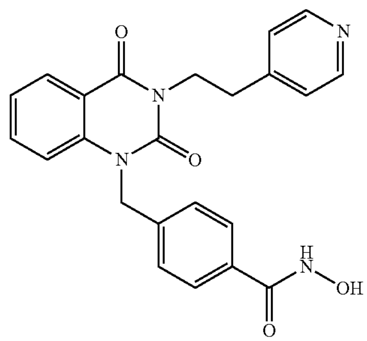 [SMILES: O=C(NO)c1ccc(Cn2c(=O)n(CCc3ccncc3)c(=O)c3ccccc32)cc1] | A = $C_6H_4$<br>B = $C_6H_4$<br>R = $CH_2CH_2$-(4-pyridine)<br>Y = null |
| 74 | N-hydroxy-4-((3-(2-methoxyethyl)-2,4-dioxo-3,4-dihydroquinazolin-1(2H)-yl)methyl)benzamide | 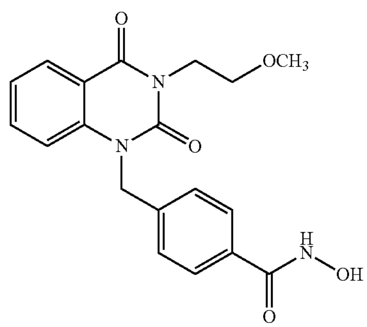 [SMILES: COCCn1c(=O)c2ccccc2n(Cc2ccc(C(=O)NO)cc2)c1=O] | A = $C_6H_4$<br>B = $C_6H_4$<br>R = $CH_2CH_2OMe$<br>Y = null |
| 75 | 4-((2,4-dioxo-3-(3-(trifluoromethyl)benzyl)-3,4-dihydroquinazolin-1(2H)-yl)methyl)-N-hydroxybenzamide | 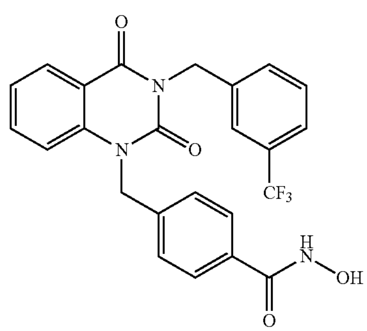 [SMILES: O=C(NO)c1ccc(Cn2c(=O)n(Cc3cccc(C(F)(F)F)c3)c(=O)c3ccccc32)cc1] | A = $C_6H_4$<br>B = $C_6H_4$<br>R = $CH_2$-(3-$CF_3$—$C_6H_4$)<br>Y = null |
| 76 | 4-((3-(2-bromophenethyl)-2,4-dioxo-3,4-dihydroquinazolin-1(2H)-yl)methyl)-N-hydroxybenzamide | 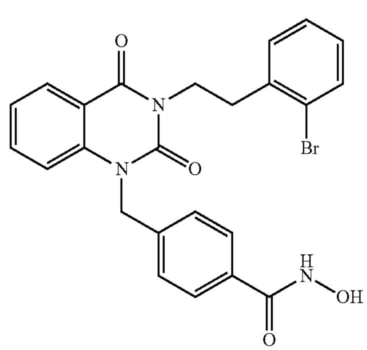 | A = $C_6H_4$<br>B = $C_6H_4$<br>R = $CH_2CH_2$-(2-Br—$C_6H_4$)<br>Y = null |

TABLE 5-continued

| Cpd No. | Chemical Name | Structure | Substituents of Formula I |
|---|---|---|---|
| 77 | 4-((2,4-dioxo-3-(2-(trifluoromethyl)benzyl)-3,4-dihydroquinazolin-1(2H)-yl)methyl)-N-hydroxybenzamide | 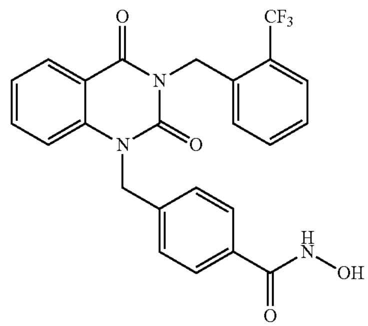 [SMILES: O=C(NO)c1ccc(Cn2c(=O)n(Cc3ccccc3C(F)(F)F)c(=O)c3ccccc32)cc1] | A = $C_6H_4$<br>B = $C_6H_4$<br>R = $CH_2$-(2-$CF_3$—$C_6H_4$)<br>Y = null |
| 78 | 4-((3-(2-fluoro-3-(trifluoromethyl)phenyl)-2,4-dioxo-3,4-dihydroquinazolin-1(2H)-yl)methyl)-N-hydroxybenzamide | 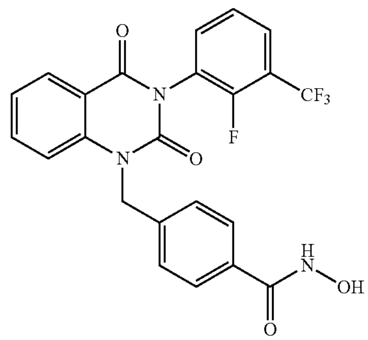 [SMILES: O=C(NO)c1ccc(Cn2c(=O)n(-c3cccc(C(F)(F)F)c3F)c(=O)c3ccccc32)cc1] | A = $C_6H_4$<br>B = $C_6H_4$<br>R = 2-F-3-$CF_3$—$C_6H_3$<br>Y = null |
| 79 | (E)-3-(4-((2,4-dioxo-3-(3-(trifluoromethyl)phenethyl)-3,4-dihydroquinazolin-1(2H)-yl)methyl)phenyl)-N-hydroxyacrylamide | 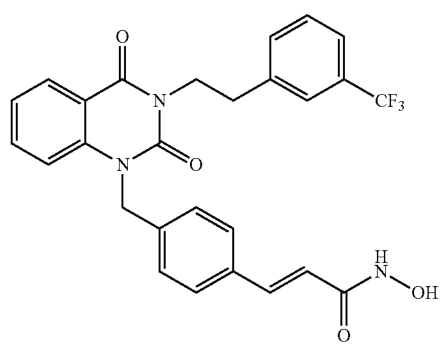 [SMILES: O=C(/C=C/c1ccc(Cn2c(=O)n(CCc3cccc(C(F)(F)F)c3)c(=O)c3ccccc32)cc1)NO] | A = $C_6H_4$<br>B = $C_6H_4$<br>R = $CH_2CH_2$-(3-$CF_3$—$C_6H_4$)<br>Y = (E)-ethylene |
| 80 | 4-((3-(2,6-diisopropylphenyl)-2,4-dioxo-3,4-dihydroquinazolin-1(2H)-yl)methyl)-N-hydroxybenzamide | 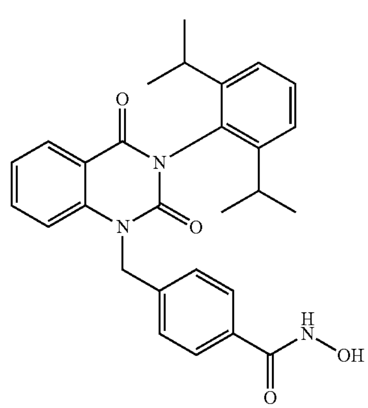 [SMILES: CC(C)c1cccc(C(C)C)c1-n1c(=O)c2ccccc2n(Cc2ccc(C(=O)NO)cc2)c1=O] | A = $C_6H_4$<br>B = $C_6H_4$<br>R = 2,6-di-iso-proyl-$C_6H_3$<br>Y = null |

TABLE 5-continued

| Cpd No. | Chemical Name | Structure | Substituents of Formula I |
|---|---|---|---|
| 81 | 4-((3-(2-ethylphenyl)-2,4-dioxo-3,4-dihydroquinazolin-1(2H)-yl)methyl)-N-hydroxybenzamide | 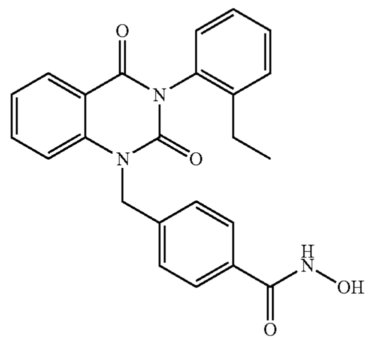 [SMILES: CCc1ccccc1-n1c(=O)c2ccccc2n(Cc2ccc(C(=O)NO)cc2)c1=O] | A = $C_6H_4$<br>B = $C_6H_4$<br>R = 2-Et—$C_6H_4$<br>Y = null |
| 82 | (E)-3-(4-((3-(2-fluorophenyl)-2,4-dioxo-3,4-dihydroquinazolin-1(2H)-yl)methyl)phenyl-N-hydroxyacrylamide | 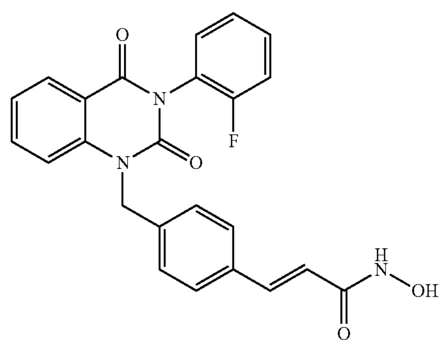 [SMILES: O=C(/C=C/c1ccc(Cn2c(=O)n(-c3ccccc3F)c(=O)c3ccccc32)cc1)NO] | A = $C_6H_4$<br>B = $C_6H_4$<br>R = 2-F—$C_6H_4$<br>Y = (E)-ethylene |
| 83 | N-hydroxy-4-((3-(2-methyl-3-(trifluoromethyl)phenyl)-2,4-dioxo-3,4-dihydroquinazolin-1(2H)-yl)methyl)benzamide | 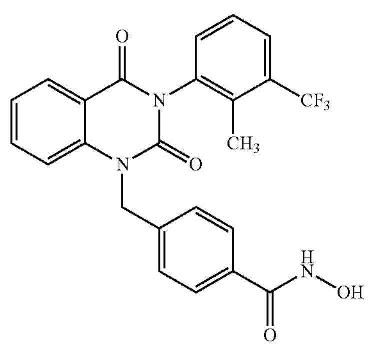 [SMILES: Cc1c(-n2c(=O)c3ccccc3n(Cc3ccc(C(=O)NO)cc3)c2=O)cccc1C(F)(F)F] | A = $C_6H_4$<br>B = $C_6H_4$<br>R = 2-Me-3-$CF_3$—$C_6H_3$<br>Y = null |
| 84 | N-hydroxy-4-((3-(3-methoxyphenethyl)-2,4-dioxo-3,4-dihydroquinazolin-1(2H)-yl)methyl)benzamide | 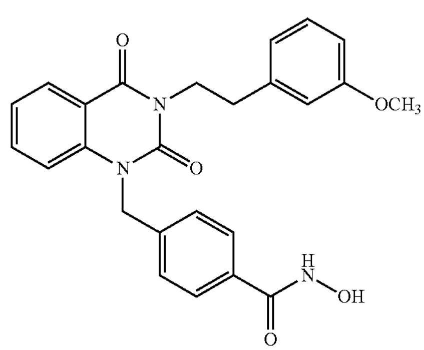 [SMILES: COc1cccc(CCn2c(=O)c3ccccc3n(Cc3ccc(C(=O)NO)cc3)c2=O)c1] | A = $C_6H_4$<br>B = $C_6H_4$<br>R = $CH_2CH_2$-(3-OMe—$C_6H_4$)<br>Y = null |

TABLE 5-continued

| Cpd No. | Chemical Name | Structure | Substituents of Formula I |
|---|---|---|---|
| 85 | 4-((3-(2-(benzo[d][1,3]dioxol-5-yl)ethyl)-2,4-dioxo-3,4-dihydroquinazolin-1(2H)-yl)methyl)-N-hydroxybenzamide | 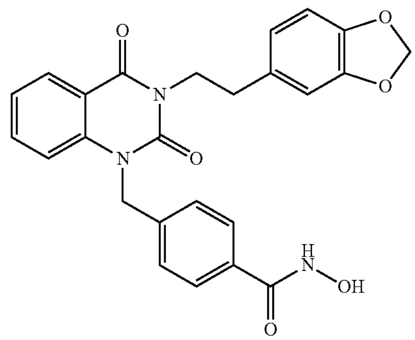 [SMILES: O=C(NO)c1ccc(Cn2c(=O)n(CCc3ccc4c(c3)OCO4)c(=O)c3ccccc32)cc1] | A = C$_6$H$_4$<br>B = C$_6$H$_4$<br>R = CH$_2$CH$_2$-(6-(1,3-benzodioxole))<br>Y = null |
| 86 | 4-((3-(3,4-dimethoxyphenethyl)-2,4-dioxo-3,4-dihydroquinazolin-1(2H)-yl)methyl)-N-hydroxybenzamide | 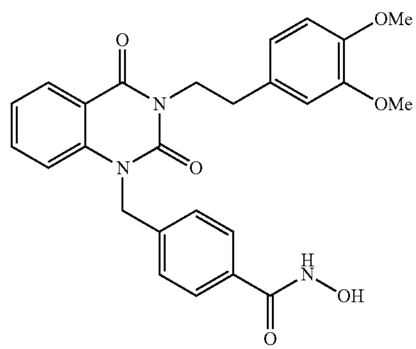 [SMILES: COc1ccc(CCn2c(=O)c3ccccc3n(Cc3ccc(C(=O)NO)cc3)c2=O)cc1OC] | A = C$_6$H$_4$<br>B = C$_6$H$_4$<br>R = CH$_2$CH$_2$-(3,4-diOMe—C$_6$H$_3$)<br>Y = null |
| 87 | 4-((6-fluoro-7-hydroxy-2,4-dioxo-3-(3-(trifluoromethyl)phenethyl)-3,4-dihydroquinazolin-1(2H)-yl)methyl)-N-hydroxybenzamide | 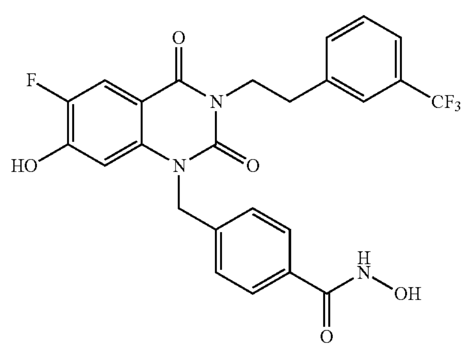 [SMILES: O=C(NO)c1ccc(Cn2c(=O)n(CCc3cccc(C(F)(F)F)c3)c(=O)c3cc(F)c(O)cc32)cc1] | A = 6-F-7-OH—C$_6$H$_2$<br>B = C$_6$H$_4$<br>R = CH$_2$CH$_2$-(3-CF$_3$—C$_6$H$_4$)<br>Y = null |
| 88 | 4-((3-(4-bromophenethyl)-2,4-dioxo-3,4-dihydroquinazolin-1(2H)-yl)methyl)-N-hydroxybenzamide | 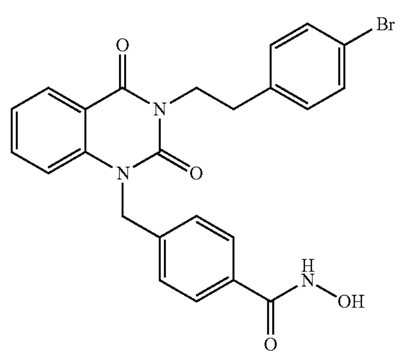 [SMILES: O=C(NO)c1ccc(Cn2c(=O)n(CCc3ccc(Br)cc3)c(=O)c3ccccc32)cc1] | A = C$_6$H$_4$<br>B = C$_6$H$_4$<br>R = CH$_2$CH$_2$-(4-Br—C$_6$H$_4$)<br>Y = null |

TABLE 5-continued

| Cpd No. | Chemical Name | Structure | Substituents of Formula I |
|---|---|---|---|
| 89 | 4-((3-(2,6-dimethylphenyl)-2,4-dioxo-3,4-dihydroquinazolin-1(2H)-yl)methyl)-N-hydroxybenzamide | 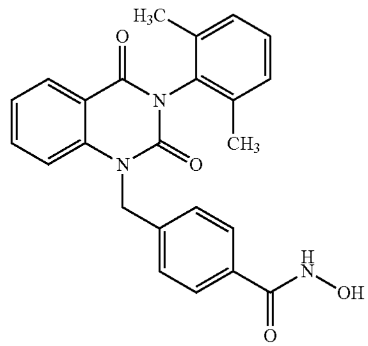 [SMILES: Cc1cccc(C)c1-n1c(=O)c2ccccc2n(Cc2ccc(C(=O)NO)cc2)c1=O] | A = $C_6H_4$<br>B = $C_6H_4$<br>R = 2,6-di-Me—$C_6H_3$<br>Y = null |
| 90 | 4-((2,4-dioxo-3-(2-(trifluoromethoxy)phenyl)-3,4-dihydroquinazolin-1(2H)-yl)methyl)-N-hydroxybenzamide | 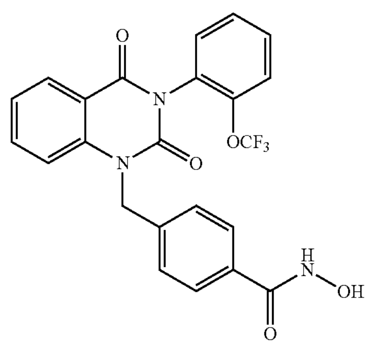 [SMILES: O=C(NO)c1ccc(Cn2c(=O)n(-c3ccccc3OC(F)(F)F)c(=O)c3ccccc32)cc1] | A = $C_6H_4$<br>B = $C_6H_4$<br>R = 2-$OCF_3$—$C_6H_4$<br>Y = null |
| 91 | 4-((2,4-dioxo-3-(o-tolyl)-3,4-dihydroquinazolin-1(2H)-yl)methyl)-N-hydroxybenzamide | 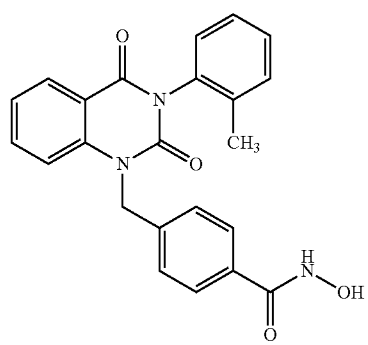 [SMILES: Cc1ccccc1-n1c(=O)c2ccccc2n(Cc2ccc(C(=O)NO)cc2)c1=O] | A = $C_6H_4$<br>B = $C_6H_4$<br>R = 2-Me—$C_6H_4$<br>Y = null |
| 92 | 4-((3-cyclohexyl-2,4-dioxo-3,4-dihydroquinazolin-1(2H)-yl)methyl)-N-hydroxybenzamide | 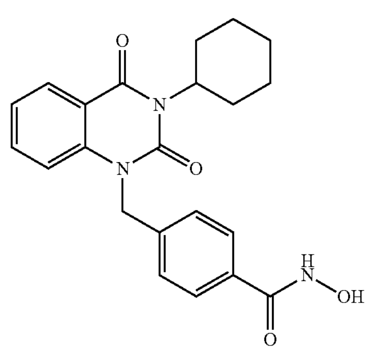 [SMILES: O=C(NO)c1ccc(Cn2c(=O)n(C3CCCCC3)c(=O)c3ccccc32)cc1] | A = $C_6H_4$<br>B = $C_6H_4$<br>R = cyclohexyl<br>Y = null |

TABLE 5-continued

| Cpd No. | Chemical Name | Structure | Substituents of Formula I |
|---|---|---|---|
| 93 | N-hydroxy-4-((3-(1-methylpiperidin-4-yl)-2,4-dioxo-3,4-dihydroquinazolin-1(2H)-yl)methyl)benzamide | 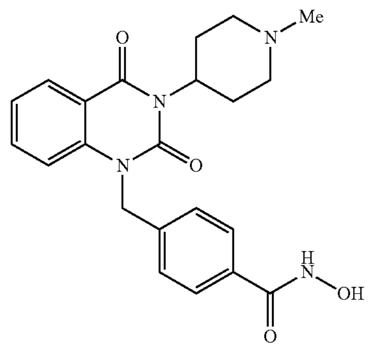 [SMILES: CN1CCC(n2c(=O)c3ccccc3n(Cc3ccc(C(=O)NO)cc3)c2=O)CC1] | A = C$_6$H$_4$<br>B = C$_6$H$_4$<br>R = 4-(N-Me-piperidine)<br>Y = null |
| 94 | 4-((2,4-dioxo-3-(pyridin-4-yl)-3,4-dihydroquinazolin-1(2H)-yl)methyl)-N-hydroxybenzamide | 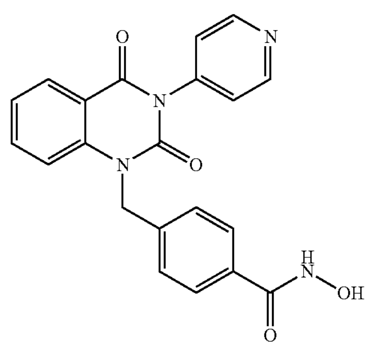 [SMILES: O=C(NO)c1ccc(Cn2c(=O)n(-c3ccncc3)c(=O)c3ccccc32)cc1] | A = C$_6$H$_4$<br>B = C$_6$H$_4$<br>R = 4-pyridine<br>Y = null |
| 95 | 4-((2,4-dioxo-3-(3-(trifluoromethyl)phenyl)-3,4-dihydroquinazolin-1(2H)-yl)methyl)-N-hydroxybenzamide | 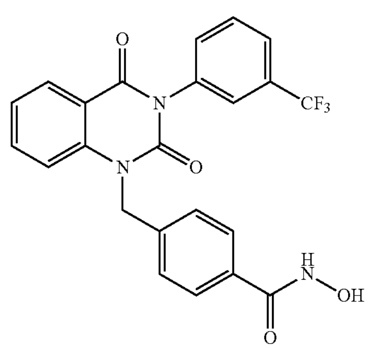 [SMILES: O=C(NO)c1ccc(Cn2c(=O)n(-c3cccc(C(F)(F)F)c3)c(=O)c3ccccc32)cc1] | A = C$_6$H$_4$<br>B = C$_6$H$_4$<br>R = 3-CF$_3$—C$_6$H$_4$<br>Y = null |
| 96 | 4-((2,4-dioxo-3-(pyridin-3-yl)-3,4-dihydroquinazolin-1(2H)-yl)methyl)-N-hydroxybenzamide | 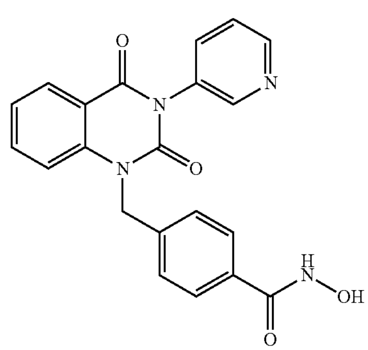 [SMILES: O=C(NO)c1ccc(Cn2c(=O)n(-c3cccnc3)c(=O)c3ccccc32)cc1] | A = C$_6$H$_4$<br>B = C$_6$H$_4$<br>R = 3-pyridine<br>Y = null |

TABLE 5-continued

| Cpd No. | Chemical Name | Structure | Substituents of Formula I |
|---|---|---|---|
| 97 | 4-((3-(3,3-difluorocyclobutyl)-2,4-dioxo-3,4-dihydroquinazolin-1(2H)-yl)methyl)-N-hydroxybenzamide | 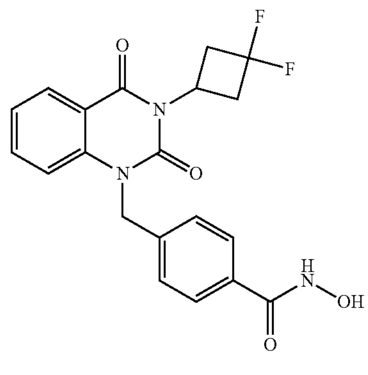 [SMILES: O=C(NO)c1ccc(Cn2c(=O)n(C3CC(F)(F)C3)c(=O)c3ccccc32)cc1] | A = C$_6$H$_4$<br>B = C$_6$H$_4$<br>R = 3,3-di-F-cyclobutayl<br>Y = null |
| 98 | 4-((2,4-dioxo-3-(piperidin-3-yl)-3,4-dihydroquinazolin-1(2H)-yl)methyl)-N-hydroxybenzamide | 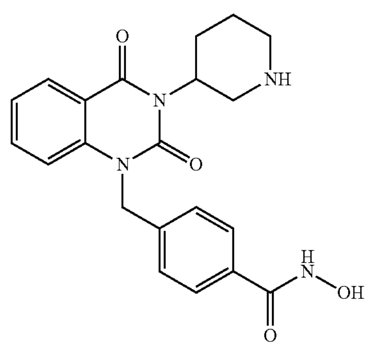 [SMILES: O=C(NO)c1ccc(Cn2c(=O)n(C3CCCNC3)c(=O)c3ccccc32)cc1] | A = C$_6$H$_4$<br>B = C$_6$H$_4$<br>R = 3-piperidine<br>Y = null |
| 99 | N-acetoxy-4-((2,4-dioxo-3-phenethyl-3,4-dihydroquinazolin-1(2H)-yl)methyl)benzamide | 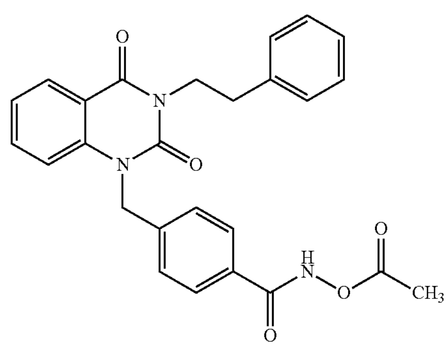 [SMILES: CC(=O)ONC(=O)c1ccc(Cn2c(=O)n(CCc3ccccc3)c(=O)c3ccccc32)cc1] | A = C$_6$H$_4$<br>B = C$_6$H$_4$<br>R = CH$_2$CH$_2$C$_6$H$_5$<br>Y = null<br>*: O-acetyl |
| 100 | 4-((2,4-dioxo-3-(3-(trifluoromethyl)phenethyl)-3,4-dihydroquinazolin-1(2H)-yl)methyl)-N-hydroxybenzamide | 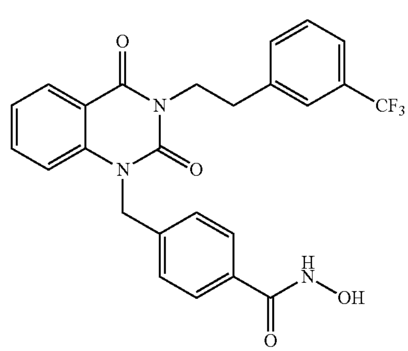 [SMILES: O=C(NO)c1ccc(Cn2c(=O)n(CCc3cccc(C(F)(F)F)c3)c(=O)c3ccccc32)cc1] | A = C$_6$H$_4$<br>B = C$_6$H$_4$<br>R = CH$_2$CH$_2$-(3-CF$_3$—C$_6$H$_4$)<br>Y = null |

TABLE 5-continued

| Cpd No. | Chemical Name | Structure | Substituents of Formula I |
|---|---|---|---|
| 101 | 4-((2,4-dioxo-3-(2-(trifluoromethoxy)benzyl)-3,4-dihydroquinazolin-1(2H)-yl)methyl)-N-hydroxybenzamideS | 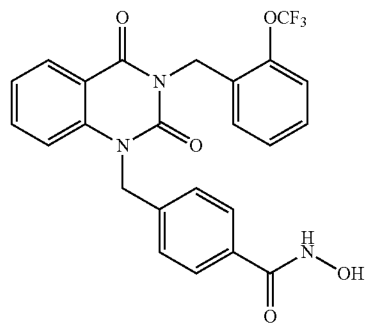 [SMILES: O=C(NO)c1ccc(Cn2c(=O)n(Cc3ccccc3OC(F)(F)F)c(=O)c3ccccc32)cc1] | A = $C_6H_4$<br>B = $C_6H_4$<br>R = $CH_2$-(2-$OCF_3$—$C_6H_4$)<br>Y = null |
| 102 | 4-((2,4-dioxo-3-(2-(trifluoromethyl)phenethyl)-3,4-dihydroquinazolin-1(2H)-yl)methyl)-N-hydroxybenzamide | 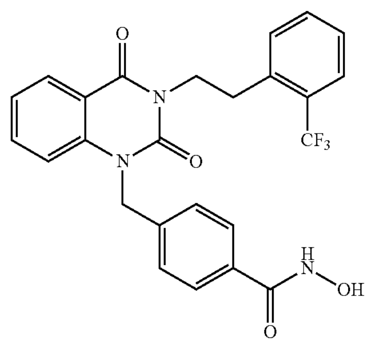 [SMILES: O=C(NO)c1ccc(Cn2c(=O)n(CCc3ccccc3C(F)(F)F)c(=O)c3ccccc32)cc1] | A = $C_6H_4$<br>B = $C_6H_4$<br>R = $CH_2CH_2$-(2-$CF_3$—$C_6H_4$)<br>Y = null |
| 103 | N-acetoxy-4-((2,4-dioxo-3-(3-(trifluoromethyl)phenethyl)-3,4-dihydroquinazolin-1(2H)-yl)methyl)benzamide | 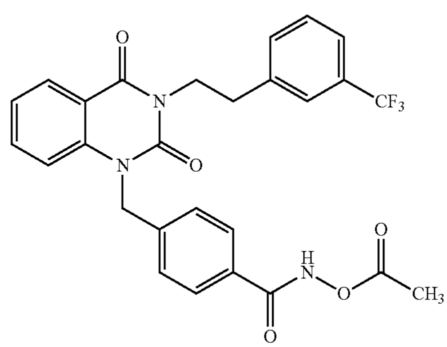 [SMILES: CC(=O)ONC(=O)c1ccc(Cn2c(=O)n(CCc3cccc(C(F)(F)F)c3)c(=O)c3ccccc32)cc1] | A = $C_6H_4$<br>B = $C_6H_4$<br>R = $CH_2CH_2$-(3-$CF_3$—$C_6H_4$)<br>Y = null<br>*: O-acetyl |
| 104 | 3-(1-(4-(hydroxycarbamoyl)benzyl)-2,4-dioxo-1,2-dihydroquinazolin-3(4H)-yl)-1,1-dimethylpiperidin-1-ium | 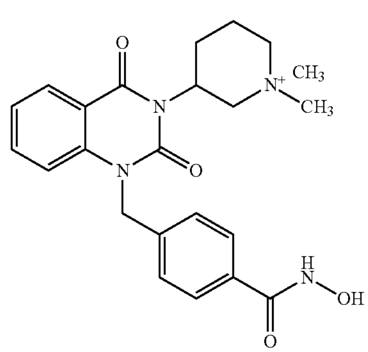 | A = $C_6H_4$<br>B = $C_6H_4$<br>R = 3-(N,N-di-Me-piperidinium)<br>Y = null |

TABLE 5-continued

| Cpd No. | Chemical Name | Structure | Substituents of Formula I |
|---|---|---|---|
| 105 | 4-((3-(1-ethylpiperidin-3-yl)-2,4-dioxo-3,4-dihydroquinazolin-1(2H)-yl)methyl)-N-hydroxybenzamide | 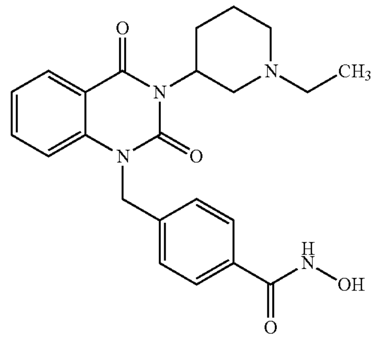 [SMILES: CCN1CCCC(n2c(=O)c3ccccc3n(Cc3ccc(C(=O)NO)cc3)c2=O)C1] | A = C$_6$H$_4$<br>B = C$_6$H$_4$<br>R = 3-(N-Et-piperidine)<br>Y = null |
| 106 | N-hydroxy-4-((3-(4-(2-hydroxyethoxy)phenethyl)-2,4-dioxo-3,4-dihydroquinazolin-1(2H)-yl)methyl)benzamide | 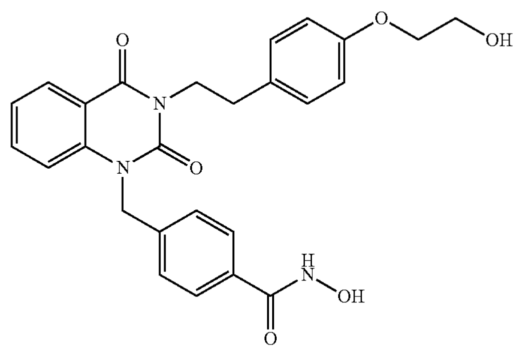 [SMILES: O=C(NO)c1ccc(Cn2c(=O)n(CCc3ccc(OCCO)cc3)c(=O)c3ccccc32)cc1] | A = C$_6$H$_4$<br>B = C$_6$H$_4$<br>R = CH$_2$CH$_2$-(4-(OCH$_2$CH$_2$OH)—C$_6$H$_4$)<br>Y = null |
| 107 | 1-((4-((2,4-dioxo-3-(3-(trifluoromethyl)phenethyl)-3,4-dihydroquinazolin-1(2H)-yl)methyl)benzamido)oxy)-3-methyl-1-oxobutan-2-aminium chloride | 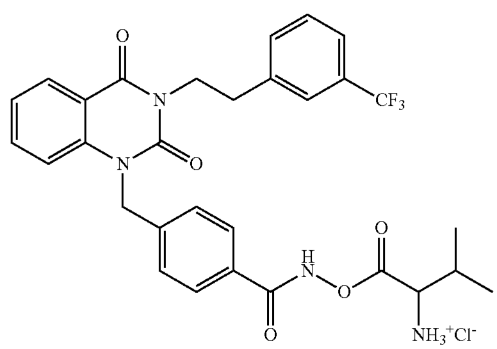 | A = C$_6$H$_4$<br>B = C$_6$H$_4$<br>R = CH$_2$CH$_2$-(3-CF$_3$—C$_6$H$_4$)<br>Y = null<br>*: N-O-Val hydrochloride salt |
| 108 | 4-((2,4-dioxo-3-phenethyl-3,4-dihydroquinazolin-1(2H)-yl)methyl)-N-hydroxy-3-methoxybenzamide | 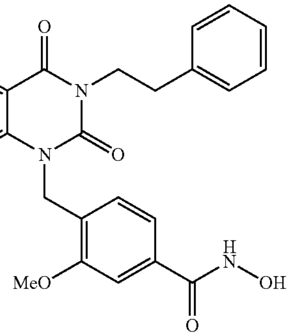 | A = C$_6$H$_4$<br>B = 3-OMe—C$_6$H$_3$<br>R = CH$_2$CH$_2$C$_6$H$_5$<br>Y = null |

TABLE 5-continued

| Cpd No. | Chemical Name | Structure | Substituents of Formula I |
|---|---|---|---|
| 109 | 4-((2,4-dioxo-3-phenethyl-3,4-dihydroquinazolin-1(2H)-yl)methyl)-N-hydroxy-2-methylbenzamide | 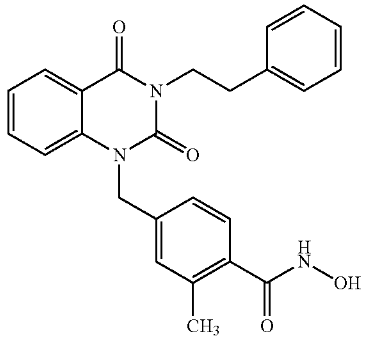 [SMILES: Cc1cc(Cn2c(=O)n(CCc3ccccc3)c(=O)c3ccccc32)ccc1C(=O)NO] | A = C$_6$H$_4$<br>B = 2-Me—C$_6$H$_3$<br>R = CH$_2$CH$_2$C$_6$H$_5$<br>Y = null |
| 110 | 4-((2,4-dioxo-3-phenethyl-3,4-dihydroquinazolin-1(2H)-yl)methyl)-2-fluoro-N-hydroxybenzamide | 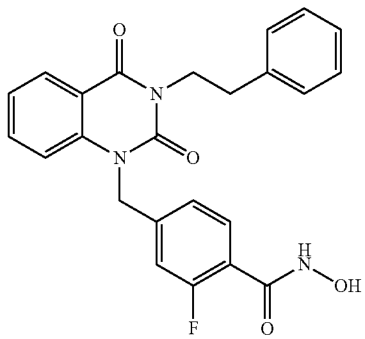 [SMILES: O=C(NO)c1ccc(Cn2c(=O)n(CCc3ccccc3)c(=O)c3ccccc32)cc1F] | A = C$_6$H$_4$<br>B = 2-F—C$_6$H$_3$<br>R = CH$_2$CH$_2$C$_6$H$_5$<br>Y = null |
| 111 | 4-((3-(3,4-dihydroxyphenethyl)-2,4-dioxo-3,4-dihydroquinazolin-1(2H)-yl)methyl)-N-hydroxybenzamide | 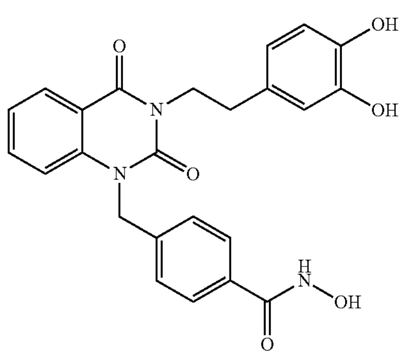 [SMILES: O=C(NO)c1ccc(Cn2c(=O)n(CCc3ccc(O)c(O)c3)c(=O)c3ccccc32)cc1] | A = C$_6$H$_4$<br>B = C$_6$H$_4$<br>R = CH$_2$CH$_2$-(3,4-di-OH—C$_6$H$_3$)<br>Y = null |
| 112 | 4-((2,4-dioxo-3-(3-(trifluoromethyl)phenethyl)-3,4-dihydroquinazolin-1(2H)-yl)methyl)-N-hydroxycyclohexane-carboxamide | 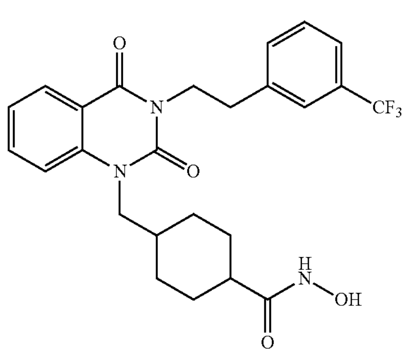 [SMILES: O=C(NO)C1CCC(Cn2c(=O)n(CCc3cccc(C(F)(F)F)c3)c(=O)c3ccccc32)CC1] | A = C$_6$H$_4$<br>B = C$_6$H$_8$<br>R = CH$_2$CH$_2$-(3-CF$_3$—C$_6$H$_4$)<br>Y = null |

TABLE 5-continued

| Cpd No. | Chemical Name | Structure | Substituents of Formula I |
|---|---|---|---|
| 113 | 4-((3-(2-chlorophenyl)-2,4-dioxo-3,4-dihydroquinazolin-1(2H)-yl)methyl)-N-hydroxybenzamide | 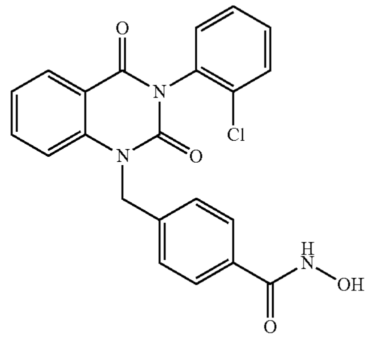 | A = C₆H₄<br>B = C₆H₄<br>R = 2-Cl—C₆H₄<br>Y = null |
| 114 | 4-((3-(3-fluorophenyl)-2,4-dioxo-3,4-dihydroquinazolin-1(2H)-yl)methyl)-N-hydroxybenzamide | 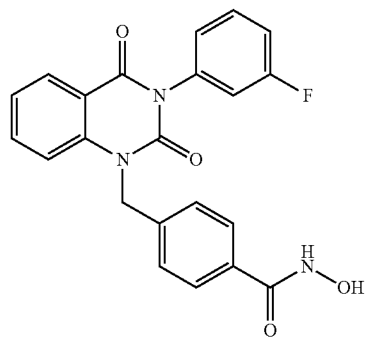 [SMILES: O=C(NO)c1ccc(Cn2c(=O)n(-c3cccc(F)c3)c(=O)c3ccccc32)cc1] | A = C₆H₄<br>B = C₆H₄<br>R = 3-F—C₆H₄<br>Y = null |
| 115 | N-acetoxy-4-((3-(2-fluorophenyl)-2,4-dioxo-3,4-dihydroquinazolin-1(2H)-yl)methyl)benzamide | 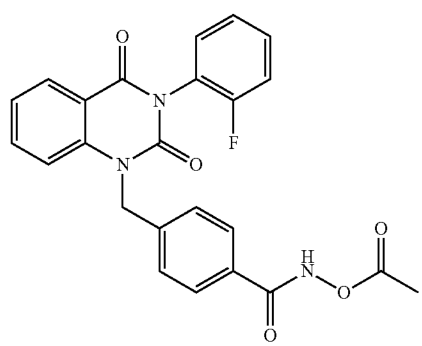 [SMILES: CC(=O)ONC(=O)c1ccc(Cn2c(=O)n(-c3ccccc3F)c(=O)c3ccccc32)cc1] | A = C₆H₄<br>B = C₆H₄<br>R = 2-F—C₆H₄<br>Y = null |
| 116 | 1-((4-((2,4-dioxo-3-phenethyl-3,4-dihydroquinazolin-1(2H)-yl)methyl)benzamido)oxy)-3-methyl-1-oxobutan-2-aminium trifluoroacetate | 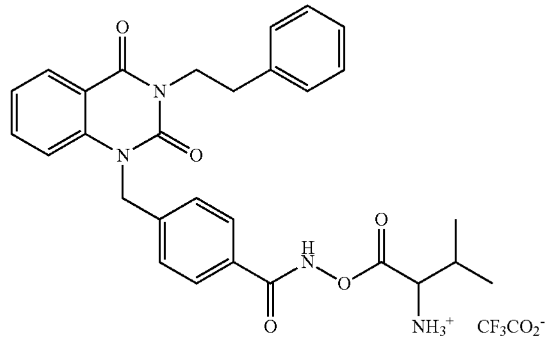 | A = C₆H₄<br>B = C₆H₄<br>R = CH₂CH₂C₆H₅<br>Y = null<br>*: N-Val trifluoroacetic acid salt |

TABLE 5-continued

| Cpd No. | Chemical Name | Structure | Substituents of Formula I |
|---|---|---|---|
| 117 | 4-((3-cyclopropyl-2,4-dioxo-3,4-dihydroquinazolin-1(2H)-yl)methyl)-N-hydroxybenzamide | 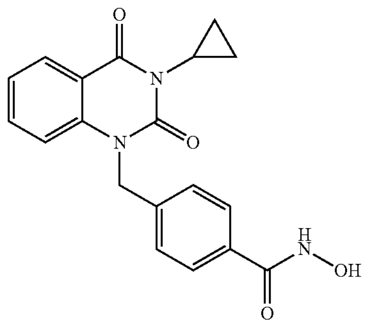 [SMILES: O=C(NO)c1ccc(Cn2c(=O)n(C3CC3)c(=O)c3ccccc32)cc1] | A = C$_6$H$_4$<br>B = C$_6$H$_4$<br>R = cyclopropyl<br>Y = null |
| 118 | 4-((3-(cyclopropylmethyl)-2,4-dioxo-3,4-dihydroquinazolin-1(2H)-yl)methyl)-N-hydroxybenzamide | 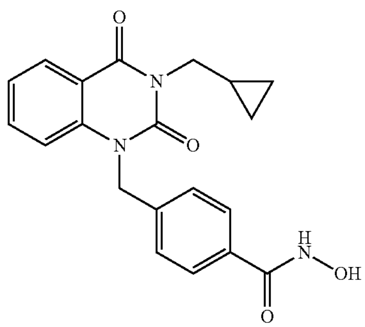 [SMILES: O=C(NO)c1ccc(Cn2c(=O)n(CC3CC3)c(=O)c3ccccc32)cc1] | A = C$_6$H$_4$<br>B = C$_6$H$_4$<br>R = CH$_2$-cyclopropyl<br>Y = null |
| 119 | 4-((2,4-dioxo-3-(4-(2-(piperidin-1-yl)ethoxy)phenethyl)-3,4-dihydroquinazolin-1(2H)-yl)methyl)-N-hydroxybenzamide | 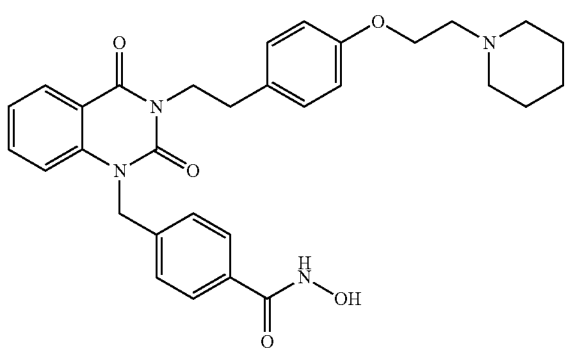 [SMILES: O=C(NO)c1ccc(Cn2c(=O)n(CCc3ccc(OCCN4CCCCC4)cc3)c(=O)c3ccccc32)cc1] | A = C$_6$H$_4$<br>B = C$_6$H$_4$<br>R = CH$_2$CH$_2$-(4-OCH$_2$CH$_2$-N-piperidine-C$_6$H$_4$)<br>Y = null |
| 120 | N-hydroxy-4-((6-(2-methoxyethoxy)-2,4-dioxo-3-phenethyl-3,4-dihydroquinazolin-1(2H)-yl)methyl)benzamide | 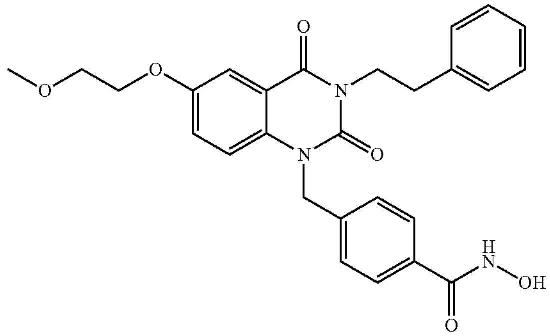 [SMILES: COCCOc1ccc2c(c1)c(=O)n(CCc1ccccc1)c(=O)n2Cc1ccc(C(=O)NO)cc1] | A = 6-(OCH$_2$CH$_2$OMe)—C$_6$H$_3$<br>B = C$_6$H$_4$<br>R = CH$_2$CH$_2$C$_6$H$_5$<br>Y = null |

TABLE 5-continued

| Cpd No. | Chemical Name | Structure | Substituents of Formula I |
|---|---|---|---|
| 121 | 6-((2,4-dioxo-3-(3-(trifluoromethyl)phenethyl)-3,4-dihydroquinazolin-1(2H)-yl)methyl)-N-hydroxynicotinamide | 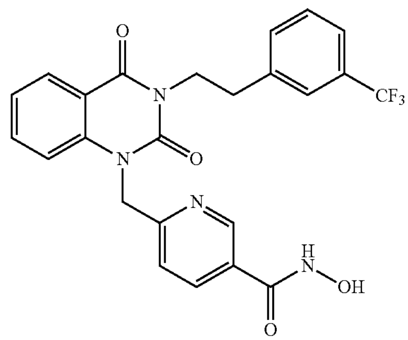 [SMILES: O=C(NO)c1ccc(Cn2c(=O)n(CCc3cccc(C(F)(F)F)c3)c(=O)c3ccccc32)nc1] | A = $C_6H_4$<br>B = 3-pyridine<br>R = $CH_2CH_2$-(3-$CF_3$—$C_6H_4$)<br>Y = null |
| 122 | 4-((3-(2-fluorocyclopentyl)-2,4-dioxo-3,4-dihydroquinazolin-1(2H)-yl)methyl)-N-hydroxybenzamide | 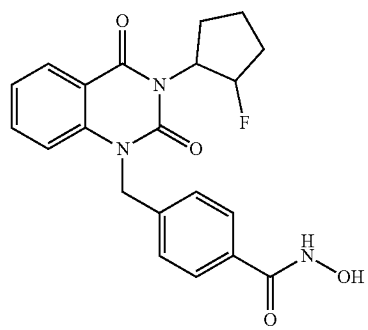 [SMILES: O=C(NO)c1ccc(Cn2c(=O)n(C3CCCC3F)c(=O)c3ccccc32)cc1] | A = $C_6H_4$<br>B = $C_6H_4$<br>R = 2-F-cyclopentyl<br>Y = null |
| 123 | 7-hydroxy-4-((3-(2-morpholinoethyl)-2,4-dioxo-3,4-dihydroquinazolin-1(2H)-yl)methyl)benzamide | 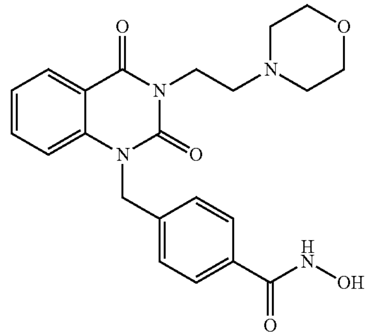 [SMILES: O=C(NO)c1ccc(Cn2c(=O)n(CCN3CCOCC3)c(=O)c3ccccc32)cc1] | A = $C_6H_4$<br>B = $C_6H_4$<br>R = $CH_2CH_2$-(N-morpholine)<br>Y = null |
| 124 | 4-((3-(2,4-difluorophenyl)-2,4-dioxo-3,4-dihydroquinazolin-1(2H)-yl)methyl)-N-hydroxybenzamide | 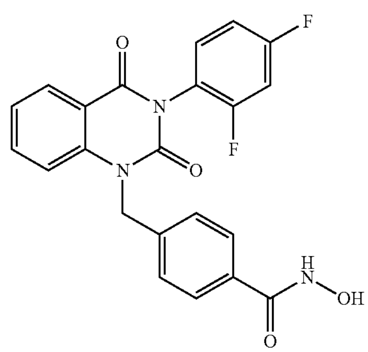 [SMILES: O=C(NO)c1ccc(Cn2c(=O)n(-c3ccc(F)cc3F)c(=O)c3ccccc32)cc1] | A = $C_6H_4$<br>B = $C_6H_4$<br>R = 2,4-di-F—$C_6H_3$<br>Y = null |

TABLE 5-continued

| Cpd No. | Chemical Name | Structure | Substituents of Formula I |
|---|---|---|---|
| 125 | 4-((2,4-dioxo-3-(pyridin-2-yl)-3,4-dihydroquinazolin-1(2H)-yl)methyl)-N-hydroxybenzamide | 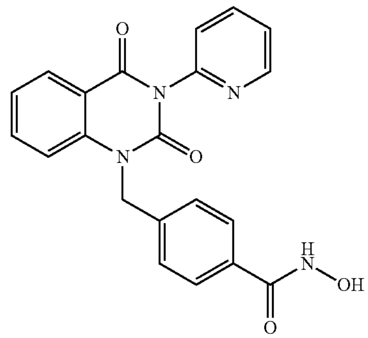 [SMILES: O=C(NO)c1ccc(Cn2c(=O)n(-c3ccccn3)c(=O)c3ccccc32)cc1] | A = C_6H_4<br>B = C_6H_4<br>R = 2-pyridine<br>Y = null |
| 126 | 4-((2,4-dioxo-3-(2-(trifluoromethyl)phenyl)-3,4-dihydroquinazolin-1(2H)-yl)methyl)-N-hydroxybenzamide | 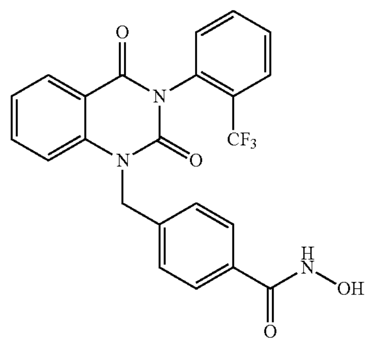 [SMILES: O=C(NO)c1ccc(Cn2c(=O)n(-c3ccccc3C(F)(F)F)c(=O)c3ccccc32)cc1] | A = C_6H_4<br>B = C_6H_4<br>R = 2-CF_3—C_6H_4<br>Y = null |
| 127 | 4-((3-(2-(tert-butyl)phenyl)-2,4-dioxo-3,4-dihydroquinazolin-1(2H)-yl)methyl)-N-hydroxybenzamide | 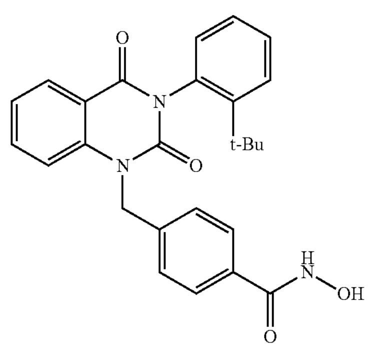 [SMILES: CC(C)(C)c1ccccc1-n1c(=O)c2ccccc2n(Cc2ccc(C(=O)NO)cc2)c1=O] | A = C_6H_4<br>B = C_6H_4<br>R = 2-t-Bu—C_6H_4<br>Y = null |
| 128 | N-hydroxy-4-((3-(4-(morpholinomethyl)phenyl)-2,4-dioxo-3,4-dihydroquinazolin-1(2H)-yl)methyl)benzamide | 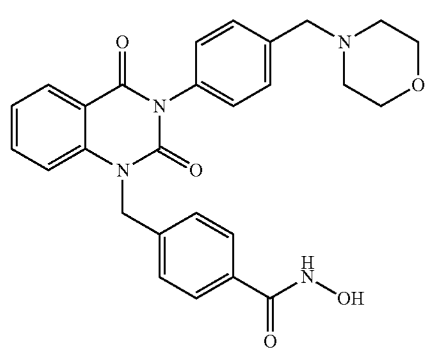 [SMILES: O=C(NO)c1ccc(Cn2c(=O)n(-c3ccc(CN4CCOCC4)cc3)c(=O)c3ccccc32)cc1] | A = C_6H_4<br>B = C_6H_4<br>R = 4-CH_2-(N-morpholine)-C_6H_4<br>Y = null |

TABLE 5-continued

| Cpd No. | Chemical Name | Structure | Substituents of Formula I |
|---|---|---|---|
| 129 | 4-((2,4-dioxo-3-(2-(3-(trifluoromethyl)phenoxy)ethyl)-3,4-dihydroquinazolin-1(2H)-yl)methyl)-N-hydroxybenzamide | 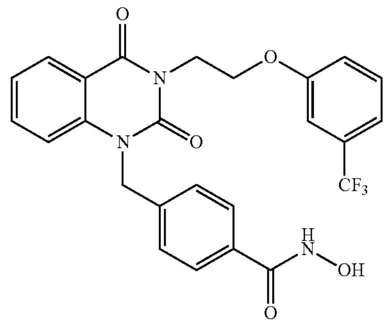 [SMILES: O=C(NO)c1ccc(Cn2c(=O)n(CCOc3cccc(C(F)(F)F)c3)c(=O)c3ccccc32)cc1] | A = C$_6$H$_4$<br>B = C$_6$H$_4$<br>R = CH$_2$CH$_2$-(O-3-CF$_3$—C$_6$H$_4$)<br>Y = null |
| 130 | 4-((2,4-dioxo-3-(2-phenylpropyl)-3,4-dihydroquinazolin-1(2H)-yl)methyl)-N-hydroxybenzamide | 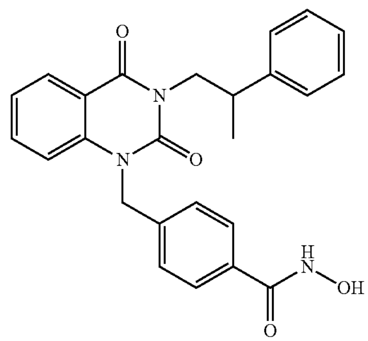 [SMILES: CC(Cn1c(=O)c2ccccc2n(Cc2ccc(C(=O)NO)cc2)c1=O)c1ccccc1] | A = C$_6$H$_4$<br>B = C$_6$H$_4$<br>R = propyl-2-C$_6$H$_5$<br>Y = null |
| 131 | N-hydroxy-4-((3-(4-(morpholinomethyl)phenethyl)-2,4-dioxo-3,4-dihydroquinazolin-1(2H)-yl)methyl)benzamide | 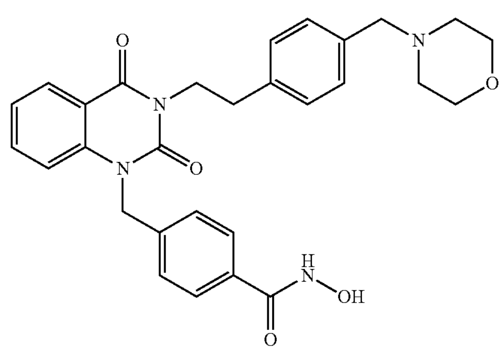 [SMILES: O=C(NO)c1ccc(Cn2c(=O)n(CCc3ccc(CN4CCOCC4)cc3)c(=O)c3ccccc32)cc1] | A = C$_6$H$_4$<br>B = C$_6$H$_4$<br>R = CH$_2$CH$_2$-(4-CH$_2$-(N-morpholine)-C$_6$H$_4$)<br>Y = null |
| 132 | 4-((2,4-dioxo-3-(4-(piperidin-1-ylmethyl)phenethyl)-3,4-dihydroquinazolin-1(2H)-yl)methyl)-N-hydroxybenzamide | 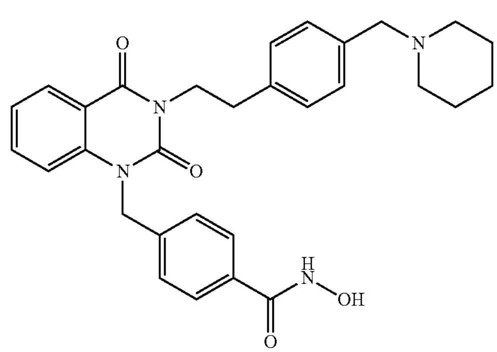 [SMILES: O=C(NO)c1ccc(Cn2c(=O)n(CCc3ccc(CN4CCCCC4)cc3)c(=O)c3ccccc32)cc1] | A = C$_6$H$_4$<br>B = C$_6$H$_4$<br>R = CH$_2$CH$_2$-(4-CH$_2$-(N-piperidine)-C$_6$H$_4$)<br>Y = null |

TABLE 5-continued

| Cpd No. | Chemical Name | Structure | Substituents of Formula I |
|---|---|---|---|
| 133 | N-hydroxy-4-((3-(4-nitrophenethyl)-2,4-dioxo-3,4-dihydroquinazolin-1(2H)-yl)methyl)benzamide | 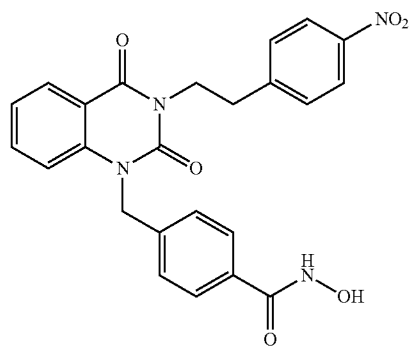 [SMILES: O=C(NO)c1ccc(Cn2c(=O)n(CCc3ccc([N+](=O)[O-])cc3)c(=O)c3ccccc32)cc1] | A = $C_6H_4$<br>B = $C_6H_4$<br>R = $CH_2CH_2$-(4-$NO_2$—$C_6H_4$)<br>Y = null |
| 134 | 4-((3-(4-aminophenethyl)-2,4-dioxo-3,4-dihydroquinazolin-1(2H)-yl)methyl)-N-hydroxybenzamide | 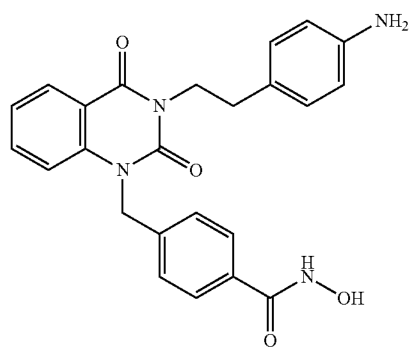 [SMILES: Nc1ccc(CCn2c(=O)c3ccccc3n(Cc3ccc(C(=O)NO)cc3)c2=O)cc1] | A = $C_6H_4$<br>B = $C_6H_4$<br>R = $CH_2CH_2$-(4-$NH_2$—$C_6H_4$)<br>Y = null |
| 135 | 4-(2-(1-(4-(hydroxycarbamoyl)benzyl)-2,4-dioxo-1,2-dihydroquinazolin-3(4H)-yl)ethyl)benzoic acid | 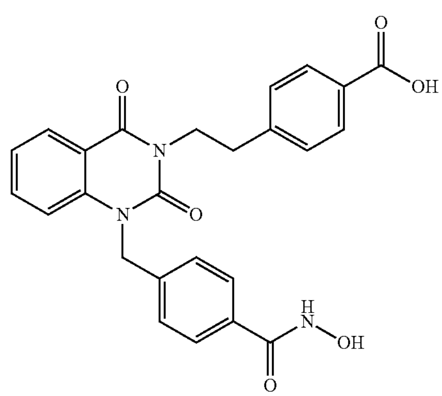 [SMILES: O=C(O)c1ccc(CCn2c(=O)c3ccccc3n(Cc3ccc(C(=O)NO)cc3)c2=O)cc1] | A = $C_6H_4$<br>B = $C_6H_4$<br>R = $CH_2CH_2$-(4-COOH—$C_6H_4$)<br>Y = null |
| 136 | 4-((3-(4-chloro-2,6-dimethylphenyl)-2,4-dioxo-3,4-dihydroquinazolin-1(2H)-yl)methyl)-N-hydroxybenzamide | 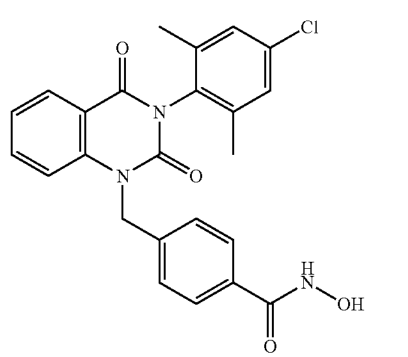 [SMILES: Cc1cc(Cl)cc(C)c1-n1c(=O)c2ccccc2n(Cc2ccc(C(=O)NO)cc2)c1=O] | A = $C_6H_4$<br>B = $C_6H_4$<br>R = (4-Cl-2,6-di-Me—$C_6H_2$)<br>Y = null |

TABLE 5-continued

| Cpd No. | Chemical Name | Structure | Substituents of Formula I |
|---|---|---|---|
| 137 | 4-((3-(4-bromo-2,6-dimethylphenyl)-2,4-dioxo-3,4-dihydroquinazolin-1(2H)-yl)methyl)-N-hydroxybenzamide | 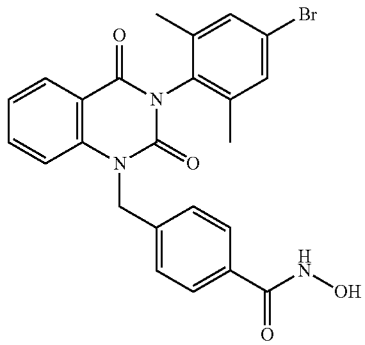 [SMILES: Cc1cc(Br)cc(C)c1-n1c(=O)c2ccccc2n(Cc2ccc(C(=O)NO)cc2)c1=O] | A = $C_6H_4$<br>B = $C_6H_4$<br>R = (4-Br-2,6-di-Me—$C_6H_2$)<br>Y = null |
| 138 | 4-((3-(2-(1H-imidazol-1-yl)ethyl)-2,4-dioxo-3,4-dihydroquinazolin-1(2H)-yl)methyl)-N-hydroxybenzamide | 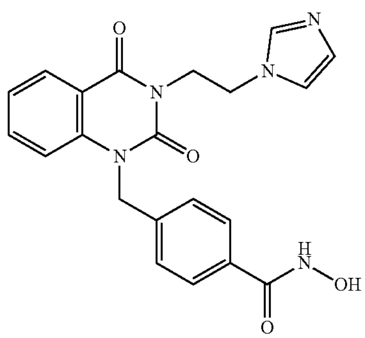 [SMILES: O=C(NO)c1ccc(Cn2c(=O)n(CCn3ccnc3)c(=O)c3ccccc32)cc1] | A = $C_6H_4$<br>B = $C_6H_4$<br>R = $CH_2CH_2$-(N-imidazole)<br>Y = null |
| 139 | 4-((2,4-dioxo-3-phenethyl-3,4-dihydroquinazolin-1(2H)-yl)methyl)-3-fluoro-N-hydroxybenzamide | 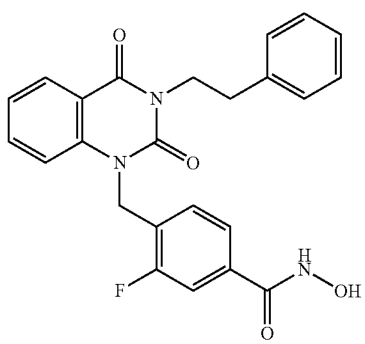 [SMILES: O=C(NO)c1ccc(Cn2c(=O)n(CCc3ccccc3)c(=O)c3ccccc32)c(F)c1] | A = $C_6H_4$<br>B = 3-F—$C_6H_3$<br>R = $CH_2CH_2C_6H_5$<br>Y = null |
| 140 | N-hydroxy-4-((7-methoxy-2,4-dioxo-3-(3-(trifluoromethyl)phenethyl)-3,4-dihydroquinazolin-1(2H)-yl)methyl)-2-methylbenzamide | 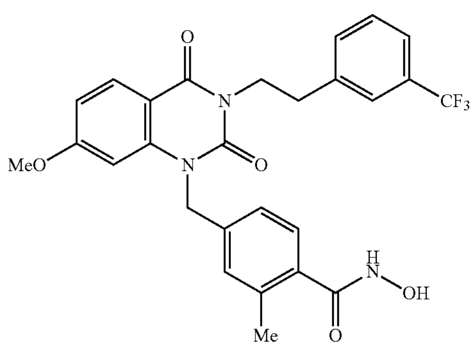 [SMILES: COc1ccc2c(=O)n(CCc3cccc(C(F)(F)F)c3)c(=O)n(Cc3ccc(C(=O)NO)c(C)c3)c2c1] | A = 7-OMe—$C_6H_3$<br>B = 2-Me—$C_6H_3$<br>R = $CH_2CH_2$-(3-$CF_3$—$C_6H_4$)<br>Y = null |

TABLE 5-continued

| Cpd No. | Chemical Name | Structure | Substituents of Formula I |
|---|---|---|---|
| 141 | 4-((2,4-dioxo-3-(4-phenylbutyl)-3,4-dihydroquinazolin-1(2H)-yl)methyl)-N-hydroxybenzamide | 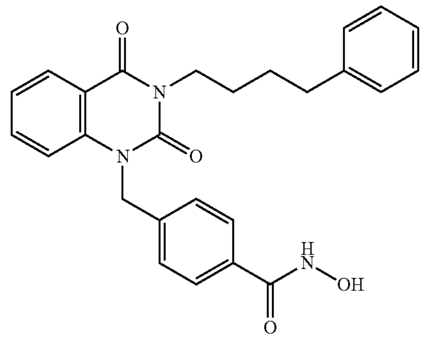 [SMILES: O=C(NO)c1ccc(Cn2c(=O)n(CCCCc3ccccc3)c(=O)c3ccccc32)cc1] | A = $C_6H_4$<br>B = $C_6H_4$<br>R = $(CH_2)_4C_6H_5$<br>Y = null |
| 142 | 4-((3-allyl-2,4-dioxo-3,4-dihydroquinazolin-1(2H)-yl)methyl)-N-hydroxybenzamide | 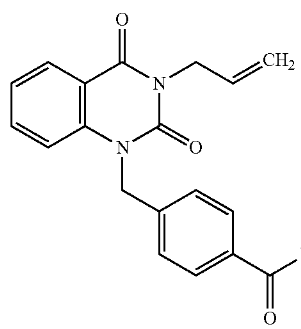 | A = $C_6H_4$<br>B = $C_6H_4$<br>R = $CH_2CHCH_2$<br>Y = null |
| 143 | 4-((3-(2-(cyclohex-1-en-1-yl)ethyl)-2,4-dioxo-3,4-dihydroquinazolin-1(2H)-yl)methyl)-N-hydroxybenzamide | 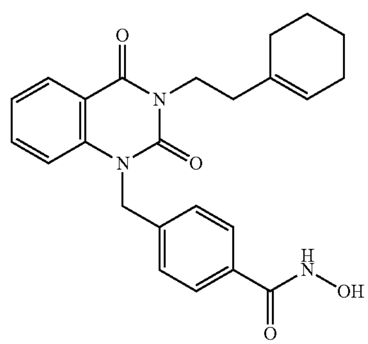 [SMILES: O=C(NO)c1ccc(Cn2c(=O)n(CCC3=CCCCC3)c(=O)c3ccccc32)cc1] | A = $C_6H_4$<br>B = $C_6H_4$<br>R = $CH_2CH_2$-(cyclohexane)<br>Y = null |
| 144 | (E)-4-((3-cinnamyl-2,4-dioxo-3,4-dihydroquinazolin-1(2H)-yl)methyl)-N-hydroxybenzamide | 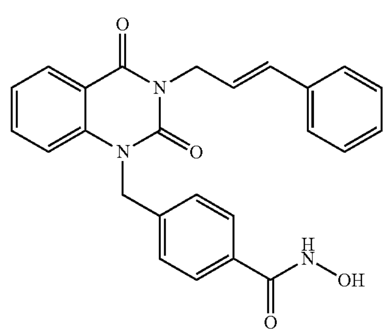 [SMILES: O=C(NO)c1ccc(Cn2c(=O)n(C/C=C/c3ccccc3)c(=O)c3ccccc32)cc1] | A = $C_6H_4$<br>B = $C_6H_4$<br>R = $CH_2CHCHC_6H_5$<br>Y = null |

TABLE 5-continued

| Cpd No. | Chemical Name | Structure | Substituents of Formula I |
|---|---|---|---|
| 145 | 4-((3-(2-(1,2-dihydroxycyclohexyl)ethyl)-2,4-dioxo-3,4-dihydroquinazolin-1(2H)-yl)methyl)-N-hydroxybenzamide | 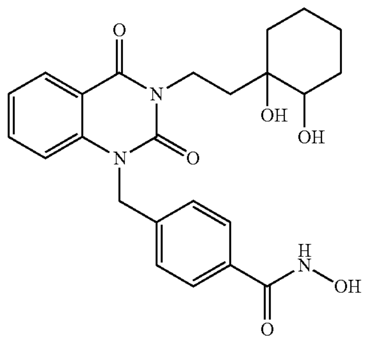 [SMILES: O=C(NO)c1ccc(Cn2c(=O)n(CCC3(O)CCCCC3O)c(=O)c3ccccc32)cc1] | A = $C_6H_4$<br>B = $C_6H_4$<br>R = $CH_2CH_2$-(1,2-OH-cyclohexane)<br>Y = null |
| 146 | 4-((8-chloro-2,4-dioxo-3-phenethyl-3,4-dihydroquinazolin-1(2H)-yl)methyl)-N-hydroxybenzamide | 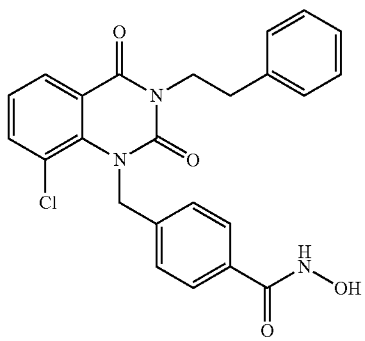 [SMILES: O=C(NO)c1ccc(Cn2c(=O)n(CCc3ccccc3)c(=O)c3cccc(Cl)c32)cc1] | A = 8-Cl—$C_6H_3$<br>B = $C_6H_4$<br>R = $CH_2CH_2C_6H_5$<br>Y = null |
| 147 | 4-((3-(2-fluoro-2-phenylethyl)-2,4-dioxo-3,4-dihydroquinazolin-1(2H)-yl)methyl)-N-hydroxybenzamide | 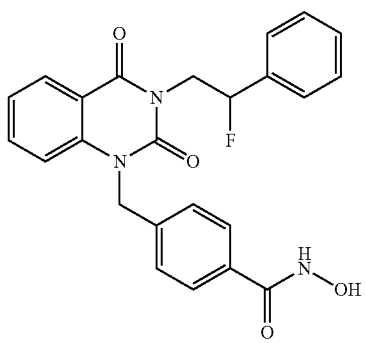 | A = $C_6H_4$<br>B = $C_6H_4$<br>R = $CH_2CHFC_6H_5$<br>Y = null |

What is claimed is:

1. A compound of Formula I

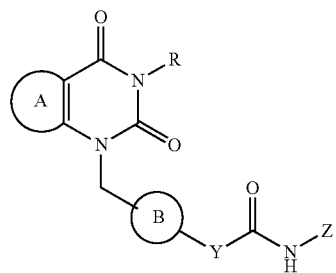

Formula I or a pharmaceutically acceptable salt thereof, wherein

R is $(C_1-C_6)$alkyl, $(C_1-C_6)$alkyl$(C_6-C_{18})$aryl, halo$(C_1-C_6)$alkyl, halo$(C_1-C_6)$alkylphenyl, halo$(C_1-C_6)$alkyl$(C_6-C_{18})$aryl$(C_1-C_6)$alkoxy, N—$(C_1-C_6)$alkylamino$(C_6-C_{18})$aryl$(C_1-C_6)$alkyl, hydroxyl$(C_6-C_{18})$aryl$(C_1-C_6)$alkyl, $(C_6-C_{18})$aryl$(C_1-C_6)$alkyl, $(C_3-C_{18})$heteroaryl$(C_1-C_6)$alkyl, halo$(C_6-C_{18})$aryl$(C_1-C_6)$alkyl, halo$(C_1-C_6)$alkoxy$(C_6-C_{18})$aryl$(C_1-C_6)$alkyl, halo$(C_1-C_6)$alkyl$(C_6-C_{18})$aryl$(C_1-C_6)$alkyl, (C1-C6)alkylamino$(C_6-C_{18})$aryl$(C_1-C_6)$alkyl, morpholinyl$(C_1-C_6)$alkyl$(C_6-C_{18})$aryl, morpholinyl$(C_6-C_{18})$aryl$(C_1-C_6)$alkyl, N,N-dimethyl$(C_6-C_{18})$aryl$(C_1-C_6)$alkyl, $(C_1-C_6)$alkoxy$(C_6-C_{18})$aryl$(C_1-C_6)$alkyl, or hydroxyl$(C_1-C_6)$alkoxy$(C_6-C_{18})$aryl$(C_1-C_6)$alkyl;

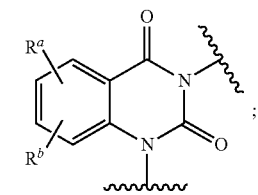

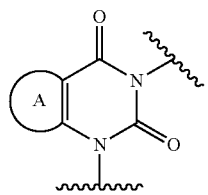

the moiety is
wherein R$^a$ and R$^b$ are independently selected from the group consisting of hydrogen, halogen, (C$_1$-C$_6$)alkyl, (C$_3$-C$_6$)cycloalkyl, (C$_1$-C$_6$)alkoxy, hydroxyl, —CN, and -CF$_3$;

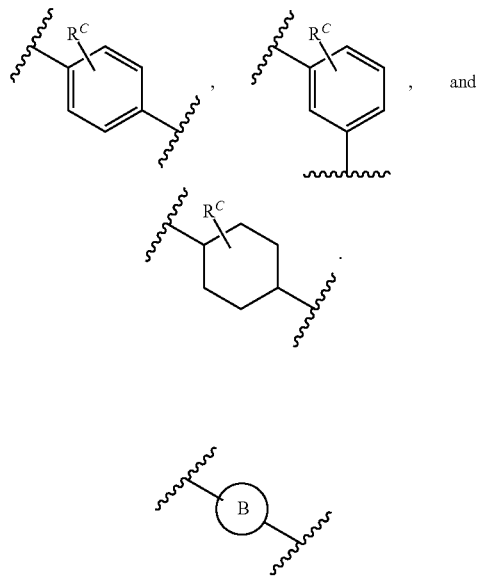

the moiety is selected from the group consisting of
in which R$^C$ is optionally present and is hydrogen, halogen, C$_1$-C$_6$alkyl, or (C$_1$-C$_6$)alkoxyl;
Y is absent or is selected from the group consisting of —CH$_2$—, —CF$_2$—, —CFH—, —CH=CH—, and —CH$_2$CH$_2$—; and
Z is —OH, —O—C(=O)—CH$_3$, -O-Valine, -O-Valine hydrochloride salt, -O-Valine trifluoroacetic acid salt, or-O—C(=O)—CH(NH2)-CH(CH$_3$)$_2$ hydrochloride or trifluoroacetic acid salt.

2. The compound or the pharmaceutically acceptable salt thereof of claim 1, wherein
R is methyl, 2-Me-C$_6$H$_4$, -CH$_2$Ph, -CH$_2$CH$_2$C$_6$H$_5$, (CH$_2$)$_4$ C$_6$H$_5$, -CH$_2$CH$_2$-(4-F—C$_6$H$_4$), -CH$_2$CH$_2$-(2-OMe-C$_6$H$_4$), -CH$^2$CH$_2$-(2-OH—C$_6$H$_4$), -CH$_2$CH$_2$-(2-thiophene), CH$_2$CH$_2$-(2-F—C$^6$H$^4$), -CH$^2$CH$_2$-(3-F—C$_6$H$_4$), -CH$_2$CH$_2$-(4-F—C$_6$H$_4$), -CH$_2$CH$_2$-(4-Cl-C$_6$H$_4$), -CH$^2$CHOH—C$_6$H$_5$, -CH$_2$CH$_2$-(3-Cl-4-OMe-C$_6$H$_3$), -CH$^2$CH$_2$-(4-NHMe-C$_6$H$_4$), -CH$_2$CH$_2$-(4-morpholine-C$_6$H$_4$), -CH$_2$CH$_2$-(4-OH—C$_6$H$_4$), CH$_2$CH$_2$-(3-OMe-C$_6$H$_4$), -CH$_2$CH$_2$-(4-OMe-C$_6$H$_4$), cyclopropyl-C$_6$H$_5$, -CH$_2$-(4-CF$_3$-C$_6$H$_4$), -CH$_2$CH$_2$-(4-CF$_3$-C$_6$H$_4$), CH$_2$CH$_2$CF$_3$, -CH$_2$CF$_3$, CH$_2$-(2-CF$_3$-C$_6$H$_4$), -CH$_2$CH$_2$-(2-CF$_3$-C$_6$H$_4$), -CH$_2$-(3-CF$_3$-C$_6$H$_4$), -CH$_2$CH$_2$-(3-CF$_3$-C$_6$H$_4$), CH$_2$CH$_2$-(2-Br-C$_6$H$_4$), CH$_2$CH$_2$-(4-Br-C$_6$H$_4$), 2-t-Bu-C$_6$H$_4$, 2-ethyl-C$_6$H$_4$, 2-Me-3-CF$_3$-C$_6$H$_3$, -CH$_2$CH$_2$-(6-(1,3-benzodioxole)), -CH$_2$CH$_2$-(3,4-diOMe-C$_6$H$_3$), 2,6-di-Me-C$_6$H$_3$, 2-methyl-C$_6$H$_4$, cyclopropyl, cyclohexyl, 3-CF$_3$-C$_6$H$_4$, 3,3-di-F-cyclobutyl,-2-OCF$_3$-C$_6$H$_4$, CH$_2$CH$_2$-(2-pyridine), -CH$_2$CH$_2$-(3-pyridine), -CH$_2$CH$_2$-(4-pyridine), CH$_2$-(2-OCF$_3$-C$_6$H$_4$), CH$_2$CH$_2$-(4-(OCH$_2$CH$_2$OH)-C$_6$H$_4$), -CH$_2$CH$_2$-(3,4-di-OH—C$_6$H$_3$), 4-CH$_2$-(N-morpholine)-C$_6$H$_4$, CH$_2$CH$_2$-(O-3-CF$_3$-C$_6$H$_4$), propyl-2-C$_6$H$_5$, CH$_2$CH$_2$-(4-CH$_2$-(N-morpholine)-C$_6$H$_4$), CH$_2$CH$_2$-(4-NH$_2$-C$_6$H$_4$), (4-Cl-2,6-di-Me-C$_6$H$_2$), (4-Br-2,6-di-Me-C$_6$H$_2$), or CH$_2$CHFC$_6$H$_5$.

3. The compound or the pharmaceutically acceptable salt thereof of claim 1, wherein

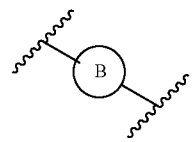

the moiety is C$_6$H$_4$, 3-F—C$_6$H$_3$, 2-F—C$_6$H$_3$, or C$_6$H$_8$.

4. The compound or the pharmaceutically acceptable salt thereof of claim 1, wherein R$^a$ and R$^b$ are independently selected from the group consisting of H, —OH, —F, Cl,-CF$_3$, —CN, —Me, -OMe, -OCH$_2$CH$_2$OMe, or –cyclopropyl.

5. The compound or the pharmaceutically acceptable salt thereof of claim 1, wherein
R is methyl, benzyl, 2-phenylethyl, 2-(4-hydroxyphenyl)ethyl, 2-(4-methoxyphenyl)ethyl, 2-(4-fluorophenyl)ethyl, 2-thiophenylethyl, 3-phenylpropyl, or 2-(4-methoxyphenyl)ethyl.

6. The compound or the pharmaceutically acceptable salt thereof of claim 1, wherein
R is phenyl, benzyl, 2-phenylethyl, 2-(4-hydroxyphenyl)ethyl, 3-phenylpropyl, or 2-(4-methoxyphenyl)ethyl.

7. A composition comprising a therapeutically effective amount of the compound or the pharmaceutically acceptable salt thereof of claim 1, and a pharmaceutically acceptable carrier or vehicle.

8. A method for treatment of a tumor in a subject in need thereof, comprising:
administering a therapeutically effective amount of the compound or the pharmaceutically acceptable salt thereof of claim 1.

9. The method of claim 8, wherein the tumor is selected from the group consisting of glioma, pancreatic carcinoma, hepatocellular carcinoma, colon tumor, breast tumor, prostate tumor, lymphoma and cutaneous tumor.

10. The method of claim 9 wherein the cutaneous tumor is melanomas or basal carcinomas.

11. A method for treatment of a tumor in a subject in need thereof, comprising:
administering a therapeutically effective amount of the compound or the pharmaceutically acceptable salt thereof of claim 1, wherein the tumor is selected from the group consisting of glioma, breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, and acute lymphocytic leukemia.

12. The compound or the pharmaceutically acceptable salt thereof of claim 2, wherein

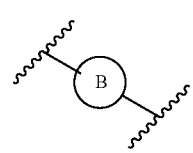

the moiety is $C_6H_4$, 3-F—$C_6H_3$, 2-F—$C_6H_3$, or $C_6H_8$.

13. The compound or the pharmaceutically acceptable salt thereof of claim 2, wherein $R^a$ and $R^b$ are independently selected from the group consisting of H, —OH, —F, Cl, -$CF_3$, —CN, —Me, -OMe, -OCH$_2$CH$_2$OMe, or —cyclopropyl.

14. The compound or the pharmaceutically acceptable salt thereof of claim 3, wherein $R^a$ and $R^b$ are independently selected from the group consisting of H, —OH, —F, Cl, -$CF_3$, —CN, —Me, -OMe, -OCH$_2$CH$_2$OMe, or —cyclopropyl.

15. A method for treatment of a tumor in a subject in need thereof, comprising:
administering a therapeutically effective amount of the compound or the pharmaceutically acceptable salt thereof of claim 2.

16. The compound or the pharmaceutically acceptable salt thereof of claim 1, wherein the compound is selected from the group consisting of

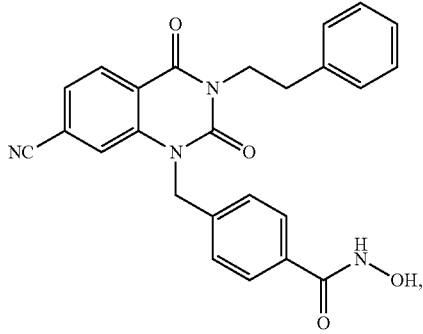

1

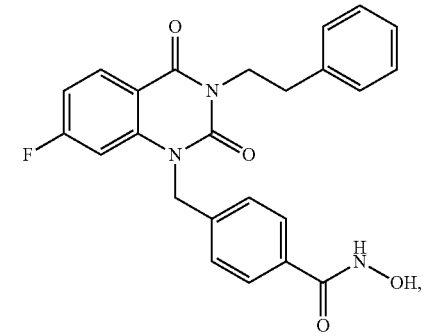

2

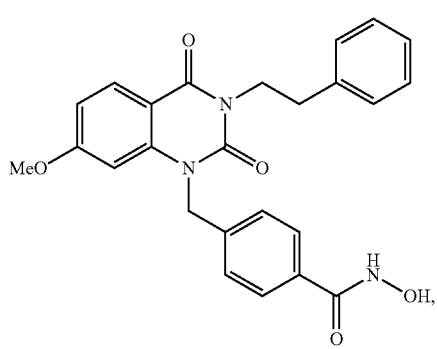

-continued

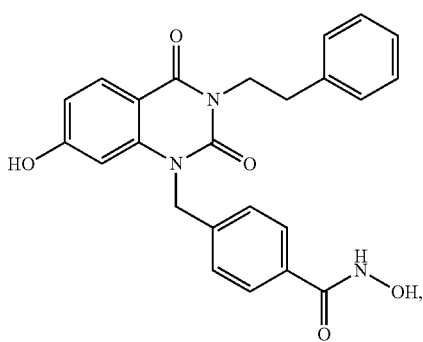

3

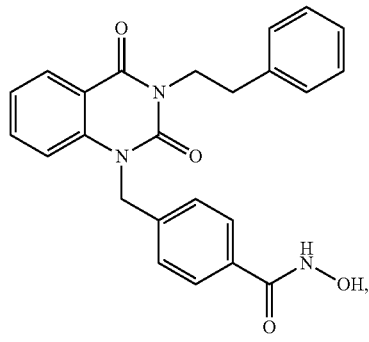

4

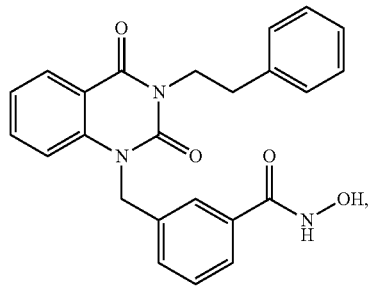

5

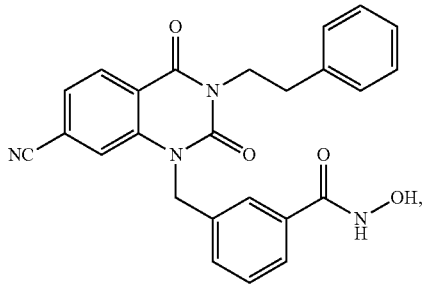

6, 7

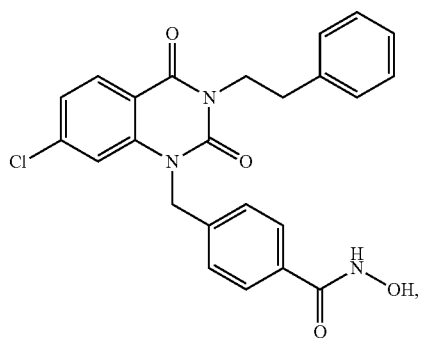
8
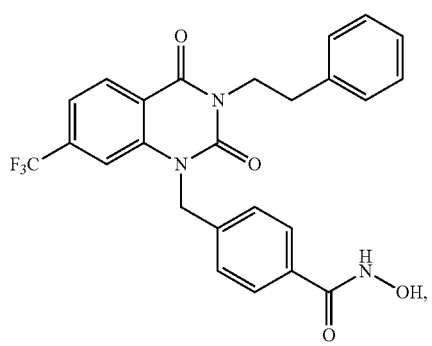
13
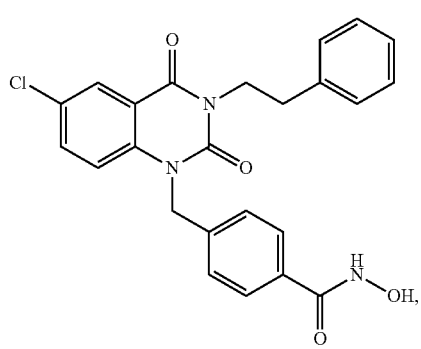
9
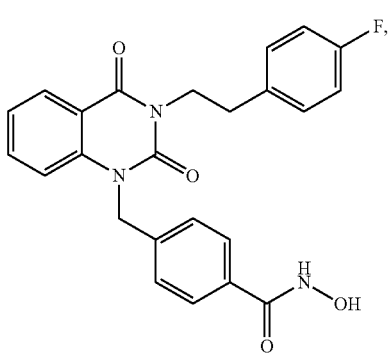
14
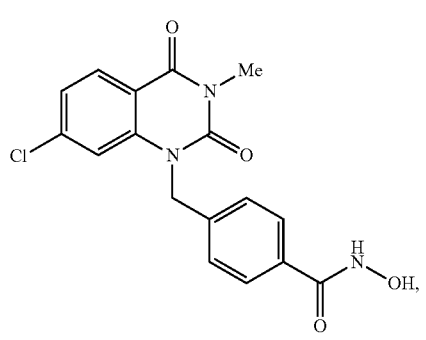
10
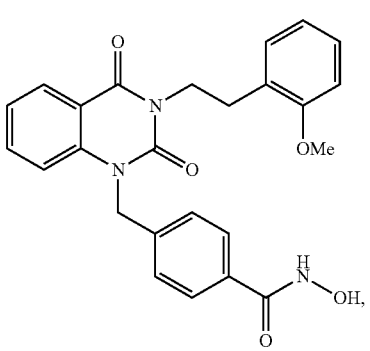
15
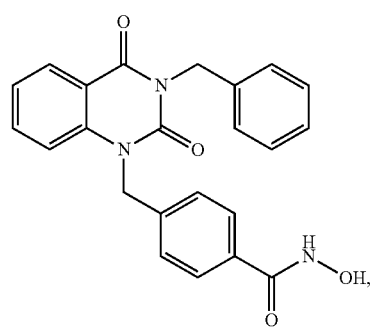
11
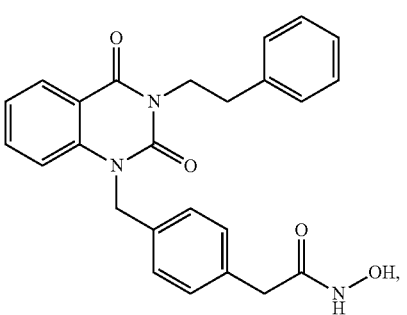
16

-continued
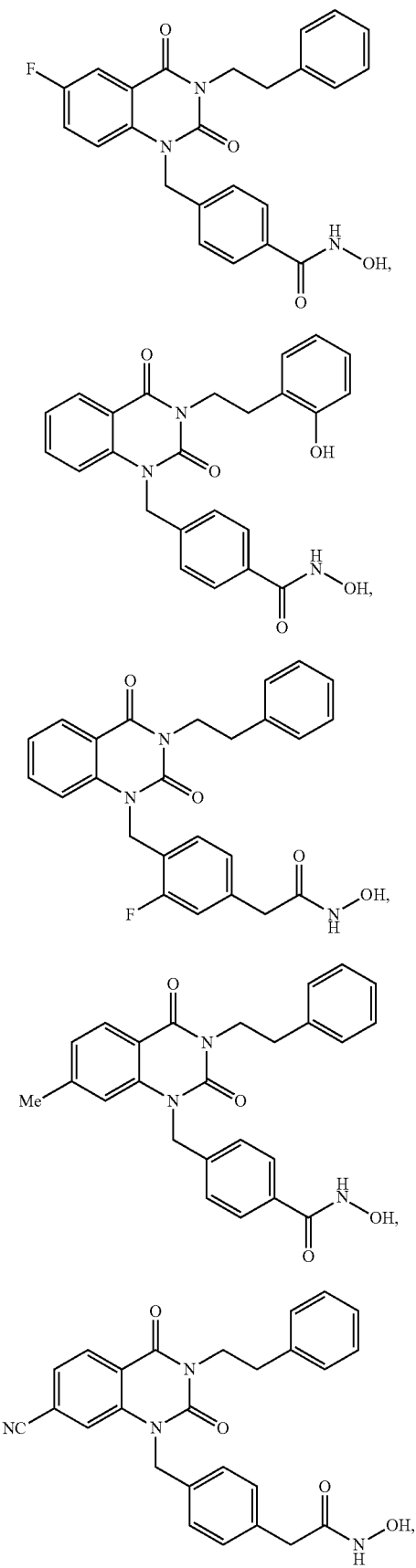
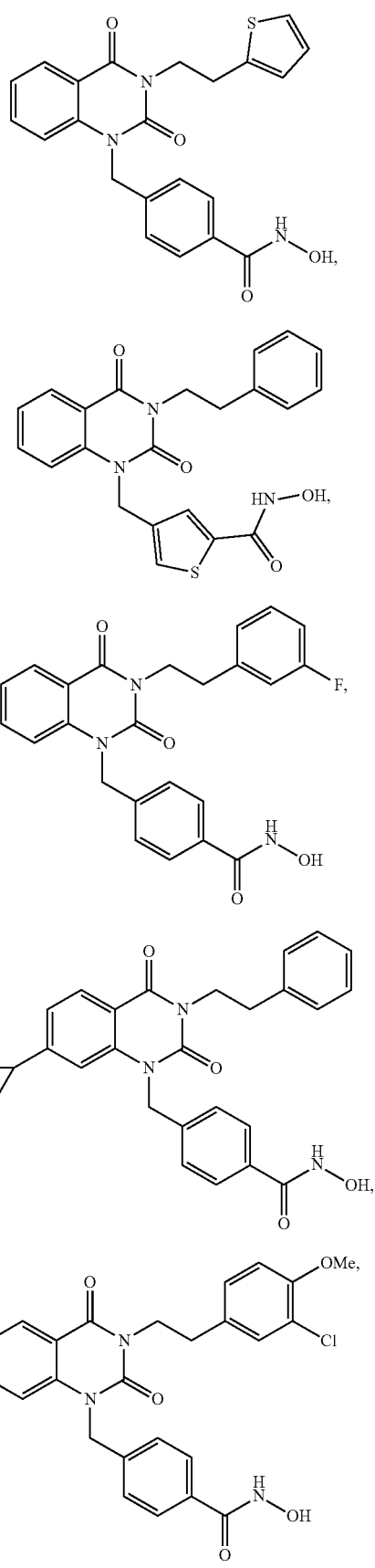

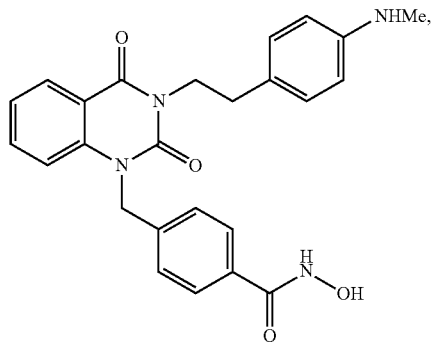
29
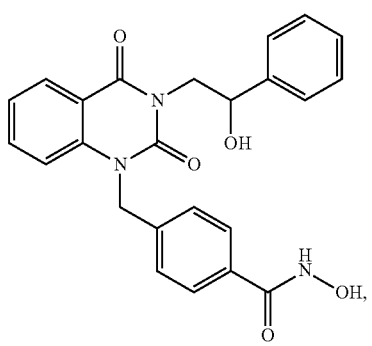
59
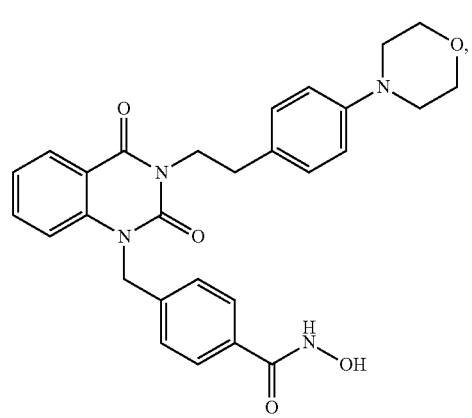
30
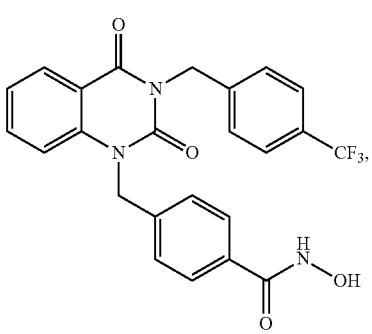
62
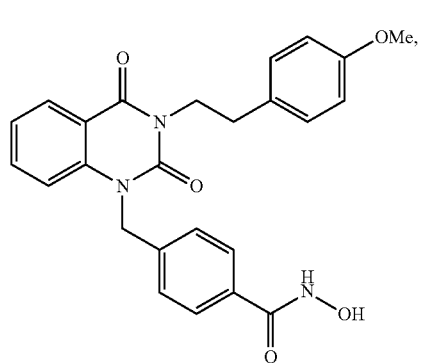
33
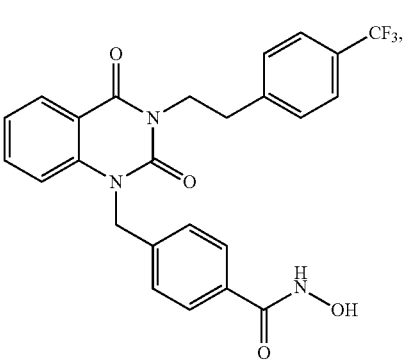
63
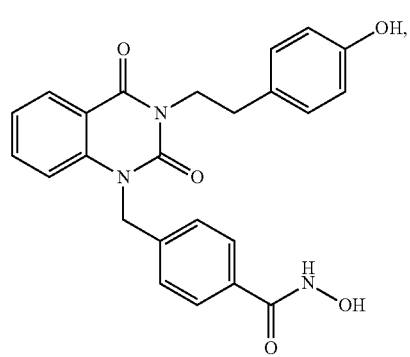
34
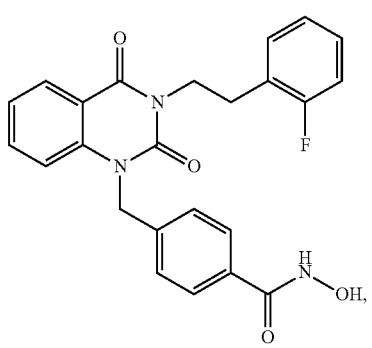
66

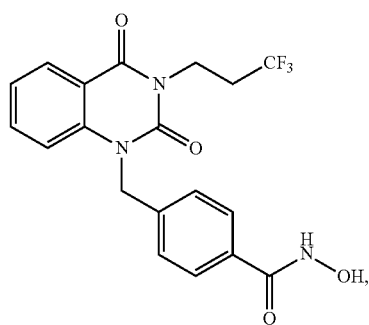
67
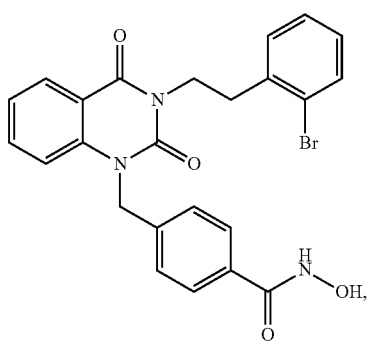
76
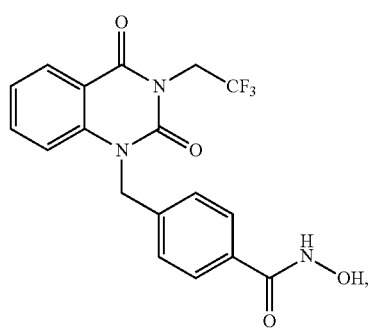
68
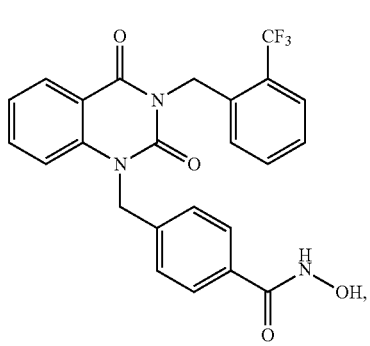
77
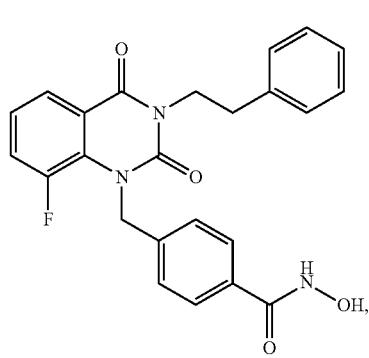
69
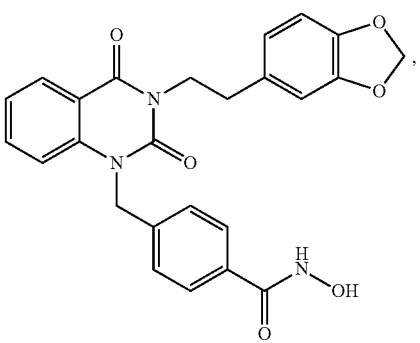
85
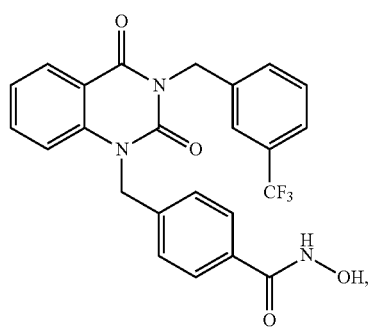
75
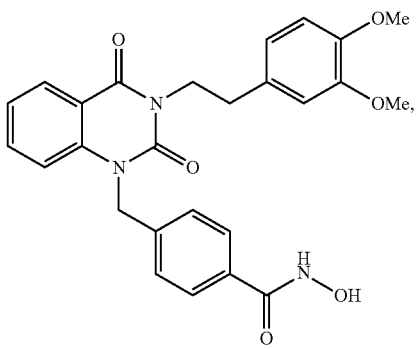
86

87
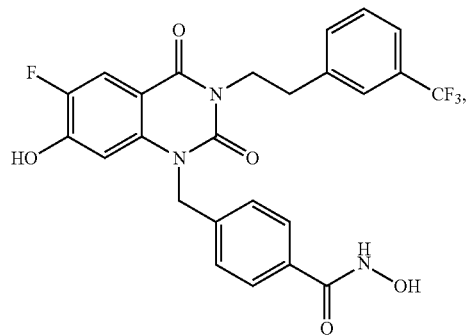
88
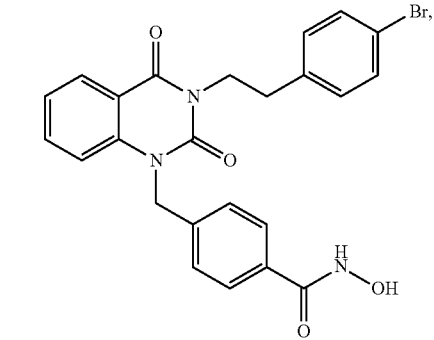
99
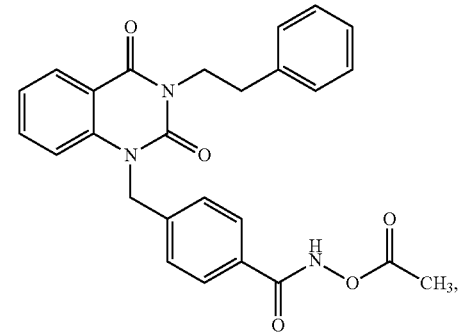
100
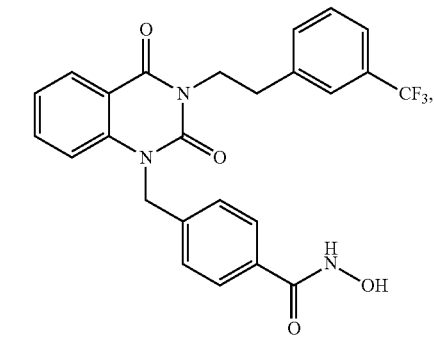
101
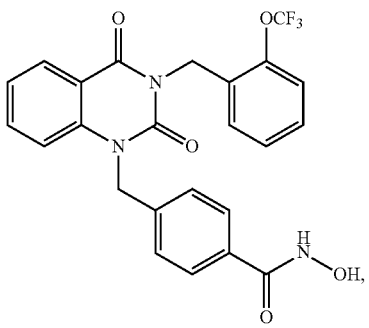
102
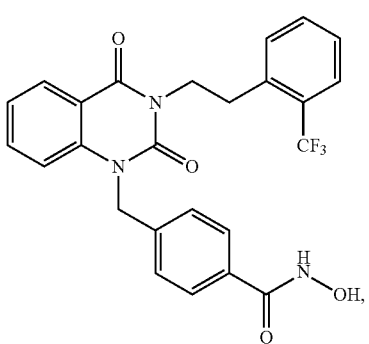
103
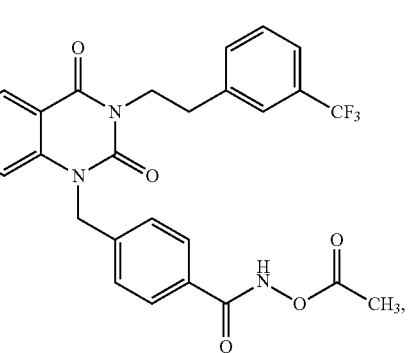
106
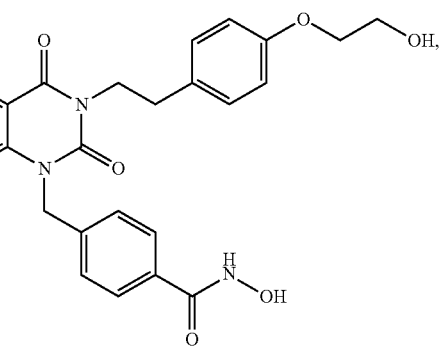

108
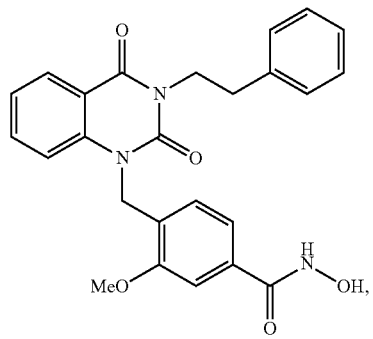
109
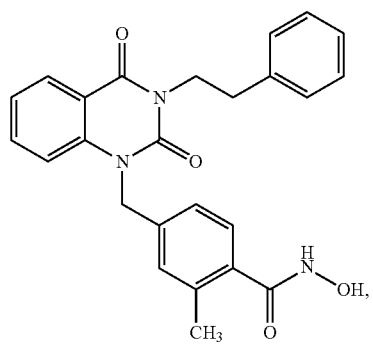
110
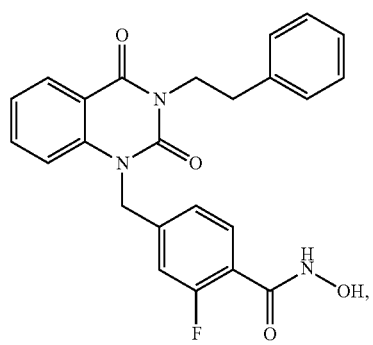
111
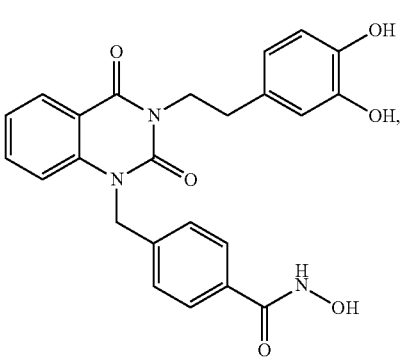
112
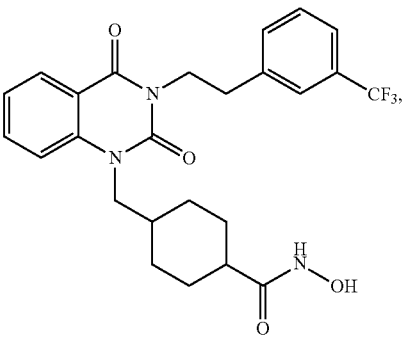
113
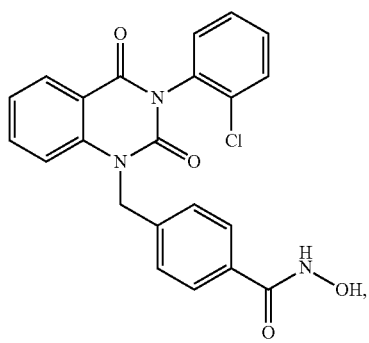
117
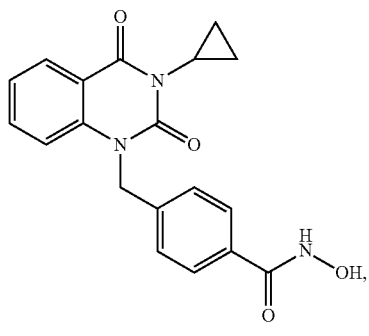
118
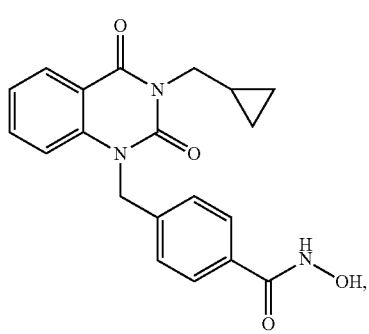

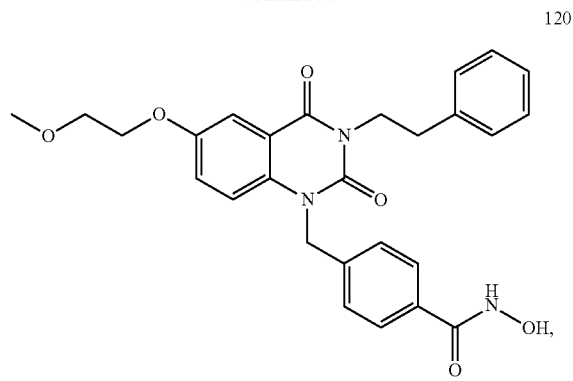
120
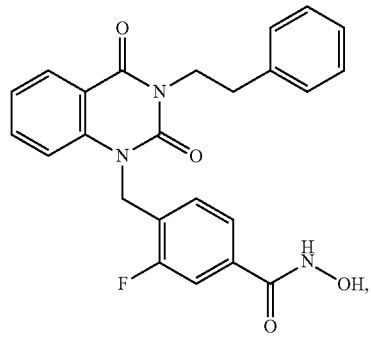
139
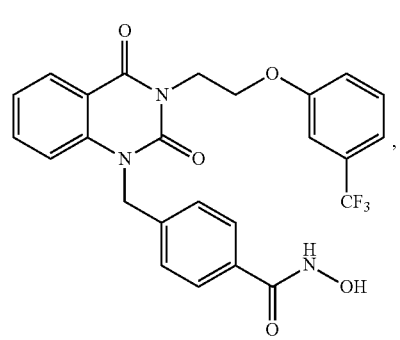
129
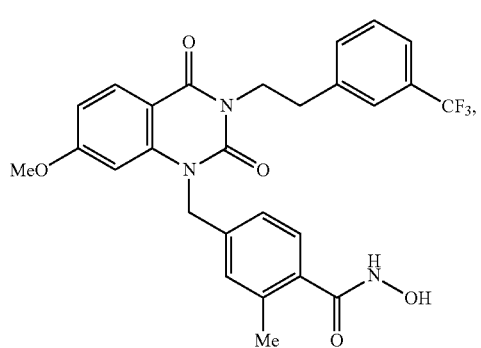
140
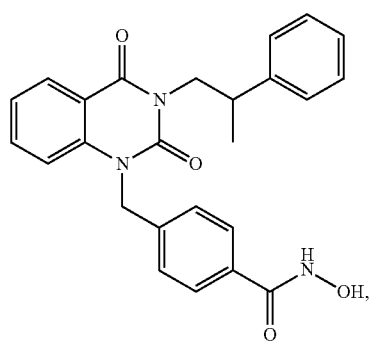
130
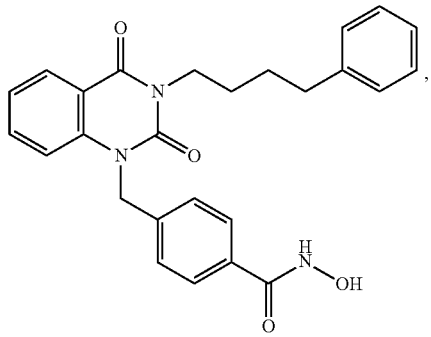
141
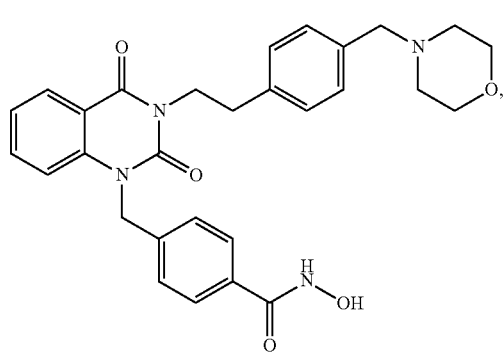
131
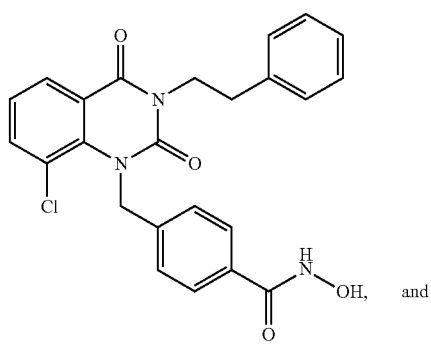
146
and -continued

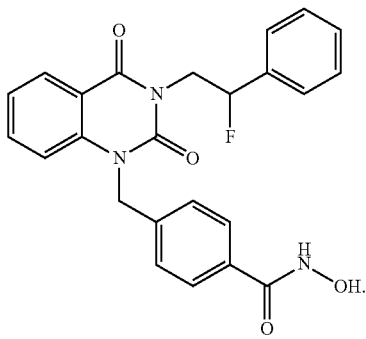

147

17. A method for treatment of a tumor in a subject in need thereof, comprising:
   administering a therapeutically effective amount of the compound or the pharmaceutically acceptable salt thereof of claim 16.

18. The method of claim 17, wherein the tumor is selected from the group consisting of glioma, breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, acute lymphocytic leukemia and cutaneous tumor.

19. The compound or the pharmaceutically acceptable salt thereof of claim 1, wherein:
   R is $(C_1-C_6)$alkyl, $(C_1-C_6)$alkyl$(C_6-C_{18})$aryl, N—$(C_1-C_6)$alkylamino$(C_6-C_{18})$aryl$(C_1-C_6)$alkyl, hydroxyl$(C_6-C_{18})$aryl$(C_1-C_6)$alkyl, $(C_3-C_{18})$heteroaryl$(C_1-C_6)$alkyl, halo$(C_6-C_{18})$aryl$(C_1-C_6)$alkyl, halo$(C_1-C_6)$alkoxy$(C_6-C_{18})$aryl$(C_1-C_6)$alkyl, morpholinyl$(C_6-C_{18})$aryl$(C_1-C_6)$alkyl, or $(C_1-C_6)$alkoxy$(C_6-C_{18})$aryl$(C_1-C_6)$alkyl, and

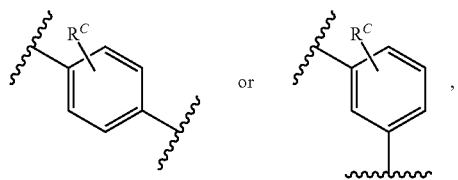

or

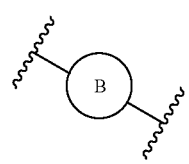

the moiety is.

20. The compound or the pharmaceutically acceptable salt thereof of claim 16, wherein the compound is selected from the group consisting of

1

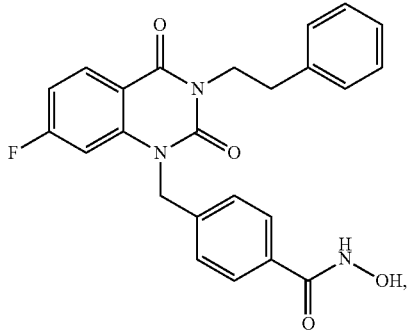

2

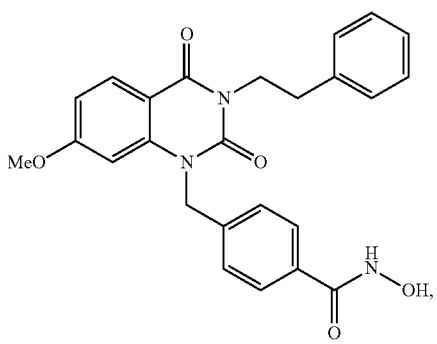

3

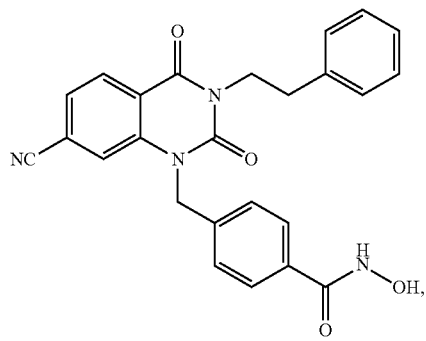

4

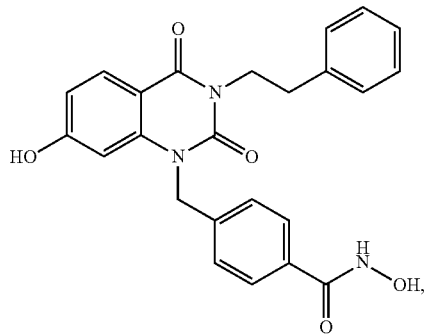

5
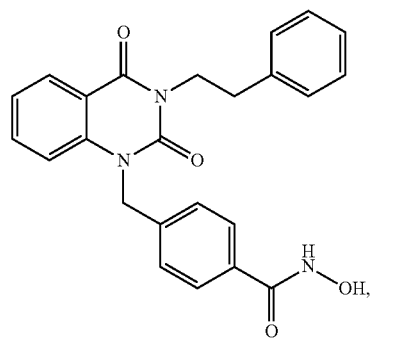
6
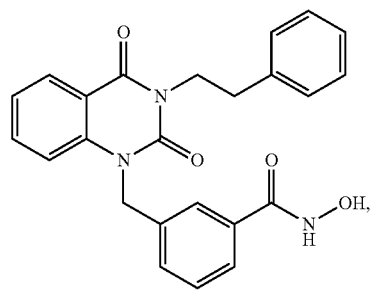
7
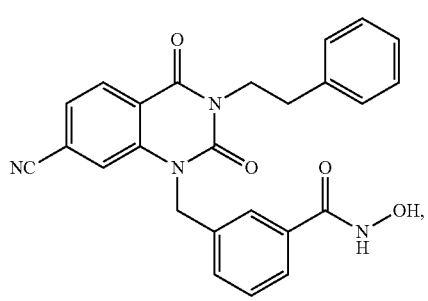
8
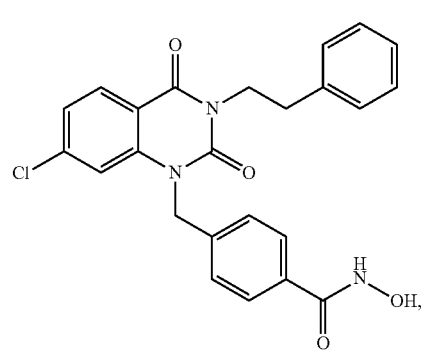
9
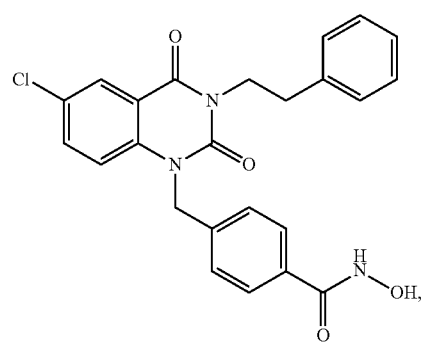
10
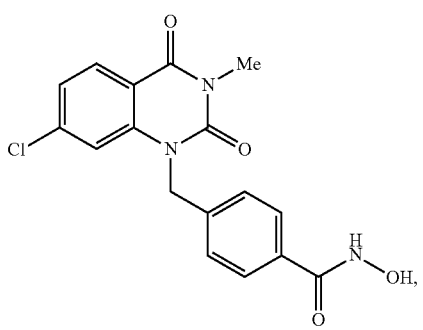
11
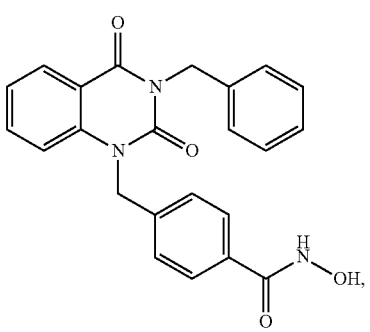
13
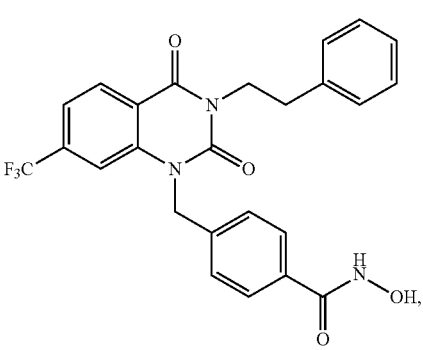
14
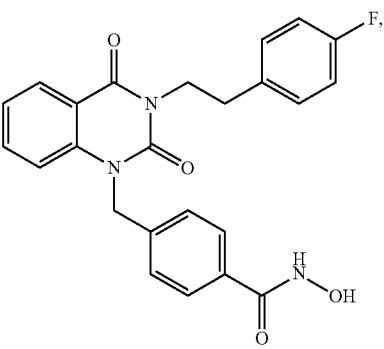

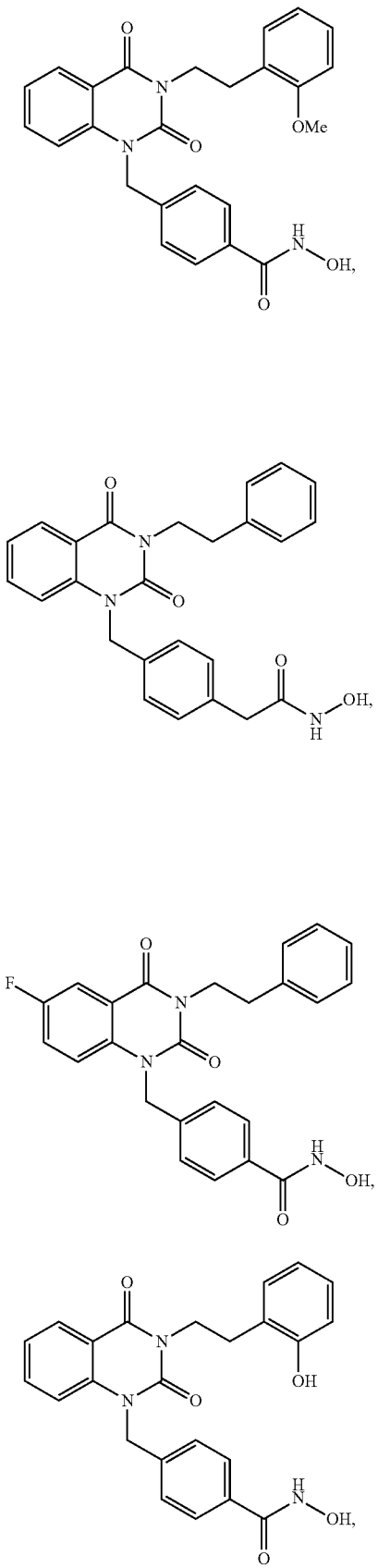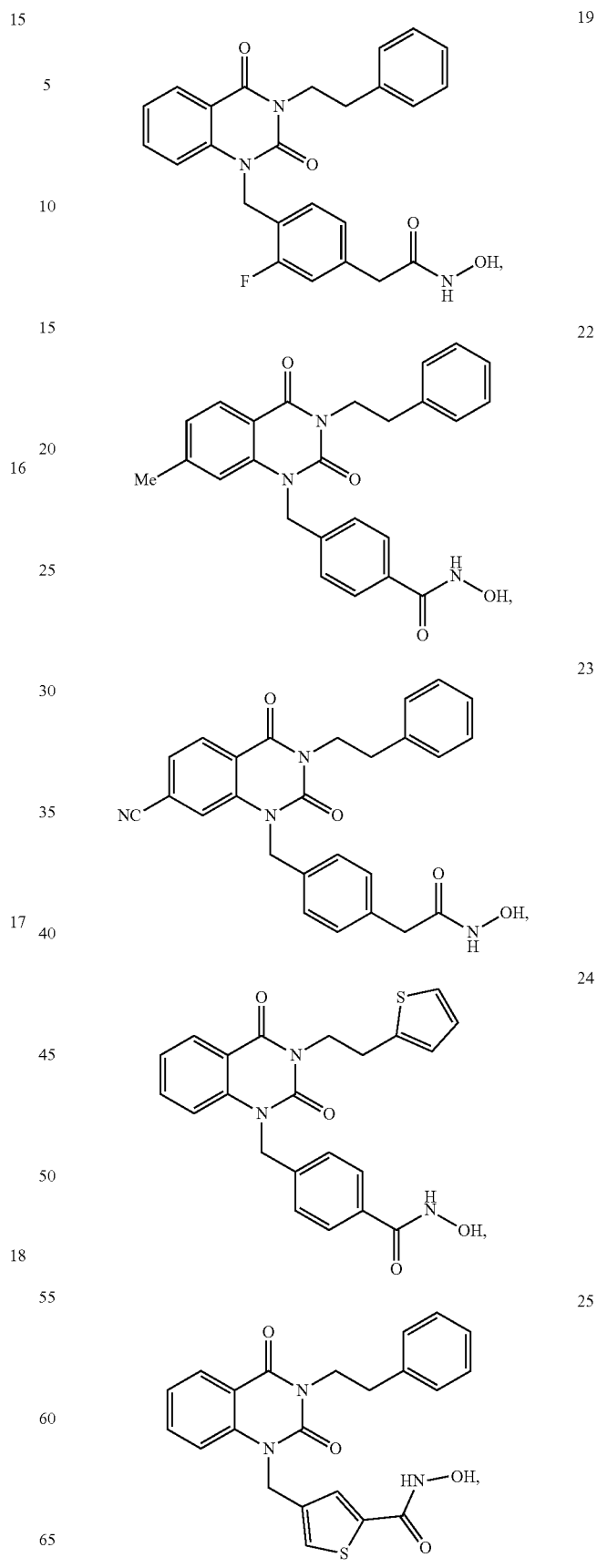

-continued
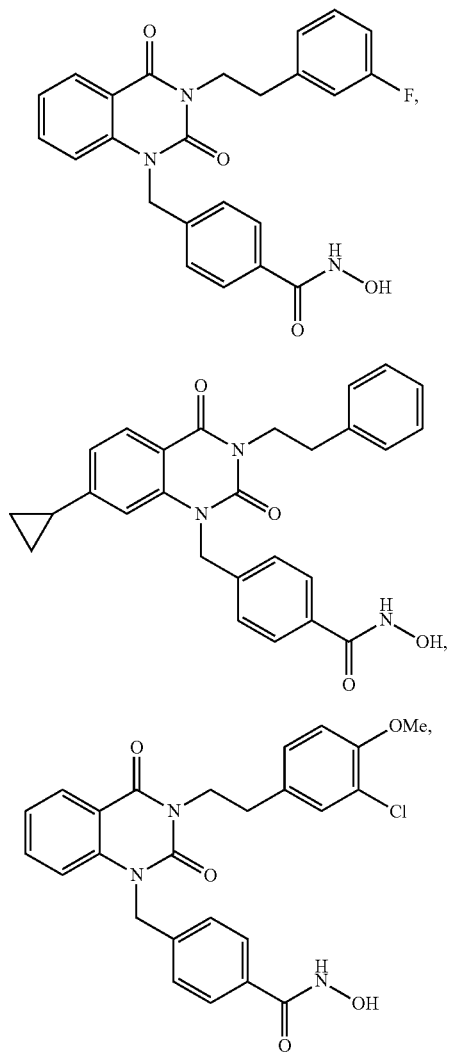
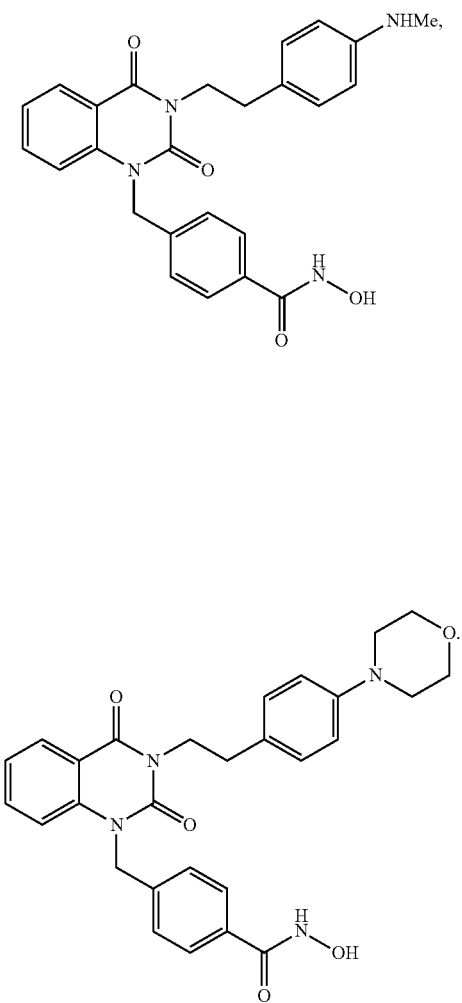
* * * * *